(12) United States Patent
Loustau et al.

(10) Patent No.: US 11,505,608 B2
(45) Date of Patent: *Nov. 22, 2022

(54) CHIMERIC ANTIGEN RECEPTORS AGAINST MULTIPLE HLA-G ISOFORMS

(71) Applicant: Invectys SA, Paris (FR)

(72) Inventors: Maria Loustau, Paris (FR); François Anna, Bourg la Reine (FR); Pierre Langlade Demoyen, Neuilly-sur-Seine (FR); Julien Caumartin, Le Vésinet (FR)

(73) Assignee: Invectys SA, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 17/739,596

(22) Filed: May 9, 2022

(65) Prior Publication Data

US 2022/0281981 A1 Sep. 8, 2022

Related U.S. Application Data

(63) Continuation of application No. 17/471,744, filed on Sep. 10, 2021, now Pat. No. 11,325,977, which is a continuation of application No. 17/077,502, filed on Oct. 22, 2020, now Pat. No. 11,117,971, which is a continuation of application No. PCT/EP2019/073257, filed on Aug. 30, 2019.

(30) Foreign Application Priority Data

Aug. 31, 2018 (EP) .................................... 18306153
Jun. 21, 2019 (EP) .................................... 19305809

(51) Int. Cl.
*C07K 16/28* (2006.01)
*C07K 14/725* (2006.01)
*C07K 14/705* (2006.01)
*C12N 5/0783* (2010.01)

(52) U.S. Cl.
CPC ...... *C07K 16/2833* (2013.01); *C07K 14/7051* (2013.01); *C07K 14/70517* (2013.01); *C07K 14/70521* (2013.01); *C07K 14/70578* (2013.01); *C12N 5/0637* (2013.01); *C07K 2317/52* (2013.01); *C07K 2317/53* (2013.01); *C07K 2317/56* (2013.01); *C07K 2317/565* (2013.01); *C07K 2317/567* (2013.01); *C07K 2317/622* (2013.01); *C07K 2317/73* (2013.01); *C07K 2319/03* (2013.01)

(58) Field of Classification Search
CPC .......... C07K 14/7051; C07K 14/70521; C07K 14/70517; C07K 16/2833; C07K 14/70578; C07K 2317/56; C07K 2317/565; C07K 2317/622; C07K 2317/503; C07K 2319/03; C12N 5/0637
See application file for complete search history.

(56) References Cited

U.S. PATENT DOCUMENTS

| | | | |
|---|---|---|---|
| 11,117,971 B2 | 9/2021 | Loustau et al. |
| 11,325,977 B2 | 5/2022 | Loustau et al. |
| 2017/0226223 A1 | 8/2017 | Williams et al. |
| 2020/0016201 A1 | 1/2020 | Epstein |
| 2020/0085868 A1 | 3/2020 | Cho et al. |
| 2021/0122825 A1 | 4/2021 | Cho et al. |
| 2021/0403574 A1 | 12/2021 | Loustau et al. |

FOREIGN PATENT DOCUMENTS

| | | |
|---|---|---|
| EP | 2730588 A1 | 5/2014 |
| WO | WO-9631604 A1 | 10/1996 |
| WO | WO-2016160622 A2 | 10/2016 |
| WO | WO-2017207775 A1 | 12/2017 |

OTHER PUBLICATIONS

Bensussan, A. et al., "Detection of Membrane-Bound HLA-G Translated Products with a Specific Monoclonal Antibody," Proc. Natl. Acad. Sci. USA, Oct. 1995, 92:10292-10296.
International Search Report and Written Opinion for International Application No. PCT/EP2019/073257 dated Oct. 2, 2019, 11 pages.
Li et al., "Increasing the safety and efficacy of chimeric antigen receptor T cell therapy," Protein Cell 2017, 8(8):573-589.
Pulè et al., "A Chimeric T Cell Antigen Receptor That Augments Cytokine Release and Supports Clonal Expansion of Primary Human T Cells," Molecular Therapy, Nov. 2005, 12(5):933-941.
Shiroishi, M. et al., "Human Inhibitory Receptors Ig-like Transcript 2 (ILT2) and ILT4 Compete with CD8 for MHC Class I Binding and Bind Preferentially to HLA-G" PNAS, Jul. 2003, 100(15):8856-8861.

*Primary Examiner* — Ruixiang Li
(74) *Attorney, Agent, or Firm* — Cooley LLP; Ivor R. Elrifi

(57) ABSTRACT

The present invention relates to chimeric antigen receptors (CAR) against multiple but not all human leukocyte antigen (HLA-G) isoforms. More specifically, the invention concerns CARs that are specific for HLA-G β2M-free or β2M-associated immunosuppressive isoforms respectively.

20 Claims, 12 Drawing Sheets
Specification includes a Sequence Listing.

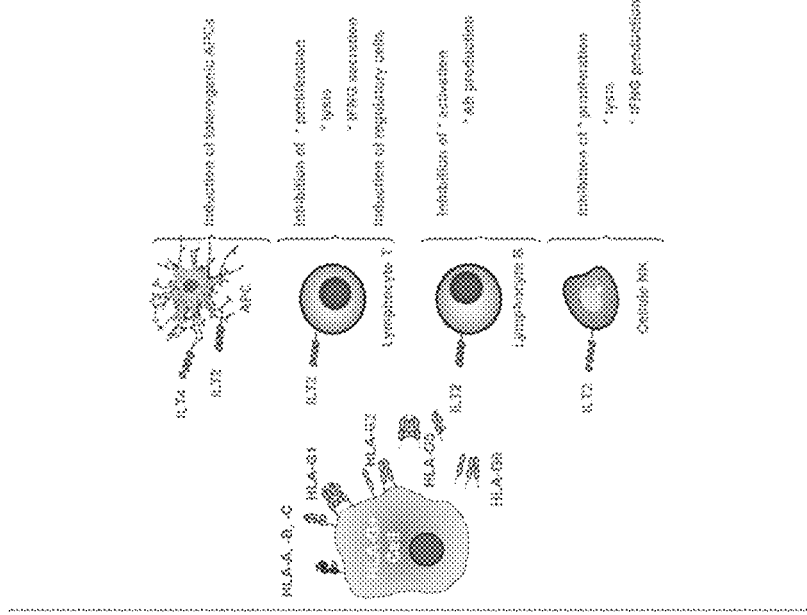
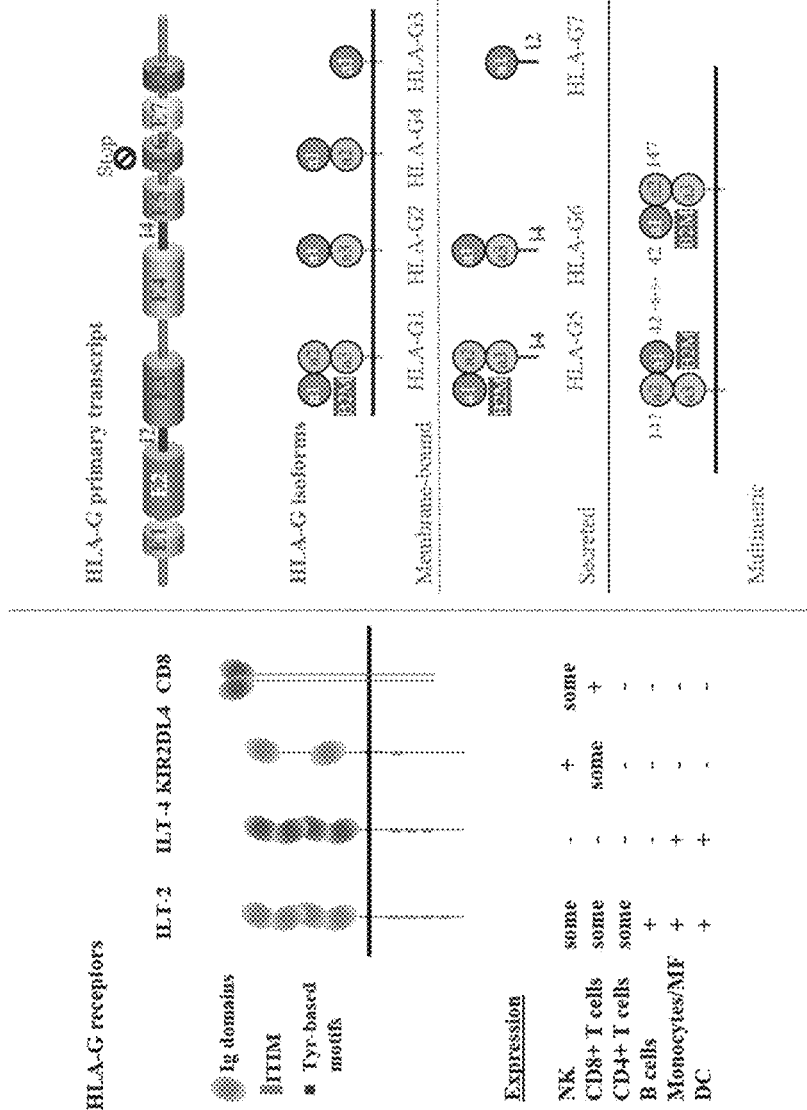

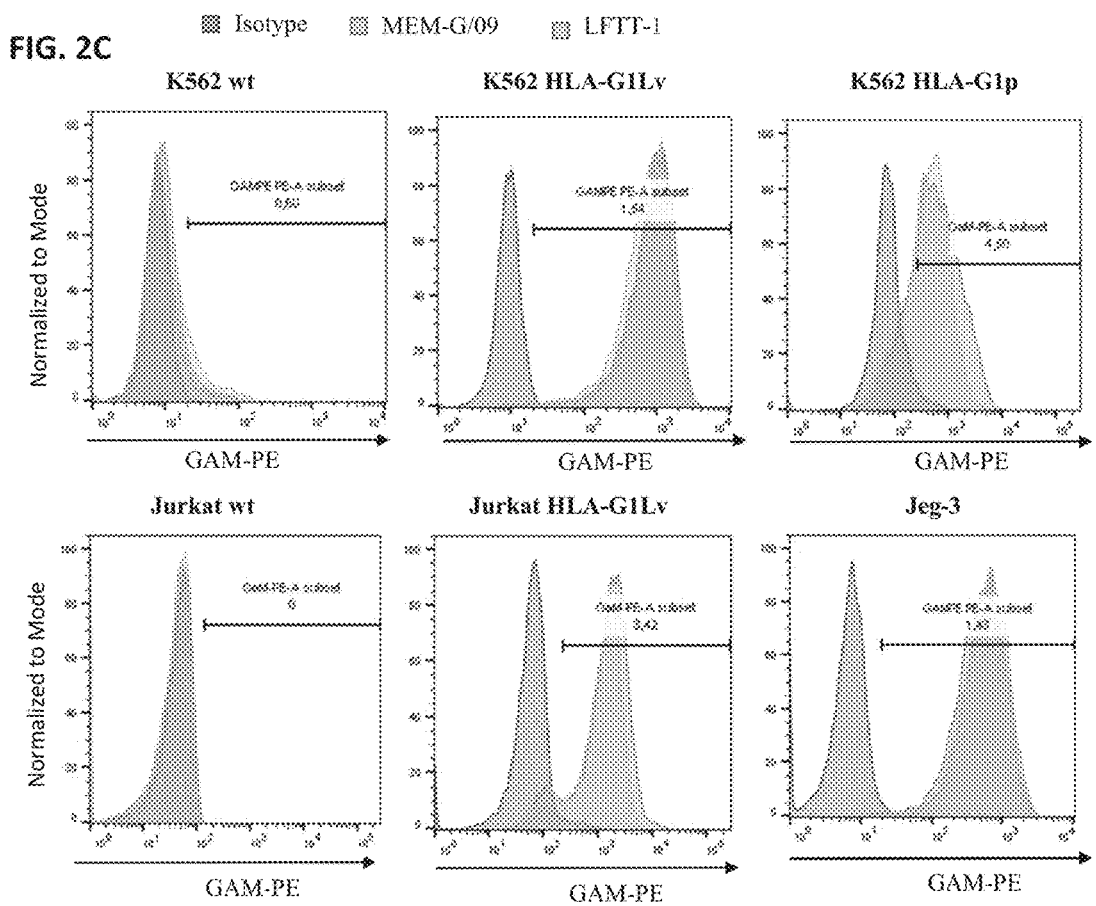
Figure 2 (Following)
FIG. 3A  15E7 28BBz
FIG. 3B  LFTT-1 28BBz

| Hinge hIgG4 + | Signal Peptide | ScFv (VL-VH) | Hinge hIgG4 | Mutated CH2 hIgG4 | CH3 hIgG4 | 28BBζ | P2A | Truncated hCD19 |

| Hinge hIgG4 + | Signal Peptide | ScFv (VL-VH) | Hinge hIgG4 | CH3 hIgG4 | 28BBζ | P2A | Truncated hCD19 |

| Hinge | Signal Peptide | ScFv (VL-VH) | Hinge hIgG4 | 28BBζ | P2A | Truncated hCD19 |

Hinge hIgG4-mCH2-CH3    Hinge hIgG4-CH3    Hinge hIgG4

FIG. 5A
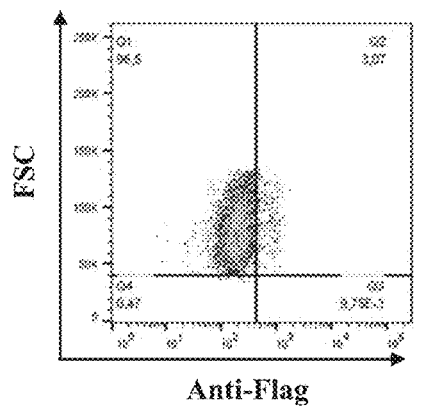
Jurkat wt
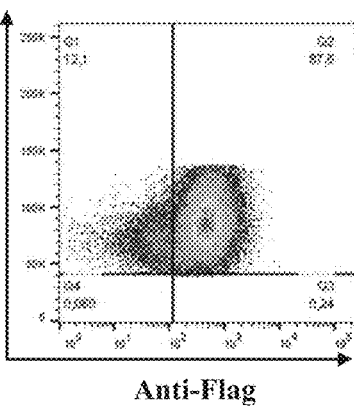
Jurkat 15E7
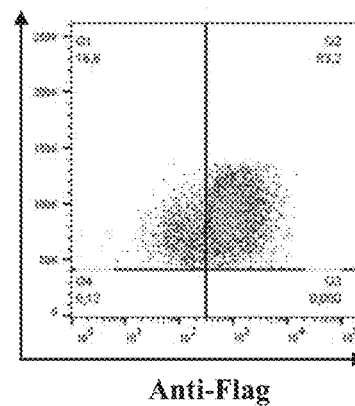
Jurkat LFTT-1
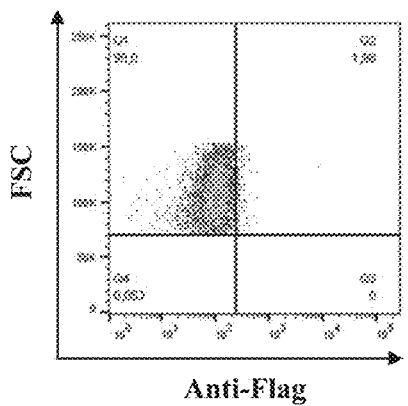
NKT1.2
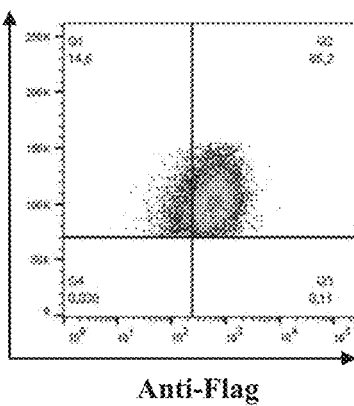
NKT1.2 15E7
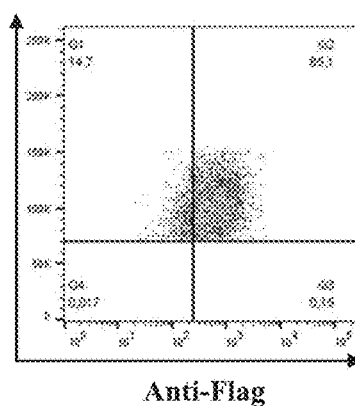
NKT1.2 LFTT-1
FIG. 5B
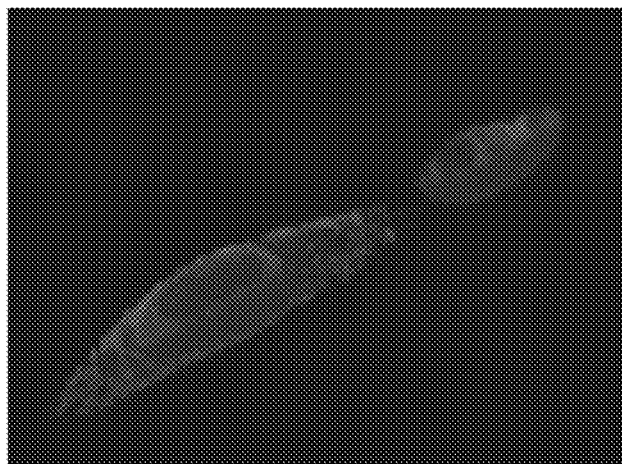

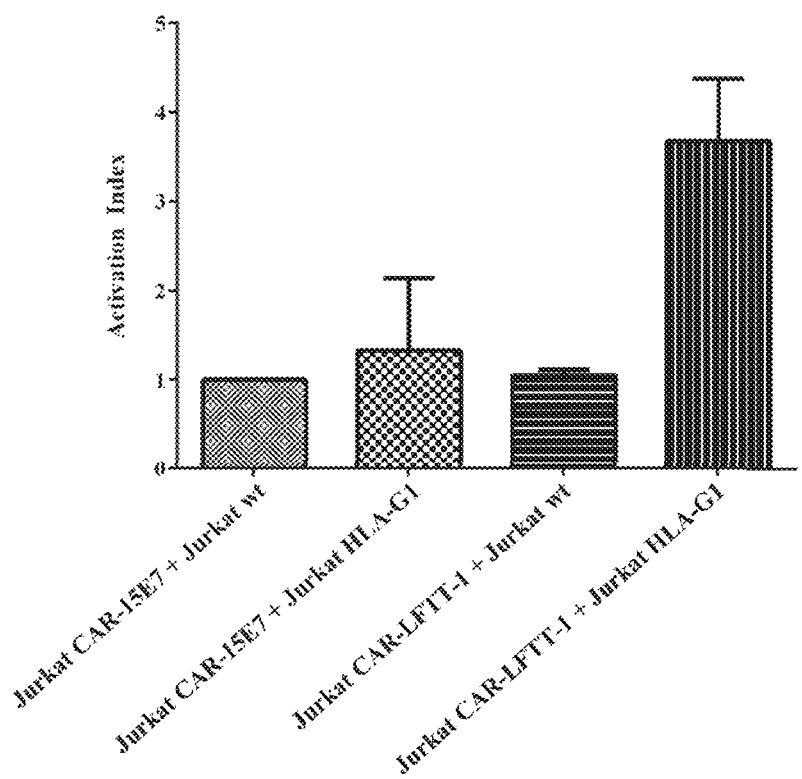
FIG. 6D
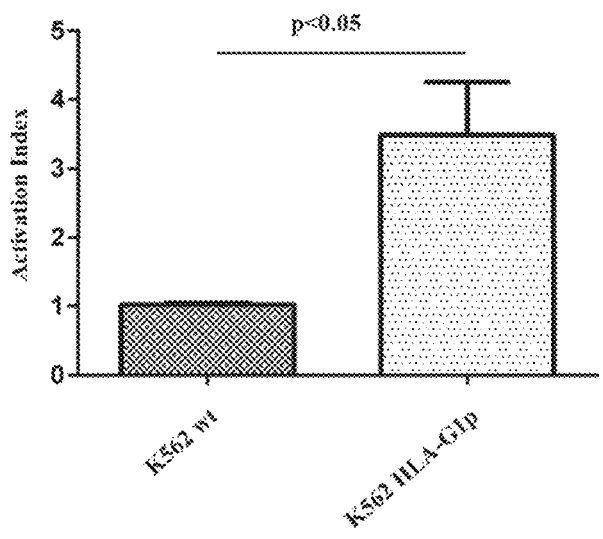 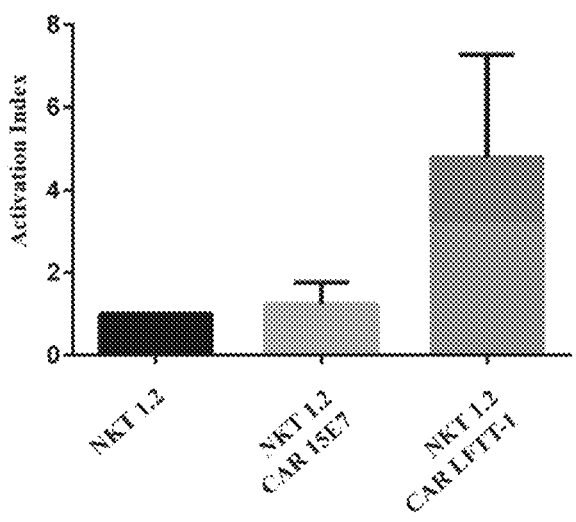
FIG. 7A    FIG. 7B 6h coincubation, n=3

- Control
- 15E7 CAR Hinge IgG4
- 15E7 CAR Hinge IgG4 + CH3
- 15E7 CAR Hinge IgG4 + mCH2-CH3
- LFTT-1 CAR Hinge IgG4
- LFTT-1 CAR Hinge IgG4 + CH3
- LFTT-1 CAR Hinge IgG4 + mCH2-CH3

CHIMERIC ANTIGEN RECEPTORS AGAINST MULTIPLE HLA-G ISOFORMS

CROSS-REFERENCE TO RELATED APPLICATIONS

This application is a continuation of U.S. patent application Ser. No. 17/471,744, filed on Sep. 10, 2021 and issued as U.S. Pat. No. 11,325,977, which is a continuation of U.S. patent application Ser. No. 17/077,502, filed on Oct. 22, 2020 and issued as U.S. Pat. No. 11,117,971, which is a continuation of International Patent Application No. PCT/EP2019/073257, filed on Aug. 30, 2019, which claims the benefit of European Patent Application No. 19305809.6, filed on Jun. 21, 2019 and European Patent Application No. 18306153.0, filed on Aug. 31, 2018, the disclosure of each of which is hereby incorporated by reference in its entirety.

DESCRIPTION OF THE TEXT FILE SUBMITTED ELECTRONICALLY

The contents of the text file submitted electronically herewith are incorporated herein by reference in their entirety: A computer readable format copy of the Sequence Listing (filename: INVE_002_03US_SeqList.txt, date recorded: May 9, 2022, file size: ~122,237 bytes).

FIELD OF THE INVENTION

The invention relates to the field of immunology, cell biology, and molecular biology. In certain aspects, the field of the invention concerns immunotherapy. More particularly, the invention relates to chimeric antigen receptors (CAR) against multiple human leukocyte antigen (HLA-G) isoforms.

BACKGROUND OF THE INVENTION

For years, the foundations of cancer treatment were surgery, chemotherapy, and radiation therapy. However, in the past several years, immunotherapy has emerged as an effective tool in cancer treatment. Advances in genetic engineering have led to the design of synthetic tumor targeting receptors, termed chimeric antigen receptors (CARs) that can be introduced into human immune cells such as T cells to redirect antigen specificity and enhance functions of effector immune cells. CARs were first developed in the mid-1980s and the interest on these receptors is growing since. They were first generated to bypass the intrinsic TCR specificity of expressing T cells by providing specific antigen recognition independently from HLA-peptides complexes. Prototypic single chain CARs were first described in a study by Eshhar and colleagues in 1993 in which specific activation and targeting of T cells was mediated through molecules consisting of a target-antigen-specific antibody domain and the γ- or ζ-signaling subunits of the Fc epsilon receptor or T-cell receptor CD3 complex, respectively (Eshhar et al., 1993, Proc Natl Acad Sci USA., 90, 720-4). Since then many groups have devised CAR molecules with single tumor-directed specificities and enhanced signaling endodomains. Nowadays, the binding domain of a CAR typically consists of an antigen-binding domain of a single-chain antibody (scFv) or antibody-binding fragment (Fab) selected from a library and comprising the light and heavy chain variable fragments of a monoclonal antibody (Mabs) joined by a flexible linker. The scFv retains the same specificity and a similar affinity as the full antibody from which it was derived and is able to specifically bind to the target of interest. CARs thus combine antigen-specificity and T cell activating properties in a single fusion molecule. Indeed, the scFv is linked to an intracellular signaling module that includes CD3ζ to induce T cell activation upon antigen binding. The modular structure has been extended from first-generation CARs with only a CD3ζ signaling domain to second and third generation CARs that link the signaling endodomains such as CD28, 4-1BB, or OX40 to CD3ζ, in an attempt to mimic co-stimulation. Generally, a spacer or hinge domain serves as a linker between the endodomains and the scFV. The incorporation of such hinge domain improves flexibility, spatial organization and/or proximity but also the expansion of CAR cells (Qin et al, Journal of Hematology & Oncology. 2017; 10:68) or tumor localization (Watanabe et al, Oncoimmunology. 2016; 5(12): e1253656). It is thus critical to develop CAR comprising an optimized hinge domain.

The CARs allow T cells to target cancers in an MHC independent mechanism. Ligand binding of a CAR differs from that of a TCR binding to peptide/MHC (pMHC) in receptor affinity, antigen density, and spatial properties; and experimental approaches to design an optimal CAR for a specific target molecule have relied on functional assays of transduced T cells in vitro or in human tumor xenograft models. Because it is unlikely that CARs will serially engage target molecules and cluster in organized synapses as it is observed with TCR/pMHC recognition, it is assumed that a higher ligand density is required for CAR recognition than for TCRs. The optimal configuration and application of these receptors, besides affinity and specificity, rely on construct design, signaling domains, vector delivery systems, recipient immune-cell populations, and manufacturing.

While many attempts to achieve the success of CART cells for solid tumors have been undertaken results have been sometimes disappointing. The three main hurdles encountered for the application of CART cell therapies to solid tumors are (1) the identification of proper Tumor Associated Antigens (TAA), (2) the limited trafficking of adoptively transferred cells to tumor sites (3) the immunosuppressive effect of tumor microenvironment and (4) the potential safety issue of unwanted or untransformed cells.

Regarding the choice of the target, the human leukocyte antigen G (HLA-G) is depicted as a molecule able to confer protection to the fetus from the immune system of its mother's recognition and destruction, providing fetal-maternal tolerance. Besides its physiologic functions, HLA-G was recently identified as an immune checkpoint (ICP) molecule, which inhibits the effector functions of infiltrating immune cell subsets through the interaction with its specific receptors. HLA-G is expressed in numerous tumor effusions of diverse origins with a highly restricted tissue expression. In several malignant transformations, the expression of HLA-G by tumor cells rises dramatically, rendering them strongly immunosuppressive. Preclinical models have shown that the expression of HLA-G on cancer cells renders them more metastatic and significantly decreases patient survival (Lin A et al., Int J Cancer. 2012 Jul. 1; 131(1):150-7. doi: 10.1002/ijc.26375; Lin A et al. Hum Immunol. 2013 April; 74(4): 439-46. doi: 10.1016/j.humimm.2012.11.021).

HLA-G is a non-classical HLA class I molecule that was first identified in choriocarcinoma cells. Unlike classic HLA class I molecules, HLA-G is characterized by a limited polymorphism and differs as well by its expression, structure and functions. The primary transcript of HLAG is alternatively spliced resulting in the expression of seven isoforms, where four are membrane-bound (HLA-G1, HLA-G2, HLA-G3 and HLA-G4) while the other three are soluble (HLA-G5, HLA-G6 and HLA-G7). HLA-G1 and HLA-G5 are the most studied isoforms and they present the typical structure of a classical HLA class I molecule: a heavy chain constituted of three globular domains non-covalently bound to β2-microglobulin (β2M) and a peptide, while the other isoforms are shorter, lacking one or two domains of the heavy chain, and should not bind β2M.

Considering that the basic criteria to develop CAR immunotherapies are the identification of proper TAA, the accessibility of transgenic effector cell and reversibility of the immunosuppressive tumor microenvironment, and also taking into account the neo-expression of HLA-G by tumor cells and its contribution to the immunosuppressive effect of tumor microenvironment and its role as an ICP and in immune escape mechanisms, HLA-G is an exceptional candidate to develop new immunotherapies able to block this molecule. Moreover, given that no stimulatory functions or cellular responses directed against allogeneic HLA-G have been reported, and that HLA-G expression is tissue-restricted, the generation of cytolytic CAR cells directed against HLA-G would open up new possibilities in the field of cancer immunotherapy.

WO2016/160622 discloses antibodies directed against HLA-G and their uses in CAR cells. However, as HLA-G mRNA is spliced into different protein isoforms, there is a need to develop CARs able to specifically recognize the different HLA-G isoforms (β2M-associated HLA isoforms and smaller β2M-free isoforms) and/or the most abundant isoforms, to eliminate most of the cells that express the immunosuppressive isoforms, but also CAR constructs that comprise an optimized spacer domain and a selectable marker to improve CAR cells expansion and selection.

SUMMARY OF THE INVENTION

Aiming at the largest number of HLA-G isoforms, the inventors developed several chimeric antigen receptors directed against HLA-G using scFv derivatives of new anti-HLA-G specific monoclonal antibodies (Mabs). These Mabs present high affinity for HLA-G and are directed to different epitopes of the molecule, considering the heterogenicity of expression of this molecule [Alegre et al, Eur. J. Immunol. 2013. 43: 1933-1939; Alegre E et al, 2014, Journal of Immunology Research, 2014: 657625]. The inventors also optimized the spacer domain between the antigen binding domain and the endodomain to improve anti-HLA-G CAR cells efficacy. The inventors finally designed a CAR construct comprising a cleavable linker and a reporter that allows the selection of transduced CAR cells.

The invention provides a chimeric antigen receptor (CAR) comprising an antigen binding domain of an anti-HLA-G antibody, a transmembrane domain and an intracellular domain, wherein said CAR specifically binds one to six HLA-G isoform(s), preferably two to five HLA-G isoforms, preferably such CAR allows the discrimination of HLA-G isoforms, i.e. the CAR does not recognize or bind all of the seven HLA-G isoforms. In one aspect, the CAR specifically binds β2M-free HLA-G or to β2M-associated HLA-G isoforms. Alternatively, the CAR specifically binds HLA-G isoform selected from the group consisting of HLA-G1, HLA-G2, HLA-G5 and HLA-G6. In another aspect, the CAR specifically binds both HLA-G1 and HLA-G5, or to both HLA-G2 and HLA-G6 and/or to both HLA-G1/β2M-free and HLA-G5/β2M-free isoforms.

The invention particularly provides an anti HLA-G chimeric antigen receptor (CAR) sequentially comprising from N to C terminus: (a) a peptide signal sequence, b) an anti-HLA-G antibody or an antigen binding fragment thereof, c) optionally a spacer domain, d) a transmembrane domain, e) an intracellular domain, and optionally f) a cleavable linker and optionally g) a truncated human CD19 domain.

In one aspect, the spacer domain comprises or consists of (i) a human IgG4 hinge domain, (ii) a human IgG4 hinge domain and a CH3 human IgG4 domain or (iii) a mutated CH2 human IgG4 domain, a human IgG4 hinge domain and a CH3 human IgG4 hinge domain. Preferably, the spacer domain comprises or consists of the sequence set forth in (i) SEQ ID No: 25, (ii) SEQ ID No: 25 and SEQ ID No: 27, or (iii) SEQ ID No: 25, SEQ ID No: 26 and SEQ ID No: 27, or a homologous sequence showing more than 80%, preferably more than 90%, still preferably more than 95% identity therewith.

In another aspect, the signal peptide is selected from the group consisting of a CD8a signal peptide, a mouse Ig Kappa signal peptide, a human IgG4 signal peptide, an IL2 signal peptide, a human IgG2 signal peptide and a *Gaussia* luc signal peptide.

In a particular aspect, the transmembrane domain is selected from CD28, CD3 and CD8 transmembrane domains, preferably the transmembrane domain is a CD28 transmembrane domain.

Preferably, the anti HLA-G CAR of the invention comprises an intracellular domain that comprises a CD3 zeta signaling domain and at least one costimulatory domain(s) selected from CD28, 41BB, CD28, CD134, ICOS, OX40, CD149, DAP10, CD30, IL2-R, IL7r6, IL21-R, NKp30, NKp44, CD27, CD137 and DNAM-1 costimulatory domains, preferably the two costimulatory domains are 41BB and CD28 costimulatory domains.

In one aspect, the cleavable linker is selected from the group consisting of P2A, T2A, E2A, B2A and F2A. In another aspect, the truncated human CD19 domain consists of the sequence set forth in SEQ ID No: 29. Particularly, the CAR, the anti-HLA-G antibody or antigen binding fragment thereof, preferably a scFV, selectively binds β2M-free HLA-G or to β2M-associated HLA-G isoforms but does not bind all HLA-G isoforms.

In another aspect, the CAR, the anti-HLA-G antibody or antigen binding fragment thereof, preferably a scFV, or the cell expressing CAR does not bind the alpha1 domain of HLA-G.

Preferably, the anti-HLA-G antibody or antigen binding fragment thereof is an anti-HLA-G scFv that comprises:

(a)(i) the heavy chain variable region comprises SEQ ID NO: 1 or a homologous sequence showing more than 80%, preferably more than 90%, still preferably more than 95% identity with SEQ ID NO: 1; and (ii) the light chain variable region comprises SEQ ID NO: 2 or a homologous sequence showing more than 80%, preferably more than 90%, still preferably more than 95% identity with SEQ ID NO: 2; or (b)(i) the heavy chain variable region comprises SEQ ID NO: 3 or a homologous sequence showing more than 80%, preferably more than 90%, still preferably more than 95% identity with SEQ ID NO: 3; and (ii) the light chain variable region comprises SEQ ID NO: 4 or a homologous sequence showing more than 80%, preferably more than 90%, still preferably more than 95% identity with SEQ ID NO: 4.

Preferably, the antigen binding domain of the CAR is a scFv that specifically binds β2M-associated HLA-G; preferably to both HLA-G1 and HLA-G5, and the scFv comprises:

(a)(i) the heavy chain variable region comprises SEQ ID NO: 1 or a homologous sequence showing more than 80%, preferably more than 90%, still preferably more than 95% identity with SEQ ID NO: 1; and (ii) the light chain variable region comprises SEQ ID NO: 2 or a homologous sequence showing more than 80%, preferably more than 90%, still preferably more than 95% identity with SEQ ID NO: 2; or (b)(i) the CDR (Complementarity Determining Region) 1, CDR2 and CDR3 of the heavy chain variable region comprises SEQ ID NO: 1; and the CDR1, CDR2 and CDR3 of the light chain variable region comprises SEQ ID NO: 2.

Alternatively, the antigen binding domain of the CAR is a scFv that specifically binds β2M-free HLA-G, preferably to both HLA-G2 and HLA-G6 and/or to both HLA-G1/β2M-free and HLA-G5/β2M-free isoforms and the scFv comprises:

(a)(i) the heavy chain variable region comprises SEQ ID NO: 3 or a homologous sequence showing more than 80%, preferably more than 90%, still preferably more than 95% identity with SEQ ID NO: 3; and (ii) the light chain variable region comprises SEQ ID NO: 4 or a homologous sequence showing more than 80%, preferably more than 90%, still preferably more than 95% identity with SEQ ID NO: 4; or (b)(i) the CDR (Complementarity Determining Region) 1, CDR2 and CDR3 of the heavy chain variable region comprises SEQ ID NO: 3; and the CDR1, CDR2 and CDR3 of the light chain variable region comprises SEQ ID NO: 4.

Preferably, the intracellular domain of the CAR comprises a CD3 zeta signaling domain and optionally at least one costimulatory domain(s) selected from CD28, 41BB, CD28, CD134, ICOS, OX40, CD149, DAP10, CD30, IL2-R, IL7r6, IL21-R, NKp30, NKp44, CD27, CD137 and DNAM-1 costimulatory domains, preferably the two costimulatory domains are 41BB and CD28 costimulatory domains.

Preferably, the transmembrane domain of the CAR is selected from CD28, CD3 and CD8 transmembrane domains, preferably the transmembrane domain is a CD28 transmembrane domain.

Preferably, the CAR further comprises a hinge region connecting the antigen binding domain to the transmembrane domain, preferably selected in the group consisting of (i) CD28 hinge, (ii) CD8 alpha hinge, (iii) a human IgG4 hinge domain, (iv) a human IgG4 hinge domain and a CH3 human IgG4 domain and (v) a mutated CH2 human IgG4 domain, a human IgG4 hinge domain and a CH3 human IgG4 hinge domain.

The invention also relates to a multispecific CAR construct which comprises at least two different antigen binding domains, a transmembrane domain and an intracellular domain, wherein at least one of the antigen binding domains specifically binds HLA-G isoforms associated with a β2M domain of HLA-G; and at least another of the antigen binding domains specifically binds HLA-G isoforms which are not associated with a β2M domain of HLA-G.

Preferably, the multispecific CAR construct is a bispecific CAR construct that comprises (i) a domain comprising CDR 1, 2 and 3 (HCDR1, HCDR2, HCDR3) comprising a sequence of SEQ ID NO: 11, 12 and 13, respectively, (ii) a domain comprising CDR 1, 2 and 3 (LCDR1, LCDR2, LCDR3) comprising a sequence of SEQ ID NO: 14, 15 and 16, respectively, (iii) a domain comprising CDR 1, 2 and 3 (HCDR1, HCDR2, HCDR3) comprising a sequence of SEQ ID NO: 5, 6 and 7, respectively, and (iv) a domain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions.

The invention also envisions a nucleic acid molecule encoding the CAR of the invention, to an expression vector, comprising the nucleic acid molecule and to a cell comprising the CAR of the invention or the nucleic acid molecule of the invention, or the expression vector of the invention, preferably wherein the cell is selected from a group consisting of a T cell, CD4+ T cell, CD8+ T cell, B cell, NK cell, NKT cell, monocyte and dendritic cell, preferably the cell being a T cell, a B cell or a NK cell.

The invention also concerns a pharmaceutical composition comprising a nucleic acid molecule, an expression vector or a cell according to the invention and optionally a pharmaceutically acceptable carrier. Preferably, the cell of the invention or the pharmaceutical composition of the invention is for use in the treatment of cancer or for use in the treatment of a viral infection. The cell or pharmaceutical composition for such uses can be administered in combination with a CAR therapy that does not target HLA-G.

In one aspect, the pharmaceutical composition comprises (i) a cell comprising a CAR specifically binding β2M-associated HLA-G; preferably to both HLA-G1 and HLA-G5, and a cell comprising a CAR specifically binding β2M-free HLA-G, preferably to both HLA-G2 and HLA-G6 and/or to both HLA-G1/β2M-free and HLA-G5/β2M-free isoforms; or (ii) a cell comprising a CAR specifically binding both HLA-G1 and HLA-G5 or to β2M-free HLA-G isoforms, and a CAR specifically binding both HLA-G2 and HLA-G6 or to β2M-associated HLA-G isoforms.

The invention finally concerns an anti-HLA-G antibody that specifically binds HLA-G β2M-associated isoforms, preferably both HLA-G1 and HLA-G5. Such antibody comprises:

(a)(i) the heavy chain variable region comprises SEQ ID NO: 1 or a homologous sequence showing more than 80%, preferably more than 90%, still preferably more than 95% identity with SEQ ID NO: 1; and (ii) the light chain variable region comprises SEQ ID NO: 2 or a homologous sequence showing more than 80%, preferably more than 90%, still preferably more than 95% identity with SEQ ID NO: 2; or (b)(i) the CDR (Complementarity Determining Region) 1, CDR2 and CDR3 of the heavy chain variable region comprises SEQ ID NO: 1; and the CDR1, CDR2 and CDR3 of the light chain variable region comprises SEQ ID NO: 2.

BRIEF DESCRIPTION OF THE DRAWINGS

FIG. 1A-FIG. 1C: (FIG. 1A) HLA-G receptors (FIG. 1B) Alternative splicing of HLA-G primary transcript generates seven HLA-G isoforms, 4 membrane bounds and 3 soluble isoforms (FIG. 1C) Immunosuppressive functions of HLA-G.

FIG. 2A-FIG. 2C: Monoclonal antibody specificity analyzed by flow-cytometry. (FIG. 2A) 15E7 monoclonal antibody is specific for β2M-free HLA-G isoforms. (FIG. 2B) Cell surface HLA-G1 expressing cell lines labeled by 15E7 antibody. (FIG. 2C) Cell surface HLA-G1 expressing cell lines labeled by LFTT-1 antibody.

FIG. 3A-FIG. 3B: (FIG. 3A) 15E7 $3^{rd}$ CAR generation structure. (FIG. 3B) LFTT-1 $3^{rd}$ CAR generation structure.

FIG. 5A-FIG. 5B: (FIG. 5A) Anti-HLA-G CAR 15E7 and LFTT-1 expressions on Jurkat and the murine NKT 1.2 cell lines were analyzed by flow-cytometry. (FIG. 5B) HLA-G CAR 15E7 and LFTT-1 cell surface expression was determined by immunofluorescence.

FIG. 6A-FIG. 6D: (FIG. 6A) Principle of activation assays. (FIG. 6B) HLA-G1 binding by 15E7 (left panel) and LFTT-1 (right panel) antibodies. (FIG. 6C) Representative figure of effector HLA-G CAR cell activation. (FIG. 6D) Effector HLA-G CAR cells were strongly activated in presence of HLA-G expressing target cells.

FIG. 7A-FIG. 7B: CAR specificity analyzed by flow-cytometry. (FIG. 7A) Jurkat HLA-G CAR 15E7 were strongly activated in presence of HLA-G/β2M$^{neg}$ expressing cells. (FIG. 7B) NKT 1.2 HLA-G CAR LFTT-1 were strongly activated in presence of Jeg-3 cell line.

DETAILED DESCRIPTION OF THE INVENTION

Introduction

Figure 2A:
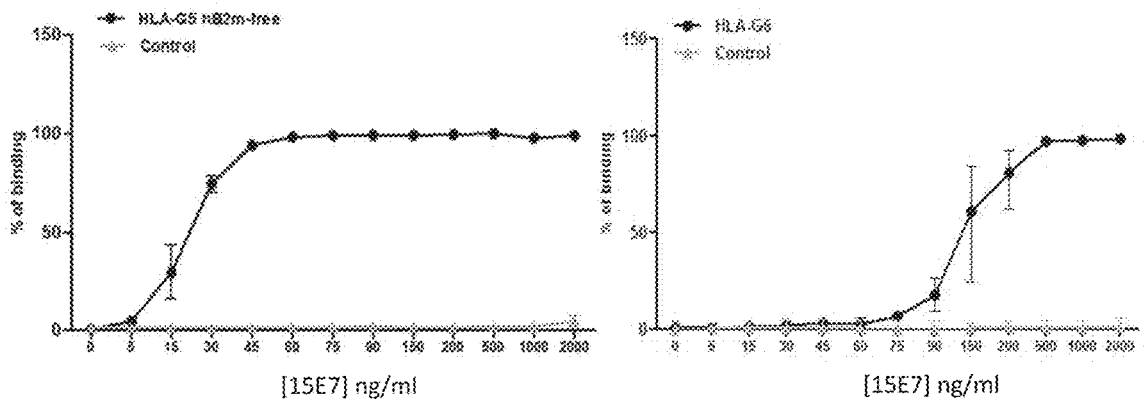

The present invention relates to a chimeric antigen receptor (CAR) comprising an extracellular domain, mostly constituted by the antigen binding domain of an anti-HLA-G specific antibody, optionally a hinge domain comprising or consisting of (i) a human IgG4 hinge domain, (ii) a human IgG4 hinge domain and a CH3 human IgG4 domain or (iii) a mutated CH2 human IgG4 domain, a human IgG4 hinge domain and a CH3 human IgG4 hinge domain, a transmembrane domain, an intracellular domain that comprises one, two or three co-stimulatory structures, depending on the generation of the CAR design, optionally a cleavable linker and optionally a reporter.

Particularly, the CAR according to the invention specifically binds to one to six, preferably two to five HLA-G isoform(s), more preferably selected from HLA-G1, HLA-G2, HLA-G5 and HLA-G6.

The invention also relates to a CAR that specifically binds to both HLA-G1 and HLA-G5 or to both HLA-G2 and HLA-G6 isoforms.

It is further provided a multispecific CAR construct, preferably a bispecific CAR construct that comprises one domain that recognizes HLA-G isoforms that are free of β2M, preferably both HLA-G2 and HLA-G6 and/or both HLA-G1/β2M free and HLA-G5/β2M free isoforms; and one domain that recognizes HLA-G isoforms associated β2M, preferably HLA-G1 and HLA-G5 isoforms.

In one aspect, the invention further relates to a CAR that specifically binds to HLA-G isoforms that are free of β2M (beta-2-microglobulin). In another aspect, the invention further relates to a CAR that specifically binds to HLA-G isoforms associated to β2M.

It particularly relates to a monoclonal antibody or a single chain variable fragment (scFv) molecule that specifically binds to both HLA-G1 and HLA-G5 or both HLA-G2 and HLA-G6 isoforms. It also relates to a monoclonal antibody or a single chain variable fragment (scFv) molecule that specifically binds to HLA-G isoforms that are free of β2M, preferably to both HLA-G2 and HLA-G6 and/or to both HLA-G1/β2M free and HLA-G5/β2M free isoforms. It further relates to a monoclonal antibody or a single chain variable fragment (scFv) molecule that specifically binds to HLA-G isoforms associated β2M, preferably HLA-G1 and HLA-G5 isoforms.

The invention also concerns nucleic acid constructs or vectors containing the nucleic acid construct that can be transduced into a cell, preferably an immune cell such as a T cell, thereby creating a recombinant immune cell engineered to express the encoded CAR. Also provided are cells that are transduced to express the CAR of the invention, cell populations, and pharmaceutical compositions containing the cells expressing CAR.

The invention may particularly relate to an immune cell that expresses two different CAR, particularly a CAR that specifically binds to HLA-G isoforms that are free of β2M, preferably to both HLA-G2 and HLA-G6 and/or both HLA-G1/β2M free and HLA-G5/β2M free isoforms; and a CAR that specifically binds to HLA-G isoforms associated β2M, preferably HLA-G1 and HLA-G5 isoforms.

Among the compositions are pharmaceutical compositions and formulations for administration, such as for adoptive cell therapy. Also provided are methods for preparing CAR expressing cells and administering the cells and compositions to subjects, e.g., patients.

Abbreviations

APC: Antigen Presenting Cell
β2M: β-2-Microglobulin
CAR: Chimeric Antigen Receptor
CTL: Cytotoxic T Lymphocyte
DC: Dendritic Cell
HLA-G: Human Leukocyte Antigen G
ICP: Immune Checkpoint
ITAM: Immunoreceptor Tyrosine-based Activation Motif
Mab(s): Monoclonal Antibody(ies)
MFI: Mean Fluorescence Intensity
MOI: Multiplicity Of Infection
NK: Natural Killer
MHC: Major Histocompatibility Complex
PBS: Phosphate Buffered Saline
PBMC: Peripheral Blood Mononuclear Cells
scFv: single-chain variable Fragment
SD: Standard Deviation
TAA: Tumor Associated Antigen
WT: wild-type Definitions To facilitate the understanding of the invention, a number of terms are defined below. The terms "Chimeric antigen receptor" (CAR), "engineered cell receptor", "chimeric cell receptor", or "chimeric immune receptor" (ICR) as used herein refer to engineered receptors, which graft an antigen binding specificity onto immune cells (e.g. T cells or NK cells), thus combining the antigen binding properties of the antigen binding domain with the immunogenic activity of the immune cell, such as the lytic capacity and self-renewal of T cells. Particularly, a CAR refers to a fused protein comprising an extracellular domain able to bind an antigen, a transmembrane domain, optionally a hinge domain and at least one intracellular domain. The terms "extracellular domain able to bind an antigen", "external domain", "ectodomain" and "antigen binding domain" are used interchangeably herein and mean any oligopeptide or polypeptide that can bind to a targeted antigen (e.g. HLA-G isoform(s)). Particularly, the term "antigen binding domain" or "antigen-specific targeting domain" as used herein refers to the region of the CAR which targets and binds to specific antigens, for example HLA-G antigen. When a CAR is expressed in a host cell, this domain forms the extracellular domain (ectodomain) of the receptor. The antigen binding domain of a CAR typically derives from an antibody and may consist of an antigen-binding domain of a single-chain antibody (scFv) or antigen-binding fragments (Fab). The terms "intracellular domain", "internal domain", "cytoplasmic domain" and "intracellular signaling domain" are used interchangeably herein and mean any oligopeptide or polypeptide known to function as a domain that transmits a signal that causes activation or inhibition of a biological process in a cell. The intracellular signaling domain may generate a signal that promotes an immune effector function of the cell transduced with a nucleic acid sequence comprising a CAR, e.g. cytolytic activity and helper activity, including the secretion of cytokines. The term "transmembrane domain" means any oligopeptide or polypeptide known to span the cell membrane and that can function to link the extracellular and signaling domains. This may be a single alpha helix, a transmembrane beta barrel, a beta-helix of gramicidin A, or any other structure. Typically, the transmembrane domain denotes a single transmembrane alpha helix of a transmembrane protein, also known as an integral protein.

A chimeric antigen receptor may optionally comprise a "hinge domain" which serves as a linker between the extracellular and transmembrane domains. As used herein the terms "hinge", "spacer", or "linker" refers to an amino acid sequence of variable length typically encoded between two or more domains of a polypeptide construct to confer for example flexibility, improved spatial organization and/or proximity. As used herein, the term "cleavable linker" refers to a peptide chain of variable length that can be proteolytically cleaved or digested by proteases or enzymes or that self-cleaves. After cleavage of the peptide linker, its integrity is generally compromised and results to the separation of the domains located on either side of the cleavable linker (C-terminus and N-terminus). A "cleavable linker" generally comprises a cleavage site. As used herein, the term "cleavage site" refers to a specific sequence of amino acids that can be cleaved specifically by a cleavage agent, such as a protease, or that self-cleaves. The term "linker" as used in the context of a scFv refers to a peptide linker that consists of amino acids such as glycine and/or serine residues used alone or in combination, to link variable heavy and variable light chain regions together.

A chimeric antigen receptor may optionally comprise a signal peptide. The terms "signal peptide" "targeting signal", "localization signal", "transit peptide" or "leader sequence" refer to a short peptide present at the N-terminus of the majority of newly synthesized proteins that are destined towards the secretory pathway. The core of the signal peptide may contain a long stretch of hydrophobic amino acids. The signal peptide may or may not be cleaved from the mature polypeptide.

As used herein, the terms "antibody" and "antibodies" refer to monoclonal antibodies, polyclonal antibodies, multispecific antibodies, human antibodies, humanized antibodies, camel antibodies, chimeric antibodies, antigen binding fragments such as single-chain variable fragment (scFv), single chain antibodies, single domain antibodies, antigen-binding fragments (Fab), F(ab') fragments, disulfide-linked variable fragment (sdFv), intrabodies, nanobodies, and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG1, $IgG_2$, $IgG_3$, $IgG_4$, IgA1 and $IgA_2$) or subclass. Unless specifically noted otherwise, the term "antibody" includes intact immunoglobulins and "antibody fragments" or "antigen binding fragments" that specifically bind to a molecule of interest (or a group of similar molecules of interest such as HLA-G isoforms) to the substantial exclusion of binding to other molecules. The term "antibody" also includes genetically engineered forms such as chimeric antibodies (for example, humanized murine antibodies), heteroconjugate antibodies (such as bispecific antibodies). Preferably, the term antibody refers to a monoclonal antibody, even more preferably to a scFv derived from a monoclonal antibody.

In terms of structure, an antibody may have heavy (H) chains and light (L) chains interconnected by disulfide bonds. There are two types of light chain, lambda (λ) and kappa (κ). Each heavy and light chain contains a constant region and a variable region (or "domain"). Light and heavy chain variable regions contain a "framework" region interrupted by three hypervariable regions, also called "complementarity-determining regions" or "CDRs". The extent of the framework region and CDRs have been defined (see, Kabat et al., Sequences of Proteins of Immunological Interest, U.S. Department of Health and Human Services, 1991, which is hereby incorporated by reference). The framework regions act to form a scaffold that provides, for positioning the CDRs in correct orientation by inter-chain, non-covalent interactions. The CDRs are primarily responsible for binding to an epitope of an antigen. The CDRs of each chain are typically referred to as CDR1, CDR2, and CDR3, numbered sequentially starting from the N-terminus. The VL and VH domain of the antibody according to the invention may comprise four framework regions or "FR's", which are referred to in the art and herein as "Framework region 1" or "FR1"; as "Framework region 2" or "FR2"; as "Framework region 3" or "FR3"; and as "Framework region 4" or "FR4", respectively. These framework regions are interrupted by three complementary determining regions or "CDR's", which are referred to in the art as "Complementarity Determining Region 1" or "CDR1"; as "Complementarity Determining Region 2" or "CDR2"; and as "Complementarity Determining Region 3" or "CDR3", respectively. These framework regions and complementary determining regions are preferably operably linked in the following order: FR1-CDR1-FR2-CDR2-FR3-CDR3-FR4 (from amino terminus to carboxy terminus).

An "antibody heavy chain" as used herein, refers to the larger of the two types of polypeptide chains present in antibody conformations.

An "antibody light chain," as used herein, refers to the smaller of the two types of polypeptide chains present in antibody conformations, K and A light chains refer to the two major antibody light chain isotypes.

The term "scFv" refers to a protein comprising at least one antibody fragment comprising a variable region of a light chain and at least one antibody fragment comprising a variable region of a heavy chain, wherein the light and heavy chain variable regions are contiguously linked, e.g., via a synthetic linker, e.g., a short flexible polypeptide linker, and capable of being expressed as a single chain polypeptide, and wherein the scFv retains the specificity of the intact antibody from which it is derived. Unless specified, as used herein a scFv may have the VL and VH variable regions in either order, e.g., with respect to the N-terminal and C-terminal ends of the polypeptide, the scFv may comprise VL-linker-VH or may comprise VH-linker-VL. The linker may comprise portions of the framework sequences.

The terms "derive from" and "derived from" as used herein refers to a compound having a structure derived from the structure of a parent compound or protein and whose structure is sufficiently similar to those disclosed herein and based upon that similarity, would be expected by one skilled in the art to exhibit the same or similar properties, activities and utilities as the claimed compounds. For example, a scFv derived from a monoclonal antibody refers to an antibody fragment that shares the same properties that the monoclonal antibody, e.g. shares identical or similar VH and VL and/or recognizes the same epitope.

As used herein, the term "antigen" refers to a compound, composition, or substance that may be specifically bound by the products of specific humoral or cellular immunity, such as an antibody molecule, a T-cell receptor or a CAR. It is readily apparent that the present invention includes intact antigen and antigen fragment thereof. It is readily apparent that an antigen can be generated synthesized or can be derived from a biological sample. Such a biological sample can include, but is not limited to a tissue sample, a tumor sample, a cell or a biological fluid. Preferably the term "antigen" refers herein to HLA-G, particularly to isoforms of HLA-G.

As used herein, the term "HLA-G" and "Human leukocyte antigen G" refers to a specific molecule associated with this name and any other molecules that have analogous biological function that share at least 80% amino acid sequence identity, preferably 90% sequence identity, more preferably at least 95% sequence identity with HLA-G, including but not limited to any one of its several isoforms, including by not limited to membrane-bound isoforms (e.g., HLA-G1, HLA-G2, HLA-G3, HLA-G4), soluble isoforms (e.g., HLA-G5, HLA-G6, HLA-G7), and soluble forms generated by proteolytic cleavage of membrane-bound isoforms (e.g. sHLA-G1). Examples of the HLA-G sequences are provided here below.

As used herein, "bind" or "binding" refer to peptides, polypeptides, proteins, fusion proteins and antibodies (including antibody fragments) that recognize and contact an antigen. Preferably, it refers to an antigen-antibody type interaction. By "specifically bind" or "immunospecifically bind" it is meant that the antibody recognizes a specific antigen, but does not substantially recognize or bind other molecules in a sample. In some instances, the terms "specific binding" or "specifically binding," can be used in reference to the interaction of an antibody, a protein, or a peptide with a second chemical species, to mean that the interaction is dependent upon the presence of a particular structure (e.g., an antigenic determinant or epitope). As used herein, the term "specific binding" means the contact between an antibody and an antigen with a binding affinity of at least $10^{-6}$ M. In certain aspects, antibodies bind with affinities of at least about $10^{-7}$ M, and preferably $10^{-8}$ M, $10^{-9}$ M, $10^{-10}$ M.

The term "antibody that specifically binds to an HLA-G isoform" or "CAR that specifically binds to an HLA-G isoform" and analogous terms, as used herein, refer to antibodies or antibody fragments that specifically recognize one or several HLA-G isoform(s) and do not or weakly recognize other antigens (including other HLA-G isoforms). Preferably, antibodies or antibody fragments that specifically bind to one or several HLA-G isoform(s) have a higher affinity to this or these HLA-G isoform(s) or a fragment thereof when compared to the affinity to other antigens or fragments thereof, including other HLA-G isoforms.

The affinity of an antibody can be a measure of its binding with a specific antigen at a single antigen-antibody site and is in essence the summation of all the attractive and repulsive forces present in the interaction between the antigen-binding site of an antibody and a particular epitope. The affinity of an antibody to a particular antigen (e.g. HLA-G isoform(s)) may be expressed by the equilibrium constant K of dissociation, defined by the equation Kd=[Ag][Ab]/[Ag Ab], which represents the affinity of the antibody-combining site; where [Ag] is the concentration of free antigen (M), [Ab] is the concentration of free antibody (M) and [Ag Ab] is the concentration (M) of the antigen-antibody complex. Where the antigen and antibody react strongly together there will be very little free antigen or free antibody, and hence the equilibrium constant or affinity of the antibody will be low. The average affinity for antibodies is a of at least $10^{-6}$ M. In certain aspects, the antigen binding domain of the CAR bind one to six, preferably two to five, HLA-G isoform(s) with affinities of at least about $10^{-6}$ M, and preferably at least $10^{-7}$ M, $10^{-8}$ M, $10^{-9}$ M or $10^{-10}$ M. The binding affinity can be measured by any method available to the person skilled in the art, in particular by surface plasmon resonance (SPR).

A "stimulatory ligand," as used herein, means a ligand that when present on an antigen presenting cell (e.g., an APC, a dendritic cell, a B-cell, and the like) can specifically bind with a cognate binding partner (referred to herein as a "stimulatory molecule") on a T cell, thereby mediating a primary response by the T cell, including, but not limited to, activation, initiation of an immune response, proliferation, and the like.

The term "co-stimulatory ligand" as used herein, includes a molecule on an antigen presenting cell (e.g., an APC, dendritic cell, B cell, and the like) that specifically binds with a cognate binding partner (referred to herein as a "stimulatory molecule") on a T cell, thereby providing a signal which, in addition to the primary signal provided by, for instance, binding of a TCR/CD3 complex with an MHC molecule loaded with peptide, mediates a T cell response, including, but not limited to, proliferation, activation, differentiation, and the like.

As used herein, a "co-stimulatory molecule" refers to a molecule expressed by an immune cell (e.g., T cell, NK cell, B cell) that provides the cytoplasmic signaling sequence(s) that regulates activation of the immune cell in a stimulatory way for at least some aspect of the immune cell signaling pathway. In one aspect, the signal is a primary signal that is initiated by, for instance, binding of a TCR/CD3 complex with an MHC molecule loaded with peptide, and which leads to mediation of a T cell response, including, but not limited to, proliferation, activation, differentiation, and the like. A primary cytoplasmic signaling sequence (also referred to as a "primary signaling domain") that acts in a stimulatory manner may contain a signaling motif which is known as an immunoreceptor tyrosine-based activation motif or ITAM. Particularly this term refers to the cognate binding partner on a T cell that specifically binds with a co-stimulatory ligand present on an antigen presenting cell, thereby mediating a co-stimulatory response by the T cell, such as, but not limited to, proliferation activation, differentiation, and the like.

A "stimulatory molecule," as used herein, means a molecule on a T cell that specifically binds with a cognate stimulatory ligand present on an antigen presenting cell.

A "co-stimulatory signal", as used herein, refers to a signal, which in combination with a primary signal, such as TCR/CD3 ligation, leads to T cell proliferation activation, differentiation, and the like, and/or upregulation or downregulation of key molecules.

By the term "stimulation" or "stimulatory" is meant a primary response induced by binding of a stimulatory molecule (e.g., a TCR/CD3 complex) with its cognate ligand thereby mediating a signal transduction event, such as, but not limited to, signal transduction via the TCR/CD3 complex. Stimulation can mediate altered expression of certain molecules, such as downregulation of TGF-β, and/or reorganization of cytoskeletal structures, and the like.

A "reporter" or "selectable marker" as used herein, refers to a polynucleotide or polypeptide that allows the detection and/or the selection of expressing cells from the population of cells sought to be transfected, particularly a cell transfected with a CAR construct. When linked to a particular construct, it allows to establish the presence and/or the quantification of such construct in a cell. "Immune cells" as used herein refers to cells involved in innate and adaptive immunity for example such as white blood cells (leukocytes) which are derived from hematopoietic stem cells (HSC) produced in the bone marrow, lymphocytes (T cells, B cells, natural killer (NK) cells and natural killer T cells (NKT)) and myeloid-derived cells (neutrophil, eosinophil, basophil, monocyte, macrophage, dendritic cells). In particular, the immune cell can be selected in the non-exhaustive list comprising B cells, T cells, in particular $CD4^+$ T cells and $CD8^+$ T cells, NK cells, NKT cells, APC cells, dendritic cells and monocytes.

According to the present invention, the donor and the recipient of the immune cells, preferably T cells, can be a single individual or different individuals, for example, autologous, allogeneic or xenogeneic individuals. As used herein, the term "autologous" refers to cells or tissues obtained from an individual and later transplanted back into the same individual. As used herein, the term "allogeneic" refers to cells or tissues obtained from different individuals of the same species, where the donor and recipient are not genetically identical. With regard to the present disclosure, an allogeneic cell transplant or tissue graft involves transplantation of cells or tissues where the donor and recipient are different individuals of the same species. The term "xenogeneic" means that which is derived or obtained from an organism of a different species. With regard to the present disclosure, a xenogeneic cell transplant or tissue graft involves transplantation of cells or tissues where the donor and recipient are different individuals of different species.

The term "treatment" refers to any act intended to ameliorate the health status of patients such as therapy, prevention, prophylaxis and retardation of the disease or of the symptoms of the disease. It designates both a curative treatment and/or a prophylactic treatment of a disease. A curative treatment is defined as a treatment resulting in cure or a treatment alleviating, improving and/or eliminating, reducing and/or stabilizing a disease or the symptoms of a disease or the suffering that it causes directly or indirectly. A prophylactic treatment comprises both a treatment resulting in the prevention of a disease and a treatment reducing and/or delaying the progression and/or the incidence of a disease or the risk of its occurrence. In certain embodiments, such a term refers to the improvement or eradication of a disease, a disorder, an infection or symptoms associated with it. In other embodiments, this term refers to minimizing the spread or the worsening of cancers. Treatments according to the present invention do not necessarily imply 100% or complete treatment. Rather, there are varying degrees of treatment of which one of ordinary skill in the art recognizes as having a potential benefit or therapeutic effect.

As used herein, the terms "disorder" or "disease" refer to the incorrectly functioning organ, part, structure, or system of the body resulting from the effect of genetic or developmental errors, infection, poisons, nutritional deficiency or imbalance, toxicity, or unfavourable environmental factors. Preferably, these terms refer to a health disorder or disease e.g. an illness that disrupts normal physical or mental functions. More preferably, the term disorder refers to immune and/or inflammatory diseases that affect animals and/or humans, such as cancer.

The term "immune disease", as used herein, refers to a condition in a subject characterized by cellular, tissue and/or organ injury caused by an immunologic reaction of the subject to its own cells, tissues and/or organs. The term "inflammatory disease" refers to a condition in a subject characterized by inflammation, e.g., chronic inflammation. Autoimmune disorders may or may not be associated with inflammation. Moreover, inflammation may or may not be caused by an autoimmune disorder.

The term "cancer" as used herein is defined as disease characterized by the rapid and uncontrolled growth of aberrant cells. Cancer cells can spread locally or through the bloodstream and lymphatic system to other parts of the body.

The term "adoptive cell therapy" or "adoptive T cell therapy" or "ACT" as used herein means the transfer of cells into a patient, where the cells have been engineered to or otherwise altered prior to transfer into the subject. An example of ACT is the harvesting from a subject's blood or tumor, an immune cell, such as a T cell. These immune cells are then stimulated ex vivo, in culture and expanded. The cells are then transduced with one or more nucleic acid constructs that allow the cell to express new molecules, such as a CAR, providing the engineered immune cells with a new mechanism for combating a disease, for instance a cancer. In some instances, the CAR comprises an antigen binding domain that specifically recognizes an antigen expressed by a tumor or cancer, such as HLA-G. Typical immune cells utilized in ACT procedures include tumor-infiltrating lymphocytes (TILs) or T cells. Immune cells used in ACT can be derived from the patient/subject themselves, or from a universal donor. ACT may also be accompanied by the optional step of lymphodepletion of the subject's own lymphocytes that may compete with the recombinant cells infused back into the subject.

The terms "CAR-therapy" or "CAR cell therapy" are used interchangeably herein and refer to a type of treatment in which immune cells are modified to express a CAR to prevent or treat a disease, for example such as viral infection or cancer. Such immune cell can be autologous or allogeneic. The immune cells can for example be B lymphocyte, T lymphocyte, natural killer cell or natural killer T cell and the like. For example, CAR cell therapy is provided by the acquisition of immune cells from a patient, transfecting the immune cells with CAR genes that allows the expression of a CAR, such CAR being directed against an antigen involved in the patient's disease, expanding the modified immune cell population, and reinfusing the cells back into the patient. The term "anti-tumor effect" as used herein, refers to a biological effect which can be manifested by a decrease in tumor volume, a decrease in the number of tumor cells, a decrease in the number of metastases, an increase in life expectancy, or amelioration of various physiological symptoms associated with the cancerous condition. An "anti-tumor effect" can also be manifested by the ability of cells and CARs of the invention in prevention of the occurrence of tumor in the first place or to limit metastasis formation.

The terms "cytolytic" or "cytotoxic" as used herein refer to the result of the immune response mediated by cytotoxic cell such as T cell or NK cells and NKT cells that leads to the death (e.g. by apoptosis) of a targeted cell.

As used herein, the term "subject", "host", "individual," or "patient" refers to human and veterinary subjects particularly to an animal, preferably to a mammal, even more preferably to a human, including adult and child. However, the term "subject" also encompasses non-human animals, in particular mammals such as dogs, cats, horses, cows, pigs, sheep and non-human primates, among others.

As used herein, the phrase "side effects" encompasses unwanted and adverse effects of a prophylactic or therapeutic agent. Side effects are always unwanted, but unwanted effects are not necessarily adverse.

An adverse effect from a therapy (e.g., a prophylactic or therapeutic agent) might be harmful, uncomfortable, or risky. Undesired effects typically experienced by patients are numerous and known in the art.

The term "in combination" as used herein refers to the use of more than one therapy (e.g., prophylactic and/or therapeutic agents). The use of the term "in combination" does not restrict the order in which therapies (e.g., prophylactic and/or therapeutic agents) are administered to a subject with a disease or disorder.

By the term "modulating," as used herein, is meant mediating a detectable increase or decrease in the level of a response in a subject compared with the level of a response in the subject in the absence of a treatment or compound, and/or compared with the level of a response in an otherwise identical but untreated subject. The term encompasses perturbing and/or affecting a native signal or response thereby mediating a beneficial therapeutic response in a subject, preferably, a human.

As used herein, a "pharmaceutical or veterinary composition" refers to a preparation of one or more of the active agents, such as comprising an antigen binding domain of an anti-HLA-G antibody according to the invention, with optional other chemical components such as physiologically suitable carriers and excipients. The purpose of a pharmaceutical or veterinary composition is to facilitate administration of the active agent to an organism. Compositions of the present invention can be in a form suitable for any conventional route of administration or use. In one embodiment, a "composition" typically intends a combination of the active agent, e.g., compound or composition, and a naturally-occurring or non-naturally-occurring carrier, inert (for example, a detectable agent or label) or active, such as an adjuvant, diluent, binder, stabilizer, buffers, salts, lipophilic solvents, preservative, adjuvant or the like and include pharmaceutically acceptable carriers.

An "acceptable vehicle" or "acceptable carrier" as referred to herein, is any known compound or combination of compounds that are known to those skilled in the art to be useful in formulating pharmaceutical or veterinary compositions.

A "therapeutically effective amount" is an amount which, when administered to a subject, is the amount of active agent that is needed to treat the targeted disease or disorder, or to produce the desired effect.

The "effective amount" will vary depending on the agent(s), the disease and its severity and the age, weight, and characteristics of the subject to be treated.

As used herein, the term "medicament" refers to any substance or composition with curative or preventive properties against disorders or diseases.

The term "transfected" or "transformed" or "transduced" are used interchangeably herein and are applied to the production of chimeric antigen receptor cells and particularly refer to the process whereby a foreign or exogenous nucleotide sequence is introduced into a cell. The exogenous nucleic acid may be introduced stably or transiently into the host cell. A "transfected" or "transformed" or "transduced" cell is one which has been transfected, transformed or transduced with exogenous nucleic acid. In some embodiments, this transduction is performed via a vector, preferably a lentiviral vector.

As used herein, the terms "nucleic acid construct" and "vector" are equivalent and refer to a nucleic acid molecule that serves to transfer a passenger nucleic acid sequence, such as DNA or RNA, into a host cell. A vector may comprise an origin of replication, a selectable marker, and optionally a suitable site for the insertion of a sequence or gene. A vector can be either a self-replicating extrachromosomal vector or a vector which integrates into a host genome. It can also comprise expression elements including, for example, a promoter, the correct translation initiation sequence such as a ribosomal binding site and a start codon, a termination codon, and a transcription termination sequence. A nucleic acid construct may also comprise other regulatory regions such as enhancers, silencers and boundary elements/insulators to direct the level of transcription of a given gene. Vectors capable of directing the expression of genes and/or nucleic acid sequence to which they are operatively linked can also be referred to herein as "expression vectors". There are several common types of vectors including nucleic acid constructs, phagemids, virus genomes, cosmids and artificial chromosomes. The nucleic acid construct can be a vector for stable or transient expression of a gene or sequence. The nucleic acid construct may comprise a nucleic acid construct origin of replication (ori). Particularly, the nucleic acid construct may be designed for genetic transfer between different hosts, including but not limited to a plasmid, a virus, a cosmid, a phage, a BAC, a YAC. Such vectors may be prepared from commercially available vectors or produced for example from baculoviruses, retroviruses, adenoviruses or AAVs according to techniques known in the art. Preferably, these terms refer to a lentiviral vector.

As used herein, the term "expression" refers to the process by which polynucleotides are transcribed into mRNA and/or the process by which the transcribed mRNA is subsequently being translated into peptides, polypeptides, or proteins. The expression level of a gene may be determined by measuring the amount of mRNA or protein in a cell or tissue sample. In one aspect, the expression level of a gene from one sample may be directly compared to the expression level of that gene from a control or reference sample. In another aspect, the expression level of a gene from one sample may be directly compared to the expression level of that gene from the same sample following administration of a compound.

The term "functional variant" or "biological equivalent" are used interchangeably as used herein and refer to a polypeptide (CAR or protein) having substantial or significant sequence identity or similarity to a parent polypeptide, which functional variant retains the biological activity of the polypeptide of which it is a variant. Unless specifically recited herein, it is contemplated that any polynucleotide, polypeptide or protein mentioned herein also includes equivalents thereof. For example, an equivalent intends at least about 70% homology or identity, or at least 80% homology or identity and alternatively, or at least about 85%, or alternatively at least about 90%, or alternatively at least about 95%, or alternatively 98% percent homology or identity and exhibits substantially equivalent biological activity to the reference protein, polypeptide or nucleic acid. Alternatively, when referring to polynucleotides, an equivalent thereof is a polynucleotide that hybridizes under stringent conditions to the reference polynucleotide or its complement. When related to antibodies, the term "equivalent" or "biological equivalent" means that the ability of the antibody to specifically bind its epitope protein or fragment thereof as measured by ELISA or other suitable methods is similar or conserved. Biologically equivalent antibodies include, but are not limited to, those antibodies, peptides, antibody fragments, antibody variant, antibody derivative and antibody mimetics that bind to the same epitope as the reference antibody. When related to CARs, functional variants encompass, for example, those variants of the CARs described herein (the parent CAR) that retain the ability to recognize target cells to a similar extent, the same extent, or to a higher extent, as the parent CAR. In reference to the parent CAR, the functional variant can, for instance, be at least about 50%, 75%, 80%, 90%, 98% or more identical in amino acid sequence to the parent CAR.

By "variant" or "equivalent", it is also meant a polypeptide sequence that differs from that of a parent polypeptide sequence by virtue of at least one amino acid modification. For instance, in the context of the invention, a variant may be a variant of a monoclonal antibody or fragment thereof or a variant of a CAR. Typically, a variant comprises from 1 to 50 amino acid modifications, preferably from 1 to 40 amino acid modifications. In particular, the variant may have from 1 to 30 amino acid changes, e.g. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid changes as compared to its parent. The variants may comprise one or several amino acid substitutions, and/or, one or several amino acid insertions, and/or one or several amino acid deletions. In some embodiments, the variant may comprise one or several conservative substitutions, e.g. as shown hereabove. In some further embodiments, the variant of an antibody or antigen binding fragment thereof, particularly a scFv, may comprise one or several amino acid modifications in the CDR domains of the parent Mab. In some other embodiments, the variant of the parent Mab may comprise one or several amino acid modifications in at least one framework domain.

By "parent polypeptide" or "polypeptide parent", as used herein, it is meant an unmodified polypeptide that is subsequently modified to generate a variant. In the context of the invention, the parent polypeptide may be an antibody, preferably a monoclonal antibody, even more preferably a scFv.

As used herein, "homology", "identity" or "similarity", when used in the context of two or more nucleic acids or polypeptide sequences, refers to two or more sequences or subsequences that are the same or have a specified percentage of nucleotides or amino acid residues that are the same, e.g., at least 60% identity, preferably at least 65%, 70%, 75%, 80%, 85%, 90%, 91%, 92%, 93%, 94%, 95%, 96%, 97%, 98%, 99%, or higher identity over a specified region (e.g., nucleotide sequence encoding an antibody described herein or amino acid sequence of an antibody described herein). Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. The term "percentage of identity" in relation to sequences designates the level of identity or homology between said sequences and may be determined by techniques known per se in the art. Typically, the percentage of identity between two nucleic acid sequences is determined by means of computer programs such as GAP provided in the GCG program package (Program Manual for the Wisconsin Package, Version 8, August 1996, Genetics Computer Group, 575 Science Drive, Madison, Wis., USA 53711) (Needleman, S. B. and Wunsch, C. D., (1970), Journal of Molecular Biology, 48, 443-453). With settings adjusted to e.g., DNA sequences (particularly: GAP creation penalty of 5.0 and GAP extension penalty of 0.3), nucleic acid molecules may be aligned to each other using the Pileup alignment software available as part of the GCG program package. The determination of percent identity between two sequences can also be accomplished using a mathematical algorithm. One, non-limiting example of a mathematical algorithm utilized for the comparison of two sequences are those described in Current Protocols in Molecular Biology (Ausubel et al., eds. 1987) Supplement 30, section 7.7.18, Table 7.7.1. or the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al, 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecule of the present invention. BLAST protein searches can be performed with the XBLAST program parameters set, e.g., to score=50, wordlength=3 to obtain amino acid sequences homologous to a protein molecule of the present invention. To obtain gapped alignments for comparison purposes, Gapped BLAST can be utilized as described in Altschul et al, 1997, Nucleic Acids Res. 25:3389-3402. Alternatively, PSI-BLAST can be used to perform an iterated search which detects distant relationships between molecules (Id). When utilizing BLAST, Gapped BLAST, and PSI-Blast programs, the default parameters of the respective programs (e.g., of XBLAST and NBLAST) can be used (see, e.g., the NCBI website). Another preferred non-limiting example of a mathematical algorithm utilized for the comparison of sequences is the algorithm of Myers and Miller, 1988, CABIOS 4:11-17. Such an algorithm is incorporated in the ALIGN program (version 2.0) which is part of the GCG sequence alignment software package. When utilizing the ALIGN program for comparing amino acid sequences, a PAM 120 weight residue table, a gap length penalty of 12, and a gap penalty of 4 can be used. The alignment and the percent homology or sequence identity can be determined using software programs known in the art, for example. Preferably, default parameters are used for alignment. A preferred alignment program is BLAST, using default parameters. In particular, preferred programs are BLASTN and BLASTP, using the following default parameters: Genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+PDB+GenBank CDS translations+SwissProtein+SPupdate+PIR. Details of these programs can be found at the following Internet address: ncbi.nlm.nih.gov/cgi-bin/BLAST. For comparing two amino acid sequences, one can use, for example, the tool "Emboss needle" for pairwise sequence alignment of proteins providing by EMBL-EBI and available on: www.ebi.ac.uk/Tools/services/web/toolform.ebi?tool=emboss_needle&context=protein, using default settings: (I) Matrix: BLOSUM62, (ii) Gap open: 10, (iii) gap extend: 0.5, (iv) output format: pair, (v) end gap penalty: false, (vi) end gap open: 10, (vii) end gap extend: 0.5.

Sequence identity between nucleotide or amino acid sequences can be determined by comparing an alignment of the sequences. When an equivalent position in the compared sequences is occupied by the same base or amino acid, then the molecules are identical at that position. Scoring an alignment as a percentage of identity is a function of the number of identical amino acids or bases at positions shared by the compared sequences. When comparing sequences, optimal alignments may require gaps to be introduced into one or more of the sequences to take into consideration possible insertions and deletions in the sequences. Sequence comparison methods may employ gap penalties so that, for the same number of identical molecules in sequences being compared, a sequence alignment with as few gaps as possible, reflecting higher relatedness between the two compared sequences, will achieve a higher score than one with many gaps. Calculation of maximum percent identity involves the production of an optimal alignment, taking into consideration gap penalties.

The terms also include sequences that have deletions and/or additions, as well as those that have substitutions, particularly conservative substitution. Preferably, identity exists over a region that is at least about 25 amino acids or nucleotides in length, or more preferably over a region that is at least 50-100 amino acids or nucleotides in length. An "unrelated" or "non-homologous" sequence shares less than 50% identity, or alternatively less than 40% identity, preferably less than 30% with one of the sequences disclosed herein.

HLA-G Antigen

"HLA-G" designates the Human leukocyte antigen G which includes at least seven isoforms. Its expression is mainly restricted to the feto-maternal interface on the extravillous cytotrophoblast; to placenta, amnion; to a few healthy adult tissues such as thymus, cornea, bronchial epithelial cells, and pancreas; and to different types of cells such as mesenchymal stem cells, a few activated monocytes, and erythroid and endothelial precursors. The soluble HLA-G is also found in body fluids such as plasma, cerebrospinal fluid, malignant ascites, pleural effusions, and sperm. Although the HLA-G gene is not active in some tissues, its expression can be induced by certain molecules such as progesterone or anticancer drugs. Furthermore, this molecule can also be neo-expressed as well in pathological conditions such as cancer, multiple sclerosis, inflammatory diseases, and viral infections or after allograft. Soluble HLA-G (sHLA-G) can be detected in the serum/plasma of individuals.

HLA-G differs from classical HLA class I molecules by its low genetic diversity, a tissue-restricted expression, the existence of seven isoforms, and immuno-inhibitory functions. This molecule exerts an immuno-inhibitory function through direct binding to three inhibitory receptors: leukocyte immunoglobulin-like receptor B1 (LILRB1/ILT2/CD85j), LILRB2 (ILT4/CD85d) and KIR2DL4 (or CD158d), schematized in FIG. 1A. For LILRB receptors, the recognition site takes place through the $\alpha 3$ domain of HLA-G and it is unlikely affected by the peptide. LILRB1 is expressed by B cells, some T cells, some NK cells, and all monocytes/dendritic cells, whereas LILRB2 is myeloid specific and its expression is restricted to monocytes/dendritic cells. KIR2DL4 is a specific receptor for HLA-G, only expressed by the CD56bright subset of NK cells. LILRB1 and LILRB2 have been shown to bind a wide range of classic HLA molecules by the $\alpha 3$ domain and the B2M, for which HLA-G is the ligand of highest affinity, whereas for KIR2DL4, HLA-G is the sole known ligand. In addition, it has been demonstrated that LILRB1 and LILRB2 present higher affinity for HLA-G multimers than monomeric structures. It is important to bring up the difference between the way LILRB1 and LILRB2 bind to their ligands: LILRB1 shows higher affinity for HLA-G heavy chain associated to the $\beta 2M$, whereas LILRB2 shows remarkably distinct MHCI-binding recognition by binding more the $\alpha 3$ domain than $\beta 2M$, involving the aromatic amino acids Phe-195 and Tyr-197. This explains the $\beta 2M$ independent HLA-G binding of the latter receptor and its higher affinity for $\beta 2M$ free isoforms.

By linking these receptors, HLA-G acts as a down-regulator of the immune system for which some of the functions had been described: inhibition of the cytolytic function of uterine and peripheral blood NK cells, the antigen-specific cytolytic function of cytotoxic T lymphocytes, the alloproliferative response of $CD4^+$ T cells, the proliferation of T cells and peripheral blood NK cells, and the maturation and function of dendritic cells, shown in FIG. 1C. Furthermore, HLA-G can induce the generation of suppressive cells. But, unlike classic HLA class I molecules, no stimulatory functions had been reported to date for HLA-G, neither responses directed against allogeneic HLA-G.

HLA-G can inhibit all the immune cell subsets; thus, it can block all the stages of the anti-tumor response. This molecule is expressed in many types of primary tumors, metastases and malignant effusions, and it can also be found on tumor cells and tumor-infiltrating cells. It was shown that HLA-G expression by tumor cell lines protects them from destruction by cytotoxic T lymphocytes and NK cells. Thus, the expression of HLA-G by malignant cells may prevent tumor immune elimination by inhibiting the activity of tumor infiltrating NK, cytotoxic T lymphocytes (CTL) and antigen presenting cells (APCs).

HLA-G expression is mainly controlled at the transcriptional level by a unique gene promoter and at the post-transcriptional level by alternative splicing, mRNA stability, translation and protein transport to the cell surface.

The primary transcript of HLA-G is alternatively spliced resulting in the expression of seven isoforms, where four are membrane-bound (HLA-G1, HLA-G2, HLA-G3 and HLA-G4) and three are soluble (HLA-G5, HLA-G6 and HLA-G7). HLA-G1 and HLA-G5 present the typical structure of a classical HLA class I molecule: a heavy chain constituted of three globular domains non-covalently bound to § 32-microglobulin ($\beta 2M$) and a peptide, while the other isoforms are shorter, lacking one or two domains of the heavy chain, and should not bind $\beta 2M$ (FIG. 1A).

HLA-G1 and HLA-G5 are considered the most abundant isoforms, probably because of the lack of antibodies diversity against other isoforms, particularly the lack of antibodies against $\beta 2M$ free isoforms. HLA-G1 isoform is the complete isoform with $\alpha 1$, $\alpha 2$ and $\alpha 3$ domains associated with § 32-microglobulin. The HLA-G2 isoform has no $\alpha 2$ domain, while HLA-G3 has no α2 and α3 domains, and HLA-G4 has no α3 domain. None of the isoforms HLA-G2, HLA-G3 and HLA-G4 binds β2M. The soluble HLA-G5 and HLA-G6 isoforms contain the same extra globular domains than HLA-G1 and HLA-G2, respectively. The HLA-G7 isoform has only the α1 domain linked to two amino acids encoded by intron 2. HLA-G5 isoform binds β2M while the isoforms HLA-G6 and HLA-G7 do not bind β2M.

In addition, HLA-G molecules can form dimers through the creation of disulfide bonds between two unique cysteine residues at positions 42 (Cys42-Cys42 bonds) and 147 (Cys42-Cys147 bonds) of the HLA-G heavy chain. The dimerization has an oblique orientation that exposes the HLA-G receptor binding sites of the α3 domain upwards, making them more accessible to the receptors. Consequently, HLA-G dimers bind receptors with higher affinity and slower dissociation rates than monomers, and signal more efficiently than monomers as well.

Alternative names are HLA-G histocompatibility antigen class I or G or MHC-G. HLA-G is described in databases under the following accession numbers: Gene ID: 3135, UniGene Hs.512152. This protein is disclosed in UniProt under accession number: P17693. The GenBank entry of the sequence of the protein and mRNA are respectively NP_002118.1. and NM_002127.5.

When comparing HLA-G isoforms sequences, HLA-G1 is generally chosen as the canonical sequence, i.e. the sequence of DNA, RNA, or amino acids that reflects the most frequent nucleic acid or base or amino acid at each position, which is why database generally refer to this isoform sequence under the name "HLA-G". HLA-G2 to G7 differ from HLA-G1 by amino acid deletion(s) and/or substitution(s). HLA-G human isoforms are described under the Uniprot accession number P17693-1 for HLA-G1, P17693-2 for HLA-G2, P17693-3 for HLA-G3, P17693-4 for HLA-G4, P17693-5 for HLA-G5, P17693-6 for HLA-G6, P17693-7 for HLA-G7.

Antibodies Against HLA-G Isoforms

The present invention provides an antibody that specifically binds one to six, preferably two to five HLA-G isoform(s) among the seven HLA-G isoforms, but does not specifically bind or recognize all the HLA-G isoforms. For instance, the antibody can specifically bind one, two, three, four, five or six HLA-G isoforms. The HLA-G isoforms can be selected from the group consisting of HLA-G1, HLA-G2, HLA-G3, HLA-G4, HLA-G5, HLA-G6 and HLA-G7, preferably from HLA-G1, HLA-G2, HLA-G5 and HLA-G6.

For example, the antibody or the antigen binding domain of the CAR according to the invention can recognize:
- HLA-G1, HLA-G4 and HLA-G5, if the epitope recognized by the antibody or antigen binding domain is on the α2 domain of HLA-G,
- HLA-G1, HLA-G2, HLA-G5 and HLA-G6, if the epitope recognized by the antibody or antigen binding domain is on the α3 domain of HLA-G,
- HLA-G1 and HLA-G5, if the epitope recognized by the antibody or antigen binding domain is on the β2M domain of HLA-G or on a domain which is specific of the HLA-G associated with the β2M domain.

In a particular embodiment the antibody or fragment thereof does not recognize all the HLA-G isoforms, i.e. the antibody or the antigen binding domain of the CAR according to the invention does not recognize an epitope of the α1 domain of HLA-G.

In one aspect, the antibody can specifically bind HLA-G1 and HLA-G5 isoforms. Then, the antibody does not substantially bind the other HLA-G isoforms, especially HLA-G2, HLA-G3, HLA-G4, HLA-G6 and HLA-G7. More specifically, the antibody is specific of the HLA-G isoforms associated with β2M. In this context, the antibody does not substantially bind HLA-G1 and HLA-G5 isoforms devoid of β2M.

It is provided herein an antibody 15E7. In particular, 15E7 is a scFv antibody having a heavy chain sequence as disclosed in SEQ ID NO: 3 and a light chain sequence as disclosed in SEQ ID NO: 4. The CDRs of the antibody 15E7 have the following sequences, according to Kabat:
Heavy chain CDR1 of SEQ ID NO: 11;
Heavy chain CDR2 of SEQ ID NO: 12,
Heavy chain CDR3 of SEQ ID NO: 13,
Light chain CDR1 of SEQ ID NO: 14,
Light chain CDR2 of SEQ ID NO: 15, and
Light chain CDR3 of SEQ ID NO: 16.

Accordingly, the present invention relates to an antibody having
(a)(i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4;
(b)(i) a heavy chain comprising CDR 1, 2 and 3 (HCDR1, HCDR2, HCDR3) comprising a sequence of SEQ ID NO: 11, 12 and 13, respectively, and (ii) a light chain comprising CDR 1, 2 and 3 (LCDR1, LCDR2, LCDR3) comprising a sequence of SEQ ID NO: 14, 15 and 16, respectively, optionally wherein each CDR may optionally comprise 1, 2, 3 or 4 amino acid substitutions, deletions or insertions; or
(c) a heavy chain variable region and a light chain variable region of SEQ ID NOS: 3 and 4 or a heavy chain variable region having at least 80, 85, 90 or 95% of identity with SEQ ID NOS: 3 and a light chain variable region having at least 80, 85, 90 or 95% of identity with SEQ ID NO: 4.

Said antibody can be a chimeric, human or humanized. Said antibody can be an antibody fragment selected from Fab, Fab', Fab'-SH, F(ab') 2, Fv, a diabody, a single-chain antibody fragment, or a multispecific antibody comprising multiple different antibody fragments. Said antibody can be conjugated or covalently bound to a toxic agent or to a detectable label.

In another aspect, the antibody can specifically bind HLA-G2 and HLA-G6 isoforms. Then, the antibody does not substantially bind the other HLA-G isoforms, especially isoforms associated with the β2M subunit such as HLA-G1, HLA-G3, HLA-G4, HLA-G5 and HLA-G7. More specifically, the antibody is specific of the β2M-free HLA-G isoforms and specifically binds both HLA-G2 and HLA-G6 and/or both HLA-G1-32M free and HLA-G5-32M free isoforms.

It is provided herein an antibody LFTT-1. In particular, LFTT-1 is a scFv antibody having a heavy chain sequence as disclosed in SEQ ID NO: 1 and a light chain sequence as disclosed in SEQ ID NO: 2. The CDRs of the antibody LFTT-1 have the following sequences, according to Kabat:
Heavy chain CDR1 of SEQ ID NO: 5;
Heavy chain CDR2 of SEQ ID NO: 6,
Heavy chain CDR3 of SEQ ID NO: 7,
Light chain CDR1 of SEQ ID NO: 8,
Light chain CDR2 of SEQ ID NO: 9, and
Light chain CDR3 of SEQ ID NO: 10.

Accordingly, the present invention relates to an antibody having
(a)(i) a heavy chain comprising CDR 1, 2 and 3 of the heavy chain variable region of SEQ ID NO: 1 and (ii) a light chain comprising CDR 1, 2 and 3 of the light chain variable region of SEQ ID NO: 2;
(b)(i) a heavy chain comprising CDR 1, 2 and 3 (HCDR1, HCDR2, HCDR3) comprising a sequence of SEQ ID NO: 5, 6 and 7, respectively, and (ii) a light chain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions; or
(c) a heavy chain variable region and a light chain variable region of SEQ ID NOS: 1 and 2 or a heavy chain variable region having at least 80, 85, 90 or 95% of identity with SEQ ID NOS: 1 and a light chain variable region having at least 80, 85, 90 or 95% of identity with SEQ ID NO: 2.

Said antibody can be a chimeric, human or humanized. Said antibody can be an antibody fragment selected from Fab, Fab', Fab'-SH, F(ab') 2, Fv, a diabody, a single-chain antibody fragment, or a multispecific antibody comprising multiple different antibody fragments. Said antibody can be conjugated or covalently bound to a toxic agent or to a detectable label.

In a particular embodiment, the antibody is a multispecific antibody, preferably a bispecific antibody. Bispecific antibodies comprise two different F(ab) fragments that recognize two different epitopes either on the same or on different antigens. Particularly, the bispecific antibody according to the invention binds different epitopes on the same HLA-G isoform(s) or different HLA-G isoforms. Preferably, the bispecific antibody specifically binds different HLA-G isoforms and comprises a F(ab) that recognizes HLA-G/β2M free isoforms and a second F(ab) that recognizes HLA-G isoforms associated with the β2M domain.

In one embodiment, the bispecific antibody comprises one F(ab) that specifically binds to HLA-G isoforms that are free of β2M, preferably to both HLA-G2 and HLA-G6 and/or to both HLA-G1/β2M free and HLA-G5/β2M free isoforms, and one other F(ab) that specifically binds to HLA-G isoforms associated with β2M, preferably HLA-G1 and HLA-G5 isoforms. In this particular embodiment, the bispecific antibody comprises one F(ab) from the LFTT-1 antibody with the CDRs described hereabove (SEQ ID No. 5-10) and one F(ab) of the 15E7 antibody with the CDRs described hereabove (SEQ ID No. 11-16).

In another embodiment, the bispecific anti-HLA-G antibody comprises a continuous heavy chain constructed of an Fc (Hinge-CH2-CH3) followed by a first antibody (antibody 1) Fab heavy chain (CH1-VH) and the successive Fab heavy chain (CH1-VH) of a second antibody (antibody 2), the latter joined by a polypeptide linker sequence. During protein expression the resulting heavy chain assembles into dimers while the co-expressed antibody 1 and antibody 2 light chains (VL-CL) associate with their cognate heavy chains to form the final tandem F(ab)'2-Fc molecule. Preferably, the antibody 1 and the antibody 2 are different, preferably are LFTT-1 antibody and 15E7 antibody respectively.

In one embodiment, the antibody or fragment thereof does not bind or recognize all of the HLA-G isoforms. Particularly, the antibody or fragment thereof that specifically binds to one or several but not all HLA-G isoform(s) has a Kd affinity constant of at least $10^{-6}$ M. In certain aspects, the antibody or fragment thereof binds one or several but not all HLA-G isoform(s) with high affinities of at least about $10^{-7}$ M, and preferably at least about $10^{-8}$ M, $10^{-9}$ M, $10^{-10}$ M.

In a particular embodiment, the antibody or fragment thereof does not bind or recognize the alpha1 domain of HLA-G isoforms. This means that such antibody or fragment thereof can bind or recognize HLA-G isoforms lacking of alpha-1 domain, for example HLA-G isoforms such as described in Tronik-Le Roux et al., Molecular Oncology 11 (2017) 1561-1578, that contain the alpha2 and alpha3 domains or only the alpha3 domain. For example, such antibody or fragment thereof can bind the alpha2, alpha3 or β2M domain.

The sequence of the antibody or antibody fragment according to the invention may be used in a method to prepare a CAR or to prepare a pharmaceutical composition. Alternatively, the antibody or antibody fragment according to the invention may be used to detect HLA-G isoform(s) in diagnosis tests such as immunoassays.

Antibodies or antibody fragments can be identified, for example, by immunoassays such as radioimmunoassays (RIAs), enzyme-linked immunosorbent assays (ELISAs) and Surface Plasmon Resonance (SPR) assays or other techniques known to those of skill in the art.

Preferably, antibodies (including antibody fragments thereof) that specifically bind to one or several HLA-G isoform(s) do not significantly cross-react with other antigens (i.e., is not detectable in routine immunological assays). An antibody binds specifically to an antigen when it binds to the antigen with higher affinity than to any cross-reactive antigen as determined using experimental techniques, such as Western blot (WB), radioimmunoassays (RIAs) and enzyme-linked immunosorbent assays (ELISAs), particularly competitive ELISA.

Chimeric Antigen Receptors (CARs) Against HLA-G Isoforms

A CAR typically comprises an ectodomain (extracellular domain) and an endodomain (cytoplasmic domain), preferably joined by a hinge domain and a transmembrane domain. Particularly, the CAR according to the invention optionally comprises a cleavable linker and a reporter. The ectodomain, expressed on the surface of the cell, comprises an antigen binding domain or receptor domain, optionally a signal peptide that directs the antigen binding domain into the endoplasmic reticulum for processing. The extracellular domain comprises an antigen binding domain that specifically recognizes a target antigen. As a non-limiting example, the antigen binding domain can be an antibody, preferably a single chain antibody, such as a scFv. The spacer region links the antigen binding domain to the transmembrane domain and is designed to be sufficiently flexible to allow the antigen binding domain to orient in a manner that allows antigen recognition. The transmembrane domain is typically a hydrophobic alpha helix, typically, that spans across the lipid bilayer of the cell membrane. The endodomain of the CAR is composed of a signal transmitting peptide that spreads an activation signal intracellularly to the cell cytoplasm, thereby stimulating the cell expressing the CAR. The endodomain may include several signaling domains, as explained vide infra.

In some embodiments, a CAR comprises at least an extracellular antigen binding domain, a transmembrane domain and a cytoplasmic signaling domain comprising a functional signaling domain derived from a stimulatory molecule and/or costimulatory molecule as defined below. In some embodiments, the set of polypeptides include a dimerization switch that, upon the presence of a dimerization molecule, can couple the polypeptides to one another, e.g., can couple an antigen binding domain to an intracellular signaling domain. In one aspect, the cytoplasmic signaling domain further comprises one or more functional signaling domains derived from at least one costimulatory molecule as defined below.

In one aspect, the CAR comprises a chimeric fusion protein comprising an extracellular antigen binding domain, a transmembrane domain and an intracellular signaling domain comprising a functional signaling domain derived from a stimulatory molecule. In one aspect, the CAR comprises a chimeric fusion protein comprising an extracellular antigen binding domain, a transmembrane domain and an intracellular signaling domain comprising a functional signaling domain derived from a costimulatory molecule and a functional signaling domain derived from a stimulatory molecule.

Preferably, the CAR comprises a chimeric fusion protein comprising an extracellular antigen binding domain, optionally a hinge domain, a transmembrane domain and an intracellular signaling domain comprising two functional signaling domains derived from one or more costimulatory molecule(s) and a functional signaling domain derived from a stimulatory molecule. In one aspect the CAR comprises an optional leader sequence or peptide signal sequence at the amino-terminus (N-ter) of the CAR fusion protein.

In a particular embodiment, the CAR further comprises a cleavable linker and a reporter, to facilitate identification and selection of expressing cells from the population of cells sought to be transfected with the CAR according to the invention, preferably sequentially at the carboxy-terminus (C-ter) of the CAR fusion protein. According to the invention, the engineered CAR has one, two, three, four, five, six, seven, eight or more components, and in some embodiments at least one component facilitates targeting or binding of the immune cell to specific HLA-G isoform(s). Preferably, this at least one component is derived from a monoclonal antibody as defined in the previous section. Preferably, this component is a scFv. Preferably, the anti-HLA-G CAR sequentially comprises or consists in, from N to C terminus: optionally a peptide signal sequence, an anti-HLA-G antibody or fragment thereof, preferably an anti-HLA-G scFv, a spacer domain, a transmembrane domain, at least one intracellular domain, a cleavable linker and a truncated human CD19 reporter. All of these components will be more specifically described herebelow. Particularly, the CAR according to the invention, particularly the antigen binding domain, the antibody or the scFv according to the invention, may specifically bind one to six, preferably two to five, HLA-G isoform(s), more preferably to one or two HLA-G isoform(s) or two or three HLA-G isoforms, but does not bind to all HLA-G isoforms. For instance, the CAR can specifically bind one, two, three, four, five or six HLA-G isoforms. The HLA-G isoforms can be selected from the group consisting of HLA-G1, HLA-G2, HLA-G3, HLA-G4, HLA-G5, HLA-G6 and HLA-G7, preferably from HLA-G1, HLA-G2, HLA-G5 and HLA-G6.

In one aspect, the CAR can specifically bind β2M-associated HLA-G isoforms, such as HLA-G1 and HLA-G5 isoforms. Then, the CAR does not substantially bind the other HLA-G isoforms, especially HLA-G2, HLA-G3, HLA-G4, HLA-G6 and HLA-G7. More specifically, the CAR is specific of the HLA-G isoforms associated with β2M. In this context, the CAR does not substantially bind HLA-G1 and HLA-G5 isoforms devoid of β2M.

In another aspect, the CAR can specifically bind HLA-G2 and HLA-G6 isoforms. Then, the CAR does not substantially bind the other HLA-G isoforms, especially HLA-G1, HLA-G3, HLA-G4, HLA-G5 and HLA-G7. More specifically, the CAR is specific of the β2M-free HLA-G isoforms and can specifically bind to both HLA-G2 and HLA-G6 and/or to both HLA-G1/β2M free and HLA-G5/β2M free isoforms.

Antigen Binding Domain

The external domain of the CAR according to the invention is an antigen binding domain. Particularly, this antigen binding domain is derived from the antibody as defined in the above section.

Antigen targeting or antigen recognition by CAR molecules most commonly involves the use of a single chain variable fragment (scFv) that has been assembled from a monoclonal antibody. However, alternative targeting moieties include ligands (Altenschmidt et al. (1996) Clin. Cancer Res. 2: 1001-8; Muniappan, et al. (2000) Cancer Gene Ther. 7: 128-134), peptides (Pameijer et al. (2007) Cancer Gene Ther. 14:91-97), chimeric ligands (Davies et al. (2012) Mol. Med. 18:565-576), receptor derivatives (Zhang et al. (2012) J Immunol. 189:2290-9), and single domain antibodies (Sharifzadeh et al. (2012) Cancer Res. 72: 1844-52). Any desired antibody or antibody fragment thereof that specifically recognizes and binds a target antigen, in particular HLA-G isoforms as defined above, may be incorporated in a CAR according to the invention.

In one embodiment, such antigen binding domain is an antibody, preferably a single chain antibody. Preferably, the antibody is a humanized antibody or a non-humanized murine antibody. Particularly, such antigen binding domain is an antibody fragment selected from fragment antigen binding (Fab) fragments, F(ab')2 fragments, Fab' fragments, Fv fragments, recombinant IgG (rIgG) fragments, single chain antibody fragments, single chain variable fragments (scFv), single domain antibodies (e.g., sdAb, sdFv, nanobody) fragments, diabodies, and multi-specific antibodies formed from antibody fragments. In particular embodiments, the antibodies are single-chain antibody fragments comprising a variable heavy chain region and/or a variable light chain region, such as scFv. Particularly, such antigen binding domain is selected from a Fab and a scFv.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that may not be produced by enzyme digestion of a naturally-occurring intact antibody. In some aspects, the antibody fragments are scFvs.

In embodiments wherein the antigen targeting domain is a scFv, the scFv can be derived from the variable heavy chain (VH) and variable light chain (VL) regions of an antigen-specific mAb linked by a flexible linker. The scFv retains the same specificity and a similar affinity as the full antibody from which it was derived (Muniappan et al. (2000) Cancer Gene Ther. 7: 128-134). Various methods for preparing an scFv can be used including methods described in U.S. Pat. No. 4,694,778; Bird et al. (1988) Science 242:423-442; Ward et al. (1989) Nature 334:54454; and Skerra et al. (1988) Science 242: 1038-1041. In certain embodiments, the scFv may be a humanized or is a fully human scFv.

The antigen binding domain that specifically binds to a particular isoform of HLA-G may be cross-reactive with related antigens, for example with one to five, preferably two to four other different HLA-G isoform(s).

In some aspects, the antigen binding domain may be derived from an antibody or fragment thereof that has one or more specified functional features, such as binding properties, including binding to particular epitopes, such as epitopes that are similar to or overlap with those of other antibodies, the ability to compete for binding with other antibodies, and/or particular binding affinities. In some embodiments, the antigen binding domain, the CARs comprising such, and the cells comprising such CARs display a binding preference for target antigen-expressing cells as compared to target antigen-negative cells. In some embodiments, the binding preference is observed where a significantly greater degree of binding is measured to the antigen-expressing, as compared to the non-expressing cells. In some cases, the total degree of observed binding to the target antigen or to the antigen-expressing cells is approximately the same, at least as great or greater than that observed for non-antigen specific domains, CARs, or cells. In any of the provided embodiments, comparison of binding properties, such as affinities or competition, may be via measurement by assays known in the art such as mentioned above.

In another embodiment, the antigen binding domain of the CAR specifically binds to one or several HLA-G isoform(s) with a Kd affinity constant of at least 106 M. In certain aspects, the antigen binding domain of the CAR binds one or several HLA-G isoform(s) with high affinities of at least about $10^{-7}$ M, and preferably at least about $10^{-8}$ M, $10^{-9}$ M, $10^{-10}$ M. Preferably, the antigen binding domain of the CAR binds one or several HLA-G isoform(s) with an affinity of about $10^{-9}$ M.

In one aspect, the antigen binding fragment of the CAR can specifically bind to both HLA-G2 and HLA-G6 and/or to both HLA-G1/β2M free and to HLA-G5/β2M free isoforms. Then, the antigen binding fragment of the CAR does not substantially bind the other HLA-G isoforms, especially HLA-G1 and HLA-G5 β2M-associated isoforms, HLA-G3, HLA-G4, and HLA-G7. More specifically, the antigen binding fragment of the CAR is specific of the β2M-free HLA-G isoforms and does not substantially bind β2M-associated HLA-G isoforms.

In a particular embodiment, the antigen binding fragment of the CAR comprises i) a heavy chain variable region that comprises SEQ ID NO: 1 or a sequence having at least 80, 85, 90 or 95% of identity with SEQ ID NO: 1; and/or (ii) the light chain variable region comprises SEQ ID NO: 2 or a sequence having at least 80, 85, 90 or 95% of identity with SEQ ID NO: 2.

In an additional particular embodiment, the antigen binding fragment of the CAR comprises (i) a heavy chain comprising CDR 1, 2 and 3 of the heavy chain variable region of SEQ ID NO: 1 and (ii) a light chain comprising CDR 1, 2 and 3 of the light chain variable region of SEQ ID NO: 2.

In a further particular embodiment, the antigen binding fragment of the CAR comprises (i) a heavy chain comprising CDR 1, 2 and 3 (HCDR1, HCDR2, HCDR3) comprising a sequence of SEQ ID NO: 5, 6 and 7, respectively, and (ii) a light chain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions.

In another aspect, the antigen binding fragment of the CAR can specifically bind the HLA-G isoforms associated with β2M such as HLA-G1 and HLA-G5 isoforms. Then, the antigen binding fragment of the CAR does not substantially bind the other HLA-G isoforms, especially β2M free isoforms such as HLA-G2, HLA-G3, HLA-G4, HLA-G6 and HLA-G7. In this context, the antigen binding fragment of the CAR does not substantially bind HLA-G1 and HLA-G5 isoforms devoid of β2M.

In a particular embodiment, the antigen binding fragment of the CAR comprises i) a heavy chain variable region that comprises SEQ ID NO: 3 or a sequence having at least 80, 85, 90 or 95% of identity with SEQ ID NO: 3; and/or (ii) the light chain variable region comprises SEQ ID NO: 4 or a sequence having at least 80, 85, 90 or 95% of identity with SEQ ID NO: 4.

In an additional particular embodiment, the antigen binding fragment of the CAR comprises (i) a heavy chain comprising CDR 1, 2 and 3 of the heavy chain variable region of SEQ ID NO: 3 and (ii) a light chain comprising CDR 1, 2 and 3 of the light chain variable region of SEQ ID NO: 4.

In a further particular embodiment, the antigen binding fragment of the CAR comprises (i) a heavy chain comprising CDR 1, 2 and 3 (HCDR1, HCDR2, HCDR3) comprising a sequence of SEQ ID NO: 11, 12 and 13, respectively, and (ii) a light chain comprising CDR 1, 2 and 3 (LCDR1, LCDR2, LCDR3) comprising a sequence of SEQ ID NO: 14, 15 and 16, respectively, optionally wherein each CDR may optionally comprise 1, 2, 3 or 4 amino acid substitutions, deletions or insertions.

Particularly, the antigen binding fragment of the CAR does not bind or recognize all of the HLA-G isoforms. In one embodiment, the antigen binding fragment of the CAR does not bind or recognize the alpha1 domain of HLA-G isoforms. This means that such antigen binding fragment can recognize HLA-G isoforms lacking of alpha-1 domain, for example HLA-G isoforms such as described in Tronik-Le Roux et al., Molecular Oncology 11 (2017) 1561-1578 that contain the alpha2 and alpha3 domains or only the alpha3 domain. For example, such antigen binding fragment can bind the alpha2, alpha3 or β2M domain.

In a particular embodiment, the antigen binding domain is a multispecific antigen binding domain, preferably a bispecific antigen binding domain. For instance, the bispecific antigen binding fragment comprises a domain that recognizes HLA-G/32M free isoforms and a second domain that recognizes HLA-G isoforms associated with the β2M domain. Even more preferably, the bispecific antigen binding domain comprises one domain that specifically binds to both HLA-G2 and HLA-G6 and/or to both HLA-G1/β2M free and HLA-G5/β2M free isoforms, and another domain that specifically binds to HLA-G1 and HLA-G5 isoforms associated with the β2M subunit. Preferably, the bispecific antigen binding fragment is derived from both LFTT-1 antibody with the CDRs described hereabove (SEQ ID No. 5-10) and the 15E7 antibody with the CDRs described hereabove (SEQ ID No. 11-16).

In a particular embodiment, the antigen binding fragment of the CAR is a bispecific antigen binding domain that comprises (i) a domain comprising CDR 1, 2 and 3 (HCDR1, HCDR2, HCDR3) comprising a sequence of SEQ ID NO: 11, 12 and 13, respectively, (ii) a domain comprising CDR 1, 2 and 3 (LCDR1, LCDR2, LCDR3) comprising a sequence of SEQ ID NO: 14, 15 and 16, respectively, (iii) a domain comprising CDR 1, 2 and 3 (HCDR1, HCDR2, HCDR3) comprising a sequence of SEQ ID NO: 5, 6 and 7, respectively, and (iv) a domain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions.

Such bispecific antigen binding domain suitable for a CAR can for example be tandem-scFv or nanobodies (De Munter et al., Molecular sciences 2018).

In some embodiments, the antigen binding domain comprises a scFv comprising the CDR sequences of an anti-HLA-G monoclonal antibody. CDRs may be determined using conventional methods. The precise amino acid sequence boundaries of a given CDR or FR can be readily determined using any of a number of well-known schemes, including those described by Kabat et al. (1991), "Sequences of Proteins of Immunological Interest," 5th Ed. Public Health Service, National Institutes of Health, Bethesda, Md. ("Kabat" numbering scheme), Al-Lazikani et al., (1997) JMB 273, 927-948 ("Chothia" numbering scheme), MacCallum et al., J. Mol. Biol. 262:732-745 (1996), "Antibody-antigen interactions: Contact analysis and binding site topography," J. Mol. Biol. 262, 732-745." ("Contact" numbering scheme), Lefranc M P et al, "IMGT unique numbering for immunoglobulin and T cell receptor variable domains and Ig superfamily V-like domains," Dev Comp Immunol, 2003 January; 27(1):55-77 ("IMGT" numbering scheme), and Honegger A and Pluckthun A, "Yet another numbering scheme for immunoglobulin variable domains: an automatic modeling and analysis tool," J Mol Biol, 2001 Jun. 8; 309(3):657-70, ("Aho" numbering scheme).

In specific embodiments, the antigen binding domain is a single-chain variable fragment (scFv). The scFv may also comprise a peptide linker. The peptide linker connecting scFv $V_H$ and $V_L$ domains joins the carboxyl terminus of one variable region domain to the amino terminus of the other variable domain without compromising the fidelity of the $V_H$-$V_L$ paring and antigen-binding sites. Peptide linkers can vary from 10 to 30 amino acids in length. In one embodiment, the scFv peptide linker is a Gly/Ser linker and comprises one or more repeats of the amino acid sequence Gly-Gly-Gly-Ser or Gly-Gly-Gly-Gly-Ser. In one embodiment, the flexible polypeptide linker includes, but is not limited to (Gly$_3$Ser)$_3$ and (Gly$_4$Ser)$_3$.

Transmembrane and Hinge Domain

Hinge Domain

When a T cell interacts with an antigen-presenting cell, an immunological synapse with an intermembrane distance of about 15 nm is formed. This distance is dictated by the architecture of TCR and the peptide-MHC complex. This spatial separation is important for effective triggering of the phosphorylation cascade and T-cell activation. When artificially shortened, this protein gets a chance to stay within the synapse, resulting in the suppression of activation signals.

Given that the position of the epitope recognized by a specific scFv on the target cell surface is generally fixed, the length and rigidity of the extracellular spacer (the hinge module) in the CAR need to be adjusted to ensure maximum steric compatibility with the scFv and the formation of a compact synapse. In some aspects, a portion of the immunoglobulin constant region serves as a spacer region between the antigen binding domain, e.g., scFv, and transmembrane domain. The spacer can be of a length that provides for increased responsiveness of the cell following antigen binding, as compared to in the absence of the spacer. The spacer domain preferably has a sequence that promotes binding of a CAR with an antigen and enhances signaling in a cell. Examples of an amino acid that is expected to promote the binding include cysteine, a charged amino acid, and serine and threonine in a potential glycosylation site, and these amino acids can be used as an amino acid constituting the spacer domain.

In some embodiments, the CAR comprises a hinge sequence between the antigen binding domain and the transmembrane domain and/or between the transmembrane domain and the cytoplasmic domain. The hinge domain can be up to 150 amino acids, preferably 10 to 100 amino acids, even more preferably 50 to 100 amino acids in length. One ordinarily skilled in the art will appreciate that a hinge sequence is a short sequence of amino acids that facilitates flexibility (see e.g., Woof et al, Nat. Rev. Immunol, 4(2): 89-99 (2004)). The hinge sequence can be any suitable sequence derived or obtained from any suitable molecule. In some embodiments, the length of the hinge sequence may be optimized based on the distance between the CAR and the binding epitope, e.g., longer hinges may be optimal for membrane proximal epitopes.

The hinge may be derived from or include at least a portion of an immunoglobulin Fc region, for example, an IgG1 Fc region, an IgG2 Fc region, an IgG3 Fc region, an IgG4 Fc region, an IgE Fc region, an IgM Fc region, or an IgA Fc region. In certain embodiments, the hinge domain includes at least a portion of an IgG1, an IgG2, an IgG3, an IgG4, an IgE, an IgM, or an IgA immunoglobulin Fc region that falls within its CH2 and CH3 domains. In some embodiments, the spacer domain may also include at least a portion of a corresponding immunoglobulin hinge region. In some embodiments, the hinge is derived from or includes at least a portion of a modified immunoglobulin Fc region, for example, a modified IgG1 Fc region, a modified IgG2 Fc region, a modified IgG3 Fc region, a modified IgG4 Fc region, a modified IgE Fc region, a modified IgM Fc region, or a modified IgA Fc region. The modified immunoglobulin Fc region may have one or more mutations (e.g., point mutations, insertions, deletions, duplications) resulting in one or more amino acid substitutions, modifications, or deletions that cause impaired binding of the spacer domain to an Fc receptor (FcR). In some aspects, the modified immunoglobulin Fc region may be designed with one or more mutations which result in one or more amino acid substitutions, modifications, or deletions that cause impaired binding of the spacer domain to one or more FcR including, but not limited to, FcγRI, FcγR2A, FcγR2BI, FcγR2B2, FcγR3A, FcγR3B, FcsRI, FcsR2, FcaRI, Fca/pK, or FcRn.

Exemplary hinges include, but are not limited to, a CD8a hinge, a CD28 hinge, IgG1/IgG4 (hinge-Fc part) sequences (in single studies, CD4, CD7, and IgD) IgG4 hinge alone, IgG4 hinge linked to CH2 and CH3 domains, or IgG4 hinge linked to the CH3 domain, those described in Hudecek et al. (2013) Clin. Cancer Res., 19:3153, international patent application publication number WO2014031687, U.S. Pat. No. 8,822,647 or published app. No. US2014/0271635. As hinge domain, the invention relates to all or a part of residues 118 to 178 of CD8a (GenBank Accession No. NP_001759.3), residues 135 to 195 of CD8 (GenBank Accession No. AAA35664), residues 315 to 396 of CD4 (GenBank Accession No. NP_000607.1), or residues 137 to 152 of CD28 (GenBank Accession No. NP_006130.1) can be used. Also, as the spacer domain, a part of a constant region of an antibody H chain or L chain (CHI region or CL region) can be used. Further, the spacer domain may be an artificially synthesized sequence. Particularly, the CAR according to the invention comprises a hinge selected from CD8a, CD28, and IgG1/IgG4 (hinge-Fc part) sequences (in single studies, CD4, CD7, and IgD). This choice is based on the fact that these sequences are relatively neutral, flexible, and have been well-characterized structurally.

Preferably, the hinge domain comprises or consists of (i) CD28 hinge, (ii) CD8 alpha hinge, (iii) a human IgG4 hinge domain, (iv) a human IgG4 hinge domain and a CH3 human IgG4 domain or (v) a mutated CH2 human IgG4 domain, a human IgG4 hinge domain and a CH3 human IgG4 hinge domain. Even more preferably, the hinge domain comprises or consists of (a) SEQ ID NO: 18, (b) SEQ ID 19, (c) SEQ ID NO: 25, (d) SEQ ID NO: 25 and SEQ ID NO: 27, or (e) SEQ ID NO: 25, SEQ ID NO: 26 and SEQ ID NO: 27, or a sequence having at least 80, 85, 90 or 95% identity thereto.

In one embodiment the hinge domain comprises or consists of (i) a human IgG4 hinge domain, (ii) a human IgG4 hinge domain and a CH3 human IgG4 domain or (iii) a mutated CH2 human IgG4 domain, a human IgG4 hinge domain and a CH3 human IgG4 hinge domain. Particularly, the hinge domain sequentially comprises or consists from the N terminus to the C terminus of (i) a human IgG4 hinge domain and a CH3 human IgG4 domain or (ii) a mutated CH2 human IgG4 domain, a human IgG4 hinge domain and a CH3 human IgG4 hinge domain.

In on embodiment, the CAR according to the invention comprises a spacer domain that comprises or consists of a human IgG4 hinge domain that comprises or consists of the sequence set forth in SEQ ID NO: 25 or a sequence having at least 80, 85, 90, 95%, 96%, 97%, 98%, 99% of identity therewith.

In another embodiment, the CAR according to the invention comprises a spacer domain that comprises or consists of (i) a CH3 human IgG4 domain that comprises or consists of the sequence set forth in SEQ ID NO: 27 or a sequence having at least 80, 85, 90, 95%, 96%, 97%, 98%, 99% of identity therewith and (ii) a human IgG4 hinge domain that comprises or consists of the sequence set forth in SEQ ID NO: 25 or a sequence having at least 80, 85, 90, 95%, 96%, 97%, 98%, 99% of identity therewith.

In one embodiment, the CAR according to the invention further comprises mutated CH2 human IgG4 domain, in which the mutation in the CH2 human IgG4 domain consists of the mutation of the amino acids EFLG(113-116)PVA and N177Q, for example as disclosed in Watanabe et al. Oncoimmunology. 2016; 5(12):e1253656. Preferably, the mutated CH2 human IgG4 domain comprises or consists of the sequence set forth in SEQ ID NO: 26 or a sequence having at least 80, 85, 90, 95%, 96%, 97%, 98%, 99% of identity therewith.

In a preferred embodiment, the CAR according to the invention comprises a hinge domain that sequentially comprises or consists of (i) a mutated CH2 human IgG4 domain comprises or consists of the sequence set forth in SEQ ID NO: 26 or a sequence having at least 80, 85, 90, 95%, 96%, 97%, 98%, 99% of identity therewith, (ii) a CH3 human IgG4 domain that comprises or consists of the sequence set forth in SEQ ID NO: 27 or a sequence having at least 80, 85, 90, 95%, 96%, 97%, 98%, 99% of identity therewith and (iii) a human IgG4 hinge domain that comprises or consists of the sequence set forth in SEQ ID NO: 25 or a sequence having at least 80, 85, 90, 95%, 96%, 97%, 98%, 99% of identity therewith.

Particularly, the CAR according to the invention comprises a CD8a hinge domain, preferably comprising or consisting in the sequence of SEQ ID NO: 18 or a sequence having at least 80, 85, 90 or 95% of identity therewith.

Another particular CAR according to the invention comprises a CD28 hinge domain, preferably comprising or consisting in the sequence of SEQ ID NO: 19 or a sequence having at least 80, 85, 90 or 95% of identity therewith.

Transmembrane Domain

The transmembrane module functions to anchor the receptor on the cell surface. With respect to the transmembrane domain, the CAR can be designed to comprise a transmembrane domain that is fused to the antigen binding domain of the CAR. Particularly, the CAR can be designed to comprise a transmembrane domain that is fused both to the antigen binding domain and the endodomain of the CAR. In one embodiment, the transmembrane domain that naturally is associated with one of the domains in the CAR is used. In some instances, the transmembrane domain can be selected or modified by amino acid substitution to avoid binding of such domains to the transmembrane domains of the same or different surface membrane proteins to minimize interactions with other members of the receptor complex. The transmembrane domain may be derived either from a natural or from a synthetic source. Where the source is natural, the domain may be derived from any membrane-bound or transmembrane protein. Typically, the transmembrane domain denotes a single transmembrane helix of a transmembrane protein, also known as an integral protein. This domain usually includes the transmembrane sequences of CD3ζ, CD28, CD8, FcRIγ and less frequently, of CD4, CD7, OX40, and MHC (H2-Kb), the choice depending on the neighboring spacer and intracellular sequences. The transmembrane modules based on CD3ζ and FcRIγ ensure efficient incorporation of CAR into endogenous TCR. For example, the CAR of WO 2008/045437 describes a transmembrane portion derived from human CD8 alpha or CD28, and particularly chimeric T cell receptor proteins with an unmodified CD8 hinge region with amino acid positions 135 to 205, 135 to 203 or 135 to 182 (according to the amino acid numbering of UniProtKB/Swiss-Prot P01732), each comprising cysteine residues in positions 164 and 181. WO 95/30014 uses the unmodified murine CD8 hinge region with amino acid positions 132 to 191 (according to the amino acid numbering of UniProtKB/Swiss-Prot P01731), comprising a cysteine residue in position 178. In particular, US 2008/0260738 uses modified CD8 hinge regions with amino acid positions 131 to 170 or 136 to 169 (according to the amino acid numbering of UniProtKB/Swiss-Prot P01732), wherein the cysteine in position 164 is substituted with serine. Therefore, it would be known by the person skilled in the art, which transmembrane domain to choose according to the CAR domains characteristics.

Transmembrane regions of particular use in this invention may be derived from (i.e. comprise at least the transmembrane region(s) of) CD28, CD3ε, CD4, CD5, CD8, CD9, CD 16, CD22, CD33, CD37, CD45, CD64, CD80, CD86, CD134, CD137, CD154, TCRα, TCRβ, H2-Kb, FcsRIy, GITR or CD3ζ and/or transmembrane regions containing functional variants thereof such as those retaining a substantial portion of the structural, e.g., transmembrane, properties thereof can be used. See e.g., Kahlon et al. (2004) Cancer Res. 64:9160-9166; Schambach et al. (2009) Methods Mol. Biol. 506: 191-205; Jensen et al. (1998) Biol. Blood Marrow Transplant 4:75-83; Patel et al. (1999) Gene Ther. 6:412; Song et al. (2012) Blood 119:696-706; Carpenito et al. (2009) Proc. Natl. Acad. Sci. USA 106: 3360-5; Hombach et al. (2012) Oncoimmunology 1:458-66) and Geiger et al. (2001) Blood 98:2364-71.

Alternatively, the transmembrane domain may be synthetic, in which case it will comprise predominantly hydrophobic residues such as leucine and valine. Preferably a triplet of phenylalanine, tryptophan and valine will be found at each end of a synthetic transmembrane domain. A transmembrane domain of the invention is thermodynamically stable in a membrane. It may be a single alpha helix, a transmembrane beta barrel, a beta-helix of gramicidin A, or any other structure.

Optionally, a short oligo- or polypeptide linker, preferably between 2 and 10 amino acids in length may form the linkage between the transmembrane domain and the intracellular signaling domain(s) of the CAR. A glycine-serine doublet may provide a suitable linker.

In one embodiment, the transmembrane domain of the CAR is selected from CD3ζ, CD28, CD8, FcRIγ CD4, CD7, OX40, and MHC (H2-Kb) transmembrane domain. Preferably, the transmembrane domain of the CAR according to the invention is selected from CD8 and CD28 transmembrane domain. Even more preferably the transmembrane domain of the CAR according to the invention is a CD28 transmembrane domain, preferably comprising or consisting in the sequence of SEQ ID NO: 20 or a sequence having at least 80, 85, 90 or 95% of identity therewith.

Intracellular Domain

In certain embodiments, a cytoplasmic or intracellular signaling domain, such as those derived from the T cell receptor ζ-chain, is employed as at least part of the chimeric receptor in order to produce stimulatory signals for T lymphocyte proliferation and effector function following engagement of the chimeric receptor with the target antigen.

The role of the signaling module of CARs is to transduce the activation signal to an immune cell as soon as the extracellular domain has recognized the antigen. In T cells, activation begins with the phosphorylation of immunoreceptor tyrosine-based activation motif (ITAMs) in the cytoplasmic portion of the CD3ζ subunit of the TCR complex. Thus, in most CAR designs implemented to date, signaling sequences from CD3ζ are used as a module that triggers cell lytic activity.

First-generation CARs, which contained the CD3ζ chain only, sent exclusively activation signal to the cell. This led to a cytotoxic reaction against tumor cells but did not provide enhanced proliferation of activated CAR T cells. In principle, the proliferation signal could potentially be provided by the native co-receptors present on the CAR T cells; however, many tumors do not express the corresponding ligands. Thus, the second-generation CARs comprise a cytoplasmic domain additionally containing the costimulatory CD28 domain, fused together with CD3ζ, to overcome this difficulty. This CAR design provides both activation and proliferation signal to the T cell; as a result, the cell is activated, destroys the target cell, and proliferates. Besides CD28, signaling sequences from costimulatory receptors, such as CD134 (TNFRSF4, OX40), CD154 (CD40L), CD137 (4-1BB), ICOS (CD278), CD27, CD244 (2B4), were successfully tested in CARs.

The third generation of CARs is based on combining two or more costimulatory sequences (such as 4-1BB-CD28-CD3ζ). These receptors secrete a broader range of cytokines (including TNFα, GM-CSF, and IFNγ), are less susceptible to activation-induced cell death, and show higher efficacy in tumor elimination in mouse models. One or multiple endodomains may be employed, as so-called third generation CARs have at least 2 or 3 signaling domains fused together for additive or synergistic effect, for example.

The CAR of the invention may be a first generation, a second generation, or a third generation CAR as described hereabove. Preferably, the CAR is a second or third generation CAR. Even more preferably, the CAR is a third generation CAR when expressed by a T cell and a first generation CAR when expressed by a NK or a NKT cell.

In some embodiments, the intracellular signaling endodomain transmits a signal into a cell when the extracellular antigen targeting domain present within the same molecule binds to an antigen.

T cell activation is transmitted by two different kinds of cytoplasmic signaling endodomains, that is, a sequence for initiating antigen-dependent primary activation via a TCR complex (primary cytoplasmic signaling endodomain) and a sequence for acting antigen-independently to provide a secondary or costimulatory signal (secondary cytoplasmic signaling endodomain or costimulatory endodomain). Therefore, while some embodiments embrace a CAR with only a primary cytoplasmic signaling endodomain, in other embodiments, a CAR of the invention includes a primary signaling endodomain and a secondary cytoplasmic signaling endodomain.

The intracellular signaling domain of the CAR of the invention triggers or elicits activation of at least one of the normal effector functions of the immune cell in which the CAR has been placed. The term "effector function" refers to a specialized function of a cell. The effector function of a T cell may, for example, be cytolytic activity or helper activity including the secretion of cytokines. While usually the entire intracellular signaling domain can be employed, in many cases it is not necessary to use the entire chain. To the extent that a truncated portion of the intracellular signaling domain is used, such truncated portion may be used in place of the intact chain as long as it transduces the effector function signal. The term intracellular signaling domain is thus meant to include any truncated portion of the intracellular signaling domain sufficient to transduce the effector function signal.

Examples of intracellular domain sequences that are of particular use in the invention include those derived from an intracellular signaling domain of a lymphocyte receptor chain, a TCR/CD3 complex protein, an Fc receptor subunit, an IL-2 receptor subunit, CD3ζ, FcRγ, FcRβ, CD3γ, CD3δ, CD3ε, CD5, CD22, CD79a, CD79b, CD66d, CD278(ICOS), FcεRI, DAP10, and DAP12. It is particularly preferred that the intracellular signaling domain in the CAR of the invention comprises a cytoplasmic signaling sequence derived from CD3ζ. Specifically, examples of the ITAM include residues 51 to 164 of CD3 (GenBank Accession No. NP_932170), residues 45 to 86 of FcεRIγ (Gen Bank Accession No. NP_004097), residues 201 to 244 of FcεRi (GenBank Accession No. NP_000130), residues 139 to 182 of CD3y (GenBank Accession No. NP_000064), residues 128 to 171 of CD3δ (GenBank Accession No. NP_000723), residues 153 to 207 of CD3ε (GenBank Accession No. NP_000724), residues 402 to 495 of CD5 (GenBank Accession No. NP_055022), residues 707 to 847 of CD22 (GenBank Accession No. NP_001762), residues 166 to 226 of CD79a (GenBank Accession No. NP_001774), residues 182 to 229 of CD79b (GenBank Accession No. NP_000611), and residues 177 to 252 of CD66d (GenBank Accession No. NP_001806), and their variants. The referenced residues are based on amino acid sequence information from GenBank and is based on the full length of the precursor (including a signal peptide sequence etc.) of each protein. Preferred examples of intracellular signaling domains for use in the CAR of the invention include the cytoplasmic sequences of the T cell receptor (TCR) and co-receptors that act in concert to initiate signal transduction following antigen receptor engagement, as well as any derivative or variant of these sequences and any synthetic sequence that has the same functional capability.

In a preferred embodiment, the cytoplasmic domain of the CAR can be designed to comprise the CD3ζ signaling domain by itself or combined with any other desired cytoplasmic domain(s) useful in the context of the CAR of the invention. In one particular aspect, the CAR of the present invention comprises the CD3ζ signaling domain, preferably comprising or consisting in the sequence of SEQ ID NO: 22 or a sequence having at least 80, 85, 90 or 95% of identity therewith.

The cytoplasmic domain of the CAR can comprise a CD3ζ chain portion and a costimulatory signaling region. The costimulatory signaling region refers to a portion of the CAR comprising the intracellular domain of a costimulatory molecule.

Examples of co-stimulatory molecules that may be used in the present invention include an MHC class I molecule, TNF receptor proteins, immunoglobulin-like proteins, cytokine receptors, integrin, signaling lymphocytic activation molecules (SLAM proteins), activating NK cell receptors, a Toll ligand receptor, B7-H3, BAFFR, BTLA, BLAME (SLAMF8), CD2, CD4, CD5, CD7, CD8a, CD8, CDI Ia, LFA-1 (CDI Ia/CD18), CDI Ib, CDI Ic, CDI Id, CD18, CD19, CD19a, CD27, CD28, CD29, CD30, CD40, CD49a, CD49D, CD49f, CD69, CD84, CD96 (Tactile), CD100 (SEMA4D), CD103, CRTAM, OX40 (CD134), 4-1BB (CD137), SLAM (SLAMF1, CD150, IPO-3), CD160 (BY55), SELPLG (CD162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), IA4, ICAM-1, IL2Rβ, IL2Rγ, IL7Ra, ITGA4, ITGA6, ITGAD, ITGAE, ITGAL, ITGAM, ITGAX, ITGB1, ITGB2, ITGB7, KIRDS2, LAT, LFA-1, LIGHT, LTBR, NKG2C, NKG2D, NKp30, NKp44, NKp46, NKp80 (KLRF1), PAG/Cbp, PD-1, PSGLI, SLAMF6 (NTB-A, Lyl08), SLAMF7, SLP-76, TNFR2, TRANCE/RANKL, VLA-I, VLA-6, a ligand that specifically binds with CD83, and the like.

Stimulatory ligands are well-known in the art and encompass, inter alia, a MHC Class I molecule loaded with a peptide, an anti-CD3 antibody, a superagonist anti-CD28 antibody, and a superagonist anti-CD2 antibody.

In one embodiment, the intracellular signaling domains comprise at least one intracellular domain selected from an intracellular signaling domain of a lymphocyte receptor chain, a TCR/CD3 complex protein, an Fc receptor subunit, an IL-2 receptor subunit, CD3, FcRγ, FcRβ, CD3γ, CD3δ, CD3ε, CD5, CD22, CD79a, CD79b, CD66d, CD278(ICOS), FcsRI, DAP10, and DAP 12.

In one embodiment, the costimulatory domain of the CAR according to the invention is selected from CD28, CD134 (TNFRSF4, OX40), CD154 (CD40L), CD137 (4-1BB), ICOS (CD278), CD27, CD244 (2B4), CD149, DAP10, CD30, IL2-R, IL7r6, IL21-R, NKp30, NKp44, CD27 and DNAM-1. These different co-stimulatory domains produce different cytokine profiles which, in turn, may produce effects on target cell-mediated cytotoxicity and the tumor microenvironment. Particularly, the costimulatory domain is fused together with CD3ζ. In one embodiment, the costimulatory domain of the CAR according to the invention is selected from CD28, 4-1BB and OX40.

While any suitable endodomain can be used in the CAR of the invention, in certain embodiments, the invention specifically contemplates the use of all or a part of the endodomains of 4-1BB and CD3ζ as the intracellular domain. The cytoplasmic signaling sequences within the intracellular signaling domain of the CAR of the invention may be linked to each other in a random or specified order. In a CAR containing more than one intracellular endodomain, an oligopeptide linker, as described above, or a polypeptide linker can be inserted between the intracellular endodomains to link the domains. Optionally, a short oligo- or polypeptide linker, preferably between 2 and 10 amino acids in length may form the linkage. A glycine-serine doublet or continuous sequence provides a particularly suitable linker. Particularly, the peptide linker may be a (Gly)$_3$-Ser linker or any repetition thereof such as doublets or triplets thereof.

As used herein, the term "4-1BB costimulatory signaling region" refers to a specific protein fragment associated with this name and any other molecules that have analogous biological function that share at least 70%, or alternatively at least 80% amino acid sequence identity, preferably 90% sequence identity, more preferably at least 95% sequence identity with the 4-1BB costimulatory signaling region sequence as shown in SEQ ID NO: 21. The example sequences of the 4-1BB costimulatory signaling region are provided in U.S. 20130266551A1.

Examples of sequences of CD28 costimulatory signaling domain are provided in U.S. Pat. No. 5,686,281; Geiger, T. L. et al., Blood 98: 2364-2371 (2001); Hombach A. et al., J Immunol 167: 6123-6131 (2001); Maher J. et al. Nat Biotechnol 20: 70-75 (2002); Haynes N. M. et al., J Immunol 169: 5780-5786 (2002); Haynes N. M. et al., Blood 100: 3155-3163 (2002).

Non-limiting example sequences of the OX40 costimulatory signaling region are disclosed in U.S. 2012/20148552 A1.

In a particular embodiment, the CAR of the invention comprises a 4-1BB costimulatory signaling region, preferably comprising or consisting in the sequence of SEQ ID NO: 21 or a sequence having at least 80, 85, 90 or 95% of identity therewith.

Signal Peptide

In addition to the antigen targeting domain, hinge domain, transmembrane domain, and signaling endodomain, the CAR of the invention can further comprise a signal peptide sequence linked to the N-terminus of the CAR. Signal peptide sequences exist at the N-terminus of many secretory proteins and membrane proteins and have typically a length of 15 to 30 amino acids. Since many of the protein molecules mentioned above have signal peptide sequences, these signal peptides can be used as a signal peptide for the CAR of this invention.

In an embodiment, the sequence comprising the antigen binding domain further comprises a signal peptide. In embodiments where the antigen binding domain comprises an antigen binding fragment, preferably a scFv, the signal peptide may be positioned at the amino terminus of the antigen binding fragment or scFv. In some embodiments, when the heavy chain variable region is N-terminal, the signal peptide may be positioned at the amino terminus of the heavy chain variable region. In some embodiments, when the light chain variable region is N-terminal, the leader sequence may be positioned at the amino terminus of the light chain variable region. The leader sequence may comprise any suitable signal sequence. In one embodiment, the CAR of the invention, preferably the antibody or the antigen binding fragment, even more preferably the scFv, comprises a signal peptide selected from the group consisting of CD8a, a mouse Ig Kappa signal peptide, a human IgG4 signal peptide, an IL2 signal peptide, a human IgG2 signal peptide and a *Gaussia* luc signal peptide. In one embodiment, the CAR of the invention, preferably the scFv, comprises a signal peptide selected from the group consisting of SEQ ID No: 17, 24, 75, 76, 77, and 78.

In a particular embodiment, the CAR of the invention comprises a CD8a signal peptide, preferably comprising or consisting in the sequence of SEQ ID NO: 17 or a sequence having at least 80, 85, 90 or 95% of identity therewith.

Cleavable Linker

In a particular embodiment, the CAR according to the invention further comprises a cleavable linker. The cleavable linker may be a peptide, a polypeptide or a part of a polypeptide, which is cleaved after the generation of the protein or polypeptide, particularly, after the translation of the CAR according to the invention.

Particularly, the cleavable linker is a self-cleavable, self-cleaving, self-cleavage peptide or linker, these terms being used interchangeably herein.

In one embodiment, the cleavable linker comprises a 2A peptide. "2A" or "2A-like" sequences are part of a large family of peptides that can cause peptide bond-skipping. Particularly, the mechanism of 2A-mediated "self-cleavage" was recently discovered to be ribosome skipping the formation of a glycyl-prolyl peptide bond at the C-terminus of the 2A peptide. The 2A-peptide-mediated cleavage commences after the translation. Successful skipping and recommencement of translation results in two "cleaved" proteins: the protein upstream of the 2A is attached to the complete 2A peptide except for the C-terminal proline, and the protein downstream of the 2A is attached to one proline at the N-terminus. Successful skipping but ribosome fall-off and discontinued translation results in only the protein upstream of 2A. Several 2A peptides have been identified in picornaviruses, insect viruses and type C rotaviruses.

Examples of cleavable linker according to the invention include, but are not limited to, porcine teschovirus-1 2A (P2A), FMDV 2A (F2A); equine rhinitis A virus (ERAV) 2A (E2A); and Thosea asigna virus 2A (T2A), cytoplasmic polyhedrosis virus 2A (BmCPV2A) and flacherie Virus 2A (BmIFV2A), or a combination thereof, for example such as described in Kim et al. (2011) PLoS ONE 6(4): e18556 and in Liu et al (2017) Sci Rep. 2017; 7: 2193.

Preferably, the cleavable linker is P2A which comprises or consists of the sequence set forth in SEQ ID NO: 28 or a sequence having at least 80, 85, 90 or 95% of identity therewith.

In one embodiment, the N-terminus of the cleavable linker is operably linked to the C-terminus of the CAR endodomain and/or the C-terminus of the cleavable linker is operably linked to the N-terminus of a reporter.

Reporter

For safety reasons, for tracking purposes or for elimination of unwanted modified CAR expressing cells, the CAR construct according to the invention may further comprise a selectable marker or reporter. Particularly, CAR cells can be engineered with self-cleaving linker to co-express CARs with a reporter, to provide the possibility of selecting or eliminating the CAR cells for example by antibodies.

In a particular embodiment, the N terminus of the reporter is connected to the anti-HLA-G CAR by a cleavable linker, such as a 2A linker as described hereabove, to allow release of the reporter molecule.

The reporter can then be used to confirm successful delivery or expression of the CAR construct to cells of interest.

Particularly, the reporter is selected in the group consisting of a c-myc tag, CD20, CD52 (Campath), truncated EGFR (EGFRt), truncated CD19 (CD19t), or any part or combination thereof, or any other marker molecule that can be expressed and/or detected in a cell.

In a preferred embodiment, the reporter is a CD19 reporter, preferably a human truncated CD19 (hCD19t) reporter in which amino-acid from position 314-556 have been removed (i.e 313 amino-acid removed). In a particular embodiment, the truncated human CD19 is the one synthesized by GeneArt containing the extracellular and transmembrane portions of human CD19 (amino acid 1-313) known under the accession number NP_001171569.1.

Preferably, the reporter is a human truncated CD19 reporter which comprises or consists of the sequence set forth in SEQ ID NO: 28 or a sequence having at least 80, 85, 90 or 95% of identity therewith.

Particular CARs of the Present Invention

In a particular embodiment, the CAR of the present invention comprises a signal peptide, preferably a CD8a signal peptide; an antigen binding domain specific of one or several HLA-G isoform(s), in particular as a scFv, preferably as detailed above; optionally a hinge, preferably comprising or consisting of (i) a human IgG4 hinge domain, (ii) a human IgG4 hinge domain and a CH3 human IgG4 domain or (iii) a mutated CH2 human IgG4 domain, a human IgG4 hinge domain and a CH3 human IgG4 domain or (iv) a CD28 hinge or (v) a CD8a hinge; a transmembrane domain, preferably a CD28 transmembrane domain; a costimulatory signaling region, preferably selected from CD28, 4-1BB and OX40 costimulatory signaling region, more preferably a 4-1BB costimulatory signaling region; and a CD3ζ signaling domain, and optionally a cleavable linker, preferably a 2A linker, and a reporter, preferably a hCD19t reporter.

In one embodiment the CAR construct is a bispecific CAR construct that comprises (i) a domain comprising CDR 1, 2 and 3 (HCDR1, HCDR2, HCDR3) comprising a sequence of SEQ ID NO: 11, 12 and 13, respectively, (ii) a domain comprising CDR 1, 2 and 3 (LCDR1, LCDR2, LCDR3) comprising a sequence of SEQ ID NO: 14, 15 and 16, respectively, (iii) a domain comprising CDR 1, 2 and 3 (HCDR1, HCDR2, HCDR3) comprising a sequence of SEQ ID NO: 5, 6 and 7, respectively, and (iv) a domain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions.

More specifically, the CAR of the present invention may comprise or consist in the polypeptide sequence of SEQ ID NO: 32, 33, 34, 35, 36, 37, 83 or 85 or a sequence having at least 80, 85, 90 or 95% of identity with the sequence of SEQ ID NO: 32, 33, 34, 35, 36, 37, 83 or 85 and having the same functions.

CAR Variations

Included in the scope of the invention are functional portions of the inventive CARs described herein. The term "functional portion" when used in reference to a CAR refers to any part or fragment of the CAR of the invention, which part or fragment retains the biological activity of the CAR of which it is a part (the parent CAR). Functional portions encompass, for example, those parts of a CAR that retain the ability to recognize antigen or target cells, or detect, treat, or prevent a disease, to a similar extent, the same extent, or to a higher extent, as the parent CAR. In reference to the parent CAR, the functional portion can comprise, for instance, about 10%, 25%, 30%, 50%, 68%, 80%, 90%, 95%, or more, of the parent CAR.

The functional portion can comprise additional amino acids at the amino or carboxy terminus of the portion, or at both termini, which additional amino acids are not found in the amino acid sequence of the parent CAR. Desirably, the additional amino acids do not interfere with the biological function, e.g., recognize target cells, detect cancer, treat or prevent cancer, etc. More desirably, the additional amino acids enhance the biological activity, as compared to the biological activity of the parent CAR.

Included in the scope of the invention are functional variants or biological equivalent of the inventive CARs or antibody described herein. A functional variant can, for example, comprise the amino acid sequence of the parent polypeptide with at least one conservative amino acid substitution. Alternatively or additionally, the functional variants can comprise the amino acid sequence of the parent polypeptide with at least one non-conservative amino acid substitution. In this case, it is preferable for the non-conservative amino acid substitution to not interfere with or inhibit the biological activity of the functional variant. The non-conservative amino acid substitution may enhance the biological activity of the functional variant, such that the biological activity of the functional variant is increased as compared to the parent polypeptide.

Such biological variant (including functional portions thereof) can comprise synthetic amino acids in place of one or more naturally-occurring amino acids.

Such biological variant (including functional portions thereof) can be glycosylated, amidated, carboxylated, phosphorylated, esterified, N-acylated, cyclized via, e.g., a disulfide bridge, or converted into an acid addition salt and/or optionally dimerized or polymerized, or conjugated.

Such biological variant (including functional portions thereof) can be obtained by methods known in the art. The polypeptides may be made by any suitable method of making polypeptides or proteins. Suitable methods of de novo synthesizing polypeptides and proteins are described in references, such as Chan et al., Fmoc Solid Phase Peptide Synthesis, Oxford University Press, Oxford, United Kingdom, 2000; Peptide and Protein Drug Analysis, ed. Reid, R., Marcel Dekker, Inc., 2000; Epitope Mapping, ed. Westwood et al., Oxford University Press, Oxford, United Kingdom, 2001 and U.S. Pat. No. 5,449,752. Also, polypeptides and proteins can be recombinantly produced using the nucleic acids described herein using standard recombinant methods. See, for instance, Sambrook et al, Molecular Cloning: A Laboratory Manual, 3rd ed., Cold Spring Harbor Press, Cold Spring Harbor, N.Y. 2001; and Ausubel et al., Current Protocols in Molecular Biology, Greene Publishing Associates and John Wiley & Sons, N Y, 1994.

Nucleic Acid Construct and Vectors for CAR Expression

The invention also relates to a nucleic acid encoding an antibody as described above or a nucleic acid encoding a CAR according to the invention. Such nucleic acid can be transduced into a cell, in particular an immune cell, to create a cell that expresses the CAR. Particularly, the nucleic acid construct comprises sequences encoding an external domain, an intracellular domain, a transmembrane, optionally a hinge domain, and optionally a cleavable linker, a reporter and/or a signal peptide as described hereabove. In one embodiment, the nucleic acid construct sequentially comprises or consists in, from N to C terminus: optionally a peptide signal sequence, an anti-HLA-G antibody or fragment thereof, preferably an anti-HLA-G scFv, a spacer domain, a transmembrane domain, at least one intracellular domain, and optionally a cleavable linker and a reporter.

In a yet further embodiment, the nucleic acid construct further comprises a tag, preferably a Flag tag. For example, the Flag tag comprises or consists in SEQ ID NO: 23, SEQ ID NO: 60, or SEQ ID NO: 79.

In some embodiments, the nucleic acid construct comprises:

(i) a nucleic acid sequence encoding an anti-HLA-G scFv as described above;

(ii) optionally a nucleic acid sequence encoding a hinge, preferably selected from the group consisting of (i) CD28 hinge, (ii) CD8 alpha hinge, (iii) a human IgG4 hinge domain, (iv) a human IgG4 hinge domain and a CH3 human IgG4 domain or (v) a mutated CH2 human IgG4 domain, a human IgG4 hinge domain and a CH3 human IgG4 hinge domain (iii) a nucleic acid sequence encoding a transmembrane domain, preferably a CD28 transmembrane domain;

(iii) a nucleic acid sequence encoding an endodomain, preferably a 4-1BB domain and/or a CD3 (domain; (iv) optionally a cleavable linker, preferably a P2A cleavable linker;

(v) optionally a reporter, preferably a hCD19t reporter; and/or (vi) optionally a signal peptide, preferably selected from the group consisting of CD8a, a mouse Ig Kappa signal peptide, a human IgG4 signal peptide and an IL2 signal peptide.

In some embodiments, the nucleic acid construct comprises:

(i) a nucleic acid sequence encoding the HCDR1, HCDR2 and HCDR 3 of SEQ ID NO: 5, 6 and 7, respectively, for instance SEQ ID NO: 42, 43 and 44, respectively; and (ii) a nucleic acid sequence encoding the LCDR1, LCDR2 and LCDR3 of SEQ ID NO: 8, 9 and 10, respectively, for instance SEQ ID NO: 45, 46 and 47 respectively.

Alternatively, the nucleic acid construct comprises:

(i) a nucleic acid sequence encoding the HCDR1, HCDR2 and HCDR 3 of SEQ ID NO: 11, 12 and 13, respectively, for instance SEQ ID NO: 48, 49 and 50, respectively, and (ii) a nucleic acid sequence encoding the LCDR1, LCDR2 and LCDR3 of SEQ ID NO: 14, 15 and 16, respectively, for instance SEQ ID NO: 51, 52 and 53, respectively.

In a particular embodiment, the nucleic acid construct comprises or essentially consists in:

(i) a nucleic acid sequence encoding SEQ ID NO: 1 or a sequence having at least 80, 85, 90 or 95% identity with SEQ ID NO: 1, for instance SEQ ID NO: 38;

(ii) a nucleic acid sequence encoding SEQ ID NO: 2 or a sequence having at least 80, 85, 90 or 95% identity with SEQ ID NO: 2, for instance SEQ ID NO: 39;

(iii) optionally a nucleic acid sequence encoding (a) SEQ ID NO: 18, (b) SEQ ID 19, (c) SEQ ID NO: 25, (d) SEQ ID NO: 25 and SEQ ID NO: 27, or (e) SEQ ID NO: 25, SEQ ID NO: 26 and SEQ ID NO: 27, or a sequence having at least 80, 85, 90 or 95% identity thereto, for instance (a) SEQ ID NO: 55, (b) SEQ ID NO: 56, (c) SEQ ID NO: 62, (d) SEQ ID NO: 62 and SEQ ID NO: 64, or (e) SEQ ID NO: 62, SEQ ID NO: 63 and SEQ ID NO:64, respectively;

(iv) a nucleic acid sequence encoding a transmembrane domain, preferably a CD28 transmembrane domain, even more preferably SEQ ID NO: 57 or SEQ ID NO:80;

(v) a nucleic acid sequence encoding an endodomain, preferably a 4-1BB domain, for instance SEQ ID NO: 58 or 81, and/or a CD3ζ endodomain, for instance SEQ ID NO: 59 or 82, preferably a 4-1BB domain and a CD3ζ endodomain;

(vi) optionally a nucleic acid sequence encoding a cleavable linker, preferably a P2A cleavable linker, even more preferably encoding SEQ ID NO: 28 or a sequence having at least 80, 85, 90 or 95% identity with SEQ ID NO: 28, for instance SEQ ID NO: 65;

(vii) optionally a nucleic acid sequence encoding a reporter, preferably a hCD19t reporter, even more preferably encoding SEQ ID NO: 29 or a sequence having at least 80, 85, 90 or 95% identity with SEQ ID NO: 29, for instance SEQ ID NO: 66;

(viii) optionally a nucleic acid sequence encoding a signal peptide, preferably a CD8 α signal peptide, even more preferably SEQ ID NO. 54 or 61.

In a yet further embodiment, the nucleic acid construct further comprises a nucleic acid sequence encoding a tag, preferably a Flag tag, for instance of SEQ ID NO: 23 or a sequence having at least 80, 85, 90 or 95% identity thereto.

In another particular embodiment, the nucleic acid construct comprises or essentially consists in:

(i) a nucleic acid sequence encoding SEQ ID NO: 3 or a sequence having at least 80, 85, 90 or 95% identity with SEQ ID NO: 3; for instance, SEQ ID NO: 40; and/or (ii) a nucleic acid sequence encoding SEQ ID NO: 4 or a sequence having at least 80, 85, 90 or 95% identity with SEQ ID NO: 4; for instance, SEQ ID NO: 41;

(iii) optionally a nucleic acid sequence encoding (a) SEQ ID NO: 18, (b) SEQ ID 19, (c) SEQ ID NO: 25, (d) SEQ ID NO: 25 and SEQ ID NO: 27, or (e) SEQ ID NO: 25, SEQ ID NO: 26 and SEQ ID NO: 27, or a sequence having at least 80, 85, 90 or 95% identity thereto, for instance (a) SEQ ID NO: 55, (b) SEQ ID NO: 56, (c) SEQ ID NO: 62, (d) SEQ ID NO: 62 and SEQ ID NO: 64, or (e) SEQ ID NO: 62, SEQ ID NO: 63 and SEQ ID NO:64, respectively;

(iv) a nucleic acid sequence encoding a transmembrane domain, preferably a CD28 transmembrane domain, even more preferably SEQ ID NO: 57 or SEQ ID NO:80;

(v) a nucleic acid sequence encoding an endodomain, preferably a 4-1BB domain, for instance SEQ ID NO: 58 or 81, and/or a CD3ζ endodomain, for instance SEQ ID NO: 59 or 82, preferably a 4-1BB domain and a CD3ζ endodomain;

(vi) optionally a nucleic acid sequence encoding a cleavable linker, preferably a P2A cleavable linker, even more preferably encoding SEQ ID NO: 28 or a sequence having at least 80, 85, 90 or 95% identity with SEQ ID NO: 28, for instance SEQ ID NO: 65;

(vii) optionally a nucleic acid sequence encoding a reporter, preferably a hCD19t reporter, even more preferably encoding SEQ ID NO: 29 or a sequence having at least 80, 85, 90 or 95% identity with SEQ ID NO: 29, for instance SEQ ID NO: 66;

(viii) optionally a nucleic acid sequence encoding a signal peptide, preferably a CD8 c signal peptide, even more preferably SEQ ID NO. 54 or 61.

In a yet further embodiment, the nucleic acid construct further comprises a nucleic acid sequence encoding a tag, preferably a Flag tag, for instance of SEQ ID NO: 23 or a sequence having at least 80, 85, 90 or 95% identity thereto.

In another particular embodiment, the nucleic acid construct sequentially comprises or consists in from N to C terminus:

(i) optionally a signal peptide, preferably a CD8a signal peptide, even more preferably SEQ ID NO: 54 or 61, (ii) a nucleic acid sequence encoding SEQ ID NO: 30 or a sequence having at least 80, 85, 90 or 95% identity with SEQ ID NO: 30; for instance SEQ ID NO: 67; or a nucleic acid sequence encoding SEQ ID NO: 31 or a sequence having at least 80, 85, 90 or 95% identity with SEQ ID NO: 31; for instance SEQ ID NO: 68;

(iii) optionally a nucleic acid sequence encoding (a) SEQ ID NO: 18, (b) SEQ ID 19, (c) SEQ ID NO: 25, (d) SEQ ID NO: 25 and SEQ ID NO: 27, or (e) SEQ ID NO: 25, SEQ ID NO: 26 and SEQ ID NO: 27, or a sequence having at least 80, 85, 90 or 95% identity thereto, for instance (a) SEQ ID NO: 55, (b) SEQ ID NO: 56, (c) SEQ ID NO: 62, (d) SEQ ID NO: 62 and SEQ ID NO: 64, or (e) SEQ ID NO: 62, SEQ ID NO: 63 and SEQ ID NO:64, respectively;

(iv) a nucleic acid sequence encoding a transmembrane domain, preferably a CD28 transmembrane domain, even more preferably SEQ ID NO: 57 or SEQ ID NO:80;

(v) a nucleic acid sequence encoding an endodomain, preferably a 4-1BB domain, for instance SEQ ID NO: 58 or 81, and/or a CD3ζ endodomain, for instance SEQ ID NO: 59 or 82, preferably a 4-1BB domain and a CD3ζ endodomain;

(vi) optionally a nucleic acid sequence encoding a cleavable linker, preferably a P2A cleavable linker, even more preferably encoding SEQ ID NO: 28 or a sequence having at least 80, 85, 90 or 95% identity with SEQ ID NO: 28, for instance SEQ ID NO: 65;

(vii) optionally a nucleic acid sequence encoding a reporter, preferably a hCD19t reporter, even more preferably encoding SEQ ID NO: 29 or a sequence having at least 80, 85, 90 or 95% identity with SEQ ID NO: 29, for instance SEQ ID NO: 66.

In a particular embodiment, the present invention provides a nucleic acid sequence encoding a particular CAR of the present invention, preferably a CAR describe in the sequence set forth in SEQ ID No: 32, 33, 34, 35, 36, 37, 83 or 85, more preferably such a nucleic acid sequence or construct comprising or consisting of SEQ ID NO: 69, 70, 71, 72, 73, 74, 84 or 86 or a sequence having at least 80, 85, 90 or 95% identity thereto.

The sequence of the open reading frame encoding the chimeric receptor can be obtained from a genomic DNA source, a cDNA source, generated by PCR from a cDNA source or else. Otherwise it can be chemically synthesized or combinations thereof. Depending upon the size of the genomic DNA and the number of introns, it may be desirable to use cDNA or a combination thereof as it is found that introns stabilize the mRNA or provide immune cell, particularly T cell-specific expression (Barthel and Goldfeld, 2003). Also, it may be further advantageous to use endogenous or exogenous non-coding regions to stabilize the mRNA. For expression of a chimeric antigen receptor of the present invention, the naturally occurring or endogenous transcriptional initiation region of the nucleic acid sequence encoding N-terminal components of the chimeric receptor can be used to generate the chimeric receptor in the target host cell. Alternatively, an exogenous transcriptional initiation region can be used that allows for constitutive or inducible expression, wherein expression can be controlled depending upon the target host, the level of expression desired, the nature of the target host, and the like.

Likewise, a signal sequence directing the chimeric receptor to the surface membrane can be the endogenous signal sequence of N-terminal component of the chimeric receptor. Optionally, in some instances, it may be desirable to exchange this sequence for a different signal sequence. However, the signal sequence selected should be compatible with the secretory pathway of the immune cell that will express the CAR so that the chimeric receptor is presented on the surface of the cell.

In accordance with the present invention, the nucleic acid construct is transformed or introduced into a cell and is transcribed and translated to produce a product (i.e. a chimeric receptor). Thus, the nucleic acid construct can further include at least one promoter for directing transcription of the CAR.

In one embodiment, the promoter is operably linked to the nucleic acid sequence encoding the chimeric receptor of the present invention, i.e., they are positioned so as to promote transcription of the messenger RNA from the DNA encoding the chimeric receptor. The promoter can be of genomic origin or synthetically generated. A variety of promoters for use in immune cells and particularly in T cells are well-known in the art (e.g., the CD4 promoter disclosed by Marodon et al. (2003)). The promoter can be constitutive or inducible, where induction is associated with the specific cell type or a specific level of maturation, or drug (e.g., tetracycline or doxorubicin) for example. Examples of inducible promoters include, but are not limited to, a metallothionine promoter, a glucocorticoid promoter, a progesterone promoter, and a tetracycline promoter. Alternatively, a number of well-known viral promoters are also suitable. Promoters of interest include the β-actin promoter, SV40 early and late promoters, immunoglobulin promoter, human cytomegalovirus promoter, retrovirus promoter, and the Friend spleen focus-forming virus promoter, mouse mammary tumor virus (MMTV), human immunodeficiency virus (HIV) long terminal repeat (LTR) promoter, MoMuLV promoter, avian leukemia virus promoter, Cytomegalovirus immediate early promoter, Rous sarcoma virus promoter, as well as human gene promoters such as, but not limited to, the actin promoter, the myosin promoter, the hemoglobin promoter, and the creatine kinase promoter. The promoters may or may not be associated with enhancers, wherein the enhancers may be naturally associated with the particular promoter or associated with a different promoter.

Similarly, a termination region may be provided by the naturally occurring or endogenous transcriptional termination region of the nucleic acid sequence encoding the C-terminal component of the chimeric receptor. Alternatively, the termination region may be derived from a different source. For the most part, the source of the termination region is generally not considered to be critical to the expression of a recombinant protein and a wide variety of termination regions can be employed without adversely affecting expression. As will be appreciated by one skilled in the art that, in some instances, a few amino acids at the ends of the antigen binding domain in the CAR can be deleted, usually not more than 10, more usually not more than 5 residues, for example. Also, it may be desirable to introduce a small number of amino acids at the borders, usually not more than 10, more usually not more than 5 residues. The deletion or insertion of amino acids may be as a result of the needs of the construction, providing for convenient restriction sites, ease of manipulation, improvement in levels of expression, or the like. In addition, the substitute of one or more amino acids with a different amino acid can occur for similar reasons, usually not substituting more than about five amino acids in any one domain.

In another embodiment, the nucleic acid construct further comprises a promoter, the correct translation initiation sequence such as a ribosomal binding site and a start codon, a termination codon, and a transcription termination sequence.

The nucleic acid construct according to the invention may also comprise other regulatory regions such as enhancers, silencers and boundary elements/insulators to direct the level of transcription of a given gene. The nucleic acid construct that encodes the chimeric receptor according to the invention can be prepared in conventional ways. Because, for the most part, natural sequences may be employed, the natural genes may be isolated and manipulated, as appropriate, so as to allow for the proper joining of the various components. Thus, the nucleic acid sequences encoding for the N-terminal and C-terminal proteins of the chimeric receptor can be isolated by employing the polymerase chain reaction (PCR), using appropriate primers that result in deletion of the undesired portions of the gene. Alternatively, restriction digests of cloned genes can be used to generate the chimeric construct. In either case, the sequences can be selected to provide for restriction sites that are blunt-ended, or have complementary overlaps.

The various manipulations for preparing the chimeric construct can be carried out in vitro and in particular embodiments the chimeric construct is introduced into vectors for cloning and expression in an appropriate host using standard transformation or transfection methods. Thus, after each manipulation, the resulting construct from joining of the DNA sequences is cloned, the vector isolated, and the sequence screened to ensure that the sequence encodes the desired chimeric receptor. The sequence can be screened by restriction analysis, sequencing, or the like.

CARs may be prepared using expression vectors. Aspects of the present disclosure relate to a nucleic acid sequence encoding a HLA-G CAR and vectors comprising a nucleic acid sequence encoding the CAR as described above.

For example, the nucleic acid construct according to the invention can be cloned into a vector including, but not limited to, a plasmid, a phagemid, a phage derivative, a virus, and a cosmid. Vectors of particular interest include expression vectors, replication vectors, probe generation vectors, and sequencing vectors. According to the nucleic acid construct and the host cell, the vector according to the invention can comprise: a promoter, a terminator, replication origin, selectable markers, multiple cloning sites, packaging sites and the like. In some other embodiments, the vector comprises, or alternatively consists essentially thereof, or yet further consists of, a Kozak consensus sequence upstream of the sequence encoding the CAR. In some embodiments, the vector comprises a polynucleotide conferring antibiotic resistance.

Particularly, the vector according to the invention may be provided to a cell in the form of a viral vector. A number of viral based systems have been developed for gene transfer into mammalian cells. Viral vector technology is well known in the art and is described, for example, in Sambrook, et al. ((2001) Molecular Cloning: A Laboratory Manual, Cold Spring Harbor Laboratory, New York), and in other virology and molecular biology manuals. Viruses, which are useful as vectors include, but are not limited to, retroviruses, adenoviruses, adeno-associated viruses, herpesviruses and lentiviruses. Preferably, the vector is an Integrative Lentiviral Vector. Lentiviral vectors have the added advantage over vectors derived from oncoretroviruses in that they can transduce non-proliferating cells and present low immunogenicity. In general, a suitable vector contains an origin of replication functional in at least one organism, a promoter sequence, convenient restriction endonuclease sites, and one or more selectable markers such as described in WO 01/96584; WO 01/29058; and U.S. Pat. No. 6,326,193.

Particularly, in order to assess the expression of a CAR, the expression vector to be introduced into a cell can also contain either a selectable marker gene or a reporter gene or both to facilitate identification and selection of expressing cells from the population of cells sought to be transfected or infected through viral vectors, in other aspects, the selectable marker may be carried on a separate piece of DNA and used in a co-transfection procedure. Both selectable markers and reporter genes may be flanked with appropriate regulatory sequences to enable expression in the host cells. Useful selectable markers include, for example, antibiotic-resistance genes and the like.

In one aspect, the term "vector" intends a recombinant vector that retains the ability to infect and transduce non-dividing and/or slowly-dividing cells and integrate into the target cell's genome. In several aspects, the vector is derived from or based on a wild-type virus. In further aspects, the vector is derived from or based on a wild-type retrovirus. Particularly, the retrovirus can be selected from a leukemia virus such as a Moloney Murine Leukemia Virus (MMLV), the Human Immunodeficiency Virus (HIV), or the Gibbon Ape Leukemia virus (GALV). The foreign enhancer and promoter may be the human cytomegalovirus (HCMV) immediate early (IE) enhancer and promoter, the enhancer and promoter (U3 region) of the Moloney Murine Sarcoma Virus (MMSV), the U3 region of Rous Sarcoma Virus (RSV), the U3 region of Spleen Focus Forming Virus (SFFV), or the HCMV IE enhancer joined to the native Moloney Murine Leukemia Virus (MMLV) promoter. Viral vectors, and especially retroviral vectors, have become the most widely used method for inserting genes into mammalian, e.g., human cells. Viral vectors can also be derived from lentivirus, poxviruses, herpes simplex virus I (HSV), Epstein Barr virus (EBV), papillomavirus, adenoviruses and adeno-associated viruses, and the like. See for example, U.S. Pat. Nos. 5,350,674 and 5,585,362.

Preferably, the vector according to the invention is a lentiviral vector. Particularly, the vector is derived from primate and non-primate lentivirus. Examples of primate lentiviruses include the human immunodeficiency virus (HIV), the causative agent of human acquired immunodeficiency syndrome (AIDS), and the simian immunodeficiency virus (SIV). The non-primate lentiviral group includes the prototype "slow virus" visna/maedi virus (VMV), as well as the related caprine arthritis-encephalitis virus (CAEV), equine infectious anemia virus (EIAV) and the more recently described feline immunodeficiency virus (FIV) and bovine immunodeficiency virus (BIV). Prior art recombinant lentiviral vectors are known in the art, e.g., see U.S. Pat. Nos. 6,924,123; 7,056,699; 7,07,993; 7,419,829 and 7,442,551, incorporated herein by reference.

Commercial retroviral vectors for use in this disclosure include, but are not limited to, pFB-neo vectors (STRATA-GENE©), Invitrogen's pLenti series versions 4, 6, and 6.2 "ViraPower" system. Manufactured by Lentigen Corp.; pHIV-7-GFP, lab generated and used by the City of Hope Research Institute; "Lenti-X" lentiviral vector, pLVX, manufactured by Clontech; pLKO.1-puro, manufactured by Sigma-Aldrich; pLemiR, manufactured by Open Biosystems; and pLV, lab generated and used by the Charite Medical School, Institute of Virology (CBF), Berlin, Germany.

It will be evident that a viral vector according to the disclosure need not be confined to the components of a particular virus. The viral vector may comprise components derived from two or more different viruses, and may also comprise synthetic components. Vector components can be manipulated to obtain desired characteristics, such as target cell specificity.

U.S. Pat. No. 6,924,123 discloses that certain retroviral sequence facilitate integration into the target cell genome. This patent teaches that each retroviral genome comprises genes called gag, pol and env which code for virion proteins and enzymes. These genes are flanked at both ends by regions called long terminal repeats (LTRs). The LTRs are responsible for proviral integration, and transcription. They also serve as enhancer-promoter sequences. Accordingly, the vector according to the invention can comprise one or more of the integration features.

In some embodiment, the components of the particles not encoded by the vector genome are provided in trans by additional nucleic acid sequences (the "packaging system", which usually includes either or both of the gag/pol and env genes) expressed in the host cell, for example using a helper virus strategy. The set of sequences required for the production of the viral vector particles may be introduced into the host cell by transient transfection, or they may be integrated into the host cell genome, or they may be provided in a mixture of ways, such as helper sequences. The techniques involved are known to those skilled in the art. For example, the retroviral constructs are packaging plasmids comprising at least one retroviral helper DNA sequence derived from a replication-incompetent retroviral genome encoding in trans all virion proteins required to package a replication incompetent retroviral vector, and for producing virion proteins capable of packaging the replication-incompetent retroviral vector at high titer, without the production of replication-competent helper virus.

In the packaging process, the packaging plasmids and retroviral vectors expressing the CAR according to the invention are transiently co-transfected into a first population of mammalian cells that are capable of producing virus, such as human embryonic kidney cells, for example 293 cells (ATCC No. CRL1573, ATCC, Rockville, Md.) to produce high titer recombinant retrovirus-containing supernatants. In another method of the invention this transiently transfected first population of cells is then co-cultivated with mammalian target cells, for example human lymphocytes, to transduce the target cells with the foreign gene at high efficiencies. In yet another method of the invention the supernatants from the above described transiently transfected first population of cells are incubated with mammalian target cells, for example human lymphocytes or hematopoietic stem cells, to transduce the target cells with the foreign gene at high efficiencies.

The nucleic acid construct according to the invention be inserted into a vector and packaged in retroviral or lentiviral particles using techniques known in the art. The recombinant virus can then be isolated and delivered to cells of the subject either in vivo or ex vivo. In a particular aspect, the packaging plasmids are stably expressed in a first population of mammalian cells that are capable of producing virus, such as human embryonic kidney cells, for example 293 cells. Retroviral or lentiviral vectors are introduced into cells by either co-transfection with a selectable marker or infection with pseudotyped virus. In both cases, the vectors integrate. Alternatively, vectors can be introduced in an episomally maintained plasmid.

Anti-HLA-G CAR Expressing Cells

The present invention relates to a cell expressing a CAR as described herein. The cell may be of any kind, including an immune cell capable of expressing the CAR or a cell, such as a bacterial cell, that harbors an expression vector that encodes the CAR.

In the context of expressing a heterologous nucleic acid sequence encoding the CAR of the invention, "host cell" refers to a cell that is capable of replicating a vector and/or expressing a heterologous gene encoded by a vector. The term "cell" also includes their progeny, which is any and all subsequent generations. It is understood that all progeny may not be identical due to deliberate or inadvertent mutations. A host cell may be transfected by the nucleic acid construct or vector according to the invention. A transformed cell includes the primary subject cell and its progeny. As used herein, the terms "engineered" and "recombinant" cells or host cells are intended to refer to a cell into which an exogenous nucleic acid sequence, such as, for example, a vector, more particularly a CAR, has been introduced. Therefore, recombinant cells are distinguishable from naturally occurring cells which do not contain a recombinantly introduced nucleic acid.

Upon transduction of a cell with a nucleic acid construct encoding a CAR, the cell will recognize the HLA-G isoform specified by the CAR. Thus, the invention also relates to cells expressing the CARs according to the invention. Particularly, the anti-HLA-G CAR expressing cells according to the invention are immune cells able to express a CAR according to the invention. In certain embodiments, immune cells are transfected to comprise at least a CAR of the present invention.

The cell can comprise a CAR that specifically binds to β2M-associated HLA-G isoforms, preferably to both HLA-G1 and HLA-G5 isoforms. Alternatively, the cell may comprise a CAR that specifically binds to β2M-free HLA-G isoforms, preferably to both HLA-G2 and HLA-G6 isoforms and/or HLA-G1/β2M free and/or HLA-G5/β2M free isoforms.

In one embodiment, the cell expresses at least two different CARs. For instance, the cell may comprise a CAR that specifically binds to β2M-associated HLA-G isoforms preferably to both HLA-G1 and HLA-G5, and another CAR that specifically binds to a different antigen. The cell may alternatively comprise a CAR that specifically binds to β2M-free HLA-G isoforms, preferably to HLA-G2 and HLA-G6, and/or HLA-G1/β2M free and/or HLA-G5/β2M free isoforms and another CAR that specifically binds to a different antigen. In particular, the cell may comprise both a CAR that specifically binds to β2M-associated HLA-G isoforms preferably to both HLA-G1 and HLA-G5, and a CAR that specifically binds to β2M-free HLA-G isoforms, preferably to HLA-G2 and HLA-G6, and/or HLA-G1/β2M free and/or HLA-G5/β2M free isoforms.

Preferably, the cell comprises a CAR comprising an antigen binding fragment derived from the LFTT-1 antibody as described hereabove and a CAR comprising an antigen binding fragment derived from the 15E7 antibody as described hereabove.

Preferably such cell thus comprises a first CAR comprising (i) one heavy chain comprising CDR 1, 2 and 3 (HCDR1, HCDR2, HCDR3) comprising a sequence of SEQ ID NO: 11, 12 and 13, respectively, and (ii) one light chain comprising CDR 1, 2 and 3 (LCDR1, LCDR2, LCDR3) comprising a sequence of SEQ ID NO: 14, 15 and 16, respectively, and a second CAR that comprises (i) one heavy chain comprising CDR 1, 2 and 3 (HCDR1, HCDR2, HCDR3) comprising a sequence of SEQ ID NO: 5, 6 and 7, respectively, and (ii) one light chain comprising CDR 1, 2 and 3 (LCDR1, LCDR2, LCDR3) comprising a sequence of SEQ ID NO: 8, 9 and 10, respectively, optionally wherein each CDR may optionally comprise 1, 2, 3 or 4 amino acid substitutions, deletions or insertions. Even more preferably, such cell thus comprises a first CAR comprising or consisting of the sequence set forth in SEQ ID NO: 32, 33, 34 or 85 or a sequence having at least 80, 85, 90 or 95% identity therewith and a second CAR comprising or consisting of SEQ ID NO: 35, 36, 37 or 83 or a sequence having at least 80, 85, 90 or 95% identity therewith.

Alternatively, the cell can express a bispecific CAR comprising a bispecific antigen binding domain as described hereabove that comprises a domain that recognizes HLA-G/β2M free isoforms, preferably both HLA-G2 and HLA-G6 and/or both HLA-G1/β2M free and HLA-G5/β2M free isoforms, and a second domain that recognizes HLA-G isoforms associated with the β2M domain preferably both HLA-G1 and HLA-G5. Optionally, the cell expressing a CAR anti-HLA-G according to the invention further expresses a CAR that targets an antigen involved in a disease, preferably such as cancer or viral infection, preferably an antigen targeted in cancer therapies or in viral therapies. It will be understood that such antigen is not HLA-G. The cell according to the invention can be a prokaryotic or a eukaryotic cell. Preferably, the cells are eukaryotic cells, such as mammalian cells, and typically are human, feline or canine cells, more typically human cells, preferably primary human cells.

Preferably, the cells are immune cells. The cells can be selected from a group consisting of a T cell, including CD4$^+$ T cell, and CD8$^+$ T cell, B cell, NK cell, NKT cell, monocyte and dendritic cell, preferably the cell being a T cell, a B cell and NK cell.

The cells can be autologous cells, syngeneic cells, allogeneic cells and even in some cases, xenogeneic cells. For instance, suitable immune cells that can be used in the invention include autologous T lymphocyte cells, allogeneic T cells, xenogeneic T cells, progenitors of any of the foregoing, transformed tumor or xenogeneic immunologic effector cells, tumor infiltrating lymphocytes (TILs), cytotoxic lymphocytes or other cells that are capable of killing target cells when activated.

The immune cells may be isolated from human or non-human subjects or may be derived from stem cells, e.g., embryonic stem cells, multipotent stem cells, pluripotent stem cells, induced pluripotent stem cells (iPSCs), adult stem cells or other reprogrammed cells. The cells for introduction of the nucleic acid constructs described herein may be isolated from a sample, such as a biological sample, e.g., one obtained from or derived from a subject. In some embodiments, the subject from which the cell is isolated is one having the disease or condition or in need of a cell therapy or to which cell therapy will be administered. The subject in some embodiments is a human in need of a particular therapeutic intervention, such as the adoptive cell therapy for which cells are being isolated, processed, and/or engineered. In some embodiments, the cells are derived from the blood, bone marrow, lymph, or lymphoid organs, are cells of the immune system, such as cells of the innate or adaptive immune systems, e.g., myeloid or lymphoid cells, including lymphocytes, typically T cells and/or NK cells.

In some embodiments, the cells include one or more subsets of T cells or other cell types, such as whole T cell populations, CD4+ cells, CD8+ cells, and subpopulations thereof, such as those defined by function, activation state, maturity, potential for differentiation, expansion, recirculation, localization, and/or persistence capacities, antigen-specificity, type of antigen receptor, presence in a particular organ or compartment, marker or cytokine secretion profile, and/or degree of differentiation.

In certain embodiments, the immune cell is a T cell, e.g., an animal T cell, a mammalian T cell, a feline T cell, a canine T cell or a human T cell. Among the sub-types and subpopulations of T cells and/or of CD4+ and/or of CD8+ T cells are naive T (TN) cells, effector T cells (TEFF), memory T cells and sub-types thereof, such as stem cell memory T (TSCM), central memory T (TCM), effector memory T (TEM), or terminally differentiated effector memory T cells, tumor-infiltrating lymphocytes (TIL), immature T cells, mature T cells, helper T cells, cytotoxic T cells, mucosa-associated invariant T (MAIT) cells, naturally occurring and adaptive regulatory T (Treg) cells, helper T cells, such as TH1 cells, TH2 cells, TH3 cells, TH17 cells, TH9 cells, TH22 cells, follicular helper T cells, α/β T cells, and δ/γ T cells. Non-limiting examples of commercially available T-cell lines include lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 cytotoxic human T cell line (ATCC # CRL-11386). Further examples include but are not limited to mature T-cell lines, e.g., such as Deglis, EBT-8, HPB-MLp-W, HUT 78, HUT 102, Karpas 384, Ki 225, My-La, Se-Ax, SKW-3, SMZ-1 and T34; and immature T-cell lines, e.g., ALL-SIL, Be13, CCRF-CEM, CML-T1, DND-41, DU.528, EU-9, HD-Mar, HPB-ALL, H-SB2, HT-1, JK-T1, Jurkat, Karpas 45, KE-37, KOPT-K1, K-T1, L-KAW, Loucy, MAT, MOLT-1, MOLT 3, MOLT-4, MOLT 13, MOLT-16, MT-1, MT-ALL, P12/Ichikawa, Peer, PER0117, PER-255, PF-382, PFI-285, RPMI-8402, ST-4, SUP-T1 to T14, TALL-1, TALL-101, TALL-103/2, TALL-104, TALL-105, TALL-106, TALL-107, TALL-197, TK-6, TLBR-1, -2, -3, and -4, CCRF-HSB-2 (CCL-120.1), J.RT3-T3.5 (ATCC TIB-153), J45.01 (ATCC CRL-1990), J.CaM1.6 (ATCC CRL-2063), RS4; 11 (ATCC CRL-1873), CCRF-CEM (ATCC CRM-CCL-119); and cutaneous T-cell lymphoma lines, e.g., HuT78 (ATCC CRM-TIB-161), MJ[G11] (ATCC CRL-8294), HuT102 (ATCCTIB-162). Non-limiting exemplary sources for such commercially available cell lines include the American Type Culture Collection, or ATCC, (http://www.atcc.org/) and the German Collection of Microorganisms and Cell Cultures (https://www.dsmz.de/).

In some embodiments, the cells are natural killer (NK) cells, Natural Killer T (NKT) cells, cytokine-induced killer (CIK) cells, tumor-infiltrating lymphocytes (TILs), lymphokine-activated killer (LAK) cells, or the like. NK cells may either be isolated or obtained from a commercially available source. Non-limiting examples of commercial NK cell lines include lines NK-92 (ATCC® CRL-2407™), NK-92MI (ATCC® CRL-2408™). Further examples include but are not limited to NK lines HANK1, KHYG-1, NKL, NK-YS, NOI-90, and YT. Non-limiting exemplary sources for such commercially available cell lines include the American Type Culture Collection, or ATCC, (http://www.atcc.org/) and the German Collection of Microorganisms and Cell Cultures (https://www.dsmz.de/).

In a particular embodiment, the host cell presenting the CAR according to the invention is selected from cytotoxic T cells (also known as TC, Cytotoxic T Lymphocyte, CTL, T Killer cell, a lytic T cell, CD8+ T cells or killer T cell) and NK cells.

In some embodiments, the cells are B cells, monocytes or granulocytes, e.g., myeloid cells, macrophages, neutrophils, dendritic cells, mast cells, eosinophils, and/or basophils.

Method for Preparing CAR Expressing Cells

Methods of introducing genes into a cell and expressing genes in a cell are known in the art.

Particularly, methods for producing cells comprising vectors and/or exogenous nucleic acids are well-known in the art. See, for example, Sambrook et al. (2001, Molecular Cloning: A Laboratory Manual, Cold Spring Harbor Laboratory, New York). In the context of an expression vector, the vector can be readily introduced into a host cell, e.g., mammalian, bacterial, yeast, or insect cell by any method in the art. For example, the expression vector can be transferred into a host cell by physical, chemical, or biological means that are more particularly described here below.

In some embodiments, the methods include isolating cells from the subject, preparing, processing, culturing, and/or engineering them, as described herein, and re-introducing them into the same patient, before or after cryopreservation.

Here is particularly provided a method of producing anti-HLA-G CAR expressing cells comprising, or alternatively consisting essentially of, or yet further consisting of the steps: (i) transducing a population of isolated cells with a nucleic acid sequence encoding the CAR as described herein; and (ii) selecting a subpopulation of said isolated cells that have been successfully transduced with said nucleic acid sequence of step (i) thereby producing anti-HLA-G CAR expressing cells. In one aspect, the isolated cells are selected from a group consisting of T cells and NK cells.

Here is even more particularly provided a method of producing anti-HLA-G CAR expressing cells comprising, or alternatively consisting essentially of, or yet further consisting of the steps: (i) acquisition of an immune cell population (e.g. blood cells) (ii) isolation of a particular cell population (e.g. T cells and/or NK cells) (iii) transducing a population of isolated cells with a nucleic acid sequence encoding the CAR as described herein; and (ii) selecting a subpopulation of said isolated cells that have been successfully transduced with said nucleic acid sequence of step (iii) thereby producing anti HLA-G CAR expressing cells. These different steps are more particularly described below.

Cell Acquisition

Prior to expansion and genetic modification of the cells disclosed herein, cells may be obtained from a subject—for instance, in embodiments involving autologous therapy—or from a commercially available culture.

The cell can be acquired from samples include tissue, body fluid (e.g. blood, plasma, serum, cerebrospinal fluid, synovial fluid, urine and sweat), and other samples taken directly from the subject, as well as samples resulting from one or more processing steps, such as separation, centrifugation, genetic engineering (e.g. transduction with viral vector), washing, and/or incubation.

Cells can be obtained from a number of non-limiting sources including whole blood, peripheral blood mononuclear cells (PBMCs), leukocytes, bone marrow, thymus tissue, lymph node tissue, cord blood, tissue from a site of infection, ascites, pleural effusion, tissue biopsy, tumor, leukemia, lymphoma, gut associated lymphoid tissue, mucosa associated lymphoid tissue, spleen, other lymphoid tissues, liver, lung, stomach, intestine, colon, kidney, pancreas, breast, bone, prostate, cervix, testes, ovaries, tonsil, or other organ, and/or cells derived therefrom. Samples include, in the context of cell therapy, e.g. adoptive cell therapy, samples from autologous and allogeneic sources.

In some examples, cells from the circulating blood of a subject are obtained, e.g., by apheresis or leukapheresis. The samples, in some aspects, contain lymphocytes, including T cells, monocytes, granulocytes, B cells, other nucleated white blood cells, red blood cells, and/or platelets, and in some aspects contain cells other than red blood cells and platelets.

In some embodiments, any number of T cell ok NK cell lines available and known to those skilled in the art, such as described hereabove may be used. In some embodiments, cells can be derived from a healthy donor, from a patient diagnosed with cancer, from a patient diagnosed with an autoimmune or inflammatory disorder or from a patient diagnosed with an infection. In some embodiments, cells can be part of a mixed population of cells which present different phenotypic characteristics.

Cell Isolation

As is known to one of skill in the art, various methods are readily available for isolating immune cells from a subject or can be adapted to the present application, for example using Life Technologies Dynabeads® system; STEMcell Technologies EasySep™, RoboSep™, RosetteSep™, SepMate™; Miltenyi Biotec MACS™ cell separation kits, cell surface marker expression and other commercially available cell separation and isolation kits (e.g., ISOCELL from Pierce, Rockford, Ill.). Particular subpopulations of immune cells may be isolated through the use of beads or other binding agents available in such kits specific to unique cell surface markers. For example, MACS™ CD4+ and CD8+ MicroBeads may be used to isolate CD4+ and CD8+ T-cells. The strategy of isolating and expanding antigen-specific T cells as a therapeutic intervention for human disease has also been validated in clinical trials (Riddell et al., 1992; Walter et al., 1995; Heslop et al., 1996).

In some embodiments, isolation of the cells includes one or more preparation and/or non-affinity-based cell separation steps. In some examples, cells are washed, centrifuged, and/or incubated in the presence of one or more reagents, for example, to remove unwanted components, enrich for desired components, lyse or remove cells sensitive to particular reagents. In some examples, cells are separated based on one or more property, such as density, adherent properties, size, sensitivity and/or resistance to particular components.

In some embodiments, the blood cells collected from the subject are washed, e.g., to remove the plasma fraction and to place the cells in an appropriate buffer or media for subsequent processing steps. In some embodiments, the cells are washed with phosphate buffered saline (PBS). In some embodiments, the wash solution lacks calcium and/or magnesium and/or many or all divalent cations. In some aspects, a washing step is accomplished by a semi-automated "flow-through" centrifuge (for example, the Cobe 2991 cell processor, Baxter) according to the manufacturer's instructions. In some aspects, a washing step is accomplished by tangential flow filtration (TFF) according to the manufacturer's instructions. In some embodiments, the cells are resuspended in a variety of biocompatible buffers after washing, such as, for example, $Ca^{2+}/Mg^{2+}$ free PBS. In certain embodiments, components of a blood cell sample are removed and the cells directly resuspended in culture media.

In some embodiments, the isolation methods include the separation of different cell types based on the expression or presence in the cell of one or more specific molecules, such as surface markers, e.g., surface proteins, intracellular markers or nucleic acid. In some embodiments, any known method for separation based on such markers may be used. In some embodiments, the separation is affinity- or immunoaffinity-based separation. For example, the isolation in some aspects includes separation of cells and cell populations based on the cells' expression or expression level of one or more markers, typically cell surface markers, for example, by incubation with an antibody or binding partner that specifically binds to such markers, followed generally by washing steps and separation of cells having bound the antibody or binding partner, from those cells having not bound to the antibody or binding partner. Such separation steps can be based on positive selection, in which the cells having bound the reagents are retained for further use, and/or negative selection, in which the cells having not bound to the antibody or binding partner are retained. In some examples, both fractions are retained for further use. In some aspects, negative selection can be particularly useful where no antibody is available that specifically identifies a cell type in a heterogeneous population, such that separation is best carried out based on markers expressed by cells other than the desired population.

In some embodiments, multiple rounds of separation steps are carried out, where the positively or negatively selected fraction from one step is subjected to another separation step, such as a subsequent positive or negative selection. In some examples, a single separation step can deplete cells expressing multiple markers simultaneously, such as by incubating cells with a plurality of antibodies or binding partners, each specific for a marker targeted for negative selection. Likewise, multiple cell types can simultaneously be positively selected by incubating cells with a plurality of antibodies or binding partners expressed on the various cell types.

For example, in some aspects, specific subpopulations of T cells, such as cells positive or expressing high levels of one or more surface markers, e.g., CD28+, CD62L+, CCR7+, CD27+, CD127+, CD4+, CD8+, CD45RA+, and/or CD45RO+ T cells, are isolated by positive or negative selection techniques. For example, CD3+ T cells can be expanded using CD3/CD28 conjugated magnetic beads (e.g., DYNABEADS® M-450 CD3/CD28 T Cell Expander).

In some embodiments, isolation is carried out by enrichment for a particular cell population by positive selection, or depletion of a particular cell population, by negative selection. In some embodiments, positive or negative selection is accomplished by incubating cells with one or more antibodies or other binding agent that specifically bind to one or more surface markers expressed or expressed (marker+) at a relatively higher level on the positively or negatively selected cells, respectively.

In some embodiments, T cells are separated from a sample by negative selection of markers expressed on non-T cells, such as B cells, monocytes, or other white blood cells, such as CD14. In some aspects, a CD4 or CD8 selection step is used to separate CD4+ helper and CD8+ cytotoxic T cells. Such CD4+ and CD8+ populations can be further sorted into sub-populations by positive or negative selection for markers expressed or expressed to a relatively higher degree on one or more naive, memory, and/or effector T cell subpopulations.

In some embodiments, CD8+ cells are further enriched for or depleted of naive, central memory, effector memory, and/or central memory stem cells, such as by positive or negative selection based on surface antigens associated with the respective subpopulation. In some embodiments, enrichment for central memory T (TCM) cells is carried out to increase efficacy, such as to improve long-term survival, expansion, and/or engraftment following administration, which in some aspects is particularly robust in such subpopulations. See Terakura et al. (2012) Blood. 1:72-82; Wang et al. (2012) J Immunother. 35(9):689-701. In some embodiments, combining TCM-enriched CD8+ T cells and CD4+ T cells further enhances efficacy. In embodiments, memory T cells are present in both CD62L+ and CD62L− subsets of CD8+ peripheral blood lymphocytes. PBMC can be enriched for or depleted of CD62L− CD8+ and/or CD62L+ CD8 fractions, such as using anti-CD8 and anti-CD62L antibodies.

In some embodiments, the enrichment for central memory T (TCM) cells is based on positive or high surface expression of CD45RO, CD62L, CCR7, CD28, CD3, and/or CD127; in some aspects, it is based on negative selection for cells expressing or highly expressing CD45RA and/or granzyme B. In some aspects, isolation of a CD8+ population enriched for TCM cells is carried out by depletion of cells expressing CD4, CD14, CD45RA, and positive selection or enrichment for cells expressing CD62L. In one aspect, enrichment for central memory T (TCM) cells is carried out starting with a negative fraction of cells selected based on CD4 expression, which is subjected to a negative selection based on expression of CD14 and CD45RA, and a positive selection based on CD62L. Such selections in some aspects are carried out simultaneously and in other aspects are carried out sequentially, in either order. In some aspects, the same CD4 expression-based selection step used in preparing the CD8+ cell population or subpopulation, also is used to generate the CD4+ cell population or sub-population, such that both the positive and negative fractions from the CD4 based separation are retained and used in subsequent steps of the methods, optionally following one or more further positive or negative selection steps.

In some embodiments, the enrichment for NK cells is based on positive or high surface expression of CD56 and CD16 and on the negative expression of CD3 and/or optionally on the presence of NKp46 or NKp30 receptors.

In some aspects, the sample or composition of cells to be separated is incubated with small, magnetizable or magnetically responsive material, such as magnetically responsive particles or micro-particles, such as paramagnetic beads (e.g., such as Dynabeads or MACS beads). The magnetically responsive material, e.g., particle, generally is directly or indirectly attached to a binding partner, e.g., an antibody, that specifically binds to a molecule, e.g., surface marker, present on the cell, cells, or population of cells that it is desired to separate, e.g., that it is desired to negatively or positively select. In some embodiments, the magnetic particle or bead comprises a magnetically responsive material bound to a specific binding member, such as an antibody or other binding partner. There are many well-known magnetically responsive materials used in magnetic separation methods. Suitable magnetic particles include those described in Molday, U.S. Pat. No. 4,452,773, and in European Patent Specification EP 452342 B, which are hereby incorporated by reference. Colloidal sized particles, such as those described in Owen U.S. Pat. No. 4,795,698, and Liberti et al., U.S. Pat. No. 5,200,084 are other examples.

The incubation generally is carried out under conditions whereby the antibodies or binding partners or molecules, such as secondary antibodies or other reagents, which specifically bind to such antibodies or binding partners, which are attached to the magnetic particle or bead, specifically bind to cell surface molecules if present on cells within the sample.

In some aspects, the sample is placed in a magnetic field, and those cells having magnetically responsive or magnetizable particles attached thereto will be attracted to the magnet and separated from the unlabeled cells. For positive selection, cells that are attracted to the magnet are retained; for negative selection, cells that are not attracted (unlabeled cells) are retained. In some aspects, a combination of positive and negative selection is performed during the same selection step, where the positive and negative fractions are retained and further processed or subject to further separation steps.

In certain embodiments, the magnetically responsive particles are coated in primary antibodies or other binding partners, secondary antibodies, lectins, enzymes, or streptavidin. In certain embodiments, the magnetic particles are attached to cells via a coating of primary antibodies specific for one or more markers. In certain embodiments, the cells, rather than the beads, are labeled with a primary antibody or binding partner, and then cell-type specific secondary antibody- or other binding partner (e.g., streptavidin)-coated magnetic particles, are added. In certain embodiments, streptavidin-coated magnetic particles are used in conjunction with biotinylated primary or secondary antibodies.

In some embodiments, the magnetically responsive particles are left attached to the cells that are to be subsequently incubated, cultured and/or engineered; in some aspects, the particles are left attached to the cells for administration to a patient. In some embodiments, the magnetizable or magnetically responsive particles are removed from the cells. Methods for removing magnetizable particles from cells are known and include, e.g., the use of competing non-labeled antibodies, magnetizable particles or antibodies conjugated to cleavable linkers, etc. In some embodiments, the magnetizable particles are biodegradable.

In certain embodiments, the isolation or separation is carried out using a system, device, or apparatus that carries out one or more of the isolation, cell preparation, separation, processing, incubation, culture, and/or formulation steps of the methods. In some aspects, the system is used to carry out each of these steps in a closed or sterile environment, for example, to minimize error, user handling and/or contamination. In one example, the system is a system as described in International Patent Application, Publication Number WO2009/072003, or US 20110003380.

In some embodiments, a cell population described herein is collected and enriched (or depleted) via flow cytometry, in which cells stained for multiple cell surface markers are carried in a fluidic stream. In some embodiments, a cell population described herein is collected and enriched (or depleted) via preparative scale (FACS)-sorting. In certain embodiments, a cell population described herein is collected and enriched (or depleted) by use of microelectromechanical systems (MEMS) chips in combination with a FACS-based detection system (see, e.g., WO 2010/033140, Cho et al. (2010) Lab Chip 10, 1567-1573; and Godin et al. (2008) J Biophoton. I(5):355-376. In both cases, cells can be labeled with multiple markers, allowing for the isolation of well-defined T cell subsets at high purity. In some embodiments, the antibodies or binding partners are labeled with one or more detectable marker, to facilitate separation for positive and/or negative selection. For example, separation may be based on binding to fluorescently labeled antibodies. In some examples, separation of cells based on binding of antibodies or other binding partners specific for one or more cell surface markers are carried in a fluidic stream, such as by fluorescence-activated cell sorting (FACS), including preparative scale (FACS) and/or microelectromechanical systems (MEMS) chips, e.g., in combination with a flow-cytometric detection system. Such methods allow for positive and negative selection based on multiple markers simultaneously.

In some embodiments, the methods include density-based cell separation methods, such as the preparation of white blood cells from peripheral blood by lysing the red blood cells and centrifugation through a Percoll or Ficoll gradient.

In any of the aforementioned separation steps, the separation does not result in 100% enrichment or removal of a particular cell population or cells expressing a particular marker. For example, positive selection of or enrichment for cells of a particular type, such as those expressing a marker, refers to increasing the number or percentage of such cells, but does not result in a complete absence of cells not expressing the marker. Likewise, negative selection, removal, or depletion of cells of a particular type, such as those expressing a marker, refers to decreasing the number or percentage of such cells, but does not result in a complete removal of all such cells.

Alternatively, cells may be obtained through commercially available cell cultures, including but not limited to, for T cells, lines BCL2 (AAA) Jurkat (ATCC® CRL-2902™), BCL2 (S70A) Jurkat (ATCC® CRL-2900™), BCL2 (S87A) Jurkat (ATCC® CRL-2901™), BCL2 Jurkat (ATCC® CRL-2899™), Neo Jurkat (ATCC® CRL-2898™), TALL-104 (ATTC® CRL-11386); and, for NK cells, lines NK-92 (ATCC® CRL-2407™), NK-92MI (ATCC® CRL-2408™) Non-limiting exemplary sources for such commercially available cell lines include the American Type Culture Collection, or ATCC, (http://www.atcc.org/) and the German Collection of Microorganisms and Cell Cultures (https://www.dsmz.de/).

Cell Preparation and Expansion

Whether prior to or after genetic modification of the immune cells to express a desirable CAR, the cells can be activated and expanded using generally known methods or from readily adapted method to the present application such as those described in U.S. Pat. Nos. 6,352,694; 6,534,055; 6,905,680; 6,692,964; 5,858,358; 6,887,466; 6,905,681; 7,144,575; 7,067,318; 7, 172,869; 7,232,566; 7, 175,843; 5,883,223; 6,905,874; 6,797,514; 6,867,041 and U.S. Patent Application Publication No. 20060121005, Life Technologies Dynabeads® system activation and expansion kits; BD Biosciences Phosflow™ activation kits, Miltenyi Biotec MACS™ activation/expansion kits, and other commercially available cell kits specific to activation moieties of the relevant cell. Stimulation with the HLA-G antigen ex vivo can activate and expand the selected CAR expressing cell subpopulation. Alternatively, the cells may be activated in vivo by interaction with HLA-G antigen.

The incubation and/or engineering may be carried out in a culture vessel, such as a unit, chamber, well, column, tube, tubing set, valve, vial, culture dish, bag, or other container for culture or cultivating cells.

In some embodiments, the cells are incubated and/or cultured prior to or in connection with genetic engineering. The incubation steps can include culture, cultivation, stimulation, activation, and/or propagation. In some embodiments, the compositions or cells are incubated in the presence of stimulating conditions or a stimulatory agent. Such conditions include those designed to induce proliferation, expansion, activation, and/or survival of cells in the population, to mimic antigen exposure, and/or to prime the cells for genetic engineering, such as for the introduction of a recombinant antigen receptor.

The conditions can include one or more of particular media, temperature, oxygen content, carbon dioxide content, time, agents, e.g., nutrients, amino acids, antibiotics, ions, and/or stimulatory factors, such as cytokines, chemokines, antigens, binding partners, fusion proteins, recombinant soluble receptors and any other agents designed to activate the cells.

In some embodiments, the immune cells of the invention can be expanded in vitro by co-culturing with tissue or cells. The cells can also be expanded in vivo, for example in the subject's blood after administrating the cell into the subject.

Generally, the T cells of the invention can be expanded, for example, by contact with an agent that stimulates a CD3 TCR complex and a co-stimulatory molecule on the surface of the T cells to create an activation signal for the T cell. For example, chemicals such as calcium ionophore A23187, phorbol 12-myristate 13-acetate (PMA), or mitogenic lectins like phytohemagglutinin (PHA) can be used to create an activation signal for the T cell.

In some embodiments, T cell populations may be stimulated in vitro by contact with, for example, an anti-CD3 antibody, or antigen-binding fragment thereof, or an anti-CD2 antibody immobilized on a surface, or by contact with a protein kinase C activator (e.g., bryostatin) in conjunction with a calcium ionophore. In some embodiments, the T cell populations may be stimulated in vitro by contact with Muromonab-CD3 (OKT3). For co-stimulation of an accessory molecule on the surface of the T cells, a ligand that binds the accessory molecule is used. For example, a population of T cells can be incubated with an anti-CD3 antibody and an anti-CD28 antibody under conditions stimulating proliferation of the T cells.

In some embodiments, the T cells are expanded by adding to the culture-initiating composition feeder cells, such as non-dividing PBMC, (e.g., such that the resulting population of cells contains at least about 5, 10, 20, or 40 or more PBMC feeder cells for each T lymphocyte in the initial population to be expanded); and incubating the culture (e.g. for a time sufficient to expand the numbers of T cells). In some aspects, the non-dividing feeder cells can comprise gamma-irradiated PBMC feeder cells. In some embodiments, the PBMC are irradiated with gamma rays in the range of about 3000 to 3600 rads to prevent cell division.

In some aspects, the feeder cells are added to culture medium prior to the addition of the populations of T cells.

In particular embodiments, co-stimulatory molecules are employed to enhance the activation, proliferation, and cytotoxicity of T cells produced by the CAR after antigen engagement. A co-stimulatory ligand can include, but is not limited to, B7-1 (CD80), B7-2 (CD86), B7-H3, BAFFR, BTLA, BLAME (SLAMF8), CD2, CD4, CD5, CD7, CD8a, CD8β, CD1a, LFA-1 (CD11a/CD18), CD1b, CD1c, CD1d, CD18, CD19, CD19a, CD27, CD28, CD29, CD30, CD30L, CD40, CD40MICA, CD49a, CD49D, CD49f, CD69, CD70, CD83, CD84, CD96 (Tactile), CD 100 (SEMA4D), CD 103, OX40 (CD134), 4-1BB (CD137), SLAM (SLAMF1, CD150, IPO-3), CD160 (BY55), SELPLG (CD 162), DNAM1 (CD226), Ly9 (CD229), SLAMF4 (CD244, 2B4), ICOS (CD278), CEACAM1, CDS, CRTAM, DAP10, GADS, GITR, HVEM (LIGHTR), HLA-G, IA4, ICAM-1, IL2R β, IL2R γ, IL7R a, ITGA4, ITGA6, ITGAD, ITGAE, ITGAL, ITGAM, ITGAX, ITGB1, ITGB2, ITGB7, KIRDS2, LAT, LFA-1, LIGHT, LTBR, MICB, NKG2C, NKG2D, NKp30, NKp44, NKp46, NKp80 (KLRF1), PAG/Cbp, PD-1, PD-L1, PD-L2, PSGL1, SLAMF6 (NTB-A, Ly108), SLAMF7, SLP-76, TNFR2, TRANCE/RANKL, VLA1, VLA-6, inducible costimulatory ligand (ICOS-L), intercellular adhesion molecule (rCAM), lymphotoxin beta receptor, 3 TR6, ILT3 and ILT4. A co-stimulatory ligand also encompasses, inter alia, an antibody that specifically binds with a co-stimulatory molecule present on a T cell, such as, but not limited to, CD27, CD28, 4-1BB, OX40, CD30, CD40, PD-1, ICOS, lymphocyte function-associated antigen-1 (LFA-1), CD2, CD7, LIGHT, NKG2C, B7-H3, and a ligand that specifically binds with CD83.

In some embodiments, NK cell populations can be expanded in vitro using interleukin-2 (IL-2) IL-15, IL-15/IL-15RA complex, IL-18 and IL-12.

Conditions appropriate for T cell and NK cell culture include an appropriate media (e.g., Minimal Essential Media or RPMI Media 1640 or, X-Vivo 10, X-Vivo 15 and X-Vivo 20 (Lonza)) that may contain factors necessary for proliferation and viability, including serum (e.g., fetal bovine or human serum), interleukin-2 (IL-2), insulin, IFN-γ, IL-4, IL-7, GM-CSF, IL-10, IL-12, IL-2, IL-15, IL-18, IL-21, TGF, and TNF, or any other additives for the growth of cells known to the skilled artisan. In a preferred embodiment, T cells are stimulated in vitro by exposure to OKT3 and IL-2. Other additives for the growth of cells include, but are not limited to, surfactant, Plasmanate, and reducing agents such as N-acetyl-cysteine and 2-mercaptoethanol. Media can include RPMI 1640, AIM-V, DMEM, MEM, a-MEM, F-12, X-Vivo 10, X-Vivo 15, and X-Vivo 20, Optimizer, with added amino acids, sodium pyruvate, and vitamins, either serum-free or supplemented with an appropriate amount of serum (or plasma) or a defined set of hormones, and/or an amount of cytokine(s) sufficient for the growth and expansion of T cells.

Antibiotics, e.g., penicillin and streptomycin, are included only in experimental cultures, not in cultures of cells that are to be infused into a subject. The target cells are maintained under conditions necessary to support growth, for example, an appropriate temperature (e.g., 37 degrees Celsius) and atmosphere (e.g., air plus 5% $CO_2$). T cells that have been exposed to varied stimulation times may exhibit different characteristics.

In some embodiments, the preparation methods include steps for freezing, e.g., cryopreserving, the cells, either before or after isolation, incubation, and/or engineering. In some embodiments, the freeze and subsequent thaw step removes granulocytes and, to some extent, monocytes in the cell population. In some embodiments, the cells are suspended in a freezing solution, e.g., following a washing step to remove plasma and platelets. Any of a variety of known freezing solutions and parameters in some aspects may be used. One example involves using PBS containing 20% DMSO and 8% human serum albumin (HSA), or other suitable cell freezing media. This is then diluted 1:1 with media so that the final concentration of DMSO and HSA are 10% and 4%, respectively. The cells are then frozen to −80° C. at a rate of 1 degree per minute and stored in the vapor phase of a liquid nitrogen storage tank.

In the inventive method the NK cells or T cells are preferably ex vivo expanded for at least about 5 days, preferably not less than about 10 days, more preferably not less than about 15 days and most preferably not less than about 20 days before administration to the patient.

In another embodiment the NK cells or T cells have been expanded at least about 100-fold, preferably at least about 200-fold, and more preferably at least about 400-fold, preferably at least about 600-fold, more preferably at least about 1000 fold and even more preferably at least about 1500 fold compared to day 0 of expansion, before administration to a patient.

Cell Transduction and Selection

The nucleic acid construct according to the invention can be transduced into immune cells to create an immune cell that expresses the anti-HLA-G CAR according to the invention. In certain embodiments, cells are transduced to comprise at least one CAR of the present invention.

It is contemplated that the chimeric nucleic acid construct can be introduced into the subject's own immune cells as naked DNA or in a suitable vector. Methods of stably transfecting immune cells, particularly T cell, by electroporation using naked DNA are known in the art. See e.g., U.S. Pat. No. 6,410,319. Naked DNA generally refers to the DNA encoding a chimeric receptor of the present invention contained in a plasmid expression vector in proper orientation for expression. Advantageously, the use of naked DNA reduces the time required to produce T cells expressing the chimeric receptor of the present invention. Physical methods for introducing a nucleic acid construct into a host cell include calcium phosphate precipitation, lipofection, particle bombardment, microinjection, electroporation, and the like. Alternatively, biological methods for introducing a polynucleotide of interest into a host cell include the use of DNA and RNA vectors. A variety of viral vectors such as vector described hereabove can be used to introduce the nucleic acid construct of the invention into immune cells. Suitable vectors for use in accordance with the method of the present invention do not replicate in the subject's immune cells.

In one embodiment, the nucleic acid construct encoding the CAR according to the invention is introduced into an immune cell by a viral vector, particularly a lentiviral vector as described hereabove.

Alternatively, chemical means for introducing a polynucleotide into a host cell include colloidal dispersion systems, such as macromolecule complexes, nanocapsules, microspheres, beads, and lipid-based systems including oil-in-water emulsions, micelles, mixed micelles, and liposomes. An exemplary colloidal system for use as a delivery vehicle in vitro and in vivo is a liposome (e.g., an artificial membrane vesicle). Regardless of the method used to introduce exogenous nucleic acids into a host cell or otherwise expose a cell to the inhibitor of the present invention, in order to confirm the presence of the recombinant DNA sequence in the host cell, a variety of assays may be performed. Such assays include, for example, "molecular biological" assays well known to those of skill in the art, such as Southern and Northern blotting, RT-PCR and PCR; "biochemical" assays, such as detecting the presence or absence of a particular peptide, e.g., by immunological means (ELISAs and Western blots) or by assays described herein to identify agents falling within the scope of the invention. Methods of testing a CAR for the ability to recognize target cells and for antigen specificity are known in the art. For instance, Clay et al, J. Immunol., 163: 507-513 (1999), teaches methods of measuring the release of cytokines (e.g., interferon-γ, granulocyte/monocyte colony stimulating factor (GM-CSF), tumor necrosis factor a (TNF-α) or interleukin 2 (IL-2)). In addition, CAR function can be evaluated by measurement of cellular cytotoxicity, as described in Zhao et al, J. Immunol., 174: 4415-4423 (2005).

Once it is established that the transfected or transduced immune cell is capable of expressing the chimeric receptor as a surface membrane protein with the desired regulation and at a desired level, it can be determined whether the chimeric receptor is functional in the host cell to provide for the desired signal induction. Subsequently, the transduced immune cells can be further reintroduced or administered to the subject to activate anti-tumor responses in the subject. To facilitate administration, the transduced T cells according to the invention can be made into a pharmaceutical composition or made into an implant appropriate for administration in vivo, with pharmaceutically acceptable carriers or diluents.

Once the cells expressing the CAR according to the invention are administered to a subject, the biological activity of the engineered cell populations and/or antibodies in some aspects is measured by any of a number of known methods. Parameters to assess include specific binding of an engineered or natural T cell or other immune cell to antigen, in vivo, e.g., by imaging, or ex vivo, e.g., by ELISA or flow cytometry.

In certain embodiments, the ability of the engineered cells to destroy target cells can be measured using any suitable method known in the art, such as cytotoxicity assays described in, for example, Kochenderfer et al., J. Immunotherapy, 32(7): 689-702 (2009), and Herman et al. J. Immunological Methods, 285(1): 25-40 (2004). In certain embodiments, the biological activity of the cells also can be measured by assaying expression and/or secretion of certain cytokines, such as GM-CSF, IL-3, MIP-1α, TNF-α, IL-10, IL-13, IFN-γ or IL-2.

In some aspects the biological activity is measured by assessing clinical outcome, such as reduction in tumor burden or load, stabilization of tumor, progression free survival, or overall survival.

Pharmaceutical or Veterinary Composition

The present invention also relates to a pharmaceutical or veterinary composition comprising the anti-HLA-G antibody or antibody fragment, the CAR, the nucleic acid construct, the vector and/or the cell as described hereabove.

In a particular aspect, the present invention relates to a pharmaceutical or veterinary composition comprising cells, preferably immune cells, comprising a CAR as described here above and/or comprising the nucleic acid construct encoding it as described hereabove. In one aspect, the pharmaceutical or veterinary composition may comprise at least two different populations of cells, a first one with cells comprising a CAR specifically binding to β2M-associated HLA-G, preferably to both HLA-G1 and HLA-G5 and a second one with cells comprising a CAR specifically binding to β2M-free HLA-G, preferably to both HLA-G2 and HLA-G6 and/or to both HLA-G1/β2M-free and HLA-G5/β2M-free isoforms. In another aspect, the pharmaceutical or veterinary composition may comprise a population of cells comprising at least two CARs, a first CAR specifically binding to β2M-associated HLA-G, preferably to both HLA-G1 and HLA-G5 and a second CAR specifically binding to β2M-free HLA-G preferably to both HLA-G2 and HLA-G6 and/or to HLA-G1/β2M-free and/or HLA-G5/β2M-free isoforms. In another aspect, the pharmaceutical or veterinary composition may comprise a population of cells comprising a bispecific CAR that allows the specific binding to β2M-associated HLA-G, preferably to both HLA-G1 and HLA-G5 and to β2M-free HLA-G preferably to both HLA-G2 and HLA-G6 and even more preferably to both HLA-G2 and HLA-G6 and/or to both HLA-G1/β2M-free and HLA-G5/β2M-free isoforms.

In a further aspect, the pharmaceutical or veterinary composition may comprise a first population of cells that express a CAR or at least two CAR or a bispecific CAR as described hereabove targeting β2M-associated HLA-G and/or β2M-free HLA-G isoforms, and a second population of cells expressing a CAR that does not recognize HLA-G but recognized an antigen known to be a target of interest in CAR therapies such as anti-tumoral and/or anti-viral therapies. It will be understood that such second population of CAR expressing cells does not target HLA-G.

The present invention also relates to a pharmaceutical or veterinary composition containing a plurality of CAR-expressing cells of the invention, such as T cells and/or NK cells. The pharmaceutical composition may additionally comprise a pharmaceutically acceptable carrier, diluent or excipient. The pharmaceutical composition may optionally comprise one or more further pharmaceutically active polypeptides and/or compounds.

In one embodiment, the concentration of the cell expressing CAR according to the invention which is included in the pharmaceutical or veterinary composition is at least 0.001 mg/ml, at least 0.1 mg/ml, at least 0.5 mg/ml, at least 1 mg/ml, at least 5 mg/ml, at least 10 mg/ml, at least 15 mg/ml, at least 20 mg/ml, at least 25 mg/ml, at least 30 mg/ml, at least 35 mg/ml, at least 40 mg/ml, at least 45 mg/ml, at least 50 mg/ml, at least 55 mg/ml, at least 60 mg/ml, at least 65 mg/ml, at least 70 mg/ml, at least 75 mg/ml, at least 80 mg/ml, at least 85 mg/ml, at least 90 mg/ml, at least 95 mg/ml, at least 100 mg/ml, at least 105 mg/ml, at least 110 mg/ml, at least 115 mg/ml, at least 120 mg/ml, at least 125 mg/ml, at least 130 mg/ml, at least 135 mg/ml, at least 140 mg/ml, at least 150 mg/ml, at least 175 mg/ml, at least 200 mg/ml, at least 250 mg/ml, at least 275 mg/ml or at least 300 mg/ml.

In another embodiment, the concentration of the cell expressing CAR according to the invention which is included in the pharmaceutical or veterinary composition is between 0.001-0.01 mg/ml, between 0.01-0.1 mg/ml, between 0.1-1 mg/ml, between 1-10 mg/ml, between 10-50 mg/ml, between 50-100 mg/ml, between 50-150 mg/ml, between 50-200 mg/ml, between 50-250 mg/ml, between 50-300 mg/ml, between 100-200 mg/ml, between 100-300 mg/ml, or between 200-300 mg/ml.

In another embodiment, the pharmaceutical or veterinary composition comprises cells expressing the CAR according to the invention, particularly at least 100 cells, at least 200 cells, at least 400 cells, at least 500 cells, at least 700 cells, at least 1000 cells, at least 1500 cells, at least 2000 cells, at least 3000 cells, at least 5000 cells, at least 10 000 cells, at least 100 000 cells, at least 1 million cells, at least 10 million cells or at least 100 million cells expressing the CAR according to the invention.

The pharmaceutical or veterinary composition according to the invention can be formulated for any conventional route of administration including a topical, enteral, oral, parenteral, intranasal, intravenous, intramuscular, subcutaneous or intraocular administration and the like.

Preferably, the pharmaceutical or veterinary composition according to the invention may be administered by enteral or parenteral route of administration. When administered parenterally, the pharmaceutical or veterinary composition according to the invention is preferably administered by intravenous route of administration. When administered enterally, the pharmaceutical or veterinary composition according to the invention is preferably administered by oral route of administration.

It will be understood by one skilled in the art that the formulations of the invention may be isotonic with human blood that is the formulations of the invention have essentially the same osmotic pressure as human blood. Such isotonic formulations generally have an osmotic pressure from about 250 mOSm to about 350 mOSm. Isotonicity can be measured by, for example, a vapor pressure or ice-freezing type osmometer. Tonicity of a formulation is adjusted by the use of tonicity modifiers. "Tonicity modifiers" are those pharmaceutically acceptable inert substances that can be added to the formulation to provide an isotonicity of the formulation. Tonicity modifiers suitable for this invention include, but are not limited to, saccharides, salts and amino acids.

Compositions and formulations for parenteral, intrathecal, or intraventricular administration may include sterile aqueous solutions that may also contain buffers, diluents and other suitable additives such as, but not limited to, penetration enhancers, carder compounds and other pharmaceutically acceptable carriers or excipients.

The pharmaceutical or veterinary composition according to the invention may further comprise a pharmaceutically acceptable vehicle. Thus, additional aspects of the invention relate to compositions comprising a carrier and one or more of the products—e.g., a cell comprising an anti-HLA-G CAR, a nucleic acid, a vector, an anti-HLA-G antibody or antibody fragment—described in the embodiments disclosed herein. The formulations can be sterilized and, if desired, mixed with auxiliary agents such as carriers and excipients which do not deleteriously interact with the products—e.g., a cell comprising an anti-HLA-G CAR, a nucleic acid, a vector, an anti-HLA-G antibody or antibody fragment—of the formulation.

Preferably, the pharmaceutical or veterinary compositions of the present invention including but not limited to any one of the claimed compositions may comprise CAR-expressing cells as described herein, in combination with one or more pharmaceutically or physiologically acceptable carriers, diluents or excipients as described hereafter. Desirably, a pharmaceutically acceptable form is employed which does not adversely affect the desired immune potentiating effects of recombinant cells according to the invention.

To facilitate administration, the transduced immune cells, preferably T cells and/or NK cells transduced with the nucleic acid construct encoding the CAR according to the invention can be made into a pharmaceutical composition for administration in vivo, with appropriate pharmaceutically acceptable carriers or diluents. The means of making such a composition have been described in the art (see, for instance, Remington: The Science and Practice of Pharmacy, Lippincott Williams & Wilkins, 21st edition (2005).

Particularly, formulations comprising populations of CAR-expressing cells may include pharmaceutically acceptable excipient(s). Excipients included in the formulations will have different purposes depending, for example, on the CAR construct, the subpopulation of cells used, and the mode of administration. The formulations comprising populations of CAR-expressing cells will typically have been prepared and cultured in the absence of any non-human components, such as animal serum (e.g., bovine serum albumin).

The formulation or composition may also contain more than one active ingredient useful for the particular indication, disease, or condition being treated with the binding molecules or cells, preferably those with activities complementary to the binding molecule or cell, where the respective activities do not adversely affect one another. Such active ingredients are suitably present in combination in amounts that are effective for the purpose intended.

The pharmaceutical or veterinary composition in some aspects can employ time-released, delayed release, and sustained release delivery systems such that the delivery of the composition occurs prior to, and with sufficient time to cause, sensitization of the site to be treated. Means known in the art can be used to prevent or minimize release and absorption of the composition until it reaches the target tissue or organ, or to ensure timed-release of the composition. Such systems can avoid repeated administrations of the composition, thereby increasing convenience to the subject and the physician.

Subject, Regimen and Administration

The present invention relates to a pharmaceutical composition of the present invention or a CAR expressing cells of the present invention for use as a medicament or for use for treating a disease or a disorder in a subject. It also relates to the use of a pharmaceutical composition of the present invention or a CAR expressing cells of the present invention in the manufacture of a medicament for treating a disease or a disorder in a subject. Finally, it relates to a method for treating a disease or a disorder in a subject comprising administering a therapeutically effective amount of a pharmaceutical composition of the present invention or a CAR expressing cells of the present invention to the subject.

The human subject according to the invention may be a human at the prenatal stage, a new-born, a child, an infant, an adolescent or an adult, in particular an adult of at least 40 years old, preferably an adult of at least 50 years old, still more preferably an adult of at least 60 years old, even more preferably an adult of at least 70 years old.

In some embodiments, the subject is a validated animal model for disease, adoptive cell therapy, and/or for assessing toxic outcomes such as cytokine release syndrome (CRS).

In some embodiments, the subject has persistent or relapsed disease, e.g., following treatment with another immunotherapy and/or other therapy, including chemotherapy, radiation, and/or hematopoietic stem cell transplantation (HSCT), e.g., allogeneic HSCT. In some embodiments, the administration effectively treats the subject despite the subject having become resistant to another therapy. In some embodiments, the subject has not relapsed but is determined to be at risk for relapse, such as at a high risk of relapse, and thus the compound or composition is administered prophylactically, e.g., to reduce the likelihood of or prevent relapse.

In some embodiments, the invention includes the administration of CAR expressing cells of the present invention or a composition containing CAR expressing cells to a subject, such as one having, at risk for, or suspected of having a disease, condition or disorder. In some embodiments, the cells, and compositions are administered to a subject having a particular disease or condition to be treated, e.g., via adoptive cell therapy, such as adoptive T cell therapy. In some embodiments, the cells or compositions are administered to the subject, such as a subject having or at risk for a disease or condition. In some aspects, the methods thereby treat, e.g., ameliorate one or more symptom of the disease or condition. In a preferred embodiment, the subject has been diagnosed with an immune disease, preferably a cancer.

Diagnostic methods of autoimmune disease or cancer are well known by the man skilled in the art.

In a particular embodiment, the subject has already received at least one line of treatment, preferably several lines of treatment, prior to the administration of immune cells according to the invention or of a pharmaceutical or veterinary composition according to the invention.

Preferably, the treatment is administered regularly, preferably between every day and every month, more preferably between every day and every two weeks, more preferably between every day and every week, even more preferably the treatment is administered every day. In a particular embodiment, the treatment is administered several times a day, preferably 2 or 3 times a day, even more preferably 3 times a day.

The duration of treatment with the vector according to the invention, with the immune cells according to the invention or with a pharmaceutical or veterinary composition according to the invention is preferably comprised between 1 day and 20 weeks, more preferably between 1 day and 10 weeks, still more preferably between 1 day and 4 weeks, even more preferably between 1 day and 2 weeks. In a particular embodiment, the duration of the treatment is of about 1 week. Alternatively, the treatment may last as long as the disease persists.

The form of the pharmaceutical or veterinary compositions, the route of administration and the dose of administration of immune cells according to the invention or of a pharmaceutical composition according to the invention can be adjusted by the man skilled in the art according to the type and severity of the infection, and to the patient, in particular its age, weight, sex, and general physical condition. The compositions of the present invention may be administered in a number of ways depending upon whether local or systemic treatment is desired.

In the case of adoptive cell therapy, methods for administration of cells for adoptive cell therapy are known and may be used in connection with the provided methods and compositions. For example, adoptive T cell therapy methods are described, e.g., in US Patent Application Publication No. 2003/0170238 to Gruenberg et al; U.S. Pat. No. 4,690,915 to Rosenberg; Rosenberg (2011) Nat Rev Clin Oncol. 8(10): 577-85). See, e.g., Themeli et al. (2013) Nat Biotechnol. 31(10): 928-933; Tsukahara et al. (2013) Biochem Biophys Res Commun 438(1): 84-9; Davila et al. (2013) PLoS ONE 8(4): e61338.

One skilled in the art will recognize that, although more than one route can be used for administration, a particular route can provide a more immediate and more effective reaction than another route. For example, intradermal delivery may be advantageously used over inhalation for the treatment of melanoma. Local or systemic delivery can be accomplished by administration comprising application or instillation of the formulation into body cavities, inhalation or insufflation of an aerosol, or by parenteral introduction, comprising intramuscular, intravenous, intraportal, intrahepatic, peritoneal, subcutaneous, or intradermal administration.

Although systemic (intravenous, IV) injection is favored in clinical applications because of its ease of administration, several preclinical studies (Carpenito, et al. (2009) Proc. Natl. Acad. Sci. USA 106:3360-3365; Song, et al. (2011) Cancer Res. 71:4617-4627; Parente-Pereira, et al. (2011) J. Clin. Immunol. 31:710-718) suggest that the regional (intratumoral, IT or intraperitoneal, IP) administration of T cells may provide optimal therapeutic effects, which may be in part due to increased T cell trafficking to the tumor. For example, it has been shown that CAR T cells remain at the site of inoculation with minimal systemic absorption when delivered via IP or IT routes (Parente-Pereira, et al. (2011) J. Clin. Immunol. 31:710-718). In contrast, after intravenous administration, CAR T cells initially reach the lungs and then are redistributed to the spleen, liver, and lymph nodes. In addition, RNA CAR-electroporated T cells may be particularly suitable for regional administration, due to the transient nature of the CAR expression on the T cells (Zhao, et al. (2010) Cancer Res. 70:9053-9061). Furthermore, clinical studies have shown the feasibility and safety of both the intratumoral and intraperitoneal injection of T cells (Canevari, et al. (1995) J. Natl. Cancer Inst. 87:1463-1469; Duval, et al. (2006) Clin. Cancer Res. 12:1229-1236). Overall, a local route of administration of the recombinant T cells may provide the optimal therapeutic effect and decrease the potential for the "on-target, off-organ" toxicity. Accordingly, in one embodiment, the CAR expressing cells according to the invention are administered locally, preferably by intratumoral and intraperitoneal injection.

The pharmaceutical composition in some embodiments contains the CAR cells in amounts effective to treat or prevent the disease or condition, such as a therapeutically effective or prophylactically effective amount. Therapeutic or prophylactic efficacy in some embodiments is monitored by periodic assessment of treated subjects. For repeated administrations over several days or longer, depending on the condition, the treatment is repeated until a desired suppression of disease symptoms occurs. However, other dosage regimens may be useful and can be determined. The desired dosage can be delivered by a single bolus administration of the composition, by multiple bolus administrations of the composition, or by continuous infusion administration of the composition. The amount of immune cells according to the invention or of a pharmaceutical composition according to the invention to be administered can be determined by standard procedure well known by those of ordinary skills in the art. Physiological data of the patient (e.g. age, size, weight and health and weight of the recipient, kind of concurrent treatment, if any, frequency of treatment and the nature of the effect desired) and the routes of administration have to be taken into account to determine the appropriate dosage, so as a therapeutically effective amount will be administered to the patient. Particularly, the appropriate dosages and dosing schedule can be based on clinical trials or well-established cell-based therapies (see, e.g., Topalian & Rosenberg (1987) Acta Haematol. 78 Suppl 1:75-6; U.S. Pat. No. 4,690,915) or an alternate continuous infusion strategy can be employed. In some embodiments, an effective amount or number of cells or pharmaceutical composition comprising those cells are administrated parenterally. In some embodiments, administration can be an intravenous administration. In some embodiments, administration can be directly done by injection within a tumor. In certain embodiments, in the context of genetically engineered cells expressing the CARs, a subject is administered the range of about one million to about 100 billion cells, such as, e.g., 1 million to about 50 billion cells (e.g., about 5 million cells, about 25 million cells, about 500 million cells, about 1 billion cells, about 5 billion cells, about 20 billion cells, about 30 billion cells, about 40 billion cells, or a range defined by any two of the foregoing values), such as about 10 million to about 100 billion cells (e.g., about 20 million cells, about 30 million cells, about 40 million cells, about 60 million cells, about 70 million cells, about 80 million cells, about 90 million cells, about 10 billion cells, about 25 billion cells, about 50 billion cells, about 75 billion cells, about 90 billion cells, or a range defined by any two of the foregoing values), and in some cases about 100 million cells to about 50 billion cells (e.g., about 120 million cells, about 250 million cells, about 350 million cells, about 450 million cells, about 650 million cells, about 800 million cells, about 900 million cells, about 3 billion cells, about 30 billion cells, about 45 billion cells) or any value in between these ranges, and/or such a number of cells per kilogram of body weight of the subject. For example, in some embodiments the administration of the cells or population of cells can comprise administration of about $10^3$ to about $10^9$ cells per kg body weight including all integer values of cell numbers within those ranges, for example, the cell compositions of the present invention can be administered in a dose, or dosages, where each dose comprises at least 10 cells/kg body weight, at least 100 cells/kg body weight; at least 1000 cells/kg body weight; at least 10,000 cells; at least 100,000 cells; at least 1 million cells; at least 10 million cells; at least 100 million cells; at least 1 billion cells or at least 10 billion cells/kg body weight.

Particularly, a sufficient number of the transduced immune cells will be introduced so as to achieve the desired therapeutic response. Desirably an effective amount or sufficient number of the isolated transduced cells is present in the composition and introduced into the subject such that long-term, specific, anti-tumor or anti-infectious agent responses are established to reduce the size or regrowth of a tumor or growth of an infectious agent than would otherwise result in the absence of such treatment. Desirably, the amount of transduced immune cells, preferably T cells, reintroduced into the subject causes a 10%, 20%, 30%, 40%, 50%, 60%, 70%, 80%, 90%, 95%, 98%, or 100% decrease in tumor size when compared to otherwise same conditions, wherein the transduced immune cells are not present.

A composition of the invention can be provided in unit dosage form wherein each dosage unit, e.g. an injection, contains a predetermined amount of the composition, alone or in appropriate combination with other active agents. The term unit dosage form, as used herein, refers to physically discrete units suitable as unitary dosages for human and animal subjects, each unit containing a predetermined quantity of the composition of the invention, alone or in combination with other active agents, calculated in an amount sufficient to produce the desired effect, in association with a pharmaceutically acceptable diluent, carrier, or vehicle, where appropriate. The specifications for the novel unit dosage forms of the invention depend on the particular pharmacodynamics associated with the pharmaceutical composition in the particular subject.

The cells or population of cells can be administered in one or more doses. In some embodiments, said effective amount or number of cells can be administered as a single dose. In some embodiments, said effective amount or number of cells can be administrated as more than one dose over a period time. Timing of administration is within the judgment of managing physician and depends on the clinical condition of the patient. While individual needs vary, determination of optimal ranges of effective amounts of a given cell type for a particular disease or conditions within the skill of the art. An effective amount means an amount which provides a therapeutic or prophylactic benefit.

For purposes of the invention, the amount or dose of the inventive CAR material administered should be sufficient to generate a therapeutic or prophylactic response in the subject over a reasonable time frame. For example, the dose of the inventive CAR material should be sufficient to bind to antigen, e.g. HLA-G isoform(s), or detect, treat or prevent disease in a period of from about 2 hours or longer, e.g., about 12 to about 24 or more hours, from the time of administration. In certain embodiments, the time period could be even longer. The dose will be determined by the efficacy of the particular inventive CAR material and the condition of the subject, as well as the body weight of the subject to be treated.

For purposes of the invention, an assay, which comprises, for example, comparing the extent to which target cells are lysed or IFN-γ is secreted by T cells expressing the inventive CAR, polypeptide, or protein upon administration of a given dose of such T cells to a mammal, among a set of mammals of which is each given a different dose of the T cells, could be used to determine a starting dose to be administered to a mammal. The extent to which target cells are lysed or IFN-γ is secreted upon administration of a certain dose can be assayed by methods known in the art.

Uses

Use in the Treatment of Disease or Disorder and in Combination Therapy

In one aspect, the disease or disorder to be treated is a condition selected from a proliferative disease or disorder, preferably cancer; an infectious disease or disorder, preferably a viral infection; an inflammatory disease or disorder; and an immune disease or disorder, preferably autoimmunity or autoimmune diseases, allergies and graft-vs-host rejection. In some embodiments, the condition may be cancer. The present invention relates to the use of an antibody, a cell, a nucleic acid construct, a vector and/or a pharmaceutical composition according to the invention for interfering or neutralizing the immune down-regulation due to HLA-G proteins in a host in need thereof.

In particular, the cell, the nucleic acid construct, the vector and/or the pharmaceutical composition according to the invention are particularly suitable for treatment of viral infections such as for example HIV-1, hepatitis B virus, and hepatitis C virus infections.

In particular, the cell, the nucleic acid construct, the vector and/or the pharmaceutical composition according to the invention are particularly suited for treatment of cancer, particularly of solid tumors or hematopoietic cancer, even more preferably when the availability of good selective single targets is limited.

The immune system can specifically identify and eliminate tumor cells based on their expression of tumor-specific antigens or molecules induced during malignant cell transformation. This process is referred to as tumor immune surveillance. Despite tumor immune surveillance, tumors can still develop in the presence of a functioning immune system. This occurs through tumor immunoediting, a process that comprises three major phases: 1) the elimination phase in which most immunogenic tumor cells are eliminated by cytotoxic T and NK cells; 2) the equilibrium phase in which tumor cells with reduced immunogenicity are selected; and 3) the escape phase in which variants that no longer respond to the host immune system are maintained (Urosevic and Dummer, 2008). HLA-G is involved in every phase of tumor immuno-editing by decreasing the elimination of tumor cells, by inhibiting the cytotoxic function of T and NK cells, and by trogocytosis, (i.e. the intercell transference of viable HLA-G molecules), which renders competent cytotoxic cells unresponsive to tumor antigens (LeMaoult et al., 2007; Caumartin et al., 2007). Therefore, the chimeric constructs of the present invention find application in subjects having or suspected of having a disease, disorder, or a particular condition, particularly subjects having or suspected of having a cancer. Particularly the chimeric constructs of the present invention find application in subjects having or suspected of having a cancer thereby reducing the size of a tumor or preventing the growth or re-growth of a tumor in these subjects or preventing the induction of an immunosuppressive microenvironment.

Accordingly, the present invention also relates to methods for inhibiting the growth of a tumor in a subject in need thereof and/or for treating a cancer patient in need thereof. The tumor may be a solid tumor, or a liquid tumor. In some embodiments, the tumor or cancer expresses or overexpresses HLA-G. In certain embodiments, these methods comprise, or alternatively consist essentially of, or yet further consist of, administering to the subject or patient an effective amount of the isolated cell. In still further embodiments, the cell expressing a CAR according to the invention is a T cell or an NK cell. The isolated cell may be allogeneic or autologous to the subject or patient being treated. In a further aspect, the tumor expresses or overexpresses HLA-G antigen and the subject has been selected for the therapy by a diagnostic.

In one embodiment, the present invention relates to a method for reducing growth or preventing tumor formation in a subject by introducing a chimeric construct of the present invention into an immune cell, preferably a T cell or a NK cell, of the subject and reintroducing into the subject the transformed immune cell, thereby expressing the CAR according to the invention and effecting anti-tumor responses to reduce or eliminate tumors in the subject. The step of delivering the nucleic acid construct to the subject generally involves introducing a nucleic acid construct of the invention into an isolated immune cell (e.g., an autologous immune cell isolated from PBMC or immune cells derived from an allogeneic third party-derived immune cell donor) and introducing into the subject the transformed immune cell, thereby effecting antitumor responses to reduce or eliminate tumors in the subject, as in an adoptive T cell therapy method. For example, the immune cell may comprise a T cell and the subject is suffering from, or is believed to be suffering from, or is diagnosed as having tumor or cancer, e.g., a HLA-G expressing cancer. For example, the anti-HLA-G CAR molecules encoded by exemplary nucleic acid constructs of the present invention may be administered to the subject in the form of a recombinant immune cell engineered to express the anti-HLA-G CAR molecule.

CAR expressing cells according to invention and obtained by the methods described above, or cell lines derived from such cells, can be used as a medicament in the treatment of a disease, disorder, or condition in a subject. In some embodiments, such a medicament can be used for treating cancer.

In some embodiments, administering the treatment to the subject may comprise adoptive cell therapy (ACT) using immune cells harvested from the subject or from one or more donors. Accordingly, the cells can be cells that are xenogeneic, allogeneic or autologous to the subject. Generally, the cells are autologous to the subject.

In some embodiments, the cell therapy, e.g., adoptive cell therapy, e.g., adoptive T cell therapy, is carried out by autologous transfer, in which the cells are isolated and/or otherwise prepared from the subject who is to receive the cell therapy, or from a sample derived from such a subject. Thus, in some aspects, the cells are derived from a subject, e.g., patient, in need of a treatment and the cells, following isolation and processing are administered to the same subject.

In some embodiments, the cell therapy, e.g., adoptive cell therapy, e.g., adoptive T cell therapy, is carried out by allogeneic transfer, in which the cells are isolated and/or otherwise prepared from a subject other than a subject who is to receive or who ultimately receives the cell therapy, e.g., a first subject. In such embodiments, the cells then are administered to a different subject, e.g., a second subject, of the same species. In some embodiments, the first and second subjects are genetically identical. In some embodiments, the first and second subjects are genetically similar. In some embodiments, the second subject expresses the same HLA class or supertype as the first subject. The cells of the present invention may be capable of killing target cells, such as cancer cells. The target cell may be recognizable by a defined pattern of antigen expression, for example the expression of antigen A or antigen B.

In some embodiments, ACT may comprise isolating primary immune cells from the subject or from one or more donors, transducing the primary immune cells with the nucleic acid construct or constructs of any of the foregoing embodiments, expressing the CAR in the transduced primary immune cells, and delivering the transduced immune cells into the subject. ACT may further comprise stimulating and/or expanding the immune cells prior to delivering the transduced immune cells to the subject.

For example, in some embodiments, ACT may comprise harvesting autologous or allogeneic T cells and transducing these T cells with one or more nucleic acid constructs, so that the T cells express a CAR mediating pro-inflammatory cytokine expression, and then infusing the cells into a subject in need thereof.

The invention also provides a method for treating cancer comprising delivering to a subject in need thereof an effective amount of the nucleic acid construct, a vector or vectors, or a transduced immune cell or pharmaceutical composition according to any of the foregoing embodiments, thereby treating the cancer. In some embodiments, the treatment of cancer may be measured by a decrease in tumor cell burden or by an increase in survival.

The invention additionally provides a method of immune therapy comprising administering to a subject a therapeutically effective amount of a nucleic acid construct or constructs, a vector or vectors, a recombinant cell or a pharmaceutical composition according to any of the foregoing embodiments. Treatment with the cells of the invention may help prevent the escape or release of tumor cells which often occurs with standard approaches.

In certain embodiments, CAR expressing cells are modified in any number of ways, such that their therapeutic or prophylactic efficacy is increased. For example, the CAR may be conjugated either directly or indirectly through a linker to a targeting moiety. The practice of conjugating compounds, e.g., the CAR, to targeting moieties is known in the art. See, for instance, Wadhwa et al., J. Drug Targeting 1995; 3(2): 111-127, and U.S. Pat. No. 5,087,616. Particularly, the present invention includes a type of cellular therapy where isolated cells are genetically modified to express CARs and the CAR cell is infused into a subject in need thereof. Such administration can promote activation of the cells (e.g., T cell activation) in a target-specific manner, such that the cells of the disease or disorder are targeted for destruction. In the case where the cell is a T cell, CAR T cells, unlike antibody therapies, are able to replicate in vivo resulting in long-term persistence that may lead to sustained control of targeted diseases, disorders, or conditions.

The CAR expressing cells as disclosed herein may be administered either alone or in combination with diluents, known anti-cancer therapeutics, and/or with other components such as cytokines or other cell populations that are immunostimulatory. They may be administered as a first line therapy, a second line therapy, a third line therapy, or further therapy.

In some embodiments, the cells expressing CAR are administered as part of a combination treatment, such as simultaneously with or sequentially with, in any order, another therapeutic intervention, such as an antibody or engineered cell or receptor or agent, such as a cytotoxic or therapeutic agent. The cells or antibodies in some embodiments are co-administered with one or more additional therapeutic agents or in connection with another therapeutic intervention, either simultaneously or sequentially in any order. In some contexts, the cells are co-administered with another therapy sufficiently close in time such that the cell populations enhance the effect of one or more additional therapeutic agents, or vice versa. In some embodiments, the cells or antibodies are administered prior to the one or more additional therapeutic agents. In some embodiments, the cells or antibodies are administered after to the one or more additional therapeutic agents, such as anti-cancer agents. An "anti-cancer" agent is capable of negatively affecting cancer in a subject, for example, by killing cancer cells, inducing apoptosis in cancer cells, reducing the growth rate of cancer cells, reducing the incidence or number of metastases, reducing tumor size, inhibiting tumor growth, reducing the blood supply to a tumor or cancer cells, promoting an immune response against cancer cells or a tumor, preventing or inhibiting the progression of cancer, or increasing the lifespan of a subject with cancer. More generally, these other compositions would be provided in a combined amount effective to kill or inhibit proliferation of the cell. This process may involve contacting the cancer cells with the cell expressing the CAR according to the invention and the agent(s) or multiple factor(s) at the same time. This may be achieved by contacting the cell with a single composition or pharmacological formulation that includes both agents, or by contacting the cell with two distinct compositions or formulations, at the same time, wherein one composition includes the expression construct and the other includes the second agent(s).

In a particular embodiment, the cells expressing a CAR against HLA-G isoforms according to the invention are administered as part of a combination treatment such as simultaneously with or sequentially with, in any order, with other CAR expressing cells that does not recognize HLA-G but are known to be useful in other CAR therapies such as anti-tumoral and/or anti-viral CAR therapies. Such CAR expressing cells targets an antigen involved in a disease, preferably such as cancer or viral infection, preferably an antigen targeted in cancer therapies or in viral therapies. It will be understood that such antigen is not HLA-G.

In the context of the present invention, it is contemplated that cell therapy could be used similarly in conjunction with chemotherapeutic, radiotherapeutic, or immunotherapeutic intervention, as well as pro-apoptotic or cell cycle regulating agents such as immune checkpoint inhibitor.

Alternatively, the present inventive therapy may precede or follow the other agent treatment by intervals ranging from minutes to weeks. In embodiments where the other agent and present invention are applied separately to the individual, one would generally ensure that a significant period of time did not expire between the times of each delivery, such that the agent and inventive therapy would still be able to exert an advantageously combined effect on the cell. In such instances, it is contemplated that one may contact the cell with both modalities within about 12-24 h of each other and, more preferably, within about 6-12 h of each other. In some situations, it may be desirable to extend the time period for treatment significantly, however, where several days (2, 3, 4, 5, 6 or 7) to several week (1, 2, 3, 4, 5, 6, 7 or 8) lapse between the respective administrations.

It is expected that the treatment cycles would be repeated as necessary. It also is contemplated that various standard therapies, as well as surgical intervention, may be applied in combination with the inventive cell therapy.

Targeted Cancers

HLA-G is aberrantly expressed in many human solid malignant tumors in situ and malignant hematopoietic diseases including breast, ovarian, clear renal cell, colorectal, gastric, esophageal, lung, and hepatocellular cancers, as well as acute myeloid leukemia and chronic lymphocytic leukemia (B-CLL). The aberrant expression of HLA-G in malignant neoplasm is significantly correlated with poor clinical outcome of patients with colorectal cancer (CRC), gastric cancer (GC), non-small cell lung cancer (NSCLC), esophageal squamous cell cancer (ESCC), breast cancer, hepatocellular cancers, and B-CLL. Furthermore, serum soluble HLA-G is increased in various types of cancer patients (including patients with melanoma, acute leukemia, multiple myeloma, neuroblastoma, lymphoproliferative disorders, breast or ovarian cancer, non-small cell lung cancer, esophageal cancer, colorectal cancer; gastric cancer and hepatocellular carcinoma), when compared to normal healthy controls or benign disease cases.

Cancers that may be treated by the CAR expressing cell, the nucleic acid construct, the vector or the pharmaceutical composition according to the invention include tumors that are not vascularized, or not yet substantially vascularized, as well as vascularized tumors.

The CAR expressing cell, the nucleic acid construct, the vector or the pharmaceutical composition according to the invention may be used to treat cancers of the oral cavity and pharynx which includes cancer of the tongue, mouth and pharynx; cancers of the digestive system which includes esophageal, gastric and colorectal cancers; cancers of the liver and biliary tree which includes hepatocellular carcinomas and cholangiocarcinomas; cancers of the respiratory system which includes bronchogenic cancers, lung cancers and cancers of the larynx; cancers of bone and joints which includes osteosarcoma; cancers of the skin which includes melanoma; breast cancer; cancers of the genital tract which include uterine, endometrium, ovarian and cervical cancer in women, prostate and testicular cancer in men; cancers of the renal tract which include renal cell carcinoma and transitional cell carcinomas of the utterers or bladder; gastrointestinal stromal tumor, pancreas cancers, kidney cancers, colon cancers, cervix cancer, brain cancers including gliomas, glioblastoma multiform and medullobastomas; cancers of the endocrine system including thyroid cancer, adrenal carcinoma and cancers associated with multiple endocrine neoplasm syndromes; lymphomas including Hodgkin's lymphoma and non-Hodgkin lymphoma; B-cell lymphoma, monocytic lymphoma, marginal zone lymphoma, Burkitt's lymphoma, T and B lymphomas, Multiple Myeloma and plasmacytomas; leukaemias both acute and chronic, prohemocytic leukemia, acute non-lymphoblastic leukemia (ANLL), acute lymphoblastic leukemia (ALL), erythroleukemia, myeloid or lymphoid leukemia; and cancers of other and unspecified sites including neuroblastoma. Preferably, the cancer is selected from the group of Renal cell carcinoma (RCC), melanoma, kidney cancer and bladder cancer.

The cancers may comprise non solid tumors (such as hematological tumors, for example, leukemia and lymphoma) or may comprise solid tumors. As used herein, "solid tumor" is an abnormal mass of tissue that usually does not contain cysts or liquid areas. Solid tumors can be benign or malignant. Different types of solid tumors are named for the type of cells that form them (such as sarcomas, carcinomas, and lymphomas).

Examples of solid tumors, such as sarcomas and carcinomas, include fibrosarcoma, myxosarcoma, liposarcoma, chondrosarcoma, osteosarcoma, and other sarcomas, synovioma, mesothelioma, Ewing's tumor, leiomyosarcoma, rhabdomyosarcoma, colon carcinoma, lymphoid malignancy, pancreatic cancer, breast cancer, lung cancers, ovarian cancer, prostate cancer, hepatocellular carcinoma, squamous cell carcinoma, basal cell carcinoma, adenocarcinoma, sweat gland carcinoma, medullary thyroid carcinoma, papillary thyroid carcinoma, pheochromocytomas sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, seminoma, bladder carcinoma, melanoma, and CNS tumors (such as a glioma (such as brainstem glioma and mixed gliomas), glioblastoma (also known as glioblastoma multiforme) astrocytoma, CNS lymphoma, germinoma, medulloblastoma, Schwannoma craniopharyogioma, ependymoma, pinealoma, hemangioblastoma, acoustic neuroma, oligodendroglioma, menangioma, neuroblastoma, retinoblastoma and brain metastases).

Hematologic cancers are cancers of the blood or bone marrow. Examples of hematological (or hematogenous) cancers include leukemias, including acute leukemias (such as acute lymphocytic leukemia, acute myelocytic leukemia, acute myelogenous leukemia and myeloblastic, promyelocytic, myelomonocytic, monocytic and erythroleukemia), chronic leukemias (such as chronic myelocytic (granulocytic) leukemia, chronic myelogenous leukemia, and chronic lymphocytic leukemia), polycythemia vera, lymphoma, Hodgkin's disease, non-Hodgkin's lymphoma (indolent and high grade forms), multiple myeloma, Waldenstrom's macroglobulinemia, heavy chain disease, myelodysplastic syndrome, hairy cell leukemia and myelodysplasia.

In some embodiments, the cancer cells express or over express HLA-G. In a particular embodiment, the cancer cells express or overexpress one to six, preferably two to five HLA-G isoform(s) selected from HLA-G1, HLA-G2, HLA-G3, HLA-G4, HLA-G5, HLA-G6 and HLA-G7, preferably from HLA-G1, HLA-G2, HLA-G5 or HLA-G6, and more preferably from HLA-G1 or HLA-G2.

Preferably, the cancer cells express or overexpress HLA-G1 and/or HLA-G5; or the cancer cells express or overexpress HLA-G2 and/or HLA-G6. Preferably, when such cancer cells express these particular HLA-G isoforms, the CAR according to the invention specifically binds to HLA-G1 and HLA-G5 or to HLA-G2 and HLA-G6, respectively.

Use in Diagnostic and Prognostic

The anti-HLA-G monoclonal antibodies or scFv disclosed herein are also useful in diagnostic and prognostic methods. As such, the present invention relates to the use of the antibodies disclosed herein in the diagnosis of HLA-G-related medical conditions in a subject.

The monoclonal antibodies or scFv disclosed herein are useful in methods known in the art relating to the localization and/or quantitation of a HLA-G polypeptide (e.g., for use in measuring levels of the HLA-G polypeptide within appropriate physiological samples, for use in diagnostic methods, for use in imaging the polypeptide, and the like). The monoclonal antibodies or scFv disclosed herein are useful in isolating a HLA-G polypeptide by standard techniques, such as western blotting, affinity chromatography methods for isolating cells or for flow cytometry-based cellular analysis or cell sorting or immunoprecipitation. A HLA-G antibody disclosed herein can facilitate the purification of natural HLA-G polypeptides from biological samples, e.g., mammalian sera or cells as well as recombinantly-produced HLA-G polypeptides expressed in a host system. Moreover, HLA-G monoclonal antibodies or scFv can be used to detect a HLA-G polypeptide (e.g., in plasma, a cellular lysate or cell supernatant) in order to evaluate the abundance and pattern of expression of the polypeptide. The HLA-G antibodies disclosed herein can be used diagnostically to monitor HLA-G levels in tissue as part of a clinical testing procedure, e.g., to determine the efficacy of a given treatment regimen. The detection can be facilitated by coupling (i.e., physically linking) the HLA-G antibodies disclosed herein to a detectable substance so as the HLA-G antibodies or fragments thereof are detectably labeled. The term "labeled", with regard to the antibody is intended to encompass direct labeling of the antibody by coupling (i.e., physically linking) a detectable substance to the antibody, as well as indirect labeling of the antibody by reactivity with another compound that is directly labeled. Non-limiting examples of indirect labeling include detection of a primary antibody using a fluorescently-labeled secondary antibody and end-labeling of a DNA probe with biotin such that it can be detected with fluorescently-labeled streptavidin.

The detection method of the present disclosure can be used to detect expression levels of HLA-G polypeptides in a biological sample in vitro as well as in vivo. In vitro techniques for detection of HLA-G polypeptides include enzyme linked immunosorbent assays (ELISAs), Western blots, flow cytometry, immunoprecipitations, radioimmunoassay, and immunofluorescence (e.g., IHC). Furthermore, in vivo techniques for detection of HLA-G polypeptides include introducing into a subject a labeled anti-HLA-G antibody. By way of example only, the antibody can be labeled with a radioactive marker whose presence and location in a subject can be detected by standard imaging techniques.

In some aspects, HLA-G antibodies containing structural modifications that facilitate rapid binding and cell uptake and/or slow release are useful in in vivo imaging detection methods. In some aspects, the HLA-G antibody contains a deletion in the CH2 constant heavy chain region of the antibody to facilitate rapid binding and cell uptake and/or slow release. In some aspects, a Fab fragment is used to facilitate rapid binding and cell uptake and/or slow release. In some aspects, a F(ab)'2 fragment is used to facilitate rapid binding and cell uptake and/or slow release.

Accordingly, the present invention also provides prognostic (or predictive) assays for determining whether a subject is at risk of developing a medical disease or condition associated with increased HLA-G polypeptide expression or activity (e.g., detection of a precancerous cell). Such assays can be used for prognostic or predictive purpose to thereby prophylactically treat an individual prior to the onset of a medical disease or condition characterized by or associated with HLA-G polypeptide expression.

Another aspect of the present disclosure provides methods for determining HLA-G expression in a subject to thereby select appropriate therapeutic or prophylactic compounds for that subject.

Alternatively, the prognostic assays can be utilized to identify a subject having or at risk for developing for developing cancer and/or solid tumors. Thus, the present disclosure provides a method for identifying a disease or condition associated with increased HLA-G isoform(s) expression levels in which a test sample is obtained from a subject and the HLA-G isoform(s) detected, wherein the presence of increased levels of HLA-G polypeptides compared to a control sample is predictive for a subject having or at risk of developing a disease or condition associated with increased HLA-G isoform(s) expression levels. In some aspects, the disease or condition associated with increased HLA-G isoform(s) expression levels is selected from the group consisting of for developing cancer and/or solid tumors.

In another embodiment, the present disclosure provides methods for determining whether a subject can be effectively treated with a compound for a disorder or condition associated with increased HLA-G expression wherein a biological sample is obtained from the subject and the HLA-G isoform(s) is/are detected using the HLA-G antibody or ScFv as described above. The expression level of the HLA-G polypeptide in the biological sample obtained from the subject is determined and compared with the HLA-G expression levels found in a biological sample obtained from a subject who is free of the disease. Elevated levels of the HLA-G in the sample obtained from the subject suspected of having the disease or condition compared with the sample obtained from the healthy subject is indicative of the HLA-G-associated disease or condition in the subject being tested.

There are a number of disease states in which the elevated expression level of HLA-G isoform(s) is known to be indicative of whether a subject with the disease is likely to respond to a particular type of therapy or treatment. Thus, the method of detecting HLA-G isoform(s) in a biological sample can be used as a method of prognosis, e.g., to evaluate the likelihood that the subject will respond to the therapy or treatment.

Further aspects of the present disclosure relate to methods for determining if a patient is likely to respond or is not likely to HLA-G CAR therapy. In specific embodiments, this method comprises contacting a tumor sample isolated from the patient with an effective amount of an HLA-G antibody and detecting the presence of any antibody bound to the tumor sample. In further embodiments, the presence of antibody bound to the tumor sample indicates that the patient is likely to respond to the HLA-G CAR therapy and the absence of antibody bound to the tumor sample indicates that the patient is not likely to respond to the HLA-G therapy. In some embodiments, the method comprises the additional step of administering an effective amount of the HLA-G CAR therapy to a patient that is determined likely to respond to the HLA-G CAR therapy.

Further aspects of the present disclosure relate to methods for determining if a patient is likely to respond or is not likely to HLA-G CAR therapy depending on the isoform(s) that is/are expressed by the tumor, particularly selected from HLA-G1, HLA-G2, HLA-G3, HLA-G4, HLA-G5, HLA-G6 and HLA-G7, preferably from HLA-G1, HLA-G2, HLA-G5 or HLA-G6, and more preferably from HLA-G1 or HLA-G2, even more preferably HLA-G1 and G5 or HLAG-2 and G6. The identification of HLA-G expressed isoform(s) prior to treatment allowed the selection of the most suitable CAR that specifically binds one to six, preferably two to five HLA-G isoform(s) selected from HLA-G1, HLA-G2, HLA-G3, HLA-G4, HLA-G5, HLA-G6 and HLA-G7, preferably from HLA-G1, HLA-G2, HLA-G5 or HLA-G6, and more preferably from HLA-G1 or HLA-G2, even more preferably binds HLA-G1 and HLA-G5 isoforms or both HLA-G2 and HLA-G6 isoforms for use in an efficient treatment such as cell therapy.

Kits

Any of the compositions described herein may be included in a kit provided by the present invention. The kits will thus include, in suitable container means, recombinant/engineered cells of the present invention, and/or vectors encoding the nucleic acid constructs of the present invention, and/or nucleic acid constructs or related reagents of the present invention. In some embodiments, the kit further includes an additional agent for treating cancer or an infectious disease, and the additional agent may be combined with the nucleic acid construct(s) or cells, or other components of the kit of the present invention or may be provided separately in the kit. In some embodiments, means of taking a sample from an individual and/or of assaying the sample may be provided in the kit. In certain embodiments the kit includes cells, buffers, cell media, vectors, primers, restriction enzymes, salts, and so forth, for example. The kits may also comprise means for containing a sterile, pharmaceutically acceptable buffer and/or other diluent. The components of the kits may be packaged either in aqueous media or in lyophilized form. The container means of the kits will generally include at least one vial, test tube, flask, bottle, syringe or other container means, into which a component may be placed, and preferably, suitably aliquoted. Where there is more than one component in the kit, the kit also will generally contain a second, third or other additional container into which the additional components may be separately placed. However, various combinations of components may be comprised in a vial. Such containers may include injection or blow-molded plastic containers into which the desired vials are retained. The kits of the present invention also will typically include a means for containing the components in close confinement for commercial sale. Such containers may include injection or blow molded plastic containers into which the desired vials are retained.

When the components of the kit are provided in one and/or more liquid solutions, the liquid solution is an aqueous solution, with a sterile aqueous solution being particularly preferred. The compositions may also be formulated into a syringe compatible composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

In particular embodiments of the invention, cells that are to be used for cell therapy are provided in a kit, and in some cases the cells are essentially the sole component of the kit. The kit may comprise reagents and materials to make the desired cell. In specific embodiments, the reagents and materials include primers for amplifying desired sequences, nucleotides, suitable buffers or buffer reagents, salt, and so forth, and in some cases the reagents include vectors and/or DNA that encodes a CAR as described herein and/or regulatory elements therefor.

In particular embodiments, there are one or more apparatuses in the kit suitable for extracting one or more samples from an individual. The apparatus may be a syringe, scalpel, and so forth.

In some cases of the invention, the kit, in addition to cell therapy embodiments, also includes a second cancer therapy, such as chemotherapy and/or immunotherapy, for example. The kit(s) may be tailored to a particular cancer for an individual and comprise respective second cancer therapies for the individual as described hereabove.

EXAMPLES

Results

Anti-HLA-G Antibody Paratope Specificity

Figure 2B:
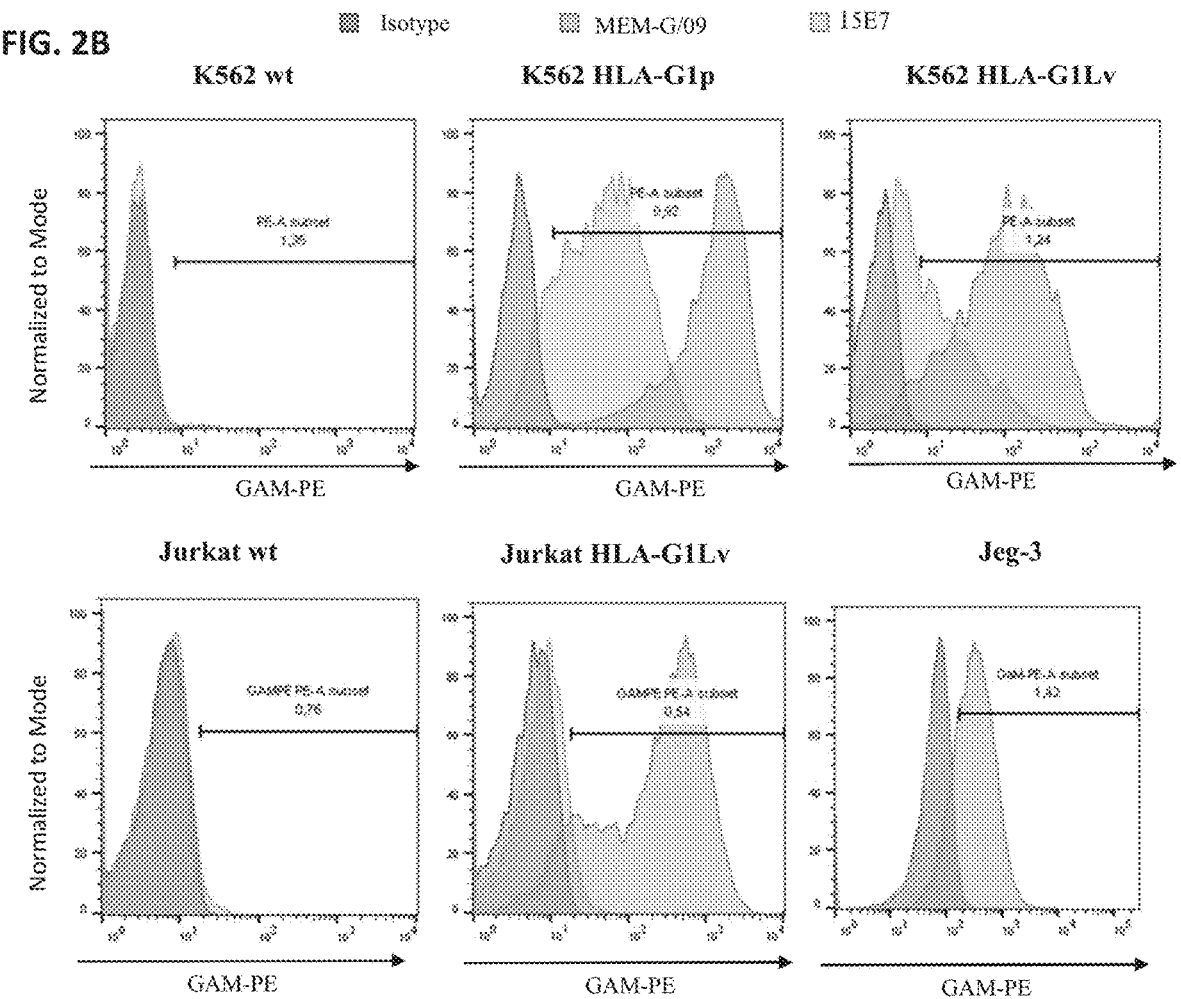

It has been previously described that different isoforms of HLA-G can be expressed containing from one to three globular domains, associated or not to β2M and a peptide. Different specific anti-HLA-G antibodies had been previously generated against different regions or "epitopes" of HLA-G. Specificity of anti-HLA-G monoclonal antibodies was previously determined against different isoforms of HLA-G. Briefly, as shown on FIG. 2A, 15E7 antibody presents a high affinity for HLA-G1/5 β2M-free and HLA-G6, demonstrating that this Mab is specific for HLA-G isoforms that are not associated to β2M. As shown on FIG. 2B, K562 HLA-G1p presents a higher proportion of HLA-G β2M-free than K562 HLA-G1Lv after staining with the 15E7 monoclonal antibody in comparison to the MEM-G/09 monoclonal antibody, specific for HLA-G β2M-associated isoforms (data not shown). Similarly, 15E7 specificity was evaluated against Jurkat wt, Jurkat HLA-G1Lv and Jeg-3 cell lines which demonstrated that the 15E7 monoclonal antibody presents high affinity for HLA-G β2M-free isoforms, as shown on FIG. 2B.

Specificity of the LFTT-1 monoclonal antibody was determined performing the same experiments. Contrary to 15E7 antibody, LFTT-1 antibody is highly specific for HLA-G β2M-associated isoforms and stained K562 HLA-G1Lv, Jurkat HLA-G1Lv and Jeg-3 cell lines, as shown on FIG. 2C.

CARs Constructions Validation

Figures 4A, 4B:
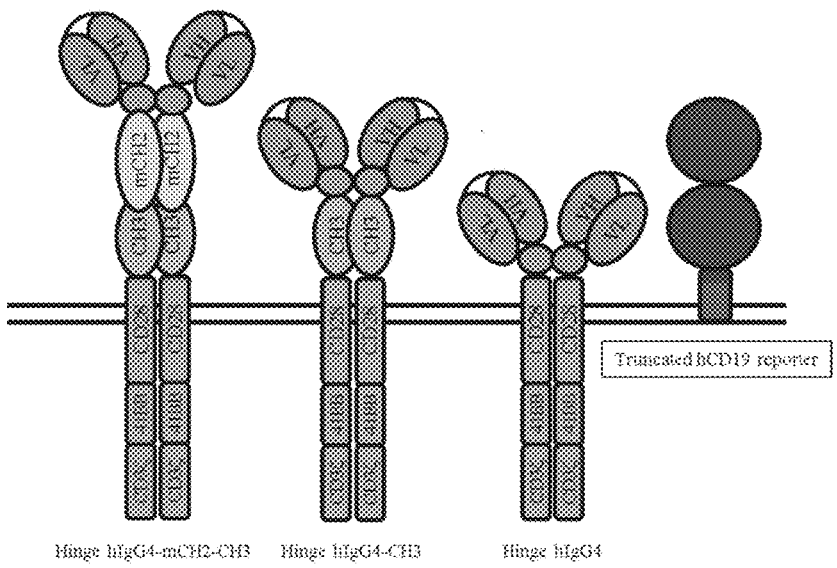
FIG. 4A-FIG. 4B: Schematic representations of (FIG. 4A) the 3 HLA-G CAR chains depending on their hinge and (FIG. 4B) the resulting HLA-G CAR proteins.

Two different chimeric antigen receptors were generated against HLA-G based on the 15E7 and LFTT-1 monoclonal antibodies paratopes. CARs design corresponded to the $3^{rd}$ generation CARs already described (Pule et al. 2005 Molecular Therapy) constituted of: a signal peptide, the scFv of either 15E7 or LFTT-1, a spacer domain that comprises or consists of (i) a CD8a or CD28 hinge, (ii) a human IgG4 hinge domain, (iii) a human IgG4 hinge domain and a CH3 human IgG4 domain or (iv) a mutated CH2 human IgG4 domain, a human IgG4 hinge domain and a CH3 human IgG4 hinge domain, a CD28 transmembrane region, and two co-activation segments: 4-1BB and CD3ζ. FIG. 3 summarizes the schematic design of the CAR structures based on 15E7 and LFTT-1 with CD8a or CD28 hinge domain and FIG. 4 summarizes the schematic design of the CAR structures based on 15E7 and LFTT-1 with the cleavable linker P2A and the truncated hCD19 as reporter.

CARs constructions were grafted in different effector host cells: Jurkat cell line (human CD4+ T cells) and NKT1.2 (murine iNKT) and CAR surface expression was evaluated by flow cytometry and immunofluorescence microscopy. 87.6% of Jurkat HLA-G-15E7 and 83.2% of HLA-G-LFTT-1 CAR transduced cells express the chimeric receptors on their surface, detected by an anti-Flag antibody demonstrating that effector cells strongly expressed CARs constructs (FIG. 5A). Similarly, NKT 1.2 HLA-G-15E7 and HLA-G-LFTT-1 CAR strongly expressed HLA-G CARs at their surface since 85.2% and 85.1% were respectively stained with the anti-Flag antibody. CARs cell surface expression was also determined by immunofluorescence microscopy as shown in FIG. 5B.

Activation Assay: Membrane Acquisition Through CAR/HLA-G1 Interaction

It was previously demonstrated that immune cells acquire cell surface membrane patches from target cells such as APC or tumor cells antigen-presenting cells. Membrane acquisition from target cells by effector cells (i) require cell-to-cell contact, (ii) is rapid, and (iii) is an active process dependent on the activation state of the acquirer cells which (iv) reflects the antigen-specific activation of the effector cells. Therefore, membrane transfers are related to the activation of functionally mature immune cells.

Based on these principles, a test was designed to determine the activation degree of the effector cells when they were confronted to the target subject: HLA-G molecules. The experiment was set up by using the Jurkat T cell line as effector and target cells allowing us to avoid any bystander protein interaction.

Figure 6A:
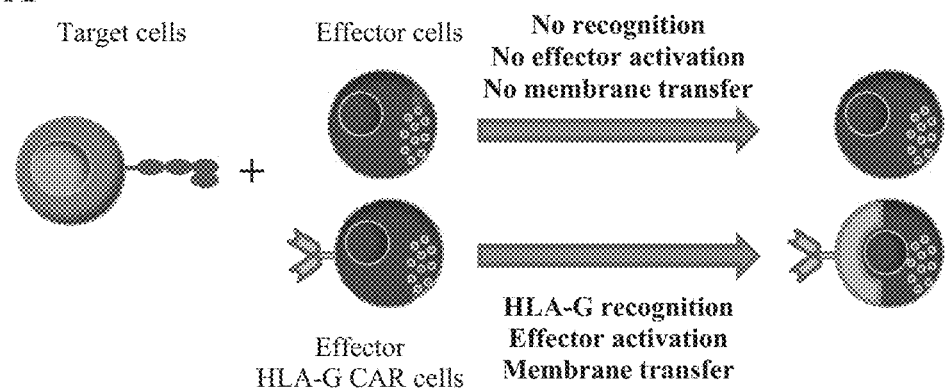

This implies that cell-to-cell contact would only be mediated by the CAR-antigen interaction. Only those cells transfected with the anti-HLA-G CAR are expected to be activated, thus, will present membrane acquisition when challenged with the target cells, and very low or no membrane transfer for control cells (Jurkat wt), as represented in FIG. 6A.

Figure 6B:
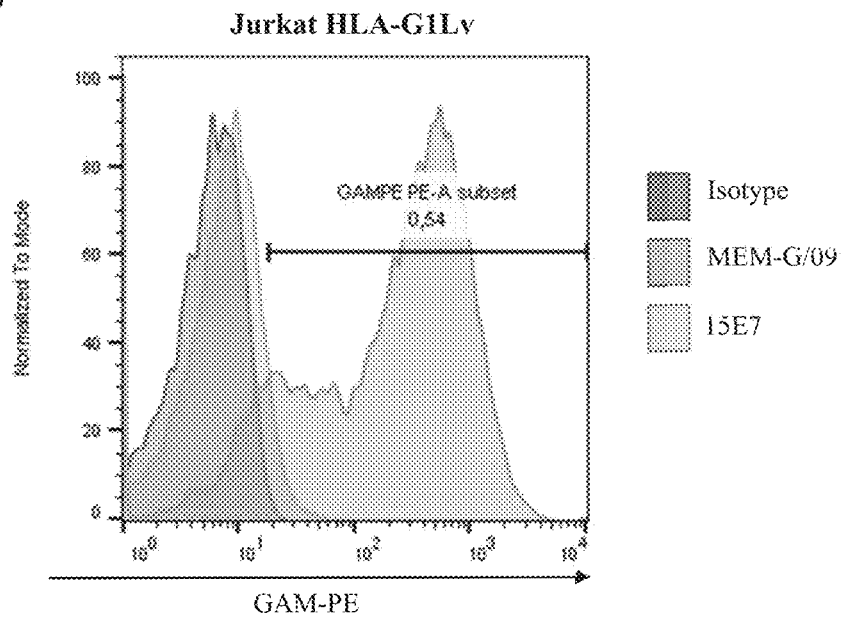

To characterize the isoforms predominantly expressed on HLA-G transduced Jurkat target cells, HLA-G isoforms expression was determined by flow cytometry using the anti-HLA-G β2M-associated MEM-G/09 antibody and the anti HLA-G-α3 β2M-free 15E7 antibody. FIG. 6B show that Jurkat HLA-G1 target cells only express HLA-G1 β2M-associated isoforms, and no staining is observed following 15E7 staining, implying that no HLA-G-α3 β2M-free isoform is expressed.

Figure 6C:
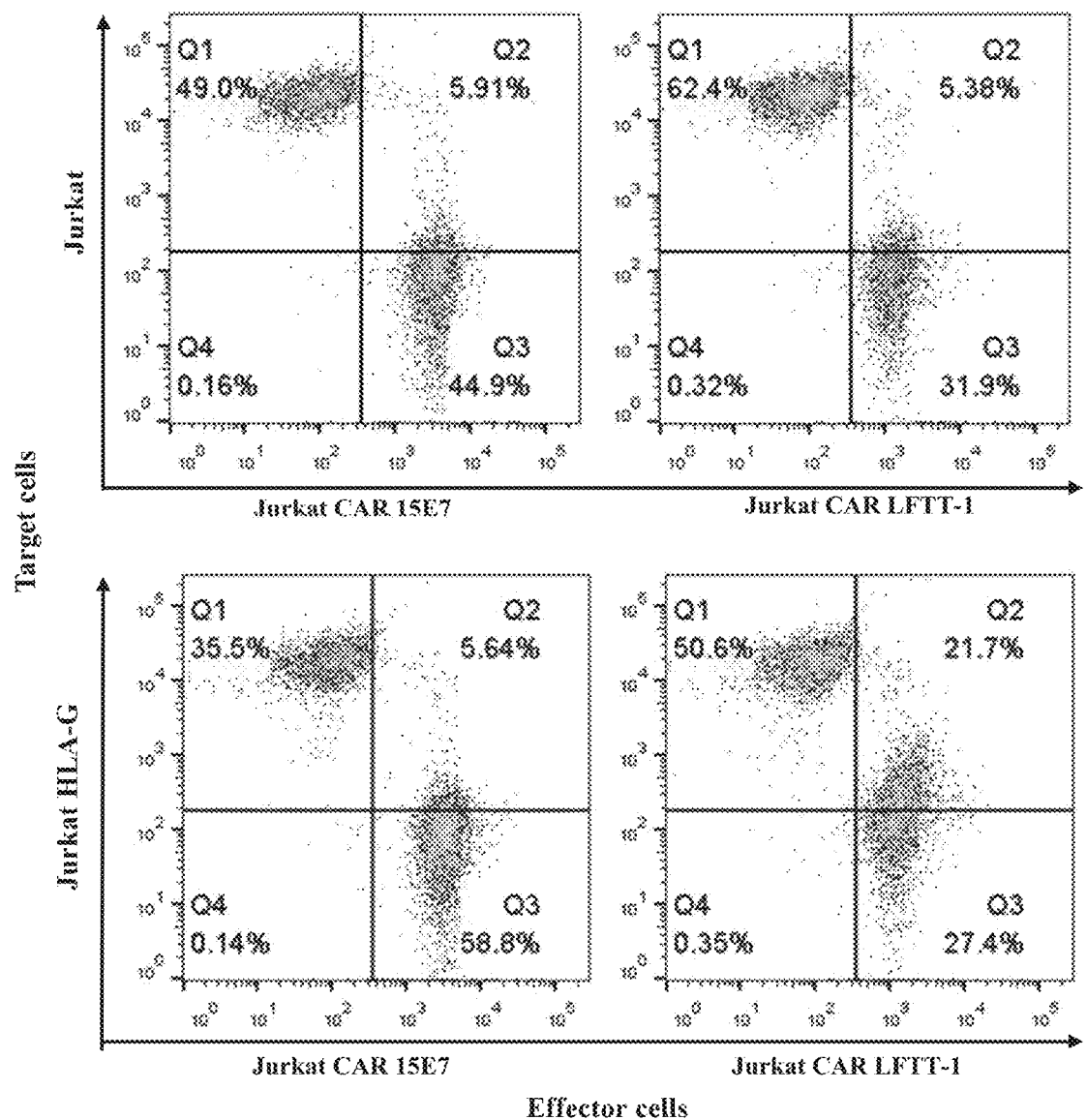

Then the level of membrane transfer was assessed, otherwise said, the degree of activation of effector cells challenged with their targets. Membrane acquisition was 5.91% and 5.38% for Jurkat HLA-G-15E7 and HLA-G-LFTT-1 CAR cells when they were confronted to control Jurkat wt. However, given the nature of the HLA-G isoforms expressed on the target cells (HLA-G1 B2M-associated), only HLA-G-LFTT-1 CAR are expected to specifically bind and ergo activate the effector cells. Indeed Jurkat HLA-G-LFTT-1 CAR acquisition increased to 21.7% whereas Jurkat HLA-G-15E7 CAR activation remained at 5.6%. These results are shown in FIG. 6C.

Afterwards, the activation degree of HLA-G-15E7 CAR and HLA-G-LFTT-1 CAR cells challenged with specific target cells was studied, based on the "Activation Index" ratio setting the baseline on the control non-specific cells: Jurkat wt cell line. As shown in FIG. 6D, Jurkat HLA-G-LFTT-1 CAR is activated more than 3 times when challenged with Jurkat HLA-G1Lv. However, activation does not increase when they are challenged with Jurkat controls, neither HLA-G-15E7 CAR cells are activated when challenged with non-specific targets (Jurkat wt and Jurkat HLA-G1Lv).

Finally, the activation status of other immune cell subsets was assessed in order to confirm the specificity and biological activity of HLA-G-15E7 CAR and HLA-G-LFTT-1 CAR constructions. As shown in FIG. 7A, Jurkat HLA-G-15E7 CAR was challenged with a specific target: K562 HLA-G1p (that express mostly β2M-free isoforms of HLA-G) using K562 wt cells as control. Again, an increase of more than 3 times of activation was observed. Also, NKT 1.2 HLA-G-15E7 and HLA-G-LFTT-1 CAR cells where tested, challenged with Jeg-3 (human choriocarcinoma cells, expressing HLA-G1 β2M-associated isoforms). Only HLA-G-LFTT-1 CAR cells were significantly activated compared to NKT 1.2 HLA-G-15E7 or NKT 1.2 control cells, as shown in FIG. 7B.

Cytolytic Function and IFN-γ Secretion of HLA-G CAR T Cells

Cytotoxic function of 15E7 and LFTT-1 CAR expressing effector cells were assessed against JEG-3, K562 and K562-HLA-G1 transfected cell lines (FIGS. 8 et 9). To do so, target cells were labelled with CFSE before being co-cultured 24 h with CAR-T cells at the indicated Effector:Target ratios (E:T). 24 h after coincubation, the medium was collected to determine the IFN-γ secretion and cells recovered to investigate target cell lysis by flow-cytometry.

Figure 8A:
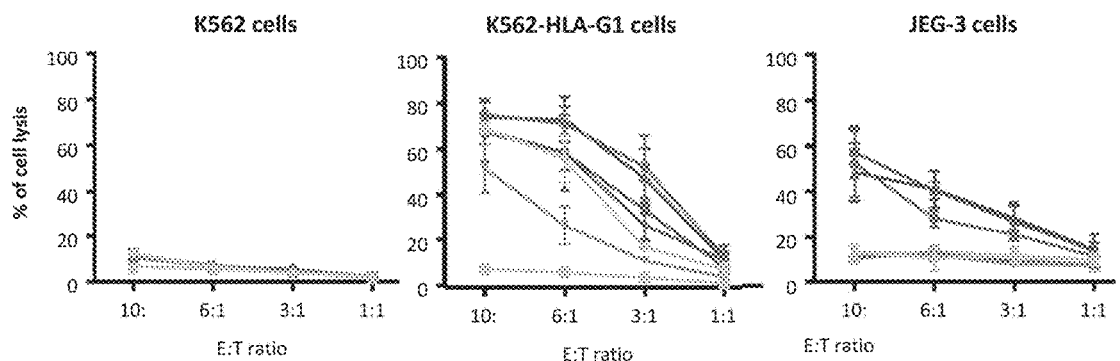
FIG. 8A-FIG. 8B: Cytolytic function of HLA-G CAR T cells was investigated on K562, K562-HLA-G1 and JEG-3 tumor cells through (FIG. 8A) tumor cell lysis was investigated and (FIG. 8B) CD107a expression on effector CARs cells.
Figure 8B:
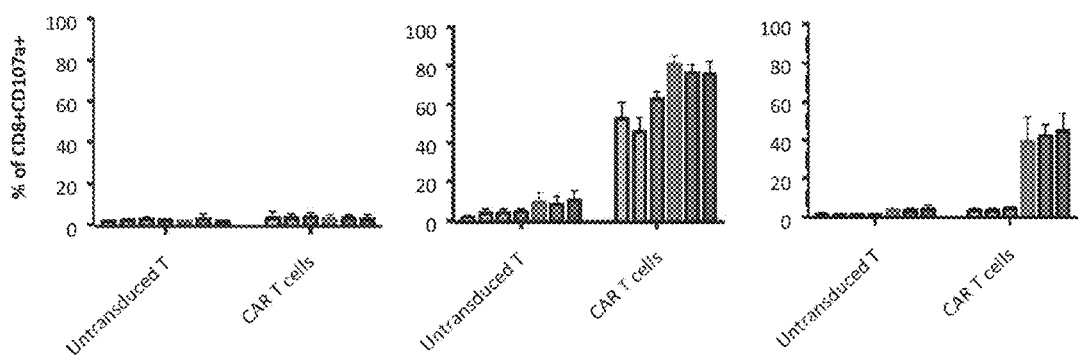

Independently of the hinge used, K562 cell line was not lysed by anti HLA-G LFTT-1 and 15E7 CAR-T cells since K562 cells did not express HLA-G protein at their surface (FIG. 8A). K562-HLA-G1P cell line expresses both HLA-G1 β2M associated and β2M free isoforms at their surface (FIGS. 2B and 2C respectively) and were almost completely lysed by LFTT-1 and 15E7 CAR-T cells at E:T ratio of 10:1 in comparison to activated but not transduced T cells. IgG4+CH3 hinge 15E7 CAR-T and LFTT-1 cells displayed a slightly lower efficiency in comparison to their IgG4 or IgG4+mCH2-CH3 counterparts. CD107a expression was determined on effector CAR-T cells accordingly to their cytotoxic function (FIG. 8B). JEG-3 cell line only expressed HLA-G1 associated to β2M isoform (FIG. 2C) and LFTT-1 CAR-T cells were capable to lyse JEG-3 tumor cells (FIG. 8A). CD107a expression was only determined on LFTT-1 CAR-T cells (FIG. 8B).

Figure 9:
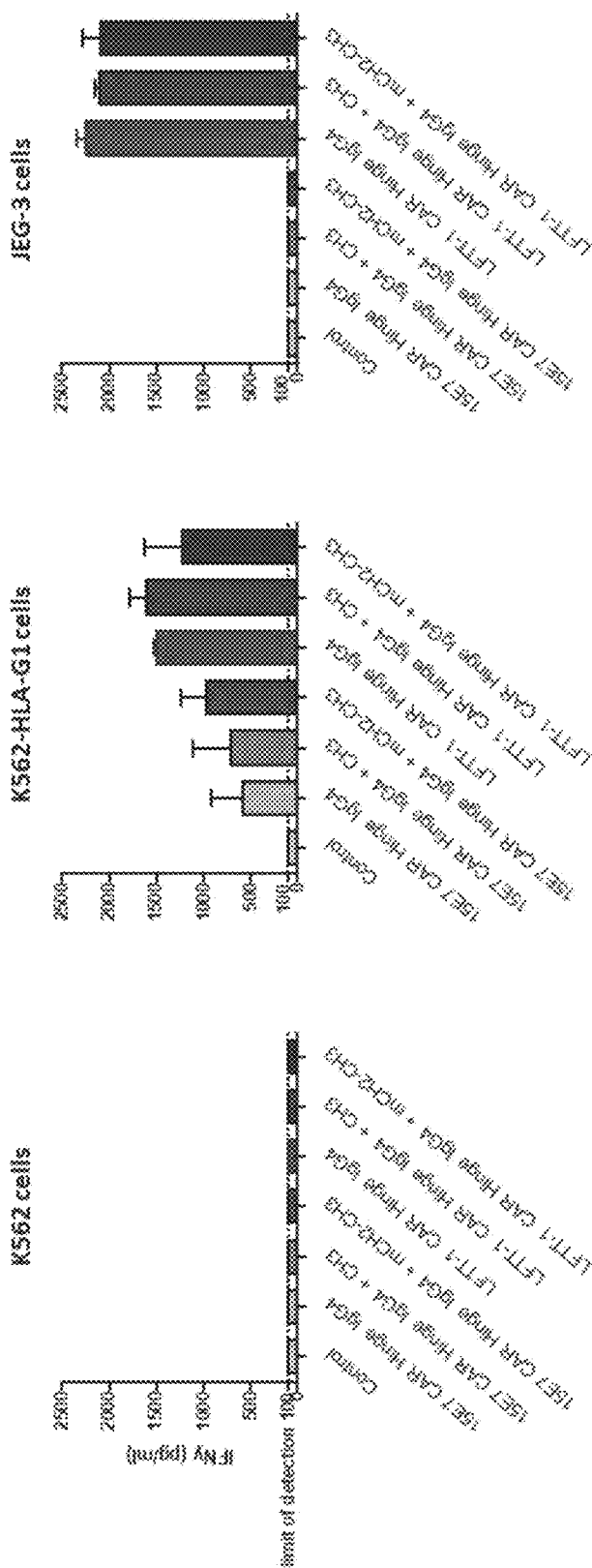
FIG. 9: IFN-γ secretion of HLA-G CARs cells was investigated after co-incubation with K562, K562-HLA-G1 and JEG-3 tumor cells.

As shown on FIG. 9, against the HLA-G negative K562 cell line, no secretion of IFN-γ was determined for LFTT-1 and 15E7 CAR-T cells whereas both CAR-T cells strongly secrete IFN-γ following incubation with the K562-HLA-G1P cell line. Against the JEG-3 cell line, only LFTT-1 CAR-T cells secreted IFN-γ, consistent with JEG-3 cells lysis and CD107a cell-surface expression on LFTT-1 CAR-T cells (FIG. 8).

In Vivo Experiment in NGS Mice

Figure 10A:
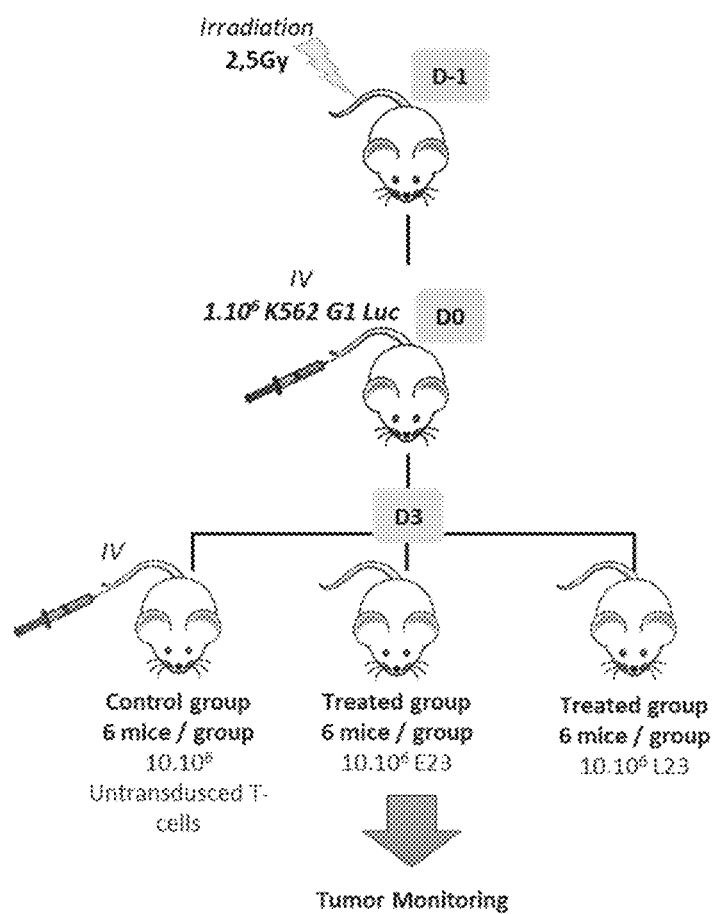
FIG. 10A-FIG. 10B: In vivo anti-tumor functions of HLA-G CAR-T cells (FIG. 10A) Scheme of in vivo experiment in mice with HLA-G CAR-T cells (FIG. 10B) CAR-T cells cytotoxicity against HLA-G tumor cells in vivo in NGS mice.
Figure 10B:
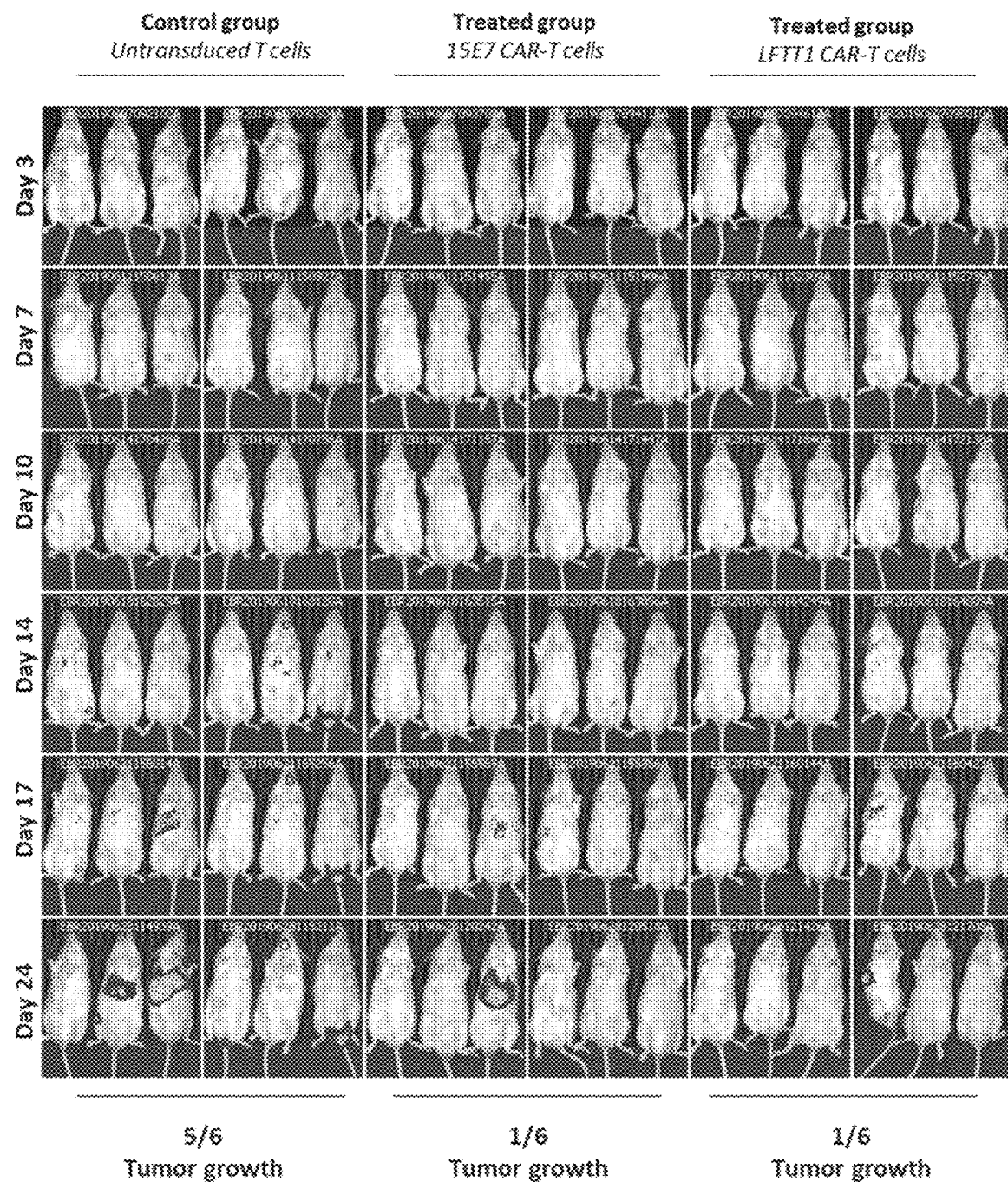

To investigate HLA-G CAR-T cells functions in vivo, K562-HLA-G1P tumor cells expressing the luciferase (K562-HLA-G1P-luc) were implanted in NGS mice followed by HLA-G CAR-T cells inoculation to monitor HLA-G CAR-T cells cytotoxicity against HLA-G tumor cells (FIG. 10).

To do so, activated control cells and HLA-G CAR transduced T cells were generated as previously described. Briefly, human T cells were sorted, activated then transduced or not with either 15E7-IgG4 hinge-CAR or LFFT1-IgG4 hinge-CAR constructs and maintained in culture until day 9 post-transduction to return to a resting state prior to in vivo experiments.

Then, 18 NGS female mice were irradiated 24 h before K562-HLA-G1P-luc cells intravenous inoculation. 3 days after K562-HLA-G1 cells inoculation, 3 groups of 6 mice were established corresponding to: (i) 6 mice were inoculated with 1.106 activated but not-transduced human CD8 T cells (control group), (ii) 6 mice were inoculated with 1.106 15E7-IgG4-CAR-T cells and (iii) 6 mice were inoculated with 1.106 LFTT1-IgG4-CAR-T cells. K562-HLA-G1P-luc tumor growth was then monitored to evaluate HLA-G CARs T-cell cytotoxicity against T cells control.

Material and Methods

Cells Lines

Jurkat cell line is human CD4+ T cells purchased from the ATCC (American Type Culture Collection TIB-152). Jurkat cell line was transduced with HLA-G1, HLA-G-LFTT-1 or HLA-G-15E7 CAR lentivirus, respectively. Jurkat wt and Jurkat transduced cell lines were cultured in RPMI 1640 (Invitrogen) supplemented with 2 mM L-glutamine, 1 mg/ml penicillin and streptomycin (Gibco), and 10% heat-inactivated FCS (Invitrogen).

NKT1.2 is a hybridoma murine cell line that was kindly provided by Dr. Kronenberg. These were also transduced with either HLA-G-LFTT-1 or HLA-G-15E7 CAR lentivirus respectively and were cultured in X-Vivo 10 (Lonza) supplemented with 1 mg/ml penicillin and streptomycin (Gibco).

K562 cells are human leukemia cells purchased from the ATCC (American Type Culture Collection CCL-243). K562-HLA-G1p cells were obtained by nucleofection of K562 wt cells with an HLA-G1 encoding vector and K562-HLA-G1Lv cells were obtained by HLA-G1 encoding lentivirus transduction. These cell lines were cultured in RPMI 1640 (Invitrogen) supplemented with 2 mM L-glutamine, 1 mg/ml penicillin and streptomycin (Gibco), and 10% heat-inactivated FCS (Invitrogen).

Jeg-3 cell line is human choriocarcinoma cells purchased from the ATCC (American Type Culture Collection HTB-36). These were cultured in MEM (X) supplemented with 1 mg/ml penicillin and streptomycin (X), and 10% heat-inactivated FCS (Invitrogen).

HLA-G CAR Jurkat cells

HLA-G-LFTT-1 and HLA-G-15E7 CAR constructs were generated as previously described [Pulé et al. 2005 Molecular Therapy]. Briefly, the anti-HLA-G-recognizing domain is a single-chain variable fragment (scFv) derived from HLA-G1/β2M associated specific antibody LFTT-1 or from the HLA-G1/β2M free specific antibody 15E7. A short spacer derived from the IgG1 hinge region was used to link this scFv to the transmembrane domain. The HLA-G CAR endodomain was constituted by the fusion of CD28, OX40 and CD3ζ activation molecules. CAR construct was cloned into a pTrip plasmid vector by digestion/ligation after extraction by PCR with specific primers, under CMV immediate early promoter. Amino acidic sequences coding for the light and heavy chains of the scFv of Mabs are detailed in SEQ ID NOs: 1 (VH), 2 ($V_L$) and 31 (scFV) for LFTT-1 and in SEQ ID NOs: 3 (VH), 4 ($V_L$) and 30 (scFV) for 15E7. The CAR sequences are disclosed in SEQ ID NOs: 83 and 84 for the 15E7 CAR (amino acid sequence and nucleic acid encoding sequence, respectively) and in SEQ ID NOs: 85 and 86 for the LFTT-1 CAR amino acid sequence and nucleic acid encoding sequence, respectively).

HLA-G Jurkat cells

HLA-G-expressing stable Jurkat cell line was generated by transduction and the lentiviral particles were generated as follows: specific sequences corresponding to native HLA-G1 cDNA (NM_002127.5) modified K334A and K335A according to Zhao et al. were cloned separately into a pTrip plasmid vector by digestion/ligation after extraction by PCR with specific primers, under CMV immediate early promoter.

Lentiviral Vectors

HIV-1-derived vector particles were produced by calcium phosphate co-transfection of HEK-293T cells (ATCC) with the recombinant plasmid pTRIP, an envelope expression plasmid encoding the glycoprotein from VSV, serotype Indiana glycoprotein, and the p8.74 encapsidation plasmid. Viral stocks were titrated by real-time PCR on cell lysates from transduced HEK-293T cells and expressed as transduction unit (TU) per ml. To generate Jurkat HLA-G-LFTT-1, HLA-G-15E7 CAR cells and Jurkat HLA-G, 1×10⁵ Jurkat cells were seeded in 12-well plate with in 500 μl of cRPMI medium and 10⁶ TU (293T) of Trip CMV-HLA-G-LFTT-1-CAR, Trip CMV-HLA-G-15E7-CAR or Trip CMV-HLA-G vectors respectively. Cells were incubated for 1 hour at 37° C. and then centrifuged 1 hour at 37° C. 1200 g. Afterwards, 1 ml of cRPMI medium was added and incubated at 37° C. Two weeks later, positive cells were sorted by flow cytometry using anti-HLA-G antibodies. The expression of HLA-G was evaluated by flow cytometry before the Jurkat HLA-G-CAR activation assay. The same procedure was carried out to obtain K562 HLA-G1Lv and NKT1.2 HLA-G-LFTT-1 CAR or HLA-G-15E7 CAR cells.

Flow Cytometry

PE-conjugated mouse IgG1 (Clone P.3.6.8.2.1. 12-4714) from eBiosciences (Paris; France), FITC-conjugated rat IgG2a from BD Biosciences (clone: R35-95 553929, Le Pont de Claix; France) and MEM-G/09 (Exbio, Praha). Flow cytometry was carried out incubating the corresponding cell line with monoclonal antibodies for 1 h at RT, washing twice and incubating for 30 min at RT with PE-conjugated goat anti-mouse IgG antibody (405307, Biolegend, USA). Flow cytometry analyses were performed using LSR FORTESSA (Beckton Dickinson, Le Pont-de-Claix, France); data were analyzed with FlowJo X software (Tree star, Ashland, USA). The % of positive labeled populations was defined as those with staining intensity higher than those exhibited by 99% of the isotype control.

Activation Assay

Jurkat HLA-G CAR effector cells and either Jurkat or Jurkat HLA-G1 tumor cells were respectively labeled with PKH26 and PKH67 fluorescent dyes (Sigma) according to the manufacturer's specifications. For activation assays based on the trogocytosis principle, Jurkat HLA-G-LFTT-1 or HLA-G-15E7 CAR ("acquirer" cells) were co-cultured with Jurkat or Jurkat HLA-G1 cells ("donor" cells) for 1 h at a 1:1 effector-tumor ratio, in a total concentration of $2 \times 10^6$ cells/mL, and at 37° C. in a 5% $CO_2$ humidified incubator as previously described [Caumartin J et al, (2007) Trogocytosis-based generation of suppressive NK cells, EMBO J 26:1423-33]. At the end of the coincubation, cells were placed on ice and all further steps were performed at less than 4° C. Acquisition of tumor cell membrane by CAR effector cells was investigated by flow cytometry.

Vector Production

HIV-1 derived vector particles were produced by transient calcium phosphate co-transfection of HEK 293 T cells (ATCC) with the vector plasmid pTRIP (encoding the glycoprotein from VSV, serotype Indiana (IND)) and the p8.74 encapsidation plasmid for the production of Integrative Lentiviral Vector particles (ILV). Vector gene transfer capacity was determined by quantitative PCR after transduction of 293T cells as previously described (Coutant, F., et al., PLoS One, 2008. 3(12): p. e3973) and was expressed as transduction unit (TU)/mL of vector.

T Cell Isolation and Activation

PBMCs were extracted from blood sample of 3 different healthy donors (EFS, Rungis) after ficoll isolation. T cells were sorted by column purification (Miltenyi), activated with CD3+ CD28+ coated microbeads (Miltenyi) and then cultured 48 hours at 37° C., 5% $CO_2$ in RPMI 1640 Glutamax (Gibco) supplemented with 10% FCS 1% Penicillin-Streptomycin (Gibco), 50 uM Beta-mercaptoethanol (Gibco), Non Essential amino acid, 10 mM Hepes (Gibco) and 1 mM Sodium Pyruvate (Gibco). Then, cells were washed and transduced with lentiviral vectors at MOI 20 in 200 µl at 1 M/ml during 4 hours under slow shaking. Cells were then transferred in a U-bottom 96-wells plate. After 24 h cells were adjusted at $1.10^6$ cells/ml and 50 U/ml of human IL2 were added (Preprotech). Every 2-3 days, cells were counted and adjusted at $1.10^6$ cells/ml in complete medium with IL2. After 8 days, cells were used for function assays.

Cytotoxicity Assays and Activation Profile

Cytotoxic assays were performed against JEG-3, K562 and K562-HLA-G1 target cells.

Briefly, 24 hour prior to the assay, 3.10s JEG-3 cells were labelled with CFSE (CellTrace, Thermofisher) at a 1/10 000; 3.105 K562 or 3.10s K562-HLA-G1 cells were labelled with CFSE at a 1/20 000 dilution. Target cells were then plated in a U-bottom 96-wells plate. CAR T cells were washed in PBS 1x (Gibco) before being co-cultured with target cells at the indicated Effector:Target ratios (E:T).

After 24 h of coincubation, medium was collected and cells recovered (detached in the case of JEG-3) in PBS-EDTA 0.1%. After washing, cells were labelled with antibodies against: CD4 (clone SK3 Percp, BD Pharmingen), CD8 (clone SK1 PE-Cy7, Biolegend), CD19 (clone LT19 FITC or PE, Miltenyi), CD25 (clone M-A251 BV421, BD Horizon), CD69 (clone FN50 BV711, BD Horizon), PD-1 (clone EH12.2H7 APC, Biolegend) and Live/dead (eFluor 780, Thermofisher) following manufacturer recommendations. Acquisition was performed with an Attune cytometer (Thermofisher) and results were analyzed with FlowJo software.

IFNγ Secretion Assays

IFNγ quantification was performed directly on co-culture medium using a CBA kit (BD Biosciences) following the manufacturer instructions.

Degranulation Assay

Co-cultured cells were prepared as described previously (E:T ratio of 10) and the anti-CD107a (clone H4A3 PE, Biolegend) was directly added to the co-culture. 1 hour after the co-incubation, Monensin (GolgiStop, BD Bioscience) was added. Cells were recovered 5 hours after co-incubation experiment and labelled with CD4, CD8, CD19 and Live/dead antibodies. Acquisition was performed with an Attune cytometer and results were analyzed with FlowJo software.

In Vivo Experiment

NOD/SCID/IL2Rγc-deficient (NSG) mice (6-8 weeks of age, The Jackson laboratory, Sacramento, Calif., USA) were irradiated (2.5 Gy) and inoculated intravenously with appropriated number of luciferase expressing K562-HLA-G1P (1.106/mouse) tumor cells. T cells (untransduced and transduced) were injected in the tail vein on day 3 for K562-HLA-G1P-Luc model. Engraftment was monitored every 3 to 4 days until day 17 post-implantation and then weekly by BLI measurements: mice received intraperitoneal 3 mg of luciferin (VivoGlo Luciferin, #P1043, Promega, Wisconsin, USA) within 10 minutes before imaging (IVIS Lumina Series III, Perkin Elmer, Massachusetts, USA).

Statistical Analyses

Data are presented as means+/−standard deviation (SD). Student t test was used and a P value less than 0.05 was taken to be significant. For figures showing representative experiments, error bars represent SD of triplicates.

CONCLUSION

Considering that the basic criteria to develop CARs immunotherapy are the identification of proper Tumor Associated Antigen, the accessibility of transgenic effector cell and reversibility of the immunosuppressive tumor microenvironment, it seems clear that HLA-G represents a very interesting candidate for this purpose. HLA-G is considered an ICP because of its key role on immune modulation, it has also been extensively described that this molecule is expressed in numerous tumor effusions of diverse origins, and no cellular or humoral response has ever been described against it. In addition, HLA-G is a singular molecule for which its function has been characterized but its protein structure turns out to be very complex and heterogeneous. Thus, solely one approach wouldn't be enough to inhibit HLA-G function. Here is proposed the generation of two CARs directed against HLA-G using the scFv of anti-HLA-G monoclonal antibodies (Mabs), directed to different epitopes of the molecule aiming most of HLA-G isoforms: classical HLA isoforms and smaller β2M-free isoforms. Therefore, it is expected to eliminate most of the cells that express HLA-G immunosuppressive isoforms. Effector cells transduced with the nucleic acid construct according to the invention were generated and these CAR molecules are highly expressed at the cell surface and are biologically functional. Also, anti-HLA-G CAR NKT cells were generated. It was previously reported that NKT cells were better immune cells for CAR therapy than T or NK counterparts. Furthermore, it was shown that CAR NKT cells infiltrate with a higher efficiency solid tumor. Since solid tumor cells highly express HLA-G (Paul et al. 1999 Cancer Research, Rouas-Freiss et al. 2007 Semin Cancer Biol, Yaghi et al. 2016 Oncotarget), anti-HLA-G NKT CAR might be an innovative way to circumvent the immunosuppressive environment linked to HLA-G.

To summarize, here is demonstrated that the 3$^{rd}$ generation recombinant construction CARs according to the invention (i) are correctly expressed on the surface of the transduced cells, (ii) that each CAR: HLA-G-15E7 CAR and HLA-G-LFTT-1 CAR are specific for HLA-G β2M-free or β2M-associated immunosuppressive isoforms respectively and (iii) that the CAR expressing effector cell against HLA-G are properly activated.

---

The invention claimed is:

1. An anti-human leukocyte antigen G (HLA-G) antibody or an antigen-binding fragment thereof, wherein the antibody or antigen-binding fragment comprises:
   (a) a heavy chain variable region (VH) comprising a heavy chain complementarity determining region 1 (HC CDR1) of SEQ ID NO: 5, a heavy chain complementarity determining region 2 (HC CDR2) of SEQ ID NO: 6, and a heavy chain complementarity determining region 3 (HC CDR3) of SEQ ID NO: 7; and
   (b) a light chain variable region (VL) comprising a light chain complementarity determining region 1 (LC CDR1) of SEQ ID NO: 8, a light chain complementarity determining region 2 (LC CDR2) of SEQ ID NO: 9 and a light chain complementarity determining region 3 (LC CDR3) of SEQ ID NO: 10.

2. The antibody or antigen-binding fragment of claim 1, wherein the VH comprises SEQ ID NO: 1 and the VL comprises SEQ ID NO: 2.

3. The antibody or antigen-binding fragment of claim 1, wherein the antibody or antigen-binding fragment is humanized or chimeric.

4. The antibody or antigen-binding fragment of claim 1, wherein the antibody or antigen-binding fragment is conjugated to a toxic agent.

5. The antigen-binding fragment of claim 1, wherein the antigen-binding fragment is a scFv, a Fv, a Fab, a Fab', or a F(ab')$_2$.

6. A pharmaceutical composition comprising the antibody or antigen-binding fragment of claim 1, and a pharmaceutically acceptable carrier.

7. A chimeric antigen receptor (CAR) comprising:
(a) an extracellular domain comprising an antigen binding domain that specifically binds to HLA-G, wherein the antigen binding domain comprises:
  (i) a VH comprising a heavy chain complementarity determining region 1 (HC CDR1) of SEQ ID NO: 5, a heavy chain complementarity determining region 2 (HC CDR2) of SEQ ID NO: 6, and a heavy chain complementarity determining region 3 (HC CDR3) of SEQ ID NO: 7; and
  (ii) a VL comprising a light chain complementarity determining region 1 (LC CDR1) of SEQ ID NO: 8, a light chain complementarity determining region 2 (LC CDR2) of SEQ ID NO: 9 and a light chain complementarity determining region 3 (LC CDR3) of SEQ ID NO: 10;
(b) a transmembrane domain; and
(c) an intracellular signaling domain.

8. The CAR of claim 7, wherein the VH comprises SEQ ID NO: 1 and the VL comprises SEQ ID NO: 2.

9. The CAR of claim 7, wherein the antigen binding domain is a scFv.

10. The CAR of claim 9, wherein the antigen binding domain comprises SEQ ID NO: 31.

11. The CAR of claim 7, wherein the transmembrane domain is a CD28 transmembrane domain; and wherein the intracellular signaling domain comprises a 4-1BB costimulatory signaling region and a CD3 zeta endodomain.

12. The CAR of claim 11, wherein:
the CD28 transmembrane domain comprises SEQ ID NO: 20,
the 4-1BB costimulatory signaling region comprises SEQ ID NO: 21, and
the CD3 zeta endodomain comprises SEQ ID NO: 22.

13. The CAR of claim 11, wherein the intracellular signaling domain further comprises a CD28 costimulatory domain.

14. The CAR of claim 7, further comprising a hinge domain connecting the antigen binding domain to the transmembrane domain.

15. The CAR of claim 14, wherein the hinge domain is (i) a human IgG4 hinge domain, (ii) a human IgG4 hinge domain and a CH3 human IgG4 domain, (iii) a mutated CH2 human IgG4 domain, a human IgG4 hinge domain and a CH3 human IgG4 hinge domain, (iv) a CD28 hinge or (v) a CD8a hinge domain.

16. The CAR of claim 7, wherein the CAR comprises SEQ ID NO: 32, SEQ ID NO: 33, SEQ ID NO: 34 or SEQ ID NO: 85.

17. A pharmaceutical composition comprising a cell comprising the CAR of claim 7, and a pharmaceutically acceptable carrier.

18. The pharmaceutical composition of claim 17, wherein the cell is a T cell, a B cell, a NK cell, a NKT cell, a monocyte cell or a dendritic cell.

19. A nucleic acid molecule encoding the CAR of claim 7.

20. An expression vector comprising the nucleic acid molecule of claim 19.

* * * * *

SEQUENCE LISTING

```
<160> NUMBER OF SEQ ID NOS: 86

<210> SEQ ID NO 1
<211> LENGTH: 122
<212> TYPE: PRT
<213> ORGANISM: Artificial Sequence
<220> FEATURE:
<223> OTHER INFORMATION: LFFT-1 VH

<400> SEQUENCE: 1

Gln Ile Gln Leu Val Gln Ser Gly Pro Glu Leu Lys Lys Pro Gly Glu
1               5                   10                  15

Thr Val Lys Ile Ser Cys Lys Ala Ser Gly Tyr Thr Phe Thr Thr Tyr
            20                  25                  30

Gly Met Ser Trp Val Lys Gln Ala Pro Gly Lys Gly Leu Lys Trp Met
        35                  40                  45

Gly Trp Ile Tyr Thr Tyr Ser Gly Val Pro Thr Tyr Ala Asp Asp Leu
    50                  55                  60

Glu Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Val Arg Asp Gly Tyr Tyr Arg Tyr Ala Met Asp Tyr Trp Gly
            100                 105                 110

Gln Gly Thr Ser Val Thr Val Ser Ser Cys
        115                 120

<210> SEQ ID NO 2
<211> LENGTH: 106
<212> TYPE: PRT
<213> ORGANISM: Artificial Sequence
<220> FEATURE:
<223> OTHER INFORMATION: LFFT-1 VL

<400> SEQUENCE: 2

Asp Ile His Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
            20                  25                  30

Ile Ala Trp Tyr Gln His Lys Pro Gly Lys Gly Pro Arg Leu Leu Ile
        35                  40                  45

His Phe Thr Ser Thr Leu Gln Ser Gly Ile Pro Ser Arg Phe Ser Gly
    50                  55                  60

Ser Gly Ser Gly Arg Asp Tyr Ser Phe Ser Ile Ser Asn Leu Glu Pro
65                  70                  75                  80

Glu Asp Ile Ala Thr Tyr Tyr Cys Leu Gln Tyr Asp Asp Leu Arg Thr
                85                  90                  95

Phe Gly Gly Gly Thr Lys Leu Glu Ile Lys
            100                 105

<210> SEQ ID NO 3
<211> LENGTH: 120
<212> TYPE: PRT
```

```
<213> ORGANISM: Artificial Sequence
<220> FEATURE:
<223> OTHER INFORMATION: 1E57 VH

<400> SEQUENCE: 3

Gln Val Gln Leu Gln Gln Pro Gly Ala Glu Leu Val Arg Pro Gly Ser
1               5                   10                  15

Ser Val Lys Leu Ser Cys Lys Ala Ser Gly Tyr Thr Phe Thr Asp Tyr
            20                  25                  30

Trp Met Asp Trp Val Lys Gln Arg Pro Gly Gln Gly Leu Glu Trp Ile
        35                  40                  45

Gly Thr Ile Tyr Pro Ser Asp Ser Ser Thr His Tyr Asn Gln Glu Phe
50                  55                  60

Lys Gly Lys Ala Thr Met Thr Val Asp Lys Ser Ser Ser Thr Ala Tyr
65                  70                  75                  80

Met His Leu Ser Ser Leu Thr Ser Glu Asp Ser Ala Val Tyr Tyr Cys
            85                  90                  95

Ala Arg Glu Gly Leu Ala Gly Val Phe Tyr Phe Asp Tyr Trp Gly Gln
            100                 105                 110

Gly Thr Thr Leu Thr Val Ser Ser
        115                 120

<210> SEQ ID NO 4
<211> LENGTH: 113
<212> TYPE: PRT
<213> ORGANISM: Artificial Sequence
<220> FEATURE:
<223> OTHER INFORMATION: 1E57 VL

<400> SEQUENCE: 4

Asp Asp Val Leu Met Thr Gln Ile Pro Phe Ser Leu Pro Val Ser Leu
1               5                   10                  15

Gly Asp Gln Ala Ser Ile Ser Cys Arg Ser Ser Gln Ser Ile Val His
            20                  25                  30

Arg Ser Gly Asn Thr Tyr Leu Glu Trp Tyr Leu Gln Lys Pro Gly Gln
        35                  40                  45

Ser Pro Lys Leu Leu Ile Tyr Lys Val Ser Asn Arg Phe Ser Gly Val
50                  55                  60

Pro Asp Arg Phe Ser Gly Ser Gly Ser Gly Thr Asp Phe Thr Leu Lys
65                  70                  75                  80

Ile Ser Arg Val Glu Ala Glu Asp Leu Gly Val Tyr Tyr Cys Phe Gln
            85                  90                  95

Gly Ser His Leu Pro Pro Thr Phe Gly Gly Gly Thr Lys Leu Glu Ile
            100                 105                 110

Lys

<210> SEQ ID NO 5
<211> LENGTH: 8
<212> TYPE: PRT
<213> ORGANISM: Artificial Sequence
<220> FEATURE:
<223> OTHER INFORMATION: LFFT-1 VH CDR1

<400> SEQUENCE: 5

Gly Tyr Thr Phe Thr Thr Tyr Gly
1               5

<210> SEQ ID NO 6
<211> LENGTH: 8
```

```
<212> TYPE: PRT
<213> ORGANISM: Artificial Sequence
<220> FEATURE:
<223> OTHER INFORMATION: LFFT-1 VH CDR2

<400> SEQUENCE: 6

Ile Tyr Thr Tyr Ser Gly Val Pro
1               5

<210> SEQ ID NO 7
<211> LENGTH: 14
<212> TYPE: PRT
<213> ORGANISM: Artificial Sequence
<220> FEATURE:
<223> OTHER INFORMATION: LFFT-1 VH CDR3

<400> SEQUENCE: 7

Ala Arg Val Arg Asp Gly Tyr Tyr Arg Tyr Ala Met Asp Tyr
1               5                   10

<210> SEQ ID NO 8
<211> LENGTH: 6
<212> TYPE: PRT
<213> ORGANISM: Artificial Sequence
<220> FEATURE:
<223> OTHER INFORMATION: LFFT-1 VL CDR1

<400> SEQUENCE: 8

Gln Asp Ile Asn Arg Tyr
1               5

<210> SEQ ID NO 9
<211> LENGTH: 3
<212> TYPE: PRT
<213> ORGANISM: Artificial Sequence
<220> FEATURE:
<223> OTHER INFORMATION: LFFT-1 VL CDR2

<400> SEQUENCE: 9

Phe Thr Ser
1

<210> SEQ ID NO 10
<211> LENGTH: 8
<212> TYPE: PRT
<213> ORGANISM: Artificial Sequence
<220> FEATURE:
<223> OTHER INFORMATION: LFFT-1 VL CDR3

<400> SEQUENCE: 10

Leu Gln Tyr Asp Asp Leu Arg Thr
1               5

<210> SEQ ID NO 11
<211> LENGTH: 8
<212> TYPE: PRT
<213> ORGANISM: Artificial Sequence
<220> FEATURE:
<223> OTHER INFORMATION: 1E57 VH CDR1

<400> SEQUENCE: 11

Gly Tyr Thr Phe Thr Asp Tyr Trp
1               5

<210> SEQ ID NO 12
<211> LENGTH: 8
<212> TYPE: PRT
```

```
<213> ORGANISM: Artificial Sequence
<220> FEATURE:
<223> OTHER INFORMATION: 1E57 VH CDR2

<400> SEQUENCE: 12

Ile Tyr Pro Ser Asp Ser Ser Thr
1               5

<210> SEQ ID NO 13
<211> LENGTH: 13
<212> TYPE: PRT
<213> ORGANISM: Artificial Sequence
<220> FEATURE:
<223> OTHER INFORMATION: 1E57 VH CDR3

<400> SEQUENCE: 13

Ala Arg Glu Gly Leu Ala Gly Val Phe Tyr Phe Asp Tyr
1               5                   10

<210> SEQ ID NO 14
<211> LENGTH: 11
<212> TYPE: PRT
<213> ORGANISM: Artificial Sequence
<220> FEATURE:
<223> OTHER INFORMATION: 1E57 VL CDR1

<400> SEQUENCE: 14

Gln Ser Ile Val His Arg Ser Gly Asn Thr Tyr
1               5                   10

<210> SEQ ID NO 15
<211> LENGTH: 3
<212> TYPE: PRT
<213> ORGANISM: Artificial Sequence
<220> FEATURE:
<223> OTHER INFORMATION: 1E57 VL CDR2

<400> SEQUENCE: 15

Lys Val Ser
1

<210> SEQ ID NO 16
<211> LENGTH: 9
<212> TYPE: PRT
<213> ORGANISM: Artificial Sequence
<220> FEATURE:
<223> OTHER INFORMATION: 1E57 VL CDR3

<400> SEQUENCE: 16

Phe Gln Gly Ser His Leu Pro Pro Thr
1               5

<210> SEQ ID NO 17
<211> LENGTH: 19
<212> TYPE: PRT
<213> ORGANISM: Artificial Sequence
<220> FEATURE:
<223> OTHER INFORMATION: Signal Peptide CD8a

<400> SEQUENCE: 17

Met Ala Leu Pro Val Thr Ala Leu Leu Leu Pro Leu Ala Leu Leu
1               5                   10                  15

His Ala Ala

<210> SEQ ID NO 18
<211> LENGTH: 90
```

```
<212> TYPE: PRT
<213> ORGANISM: Artificial Sequence
<220> FEATURE:
<223> OTHER INFORMATION: CD8a Hinge

<400> SEQUENCE: 18

Ala Leu Ser Asn Ser Ile Met Tyr Phe Ser His Phe Val Pro Val Phe
1               5                   10                  15

Leu Pro Ala Lys Pro Thr Thr Thr Pro Ala Pro Arg Pro Pro Thr Pro
            20                  25                  30

Ala Pro Thr Ile Ala Ser Gln Pro Leu Ser Leu Arg Pro Glu Ala Cys
        35                  40                  45

Arg Pro Ala Ala Gly Gly Ala Val His Thr Arg Gly Leu Asp Phe Ala
    50                  55                  60

Cys Asp Phe Trp Val Leu Val Val Val Gly Gly Val Leu Ala Cys Tyr
65                  70                  75                  80

Ser Leu Leu Val Thr Val Ala Phe Ile Ile
                85                  90

<210> SEQ ID NO 19
<211> LENGTH: 64
<212> TYPE: PRT
<213> ORGANISM: Artificial Sequence
<220> FEATURE:
<223> OTHER INFORMATION: CD28 Hinge

<400> SEQUENCE: 19

Lys Ile Glu Val Met Tyr Pro Pro Pro Tyr Leu Asp Asn Glu Lys Ser
1               5                   10                  15

Asn Gly Thr Ile Ile His Val Lys Gly Lys His Leu Cys Pro Ser Pro
            20                  25                  30

Leu Phe Pro Gly Pro Ser Lys Pro Phe Trp Val Leu Val Val Val Gly
            35                  40                  45

Gly Val Leu Ala Cys Tyr Ser Leu Leu Val Thr Val Ala Phe Ile Ile
    50                  55                  60

<210> SEQ ID NO 20
<211> LENGTH: 68
<212> TYPE: PRT
<213> ORGANISM: Artificial Sequence
<220> FEATURE:
<223> OTHER INFORMATION: CD28 human

<400> SEQUENCE: 20

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
            35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 21
<211> LENGTH: 42
<212> TYPE: PRT
<213> ORGANISM: Artificial Sequence
<220> FEATURE:
<223> OTHER INFORMATION: 4-1BB human
```

<400> SEQUENCE: 21

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
            35                  40

<210> SEQ ID NO 22
<211> LENGTH: 112
<212> TYPE: PRT
<213> ORGANISM: Artificial Sequence
<220> FEATURE:
<223> OTHER INFORMATION: CD3z human endodomain

<400> SEQUENCE: 22

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
            35                  40                  45

Pro Arg Arg Lys Asn Pro Gln Glu Gly Leu Tyr Asn Glu Leu Gln Lys
50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

<210> SEQ ID NO 23
<211> LENGTH: 24
<212> TYPE: PRT
<213> ORGANISM: Artificial Sequence
<220> FEATURE:
<223> OTHER INFORMATION: Flag Tag

<400> SEQUENCE: 23

Gly Ala Cys Thr Ala Cys Ala Ala Gly Ala Cys Gly Ala Cys Gly
1               5                   10                  15

Ala Thr Gly Ala Cys Ala Ala Gly
            20

<210> SEQ ID NO 24
<211> LENGTH: 19
<212> TYPE: PRT
<213> ORGANISM: Artificial Sequence
<220> FEATURE:
<223> OTHER INFORMATION: Mouse IgKappa Signal Peptide

<400> SEQUENCE: 24

Met Lys Leu Pro Val Arg Leu Leu Val Leu Met Phe Trp Ile Pro Ala
1               5                   10                  15

Ser Ser Ser

<210> SEQ ID NO 25
<211> LENGTH: 12
<212> TYPE: PRT
<213> ORGANISM: Artificial Sequence
<220> FEATURE:
<223> OTHER INFORMATION: Hinge hIgG4

<400> SEQUENCE: 25

Glu Ser Lys Tyr Gly Pro Pro Cys Pro Pro Cys Pro
1               5                   10

<210> SEQ ID NO 26
<211> LENGTH: 109
<212> TYPE: PRT
<213> ORGANISM: Artificial Sequence
<220> FEATURE:
<223> OTHER INFORMATION: Mutated CH2 human IgG4

<400> SEQUENCE: 26

Ala Pro Pro Val Ala Gly Pro Ser Val Phe Leu Phe Pro Pro Lys Pro
1               5                   10                  15

Lys Asp Thr Leu Met Ile Ser Arg Thr Pro Glu Val Thr Cys Val Val
            20                  25                  30

Val Asp Val Ser Gln Glu Asp Pro Glu Val Gln Phe Asn Trp Tyr Val
        35                  40                  45

Asp Gly Val Glu Val His Asn Ala Lys Thr Lys Pro Arg Glu Glu Gln
    50                  55                  60

Phe Gln Ser Thr Tyr Arg Val Val Ser Val Leu Thr Val Leu His Gln
65                  70                  75                  80

Asp Trp Leu Asn Gly Lys Glu Tyr Lys Cys Lys Val Ser Asn Lys Gly
                85                  90                  95

Leu Pro Ser Ser Ile Glu Lys Thr Ile Ser Lys Ala Lys
            100                 105

<210> SEQ ID NO 27
<211> LENGTH: 107
<212> TYPE: PRT
<213> ORGANISM: Artificial Sequence
<220> FEATURE:
<223> OTHER INFORMATION: CH3 human IgG4

<400> SEQUENCE: 27

Gly Gln Pro Arg Glu Pro Gln Val Tyr Thr Leu Pro Pro Ser Gln Glu
1               5                   10                  15

Glu Met Thr Lys Asn Gln Val Ser Leu Thr Cys Leu Val Lys Gly Phe
            20                  25                  30

Tyr Pro Ser Asp Ile Ala Val Glu Trp Glu Ser Asn Gly Gln Pro Glu
        35                  40                  45

Asn Asn Tyr Lys Thr Thr Pro Pro Val Leu Asp Ser Asp Gly Ser Phe
    50                  55                  60

Phe Leu Tyr Ser Arg Leu Thr Val Asp Lys Ser Arg Trp Gln Glu Gly
65                  70                  75                  80

Asn Val Phe Ser Cys Ser Val Met His Glu Ala Leu His Asn His Tyr
                85                  90                  95

Thr Gln Lys Ser Leu Ser Leu Ser Leu Gly Lys
            100                 105

<210> SEQ ID NO 28
<211> LENGTH: 22
<212> TYPE: PRT
<213> ORGANISM: Artificial Sequence
<220> FEATURE:
<223> OTHER INFORMATION: P2A Cleavage peptide

<400> SEQUENCE: 28

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 29
<211> LENGTH: 313
<212> TYPE: PRT
<213> ORGANISM: Artificial Sequence
<220> FEATURE:
<223> OTHER INFORMATION: Truncated human CD19 Reporter

<400> SEQUENCE: 29

Met Pro Pro Pro Arg Leu Leu Phe Phe Leu Leu Phe Leu Thr Pro Met
1               5                   10                  15

Glu Val Arg Pro Glu Glu Pro Leu Val Val Lys Val Glu Glu Gly Asp
            20                  25                  30

Asn Ala Val Leu Gln Cys Leu Lys Gly Thr Ser Asp Gly Pro Thr Gln
        35                  40                  45

Gln Leu Thr Trp Ser Arg Glu Ser Pro Leu Lys Pro Phe Leu Lys Leu
    50                  55                  60

Ser Leu Gly Leu Pro Gly Leu Gly Ile His Met Arg Pro Leu Ala Ile
65                  70                  75                  80

Trp Leu Phe Ile Phe Asn Val Ser Gln Gln Met Gly Gly Phe Tyr Leu
                85                  90                  95

Cys Gln Pro Gly Pro Pro Ser Glu Lys Ala Trp Gln Pro Gly Trp Thr
            100                 105                 110

Val Asn Val Glu Gly Ser Gly Glu Leu Phe Arg Trp Asn Val Ser Asp
        115                 120                 125

Leu Gly Gly Leu Gly Cys Gly Leu Lys Asn Arg Ser Ser Glu Gly Pro
    130                 135                 140

Ser Ser Pro Ser Gly Lys Leu Met Ser Pro Lys Leu Tyr Val Trp Ala
145                 150                 155                 160

Lys Asp Arg Pro Glu Ile Trp Glu Gly Glu Pro Pro Cys Leu Pro Pro
                165                 170                 175

Arg Asp Ser Leu Asn Gln Ser Leu Ser Gln Asp Leu Thr Met Ala Pro
            180                 185                 190

Gly Ser Thr Leu Trp Leu Ser Cys Gly Val Pro Pro Asp Ser Val Ser
        195                 200                 205

Arg Gly Pro Leu Ser Trp Thr His Val His Pro Lys Gly Pro Lys Ser
    210                 215                 220

Leu Leu Ser Leu Glu Leu Lys Asp Asp Arg Pro Ala Arg Asp Met Trp
225                 230                 235                 240

Val Met Glu Thr Gly Leu Leu Leu Pro Arg Ala Thr Ala Gln Asp Ala
                245                 250                 255

Gly Lys Tyr Tyr Cys His Arg Gly Asn Leu Thr Met Ser Phe His Leu
            260                 265                 270

Glu Ile Thr Ala Arg Pro Val Leu Trp His Trp Leu Leu Arg Thr Gly
        275                 280                 285

Gly Trp Lys Val Ser Ala Val Thr Leu Ala Tyr Leu Ile Phe Cys Leu
    290                 295                 300

Cys Ser Leu Val Gly Ile Leu His Leu
305                 310

<210> SEQ ID NO 30

```
<211> LENGTH: 247
<212> TYPE: PRT
<213> ORGANISM: Artificial Sequence
<220> FEATURE:
<223> OTHER INFORMATION: ScFV 15E7

<400> SEQUENCE: 30

Asp Val Leu Met Thr Gln Ile Pro Phe Ser Leu Pro Val Ser Leu Gly
1               5                   10                  15

Asp Gln Ala Ser Ile Ser Cys Arg Ser Ser Gln Ser Ile Val His Arg
            20                  25                  30

Ser Gly Asn Thr Tyr Leu Glu Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Leu Pro Pro Thr Phe Gly Gly Gly Thr Thr Leu Glu Ile Lys
            100                 105                 110

Gly Gly Gly Gly Ser Gly Gly Gly Gly Ser Gly Gly Gly Gly Ser Gln
        115                 120                 125

Val Gln Leu Gln Gln Pro Gly Ala Glu Leu Val Arg Pro Gly Ser Ser
    130                 135                 140

Val Lys Leu Ser Cys Lys Ala Ser Gly Tyr Thr Phe Thr Asp Tyr Trp
145                 150                 155                 160

Met Asp Trp Val Lys Gln Arg Pro Gly Gln Gly Leu Glu Trp Ile Gly
                165                 170                 175

Thr Ile Tyr Pro Ser Asp Ser Thr His Tyr Asn Gln Glu Phe Lys
            180                 185                 190

Gly Lys Ala Thr Met Thr Val Asp Lys Ser Ser Ser Thr Ala Tyr Met
        195                 200                 205

His Leu Ser Ser Leu Thr Ser Glu Asp Ser Ala Val Tyr Tyr Cys Ala
    210                 215                 220

Arg Glu Gly Leu Ala Gly Val Phe Tyr Phe Asp Tyr Trp Gly Gln Gly
225                 230                 235                 240

Thr Thr Leu Thr Val Ser Ser
            245

<210> SEQ ID NO 31
<211> LENGTH: 242
<212> TYPE: PRT
<213> ORGANISM: Artificial Sequence
<220> FEATURE:
<223> OTHER INFORMATION: ScFV LFTT1

<400> SEQUENCE: 31

Asp Ile His Met Thr Gln Ser Pro Ser Ser Leu Ser Ala Ser Leu Gly
1               5                   10                  15

Gly Lys Val Thr Ile Thr Cys Lys Ala Ser Gln Asp Ile Asn Arg Tyr
            20                  25                  30

Ile Ala Trp Tyr Gln His Lys Pro Gly Lys Gly Pro Arg Leu Leu Ile
        35                  40                  45

His Phe Thr Ser Thr Leu Gln Ser Gly Ile Pro Ser Arg Phe Ser Gly
    50                  55                  60

Ser Gly Ser Gly Arg Asp Tyr Ser Phe Ser Ile Ser Asn Leu Glu Pro
```

```
                65                  70                  75                  80
Glu Asp Ile Ala Thr Tyr Tyr Cys Leu Gln Tyr Asp Asp Leu Arg Thr
                    85                  90                  95
Phe Gly Gly Gly Thr Lys Leu Glu Ile Lys Gly Gly Gly Gly Ser Gly
                100                 105                 110
Gly Gly Gly Ser Gly Gly Gly Ser Gln Ile Gln Leu Val Gln Ser
            115                 120                 125
Gly Pro Glu Leu Lys Lys Pro Gly Glu Thr Val Lys Ile Ser Cys Lys
130                 135                 140
Ala Ser Gly Tyr Thr Phe Thr Thr Tyr Gly Met Ser Trp Val Lys Gln
145                 150                 155                 160
Ala Pro Gly Lys Gly Leu Lys Trp Met Gly Trp Ile Tyr Thr Tyr Ser
                165                 170                 175
Gly Val Pro Thr Tyr Ala Asp Asp Leu Glu Gly Arg Phe Ala Phe Ser
            180                 185                 190
Leu Glu Thr Ser Ala Ser Thr Ala Tyr Leu Gln Ile Asn Asn Leu Lys
                195                 200                 205
Asn Glu Asp Thr Ala Thr Tyr Phe Cys Ala Arg Val Arg Asp Gly Tyr
        210                 215                 220
Tyr Arg Tyr Ala Met Asp Tyr Trp Gly Gln Gly Thr Ser Val Thr Val
225                 230                 235                 240
Ser Ser

<210> SEQ ID NO 32
<211> LENGTH: 1046
<212> TYPE: PRT
<213> ORGANISM: Artificial Sequence
<220> FEATURE:
<223> OTHER INFORMATION: LFTT1 HingeCH2CH3 hIgG4

<400> SEQUENCE: 32

Met Lys Leu Pro Val Arg Leu Leu Val Leu Met Phe Trp Ile Pro Ala
1               5                   10                  15
Ser Ser Ser Asp Ile His Met Thr Gln Ser Pro Ser Ser Leu Ser Ala
                20                  25                  30
Ser Leu Gly Gly Lys Val Thr Ile Thr Cys Lys Ala Ser Gln Asp Ile
            35                  40                  45
Asn Arg Tyr Ile Ala Trp Tyr Gln His Lys Pro Gly Lys Gly Pro Arg
        50                  55                  60
Leu Leu Ile His Phe Thr Ser Thr Leu Gln Ser Gly Ile Pro Ser Arg
65                  70                  75                  80
Phe Ser Gly Ser Gly Ser Gly Arg Asp Tyr Ser Phe Ser Ile Ser Asn
                85                  90                  95
Leu Glu Pro Glu Asp Ile Ala Thr Tyr Tyr Cys Leu Gln Tyr Asp Asp
                100                 105                 110
Leu Arg Thr Phe Gly Gly Gly Thr Lys Leu Glu Ile Lys Gly Gly Gly
            115                 120                 125
Gly Ser Gly Gly Gly Gly Ser Gly Gly Gly Ser Gln Ile Gln Leu
        130                 135                 140
Val Gln Ser Gly Pro Glu Leu Lys Lys Pro Gly Glu Thr Val Lys Ile
145                 150                 155                 160
Ser Cys Lys Ala Ser Gly Tyr Thr Phe Thr Thr Tyr Gly Met Ser Trp
                165                 170                 175
Val Lys Gln Ala Pro Gly Lys Gly Leu Lys Trp Met Gly Trp Ile Tyr
                180                 185                 190
```

-continued

Thr Tyr Ser Gly Val Pro Thr Tyr Ala Asp Asp Leu Glu Gly Arg Phe
        195                 200                 205
Ala Phe Ser Leu Glu Thr Ser Ala Ser Thr Ala Tyr Leu Gln Ile Asn
        210                 215                 220
Asn Leu Lys Asn Glu Asp Thr Ala Thr Tyr Phe Cys Ala Arg Val Arg
225                 230                 235                 240
Asp Gly Tyr Tyr Arg Tyr Ala Met Asp Tyr Trp Gly Gln Gly Thr Ser
                245                 250                 255
Val Thr Val Ser Ser Glu Ser Lys Tyr Gly Pro Pro Cys Pro Pro Cys
                260                 265                 270
Pro Ala Pro Pro Val Ala Gly Pro Ser Val Phe Leu Phe Pro Pro Lys
        275                 280                 285
Pro Lys Asp Thr Leu Met Ile Ser Arg Thr Pro Glu Val Thr Cys Val
        290                 295                 300
Val Val Asp Val Ser Gln Glu Asp Pro Glu Val Gln Phe Asn Trp Tyr
305                 310                 315                 320
Val Asp Gly Val Glu Val His Asn Ala Lys Thr Lys Pro Arg Glu Glu
                325                 330                 335
Gln Phe Gln Ser Thr Tyr Arg Val Val Ser Val Leu Thr Val Leu His
        340                 345                 350
Gln Asp Trp Leu Asn Gly Lys Glu Tyr Lys Cys Lys Val Ser Asn Lys
        355                 360                 365
Gly Leu Pro Ser Ser Ile Glu Lys Thr Ile Ser Lys Ala Lys Gly Gln
        370                 375                 380
Pro Arg Glu Pro Gln Val Tyr Thr Leu Pro Pro Ser Gln Glu Glu Met
385                 390                 395                 400
Thr Lys Asn Gln Val Ser Leu Thr Cys Leu Val Lys Gly Phe Tyr Pro
                405                 410                 415
Ser Asp Ile Ala Val Glu Trp Glu Ser Asn Gly Gln Pro Glu Asn Asn
        420                 425                 430
Tyr Lys Thr Thr Pro Pro Val Leu Asp Ser Asp Gly Ser Phe Phe Leu
        435                 440                 445
Tyr Ser Arg Leu Thr Val Asp Lys Ser Arg Trp Gln Glu Gly Asn Val
        450                 455                 460
Phe Ser Cys Ser Val Met His Glu Ala Leu His Asn His Tyr Thr Gln
465                 470                 475                 480
Lys Ser Leu Ser Leu Ser Leu Gly Lys Phe Trp Val Leu Val Val Val
                485                 490                 495
Gly Gly Val Leu Ala Cys Tyr Ser Leu Leu Val Thr Val Ala Phe Ile
        500                 505                 510
Ile Phe Trp Val Arg Ser Lys Arg Ser Arg Leu Leu His Ser Asp Tyr
        515                 520                 525
Met Asn Met Thr Pro Arg Arg Pro Gly Pro Thr Arg Lys His Tyr Gln
        530                 535                 540
Pro Tyr Ala Pro Pro Arg Asp Phe Ala Ala Tyr Arg Ser Lys Arg Gly
545                 550                 555                 560
Arg Lys Lys Leu Leu Tyr Ile Phe Lys Gln Pro Phe Met Arg Pro Val
                565                 570                 575
Gln Thr Thr Gln Glu Glu Asp Gly Cys Ser Cys Arg Phe Pro Glu Glu
        580                 585                 590
Glu Glu Gly Gly Cys Glu Leu Arg Val Lys Phe Ser Arg Ser Ala Asp
        595                 600                 605

-continued

```
Ala Pro Ala Tyr Gln Gln Gly Gln Asn Gln Leu Tyr Asn Glu Leu Asn
610                 615                 620

Leu Gly Arg Arg Glu Glu Tyr Asp Val Leu Asp Lys Arg Arg Gly Arg
625                 630                 635                 640

Asp Pro Glu Met Gly Gly Lys Pro Arg Arg Lys Asn Pro Gln Glu Gly
            645                 650                 655

Leu Tyr Asn Glu Leu Gln Lys Asp Lys Met Ala Glu Ala Tyr Ser Glu
            660                 665                 670

Ile Gly Met Lys Gly Glu Arg Arg Arg Gly Lys Gly His Asp Gly Leu
            675                 680                 685

Tyr Gln Gly Leu Ser Thr Ala Thr Lys Asp Thr Tyr Asp Ala Leu His
690                 695                 700

Met Gln Ala Leu Pro Pro Arg Gly Ser Gly Ala Thr Asn Phe Ser Leu
705                 710                 715                 720

Leu Lys Gln Ala Gly Asp Val Glu Glu Asn Pro Gly Pro Met Pro Pro
            725                 730                 735

Pro Arg Leu Leu Phe Phe Leu Leu Phe Leu Thr Pro Met Glu Val Arg
            740                 745                 750

Pro Glu Glu Pro Leu Val Val Lys Val Glu Glu Gly Asp Asn Ala Val
            755                 760                 765

Leu Gln Cys Leu Lys Gly Thr Ser Asp Gly Pro Thr Gln Gln Leu Thr
770                 775                 780

Trp Ser Arg Glu Ser Pro Leu Lys Pro Phe Leu Lys Leu Ser Leu Gly
785                 790                 795                 800

Leu Pro Gly Leu Gly Ile His Met Arg Pro Leu Ala Ile Trp Leu Phe
            805                 810                 815

Ile Phe Asn Val Ser Gln Gln Met Gly Gly Phe Tyr Leu Cys Gln Pro
            820                 825                 830

Gly Pro Pro Ser Glu Lys Ala Trp Gln Pro Gly Trp Thr Val Asn Val
            835                 840                 845

Glu Gly Ser Gly Glu Leu Phe Arg Trp Asn Val Ser Asp Leu Gly Gly
850                 855                 860

Leu Gly Cys Gly Leu Lys Asn Arg Ser Ser Glu Gly Pro Ser Ser Pro
865                 870                 875                 880

Ser Gly Lys Leu Met Ser Pro Lys Leu Tyr Val Trp Ala Lys Asp Arg
            885                 890                 895

Pro Glu Ile Trp Glu Gly Glu Pro Pro Cys Leu Pro Pro Arg Asp Ser
            900                 905                 910

Leu Asn Gln Ser Leu Ser Gln Asp Leu Thr Met Ala Pro Gly Ser Thr
            915                 920                 925

Leu Trp Leu Ser Cys Gly Val Pro Pro Asp Ser Val Ser Arg Gly Pro
930                 935                 940

Leu Ser Trp Thr His Val His Pro Lys Gly Pro Lys Ser Leu Leu Ser
945                 950                 955                 960

Leu Glu Leu Lys Asp Asp Arg Pro Ala Arg Asp Met Trp Val Met Glu
            965                 970                 975

Thr Gly Leu Leu Leu Pro Arg Ala Thr Ala Gln Asp Ala Gly Lys Tyr
            980                 985                 990

Tyr Cys His Arg Gly Asn Leu Thr Met Ser Phe His Leu Glu Ile Thr
            995                 1000                1005

Ala Arg Pro Val Leu Trp His Trp Leu Leu Arg Thr Gly Gly Trp
    1010                1015                1020

Lys Val Ser Ala Val Thr Leu Ala Tyr Leu Ile Phe Cys Leu Cys
```

Ser Leu Val Gly Ile Leu His Leu
       1040                1045

<210> SEQ ID NO 33
<211> LENGTH: 937
<212> TYPE: PRT
<213> ORGANISM: Artificial Sequence
<220> FEATURE:
<223> OTHER INFORMATION: LFTT1 CH3 hIgG4

<400> SEQUENCE: 33

Met Lys Leu Pro Val Arg Leu Leu Val Leu Met Phe Trp Ile Pro Ala
1               5                   10                  15

Ser Ser Ser Asp Ile His Met Thr Gln Ser Pro Ser Ser Leu Ser Ala
            20                  25                  30

Ser Leu Gly Gly Lys Val Thr Ile Thr Cys Lys Ala Ser Gln Asp Ile
        35                  40                  45

Asn Arg Tyr Ile Ala Trp Tyr Gln His Lys Pro Gly Lys Gly Pro Arg
    50                  55                  60

Leu Leu Ile His Phe Thr Ser Thr Leu Gln Ser Gly Ile Pro Ser Arg
65                  70                  75                  80

Phe Ser Gly Ser Gly Ser Gly Arg Asp Tyr Ser Phe Ser Ile Ser Asn
                85                  90                  95

Leu Glu Pro Glu Asp Ile Ala Thr Tyr Tyr Cys Leu Gln Tyr Asp Asp
            100                 105                 110

Leu Arg Thr Phe Gly Gly Gly Thr Lys Leu Glu Ile Lys Gly Gly Gly
        115                 120                 125

Gly Ser Gly Gly Gly Gly Ser Gly Gly Gly Gly Ser Gln Ile Gln Leu
    130                 135                 140

Val Gln Ser Gly Pro Glu Leu Lys Lys Pro Gly Glu Thr Val Lys Ile
145                 150                 155                 160

Ser Cys Lys Ala Ser Gly Tyr Thr Phe Thr Thr Tyr Gly Met Ser Trp
                165                 170                 175

Val Lys Gln Ala Pro Gly Lys Gly Leu Lys Trp Met Gly Trp Ile Tyr
            180                 185                 190

Thr Tyr Ser Gly Val Pro Thr Tyr Ala Asp Asp Leu Glu Gly Arg Phe
        195                 200                 205

Ala Phe Ser Leu Glu Thr Ser Ala Ser Thr Ala Tyr Leu Gln Ile Asn
    210                 215                 220

Asn Leu Lys Asn Glu Asp Thr Ala Thr Tyr Phe Cys Ala Arg Val Arg
225                 230                 235                 240

Asp Gly Tyr Tyr Arg Tyr Ala Met Asp Tyr Trp Gly Gln Gly Thr Ser
                245                 250                 255

Val Thr Val Ser Ser Glu Ser Lys Tyr Gly Pro Pro Cys Pro Pro Cys
            260                 265                 270

Pro Gly Gln Pro Arg Glu Pro Gln Val Tyr Thr Leu Pro Pro Ser Gln
        275                 280                 285

Glu Glu Met Thr Lys Asn Gln Val Ser Leu Thr Cys Leu Val Lys Gly
    290                 295                 300

Phe Tyr Pro Ser Asp Ile Ala Val Glu Trp Glu Ser Asn Gly Gln Pro
305                 310                 315                 320

Glu Asn Asn Tyr Lys Thr Thr Pro Pro Val Leu Asp Ser Asp Gly Ser
                325                 330                 335

Phe Phe Leu Tyr Ser Arg Leu Thr Val Asp Lys Ser Arg Trp Gln Glu

```
                340             345             350
Gly Asn Val Phe Ser Cys Ser Val Met His Glu Ala Leu His Asn His
            355                 360             365

Tyr Thr Gln Lys Ser Leu Ser Leu Ser Leu Gly Lys Phe Trp Val Leu
    370                 375             380

Val Val Val Gly Gly Val Leu Ala Cys Tyr Ser Leu Leu Val Thr Val
385                 390                 395                 400

Ala Phe Ile Ile Phe Trp Val Arg Ser Lys Arg Ser Arg Leu Leu His
                405                 410                 415

Ser Asp Tyr Met Asn Met Thr Pro Arg Arg Pro Gly Pro Thr Arg Lys
            420                 425             430

His Tyr Gln Pro Tyr Ala Pro Pro Arg Asp Phe Ala Ala Tyr Arg Ser
        435                 440                 445

Lys Arg Gly Arg Lys Lys Leu Leu Tyr Ile Phe Lys Gln Pro Phe Met
    450                 455                 460

Arg Pro Val Gln Thr Thr Gln Glu Glu Asp Gly Cys Ser Cys Arg Phe
465                 470                 475                 480

Pro Glu Glu Glu Glu Gly Gly Cys Glu Leu Arg Val Lys Phe Ser Arg
                485                 490                 495

Ser Ala Asp Ala Pro Ala Tyr Gln Gln Gly Gln Asn Gln Leu Tyr Asn
            500                 505                 510

Glu Leu Asn Leu Gly Arg Arg Glu Glu Tyr Asp Val Leu Asp Lys Arg
        515                 520                 525

Arg Gly Arg Asp Pro Glu Met Gly Gly Lys Pro Arg Arg Lys Asn Pro
    530                 535                 540

Gln Glu Gly Leu Tyr Asn Glu Leu Gln Lys Asp Lys Met Ala Glu Ala
545                 550                 555                 560

Tyr Ser Glu Ile Gly Met Lys Gly Glu Arg Arg Arg Gly Lys Gly His
                565                 570                 575

Asp Gly Leu Tyr Gln Gly Leu Ser Thr Ala Thr Lys Asp Thr Tyr Asp
            580                 585                 590

Ala Leu His Met Gln Ala Leu Pro Pro Arg Gly Ser Gly Ala Thr Asn
        595                 600                 605

Phe Ser Leu Leu Lys Gln Ala Gly Asp Val Glu Glu Asn Pro Gly Pro
    610                 615                 620

Met Pro Pro Pro Arg Leu Leu Phe Phe Leu Leu Phe Leu Thr Pro Met
625                 630                 635                 640

Glu Val Arg Pro Glu Glu Pro Leu Val Val Lys Val Glu Glu Gly Asp
                645                 650                 655

Asn Ala Val Leu Gln Cys Leu Lys Gly Thr Ser Asp Gly Pro Thr Gln
            660                 665                 670

Gln Leu Thr Trp Ser Arg Glu Ser Pro Leu Lys Pro Phe Leu Lys Leu
        675                 680                 685

Ser Leu Gly Leu Pro Gly Leu Gly Ile His Met Arg Pro Leu Ala Ile
    690                 695                 700

Trp Leu Phe Ile Phe Asn Val Ser Gln Gln Met Gly Gly Phe Tyr Leu
705                 710                 715                 720

Cys Gln Pro Gly Pro Pro Ser Glu Lys Ala Trp Gln Pro Gly Trp Thr
                725                 730                 735

Val Asn Val Glu Gly Ser Gly Glu Leu Phe Arg Trp Asn Val Ser Asp
            740                 745                 750

Leu Gly Gly Leu Gly Cys Gly Leu Lys Asn Arg Ser Ser Glu Gly Pro
        755                 760                 765
```

```
Ser Ser Pro Ser Gly Lys Leu Met Ser Pro Lys Leu Tyr Val Trp Ala
    770                 775                 780
Lys Asp Arg Pro Glu Ile Trp Glu Gly Glu Pro Cys Leu Pro Pro
785                 790                 795                 800
Arg Asp Ser Leu Asn Gln Ser Leu Ser Gln Asp Leu Thr Met Ala Pro
                805                 810                 815
Gly Ser Thr Leu Trp Leu Ser Cys Gly Val Pro Pro Asp Ser Val Ser
            820                 825                 830
Arg Gly Pro Leu Ser Trp Thr His Val His Pro Lys Gly Pro Lys Ser
            835                 840                 845
Leu Leu Ser Leu Glu Leu Lys Asp Asp Arg Pro Ala Arg Asp Met Trp
    850                 855                 860
Val Met Glu Thr Gly Leu Leu Pro Arg Ala Thr Ala Gln Asp Ala
865                 870                 875                 880
Gly Lys Tyr Tyr Cys His Arg Gly Asn Leu Thr Met Ser Phe His Leu
                885                 890                 895
Glu Ile Thr Ala Arg Pro Val Leu Trp His Trp Leu Leu Arg Thr Gly
            900                 905                 910
Gly Trp Lys Val Ser Ala Val Thr Leu Ala Tyr Leu Ile Phe Cys Leu
    915                 920                 925
Cys Ser Leu Val Gly Ile Leu His Leu
    930                 935
```

<210> SEQ ID NO 34
<211> LENGTH: 830
<212> TYPE: PRT
<213> ORGANISM: Artificial Sequence
<220> FEATURE:
<223> OTHER INFORMATION: LFTT1 hIgG4

<400> SEQUENCE: 34

```
Met Lys Leu Pro Val Arg Leu Leu Val Leu Met Phe Trp Ile Pro Ala
1               5                   10                  15
Ser Ser Ser Asp Ile His Met Thr Gln Ser Pro Ser Ser Leu Ser Ala
                20                  25                  30
Ser Leu Gly Gly Lys Val Thr Ile Thr Cys Lys Ala Ser Gln Asp Ile
            35                  40                  45
Asn Arg Tyr Ile Ala Trp Tyr Gln His Lys Pro Gly Lys Gly Pro Arg
    50                  55                  60
Leu Leu Ile His Phe Thr Ser Thr Leu Gln Ser Gly Ile Pro Ser Arg
65                  70                  75                  80
Phe Ser Gly Ser Gly Ser Gly Arg Asp Tyr Ser Phe Ser Ile Ser Asn
                85                  90                  95
Leu Glu Pro Glu Asp Ile Ala Thr Tyr Tyr Cys Leu Gln Tyr Asp Asp
                100                 105                 110
Leu Arg Thr Phe Gly Gly Gly Thr Lys Leu Glu Ile Lys Gly Gly Gly
            115                 120                 125
Gly Ser Gly Gly Gly Gly Ser Gly Gly Gly Gly Ser Gln Ile Gln Leu
    130                 135                 140
Val Gln Ser Gly Pro Glu Leu Lys Lys Pro Gly Glu Thr Val Lys Ile
145                 150                 155                 160
Ser Cys Lys Ala Ser Gly Tyr Thr Phe Thr Thr Tyr Gly Met Ser Trp
                165                 170                 175
Val Lys Gln Ala Pro Gly Lys Gly Leu Lys Trp Met Gly Trp Ile Tyr
                180                 185                 190
```

```
Thr Tyr Ser Gly Val Pro Thr Tyr Ala Asp Asp Leu Glu Gly Arg Phe
        195                 200                 205

Ala Phe Ser Leu Glu Thr Ser Ala Ser Thr Ala Tyr Leu Gln Ile Asn
        210                 215                 220

Asn Leu Lys Asn Glu Asp Thr Ala Thr Tyr Phe Cys Ala Arg Val Arg
225                 230                 235                 240

Asp Gly Tyr Tyr Arg Tyr Ala Met Asp Tyr Trp Gly Gln Gly Thr Ser
                245                 250                 255

Val Thr Val Ser Ser Glu Ser Lys Tyr Gly Pro Pro Cys Pro Pro Cys
            260                 265                 270

Pro Phe Trp Val Leu Val Val Gly Val Leu Ala Cys Tyr Ser
        275                 280                 285

Leu Leu Val Thr Val Ala Phe Ile Ile Phe Trp Val Arg Ser Lys Arg
        290                 295                 300

Ser Arg Leu Leu His Ser Asp Tyr Met Asn Met Thr Pro Arg Arg Pro
305                 310                 315                 320

Gly Pro Thr Arg Lys His Tyr Gln Pro Tyr Ala Pro Pro Arg Asp Phe
                325                 330                 335

Ala Ala Tyr Arg Ser Lys Arg Gly Arg Lys Lys Leu Leu Tyr Ile Phe
            340                 345                 350

Lys Gln Pro Phe Met Arg Pro Val Gln Thr Thr Gln Glu Glu Asp Gly
        355                 360                 365

Cys Ser Cys Arg Phe Pro Glu Glu Glu Glu Gly Gly Cys Glu Leu Arg
        370                 375                 380

Val Lys Phe Ser Arg Ser Ala Asp Ala Pro Ala Tyr Gln Gln Gly Gln
385                 390                 395                 400

Asn Gln Leu Tyr Asn Glu Leu Asn Leu Gly Arg Arg Glu Glu Tyr Asp
                405                 410                 415

Val Leu Asp Lys Arg Arg Gly Arg Asp Pro Glu Met Gly Gly Lys Pro
            420                 425                 430

Arg Arg Lys Asn Pro Gln Glu Gly Leu Tyr Asn Glu Leu Gln Lys Asp
        435                 440                 445

Lys Met Ala Glu Ala Tyr Ser Glu Ile Gly Met Lys Gly Glu Arg Arg
450                 455                 460

Arg Gly Lys Gly His Asp Gly Leu Tyr Gln Gly Leu Ser Thr Ala Thr
465                 470                 475                 480

Lys Asp Thr Tyr Asp Ala Leu His Met Gln Ala Leu Pro Pro Arg Gly
                485                 490                 495

Ser Gly Ala Thr Asn Phe Ser Leu Leu Lys Gln Ala Gly Asp Val Glu
            500                 505                 510

Glu Asn Pro Gly Pro Met Pro Pro Arg Leu Leu Phe Phe Leu Leu
        515                 520                 525

Phe Leu Thr Pro Met Glu Val Arg Pro Glu Glu Pro Leu Val Val Lys
        530                 535                 540

Val Glu Glu Gly Asp Asn Ala Val Leu Gln Cys Leu Lys Gly Thr Ser
545                 550                 555                 560

Asp Gly Pro Thr Gln Gln Leu Thr Trp Ser Arg Glu Ser Pro Leu Lys
                565                 570                 575

Pro Phe Leu Lys Leu Ser Leu Gly Leu Pro Gly Leu Gly Ile His Met
            580                 585                 590

Arg Pro Leu Ala Ile Trp Leu Phe Ile Phe Asn Val Ser Gln Gln Met
        595                 600                 605
```

Gly Gly Phe Tyr Leu Cys Gln Pro Gly Pro Ser Glu Lys Ala Trp
            610                 615                 620

Gln Pro Gly Trp Thr Val Asn Val Glu Gly Ser Gly Glu Leu Phe Arg
625                 630                 635                 640

Trp Asn Val Ser Asp Leu Gly Leu Gly Cys Gly Leu Lys Asn Arg
                645                 650                 655

Ser Ser Glu Gly Pro Ser Pro Ser Gly Lys Leu Met Ser Pro Lys
            660                 665                 670

Leu Tyr Val Trp Ala Lys Asp Arg Pro Glu Ile Trp Glu Gly Pro
            675                 680                 685

Pro Cys Leu Pro Pro Arg Asp Ser Leu Asn Gln Ser Leu Ser Gln Asp
690                 695                 700

Leu Thr Met Ala Pro Gly Ser Thr Leu Trp Leu Ser Cys Gly Val Pro
705                 710                 715                 720

Pro Asp Ser Val Ser Arg Gly Pro Leu Ser Trp Thr His Val His Pro
                725                 730                 735

Lys Gly Pro Lys Ser Leu Leu Ser Leu Glu Leu Lys Asp Asp Arg Pro
            740                 745                 750

Ala Arg Asp Met Trp Val Met Glu Thr Gly Leu Leu Leu Pro Arg Ala
            755                 760                 765

Thr Ala Gln Asp Ala Gly Lys Tyr Tyr Cys His Arg Gly Asn Leu Thr
770                 775                 780

Met Ser Phe His Leu Glu Ile Thr Ala Arg Pro Val Leu Trp His Trp
785                 790                 795                 800

Leu Leu Arg Thr Gly Gly Trp Lys Val Ser Ala Val Thr Leu Ala Tyr
                805                 810                 815

Leu Ile Phe Cys Leu Cys Ser Leu Val Gly Ile Leu His Leu
            820                 825                 830

<210> SEQ ID NO 35
<211> LENGTH: 1051
<212> TYPE: PRT
<213> ORGANISM: Artificial Sequence
<220> FEATURE:
<223> OTHER INFORMATION: 15E7 CH2CH3 hIgG4

<400> SEQUENCE: 35

Met Lys Leu Pro Val Arg Leu Leu Val Leu Met Phe Trp Ile Pro Ala
1               5                   10                  15

Ser Ser Ser Asp Val Leu Met Thr Gln Ile Pro Phe Ser Leu Pro Val
                20                  25                  30

Ser Leu Gly Asp Gln Ala Ser Ile Ser Cys Arg Ser Ser Gln Ser Ile
            35                  40                  45

Val His Arg Ser Gly Asn Thr Tyr Leu Glu Trp Tyr Leu Gln Lys Pro
        50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Leu Pro Pro Thr Phe Gly Gly Gly Thr Thr Leu
        115                 120                 125

Glu Ile Lys Gly Gly Gly Gly Ser Gly Gly Gly Gly Ser Gly Gly Gly
    130                 135                 140

```
Gly Ser Gln Val Gln Leu Gln Gln Pro Gly Ala Glu Leu Val Arg Pro
145                 150                 155                 160

Gly Ser Ser Val Lys Leu Ser Cys Lys Ala Ser Gly Tyr Thr Phe Thr
                165                 170                 175

Asp Tyr Trp Met Asp Trp Val Lys Gln Arg Pro Gly Gln Gly Leu Glu
            180                 185                 190

Trp Ile Gly Thr Ile Tyr Pro Ser Asp Ser Thr His Tyr Asn Gln
        195                 200                 205

Glu Phe Lys Gly Lys Ala Thr Met Thr Val Asp Lys Ser Ser Ser Thr
    210                 215                 220

Ala Tyr Met His Leu Ser Ser Leu Thr Ser Glu Asp Ser Ala Val Tyr
225                 230                 235                 240

Tyr Cys Ala Arg Glu Gly Leu Ala Gly Val Phe Tyr Phe Asp Tyr Trp
                245                 250                 255

Gly Gln Gly Thr Thr Leu Thr Val Ser Ser Glu Ser Lys Tyr Gly Pro
            260                 265                 270

Pro Cys Pro Pro Cys Pro Ala Pro Val Ala Gly Pro Ser Val Phe
        275                 280                 285

Leu Phe Pro Pro Lys Pro Lys Asp Thr Leu Met Ile Ser Arg Thr Pro
290                 295                 300

Glu Val Thr Cys Val Val Asp Val Ser Gln Glu Asp Pro Glu Val
305                 310                 315                 320

Gln Phe Asn Trp Tyr Val Asp Gly Val Glu Val His Asn Ala Lys Thr
                325                 330                 335

Lys Pro Arg Glu Glu Gln Phe Gln Ser Thr Tyr Arg Val Val Ser Val
            340                 345                 350

Leu Thr Val Leu His Gln Asp Trp Leu Asn Gly Lys Glu Tyr Lys Cys
        355                 360                 365

Lys Val Ser Asn Lys Gly Leu Pro Ser Ser Ile Glu Lys Thr Ile Ser
    370                 375                 380

Lys Ala Lys Gly Gln Pro Arg Glu Pro Gln Val Tyr Thr Leu Pro Pro
385                 390                 395                 400

Ser Gln Glu Glu Met Thr Lys Asn Gln Val Ser Leu Thr Cys Leu Val
                405                 410                 415

Lys Gly Phe Tyr Pro Ser Asp Ile Ala Val Glu Trp Glu Ser Asn Gly
            420                 425                 430

Gln Pro Glu Asn Asn Tyr Lys Thr Thr Pro Pro Val Leu Asp Ser Asp
        435                 440                 445

Gly Ser Phe Phe Leu Tyr Ser Arg Leu Thr Val Asp Lys Ser Arg Trp
450                 455                 460

Gln Glu Gly Asn Val Phe Ser Cys Ser Val Met His Glu Ala Leu His
465                 470                 475                 480

Asn His Tyr Thr Gln Lys Ser Leu Ser Leu Ser Leu Gly Lys Phe Trp
                485                 490                 495

Val Leu Val Val Val Gly Gly Val Leu Ala Cys Tyr Ser Leu Leu Val
            500                 505                 510

Thr Val Ala Phe Ile Ile Phe Trp Val Arg Ser Lys Arg Ser Arg Leu
        515                 520                 525

Leu His Ser Asp Tyr Met Asn Met Thr Pro Arg Arg Pro Gly Pro Thr
    530                 535                 540

Arg Lys His Tyr Gln Pro Tyr Ala Pro Pro Arg Asp Phe Ala Ala Tyr
545                 550                 555                 560

Arg Ser Lys Arg Gly Arg Lys Lys Leu Leu Tyr Ile Phe Lys Gln Pro
```

```
                    565                 570                 575
        Phe Met Arg Pro Val Gln Thr Thr Gln Glu Glu Asp Gly Cys Ser Cys
                        580                 585                 590

Arg Phe Pro Glu Glu Glu Gly Gly Cys Glu Leu Arg Val Lys Phe
                        595                 600                 605

Ser Arg Ser Ala Asp Ala Pro Ala Tyr Gln Gly Gln Asn Gln Leu
                        610                 615                 620

Tyr Asn Glu Leu Asn Leu Gly Arg Arg Glu Glu Tyr Asp Val Leu Asp
        625                 630                 635                 640

Lys Arg Arg Gly Arg Asp Pro Glu Met Gly Gly Lys Pro Arg Arg Lys
                        645                 650                 655

Asn Pro Gln Glu Gly Leu Tyr Asn Glu Leu Gln Lys Asp Lys Met Ala
                        660                 665                 670

Glu Ala Tyr Ser Glu Ile Gly Met Lys Gly Glu Arg Arg Arg Gly Lys
                        675                 680                 685

Gly His Asp Gly Leu Tyr Gln Gly Leu Ser Thr Ala Thr Lys Asp Thr
                        690                 695                 700

Tyr Asp Ala Leu His Met Gln Ala Leu Pro Pro Arg Gly Ser Gly Ala
        705                 710                 715                 720

Thr Asn Phe Ser Leu Leu Lys Gln Ala Gly Asp Val Glu Glu Asn Pro
                        725                 730                 735

Gly Pro Met Pro Pro Pro Arg Leu Leu Phe Phe Leu Leu Phe Leu Thr
                        740                 745                 750

Pro Met Glu Val Arg Pro Glu Glu Pro Leu Val Val Lys Val Glu Glu
                        755                 760                 765

Gly Asp Asn Ala Val Leu Gln Cys Leu Lys Gly Thr Ser Asp Gly Pro
                        770                 775                 780

Thr Gln Gln Leu Thr Trp Ser Arg Glu Ser Pro Leu Lys Pro Phe Leu
        785                 790                 795                 800

Lys Leu Ser Leu Gly Leu Pro Gly Leu Gly Ile His Met Arg Pro Leu
                        805                 810                 815

Ala Ile Trp Leu Phe Ile Phe Asn Val Ser Gln Gln Met Gly Gly Phe
                        820                 825                 830

Tyr Leu Cys Gln Pro Gly Pro Pro Ser Glu Lys Ala Trp Gln Pro Gly
                        835                 840                 845

Trp Thr Val Asn Val Glu Gly Ser Gly Glu Leu Phe Arg Trp Asn Val
                        850                 855                 860

Ser Asp Leu Gly Gly Leu Gly Cys Gly Leu Lys Asn Arg Ser Ser Glu
        865                 870                 875                 880

Gly Pro Ser Ser Pro Ser Gly Lys Leu Met Ser Pro Lys Leu Tyr Val
                        885                 890                 895

Trp Ala Lys Asp Arg Pro Glu Ile Trp Glu Gly Glu Pro Pro Cys Leu
                        900                 905                 910

Pro Pro Arg Asp Ser Leu Asn Gln Ser Leu Ser Gln Asp Leu Thr Met
                        915                 920                 925

Ala Pro Gly Ser Thr Leu Trp Leu Ser Cys Gly Val Pro Pro Asp Ser
                        930                 935                 940

Val Ser Arg Gly Pro Leu Ser Trp Thr His Val His Pro Lys Gly Pro
        945                 950                 955                 960

Lys Ser Leu Leu Ser Leu Glu Leu Lys Asp Asp Arg Pro Ala Arg Asp
                        965                 970                 975

Met Trp Val Met Glu Thr Gly Leu Leu Leu Pro Arg Ala Thr Ala Gln
                        980                 985                 990
```

Asp Ala Gly Lys Tyr Tyr Cys His Arg Gly Asn Leu Thr Met Ser Phe
         995                 1000                1005

His Leu Glu Ile Thr Ala Arg Pro Val Leu Trp His Trp Leu Leu
    1010                1015                1020

Arg Thr Gly Gly Trp Lys Val Ser Ala Val Thr Leu Ala Tyr Leu
    1025                1030                1035

Ile Phe Cys Leu Cys Ser Leu Val Gly Ile Leu His Leu
    1040                1045                1050

<210> SEQ ID NO 36
<211> LENGTH: 942
<212> TYPE: PRT
<213> ORGANISM: Artificial Sequence
<220> FEATURE:
<223> OTHER INFORMATION: 15E7 CH3 hIgG4

<400> SEQUENCE: 36

Met Lys Leu Pro Val Arg Leu Leu Val Leu Met Phe Trp Ile Pro Ala
1               5                   10                  15

Ser Ser Ser Asp Val Leu Met Thr Gln Ile Pro Phe Ser Leu Pro Val
            20                  25                  30

Ser Leu Gly Asp Gln Ala Ser Ile Ser Cys Arg Ser Ser Gln Ser Ile
        35                  40                  45

Val His Arg Ser Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Leu Pro Pro Thr Phe Gly Gly Gly Thr Thr Leu
        115                 120                 125

Glu Ile Lys Gly Gly Gly Gly Ser Gly Gly Gly Gly Ser Gly Gly Gly
    130                 135                 140

Gly Ser Gln Val Gln Leu Gln Gln Pro Gly Ala Glu Leu Val Arg Pro
145                 150                 155                 160

Gly Ser Ser Val Lys Leu Ser Cys Lys Ala Ser Gly Tyr Thr Phe Thr
                165                 170                 175

Asp Tyr Trp Met Asp Trp Val Lys Gln Arg Pro Gly Gln Gly Leu Glu
            180                 185                 190

Trp Ile Gly Thr Ile Tyr Pro Ser Asp Ser Thr His Tyr Asn Gln
        195                 200                 205

Glu Phe Lys Gly Lys Ala Thr Met Thr Val Asp Lys Ser Ser Ser Thr
    210                 215                 220

Ala Tyr Met His Leu Ser Ser Leu Thr Ser Glu Asp Ser Ala Val Tyr
225                 230                 235                 240

Tyr Cys Ala Arg Glu Gly Leu Ala Gly Val Phe Tyr Phe Asp Tyr Trp
                245                 250                 255

Gly Gln Gly Thr Thr Leu Thr Val Ser Ser Glu Ser Lys Tyr Gly Pro
            260                 265                 270

Pro Cys Pro Pro Cys Pro Gly Gln Pro Arg Glu Pro Gln Val Tyr Thr
        275                 280                 285

Leu Pro Pro Ser Gln Glu Glu Met Thr Lys Asn Gln Val Ser Leu Thr
    290                 295                 300

```
Cys Leu Val Lys Gly Phe Tyr Pro Ser Asp Ile Ala Val Glu Trp Glu
305                 310                 315                 320

Ser Asn Gly Gln Pro Glu Asn Asn Tyr Lys Thr Thr Pro Pro Val Leu
                325                 330                 335

Asp Ser Asp Gly Ser Phe Phe Leu Tyr Ser Arg Leu Thr Val Asp Lys
            340                 345                 350

Ser Arg Trp Gln Glu Gly Asn Val Phe Ser Cys Ser Val Met His Glu
        355                 360                 365

Ala Leu His Asn His Tyr Thr Gln Lys Ser Leu Ser Leu Ser Leu Gly
    370                 375                 380

Lys Phe Trp Val Leu Val Val Gly Val Leu Ala Cys Tyr Ser
385                 390                 395                 400

Leu Leu Val Thr Val Ala Phe Ile Ile Phe Trp Val Arg Ser Lys Arg
                405                 410                 415

Ser Arg Leu Leu His Ser Asp Tyr Met Asn Met Thr Pro Arg Arg Pro
            420                 425                 430

Gly Pro Thr Arg Lys His Tyr Gln Pro Tyr Ala Pro Pro Arg Asp Phe
        435                 440                 445

Ala Ala Tyr Arg Ser Lys Arg Gly Arg Lys Lys Leu Leu Tyr Ile Phe
    450                 455                 460

Lys Gln Pro Phe Met Arg Pro Val Gln Thr Thr Gln Glu Glu Asp Gly
465                 470                 475                 480

Cys Ser Cys Arg Phe Pro Glu Glu Glu Glu Gly Gly Cys Glu Leu Arg
                485                 490                 495

Val Lys Phe Ser Arg Ser Ala Asp Ala Pro Ala Tyr Gln Gln Gly Gln
            500                 505                 510

Asn Gln Leu Tyr Asn Glu Leu Asn Leu Gly Arg Arg Glu Glu Tyr Asp
        515                 520                 525

Val Leu Asp Lys Arg Arg Gly Arg Asp Pro Glu Met Gly Gly Lys Pro
    530                 535                 540

Arg Arg Lys Asn Pro Gln Glu Gly Leu Tyr Asn Glu Leu Gln Lys Asp
545                 550                 555                 560

Lys Met Ala Glu Ala Tyr Ser Glu Ile Gly Met Lys Gly Glu Arg Arg
                565                 570                 575

Arg Gly Lys Gly His Asp Gly Leu Tyr Gln Gly Leu Ser Thr Ala Thr
            580                 585                 590

Lys Asp Thr Tyr Asp Ala Leu His Met Gln Ala Leu Pro Pro Arg Gly
        595                 600                 605

Ser Gly Ala Thr Asn Phe Ser Leu Leu Lys Gln Ala Gly Asp Val Glu
    610                 615                 620

Glu Asn Pro Gly Pro Met Pro Pro Arg Leu Leu Phe Phe Leu Leu
625                 630                 635                 640

Phe Leu Thr Pro Met Glu Val Arg Pro Glu Glu Pro Leu Val Val Lys
                645                 650                 655

Val Glu Glu Gly Asp Asn Ala Val Leu Gln Cys Leu Lys Gly Thr Ser
            660                 665                 670

Asp Gly Pro Thr Gln Gln Leu Thr Trp Ser Arg Glu Ser Pro Leu Lys
        675                 680                 685

Pro Phe Leu Lys Leu Ser Leu Gly Leu Pro Gly Leu Gly Ile His Met
    690                 695                 700

Arg Pro Leu Ala Ile Trp Leu Phe Ile Phe Asn Val Ser Gln Gln Met
705                 710                 715                 720
```

-continued

```
Gly Gly Phe Tyr Leu Cys Gln Pro Gly Pro Ser Glu Lys Ala Trp
            725                 730                 735

Gln Pro Gly Trp Thr Val Asn Val Glu Gly Ser Gly Glu Leu Phe Arg
        740                 745                 750

Trp Asn Val Ser Asp Leu Gly Leu Gly Cys Gly Leu Lys Asn Arg
        755                 760                 765

Ser Ser Glu Gly Pro Ser Pro Ser Gly Lys Leu Met Ser Pro Lys
        770                 775                 780

Leu Tyr Val Trp Ala Lys Asp Arg Pro Glu Ile Trp Glu Gly Glu Pro
785                 790                 795                 800

Pro Cys Leu Pro Pro Arg Asp Ser Leu Asn Gln Ser Leu Ser Gln Asp
                805                 810                 815

Leu Thr Met Ala Pro Gly Ser Thr Leu Trp Leu Ser Cys Gly Val Pro
            820                 825                 830

Pro Asp Ser Val Ser Arg Gly Pro Leu Ser Trp Thr His Val His Pro
        835                 840                 845

Lys Gly Pro Lys Ser Leu Leu Ser Leu Glu Leu Lys Asp Asp Arg Pro
        850                 855                 860

Ala Arg Asp Met Trp Val Met Glu Thr Gly Leu Leu Leu Pro Arg Ala
865                 870                 875                 880

Thr Ala Gln Asp Ala Gly Lys Tyr Tyr Cys His Arg Gly Asn Leu Thr
                885                 890                 895

Met Ser Phe His Leu Glu Ile Thr Ala Arg Pro Val Leu Trp His Trp
            900                 905                 910

Leu Leu Arg Thr Gly Gly Trp Lys Val Ser Ala Val Thr Leu Ala Tyr
        915                 920                 925

Leu Ile Phe Cys Leu Cys Ser Leu Val Gly Ile Leu His Leu
        930                 935                 940

<210> SEQ ID NO 37
<211> LENGTH: 835
<212> TYPE: PRT
<213> ORGANISM: Artificial Sequence
<220> FEATURE:
<223> OTHER INFORMATION: 15E7 hIgG4

<400> SEQUENCE: 37

Met Lys Leu Pro Val Arg Leu Leu Val Leu Met Phe Trp Ile Pro Ala
1               5                   10                  15

Ser Ser Ser Asp Val Leu Met Thr Gln Ile Pro Phe Ser Leu Pro Val
            20                  25                  30

Ser Leu Gly Asp Gln Ala Ser Ile Ser Cys Arg Ser Ser Gln Ser Ile
        35                  40                  45

Val His Arg Ser Gly Asn Thr Tyr Leu Glu Trp Tyr Leu Gln Lys Pro
    50                  55                  60

Gly Gln Ser Pro Lys Leu Leu Ile Tyr Lys Val Ser Asn Arg Phe Ser
65                  70                  75                  80

Gly Val Pro Asp Arg Phe Ser Gly Ser Gly Ser Gly Thr Asp Phe Thr
                85                  90                  95

Leu Lys Ile Ser Arg Val Glu Ala Glu Asp Leu Gly Val Tyr Tyr Cys
            100                 105                 110

Phe Gln Gly Ser His Leu Pro Pro Thr Phe Gly Gly Gly Thr Thr Leu
        115                 120                 125

Glu Ile Lys Gly Gly Gly Gly Ser Gly Gly Gly Gly Ser Gly Gly Gly
        130                 135                 140
```

-continued

Gly Ser Gln Val Gln Leu Gln Gln Pro Gly Ala Glu Leu Val Arg Pro
145                 150                 155                 160

Gly Ser Ser Val Lys Leu Ser Cys Lys Ala Ser Gly Tyr Thr Phe Thr
                165                 170                 175

Asp Tyr Trp Met Asp Trp Val Lys Gln Arg Pro Gly Gln Gly Leu Glu
            180                 185                 190

Trp Ile Gly Thr Ile Tyr Pro Ser Asp Ser Thr His Tyr Asn Gln
        195                 200                 205

Glu Phe Lys Gly Lys Ala Thr Met Thr Val Asp Lys Ser Ser Ser Thr
    210                 215                 220

Ala Tyr Met His Leu Ser Ser Leu Thr Ser Glu Asp Ser Ala Val Tyr
225                 230                 235                 240

Tyr Cys Ala Arg Glu Gly Leu Ala Gly Val Phe Tyr Phe Asp Tyr Trp
                245                 250                 255

Gly Gln Gly Thr Thr Leu Thr Val Ser Ser Glu Ser Lys Tyr Gly Pro
            260                 265                 270

Pro Cys Pro Pro Cys Pro Phe Trp Val Leu Val Val Val Gly Gly Val
        275                 280                 285

Leu Ala Cys Tyr Ser Leu Leu Val Thr Val Ala Phe Ile Ile Phe Trp
290                 295                 300

Val Arg Ser Lys Arg Ser Arg Leu Leu His Ser Asp Tyr Met Asn Met
305                 310                 315                 320

Thr Pro Arg Arg Pro Gly Pro Thr Arg Lys His Tyr Gln Pro Tyr Ala
                325                 330                 335

Pro Pro Arg Asp Phe Ala Ala Tyr Arg Ser Lys Arg Gly Arg Lys Lys
            340                 345                 350

Leu Leu Tyr Ile Phe Lys Gln Pro Phe Met Arg Pro Val Gln Thr Thr
        355                 360                 365

Gln Glu Glu Asp Gly Cys Ser Cys Arg Phe Pro Glu Glu Glu Glu Gly
    370                 375                 380

Gly Cys Glu Leu Arg Val Lys Phe Ser Arg Ser Ala Asp Ala Pro Ala
385                 390                 395                 400

Tyr Gln Gln Gly Gln Asn Gln Leu Tyr Asn Glu Leu Asn Leu Gly Arg
                405                 410                 415

Arg Glu Glu Tyr Asp Val Leu Asp Lys Arg Arg Gly Arg Asp Pro Glu
            420                 425                 430

Met Gly Gly Lys Pro Arg Arg Lys Asn Pro Gln Glu Gly Leu Tyr Asn
        435                 440                 445

Glu Leu Gln Lys Asp Lys Met Ala Glu Ala Tyr Ser Glu Ile Gly Met
    450                 455                 460

Lys Gly Glu Arg Arg Arg Gly Lys Gly His Asp Gly Leu Tyr Gln Gly
465                 470                 475                 480

Leu Ser Thr Ala Thr Lys Asp Thr Tyr Asp Ala Leu His Met Gln Ala
                485                 490                 495

Leu Pro Pro Arg Gly Ser Gly Ala Thr Asn Phe Ser Leu Leu Lys Gln
            500                 505                 510

Ala Gly Asp Val Glu Glu Asn Pro Gly Pro Met Pro Pro Pro Arg Leu
        515                 520                 525

Leu Phe Phe Leu Leu Phe Leu Thr Pro Met Glu Val Arg Pro Glu Glu
    530                 535                 540

Pro Leu Val Val Lys Val Glu Glu Gly Asp Asn Ala Val Leu Gln Cys
545                 550                 555                 560

Leu Lys Gly Thr Ser Asp Gly Pro Thr Gln Gln Leu Thr Trp Ser Arg

```
                    565                 570                 575
Glu Ser Pro Leu Lys Pro Phe Leu Lys Leu Ser Leu Gly Leu Pro Gly
                580                 585                 590

Leu Gly Ile His Met Arg Pro Leu Ala Ile Trp Leu Phe Ile Phe Asn
            595                 600                 605

Val Ser Gln Gln Met Gly Gly Phe Tyr Leu Cys Gln Pro Gly Pro Pro
        610                 615                 620

Ser Glu Lys Ala Trp Gln Pro Gly Trp Thr Val Asn Val Glu Gly Ser
625                 630                 635                 640

Gly Glu Leu Phe Arg Trp Asn Val Ser Asp Leu Gly Gly Leu Gly Cys
                645                 650                 655

Gly Leu Lys Asn Arg Ser Ser Glu Gly Pro Ser Ser Pro Ser Gly Lys
            660                 665                 670

Leu Met Ser Pro Lys Leu Tyr Val Trp Ala Lys Asp Arg Pro Glu Ile
        675                 680                 685

Trp Glu Gly Glu Pro Pro Cys Leu Pro Pro Arg Asp Ser Leu Asn Gln
690                 695                 700

Ser Leu Ser Gln Asp Leu Thr Met Ala Pro Gly Ser Thr Leu Trp Leu
705                 710                 715                 720

Ser Cys Gly Val Pro Pro Asp Ser Val Ser Arg Gly Pro Leu Ser Trp
                725                 730                 735

Thr His Val His Pro Lys Gly Pro Lys Ser Leu Leu Ser Leu Glu Leu
            740                 745                 750

Lys Asp Asp Arg Pro Ala Arg Asp Met Trp Val Met Glu Thr Gly Leu
        755                 760                 765

Leu Leu Pro Arg Ala Thr Ala Gln Asp Ala Gly Lys Tyr Tyr Cys His
        770                 775                 780

Arg Gly Asn Leu Thr Met Ser Phe His Leu Glu Ile Thr Ala Arg Pro
785                 790                 795                 800

Val Leu Trp His Trp Leu Leu Arg Thr Gly Gly Trp Lys Val Ser Ala
                805                 810                 815

Val Thr Leu Ala Tyr Leu Ile Phe Cys Leu Cys Ser Leu Val Gly Ile
            820                 825                 830

Leu His Leu
        835

<210> SEQ ID NO 38
<211> LENGTH: 366
<212> TYPE: DNA
<213> ORGANISM: Artificial Sequence
<220> FEATURE:
<223> OTHER INFORMATION: LFFT-1 VH

<400> SEQUENCE: 38
cagattcagc ttgtacaatc tgggcctgag ctgaagaaac ccggagaaac cgtcaagatc      60
agctgcaaag caagtgggta tactttcacg acgtatggca tgtcttgggt caagcaagct     120
cctgggaaag ggctgaaatg gatgggctgg atttacacct attctggagt tcctacatat     180
gccgacgatc tggaagggcg ctttgccttc agcctggaga ctagcgcctc aaccgcttat     240
ttgcagatca caacctcaa gaacgaagat acggcgacct atttctgtgc cagagttcgg     300
gatggctact atagatacgc catggattat tggggccaag gtacatccgt gaccgtttca     360
agctgc                                                                366

<210> SEQ ID NO 39
```

```
<211> LENGTH: 318
<212> TYPE: DNA
<213> ORGANISM: Artificial Sequence
<220> FEATURE:
<223> OTHER INFORMATION: LFFT-1 VL

<400> SEQUENCE: 39
gatatccata tgacccagag tccaagctct ctgagcgcta gcctgggcgg caaagtgacc      60
ataacatgca aggctagcca ggacattaac cggtacatag cctggtacca gcataagccc     120
ggaaaaggcc ccagactgct gatccacttc acctccacac tgcagtccgg gattccctca     180
cgattctccg gatcaggttc aggtcgagac tactccttta gcatttccaa cctcgaacct     240
gaggacatcg ccacatacta ctgtctgcag tatgacgacc ttcgcacttt tggcggtgga     300
actaaactgg agatcaag                                                   318

<210> SEQ ID NO 40
<211> LENGTH: 360
<212> TYPE: DNA
<213> ORGANISM: Artificial Sequence
<220> FEATURE:
<223> OTHER INFORMATION: 1E57 VH

<400> SEQUENCE: 40
caggtgcagt tgcagcaacc cggggccgaa ctggtcagac cgggctcctc tgtgaagctg      60
tcatgcaagg ctagtggcta taccttcacc gactattgga tggattgggt aaagcagcgg     120
ccaggacaag gactggaatg gattgggacc atttacccca gcgacagttc tacgcactac     180
aatcaggagt tcaaaggcaa ggctacaatg acagtggaca gtccagttc  acagcctac      240
atgcaccttt ctagcctcac atcagaggat tccgcagtgt actattgtgc acgtgaaggc     300
ctggctggag tgtttttactt cgactactgg ggacagggga ccaccttgac ggttagctcc     360

<210> SEQ ID NO 41
<211> LENGTH: 339
<212> TYPE: DNA
<213> ORGANISM: Artificial Sequence
<220> FEATURE:
<223> OTHER INFORMATION: 1E57 VL

<400> SEQUENCE: 41
gacgatgtcc tgatgacaca aatcccattt agcctgcctg tatccctggg tgatcaggcc      60
agcattagct gtcgctcctc ccagtccatc gttcaccggt ctggcaacac gtatctggaa     120
tggtacctcc agaaacccgg ccaatcccct aagctcctta tttacaaagt gagcaatcgc     180
ttttctggag tgcctgatag attctcagga agtggttcag aactgactt  caccccttaag    240
attagccggg ttgaggccga ggatcttggt gtgtactact gctttcaagg gagtcacctt     300
cctcccacat ttggcggcgg cacaactctg gagatcaaa                            339

<210> SEQ ID NO 42
<211> LENGTH: 24
<212> TYPE: DNA
<213> ORGANISM: Artificial Sequence
<220> FEATURE:
<223> OTHER INFORMATION: LFFT-1 VH CDR1

<400> SEQUENCE: 42
gggtatactt tcacgacgta tggc                                             24

<210> SEQ ID NO 43
<211> LENGTH: 24
```

```
<212> TYPE: DNA
<213> ORGANISM: Artificial Sequence
<220> FEATURE:
<223> OTHER INFORMATION: LFFT-1 VH CDR2

<400> SEQUENCE: 43
atttacacct attctggagt tcct                                          24

<210> SEQ ID NO 44
<211> LENGTH: 42
<212> TYPE: DNA
<213> ORGANISM: Artificial Sequence
<220> FEATURE:
<223> OTHER INFORMATION: LFFT-1 VH CDR3

<400> SEQUENCE: 44
gccagagttc gggatggcta ctatagatac gccatggatt at                      42

<210> SEQ ID NO 45
<211> LENGTH: 18
<212> TYPE: DNA
<213> ORGANISM: Artificial Sequence
<220> FEATURE:
<223> OTHER INFORMATION: LFFT-1 VL CDR1

<400> SEQUENCE: 45
caggacatta accggtac                                                 18

<210> SEQ ID NO 46
<211> LENGTH: 9
<212> TYPE: DNA
<213> ORGANISM: Artificial Sequence
<220> FEATURE:
<223> OTHER INFORMATION: LFFT-1 VL CDR2

<400> SEQUENCE: 46 ttcacctcc                                                            9

<210> SEQ ID NO 47
<211> LENGTH: 24
<212> TYPE: DNA
<213> ORGANISM: Artificial Sequence
<220> FEATURE:
<223> OTHER INFORMATION: LFFT-1 VL CDR3

<400> SEQUENCE: 47
ctgcagtatg acgaccttcg cact                                          24

<210> SEQ ID NO 48
<211> LENGTH: 24
<212> TYPE: DNA
<213> ORGANISM: Artificial Sequence
<220> FEATURE:
<223> OTHER INFORMATION: 1E57 VH CDR1

<400> SEQUENCE: 48
ggctatacct tcaccgacta ttgg                                          24

<210> SEQ ID NO 49
<211> LENGTH: 24
<212> TYPE: DNA
<213> ORGANISM: Artificial Sequence
<220> FEATURE:
<223> OTHER INFORMATION: 1E57 VH CDR2

<400> SEQUENCE: 49
```
atttacccca gcgacagttc tacg                                           24

<210> SEQ ID NO 50
<211> LENGTH: 39
<212> TYPE: DNA
<213> ORGANISM: Artificial Sequence
<220> FEATURE:
<223> OTHER INFORMATION: 1E57 VH CDR3

<400> SEQUENCE: 50
gcacgtgaag gcctggctgg agtgttttac ttcgactac                           39

<210> SEQ ID NO 51
<211> LENGTH: 33
<212> TYPE: DNA
<213> ORGANISM: Artificial Sequence
<220> FEATURE:
<223> OTHER INFORMATION: 1E57 VL CDR1

<400> SEQUENCE: 51
cagtccatcg ttcaccggtc tggcaacacg tat                                 33

<210> SEQ ID NO 52
<211> LENGTH: 9
<212> TYPE: DNA
<213> ORGANISM: Artificial Sequence
<220> FEATURE:
<223> OTHER INFORMATION: 1E57 VL CDR2

<400> SEQUENCE: 52 aaagtgagc                                                             9

<210> SEQ ID NO 53
<211> LENGTH: 27
<212> TYPE: DNA
<213> ORGANISM: Artificial Sequence
<220> FEATURE:
<223> OTHER INFORMATION: 1E57 VL CDR3

<400> SEQUENCE: 53
tttcaaggga gtcaccttcc tcccaca                                        27

<210> SEQ ID NO 54
<211> LENGTH: 57
<212> TYPE: DNA
<213> ORGANISM: Artificial Sequence
<220> FEATURE:
<223> OTHER INFORMATION: Signal Peptide CD8a

<400> SEQUENCE: 54
atggctctcc ctgtaaccgc actccttctg ccattggctc tcctgcttca tgccgcc       57

<210> SEQ ID NO 55
<211> LENGTH: 270
<212> TYPE: DNA
<213> ORGANISM: Artificial Sequence
<220> FEATURE:
<223> OTHER INFORMATION: CD8a Hinge

<400> SEQUENCE: 55
gccctgtcca acagcattat gtacttctca catttcgttc ctgtgtttct gcccgcaaaa    60
cctactacaa ccctgccccc tcgaccacca actccagctc ccactatagc ctctcagccc   120
ctgtctctca gaccagaggc ctgtaggcct gctgcgggag gagccgtgca tacccgcggg   180
ttggacttcg cctgcgattt ctgggtgctg gttgtagtag gcggagtctt ggcctgttat   240
tcactgttgg ttacagtggc ctttatcata                                      270

<210> SEQ ID NO 56
<211> LENGTH: 192
<212> TYPE: DNA
<213> ORGANISM: Artificial Sequence
<220> FEATURE:
<223> OTHER INFORMATION: CD28 Hinge

<400> SEQUENCE: 56
aagatcgaag tgatgtaccc tcctccctat ctcgacaatg agaaatccaa tggaaccatt      60
atacacgtca aggggaagca cctgtgtccc agccctctgt tccgggaccc tctaaaccca    120
ttttgggtgc tggtggtggt aggaggagtt ctcgcgtgct atagcctgtt ggtgactgtc    180
gcattcatca tc                                                         192

<210> SEQ ID NO 57
<211> LENGTH: 204
<212> TYPE: DNA
<213> ORGANISM: Artificial Sequence
<220> FEATURE:
<223> OTHER INFORMATION: CD28 human

<400> SEQUENCE: 57
ttttgggtgc tggtggtggt gggaggcgtg ctggcctgtt attctctgct ggtgaccgtg      60
gccttcatca tcttttgggt gcgcagcaag cggagccggc tgctgcactc cgactacatg    120
aacatgaccc caagacggcc cggaccaaca aggaagcact accagcctta tgcaccaccc    180
cgcgattttg cagcataccg gagc                                           204

<210> SEQ ID NO 58
<211> LENGTH: 126
<212> TYPE: DNA
<213> ORGANISM: Artificial Sequence
<220> FEATURE:
<223> OTHER INFORMATION: 4-1BB human

<400> SEQUENCE: 58
aagagaggca ggaagaagct gctgtatatc ttcaagcagc ccttcatgcg gcccgtgcag      60
accacacagg aggaggacgg ctgctcctgt aggttccctg aagaggagga gggaggatgc    120
gagctg                                                                126

<210> SEQ ID NO 59
<211> LENGTH: 336
<212> TYPE: DNA
<213> ORGANISM: Artificial Sequence
<220> FEATURE:
<223> OTHER INFORMATION: CD3z human endodomain

<400> SEQUENCE: 59
agagtgaagt tttctaggag cgccgatgca ccagcatacc agcagggaca gaatcagctg      60
tataacgagc tgaatctggg caggcgcgag gagtacgacg tgctggataa gaggagagga    120
cgggaccccg agatggggag caagccaagg cgcaagaacc cccaggaggg cctgtacaat    180
gagctgcaga aggacaagat ggccgaggcc tatagcgaga tcggcatgaa gggagagcgg    240
agaaggggca agggacacga tggcctgtac cagggcctgt ccaccgccac aaaggacacc    300
tatgatgccc tgcacatgca ggccctgcct ccaagg                              336

<210> SEQ ID NO 60

```
<211> LENGTH: 24
<212> TYPE: DNA
<213> ORGANISM: Artificial Sequence
<220> FEATURE:
<223> OTHER INFORMATION: Flag Tag

<400> SEQUENCE: 60
gattacaagg atgacgacga caaa                                     24

<210> SEQ ID NO 61
<211> LENGTH: 57
<212> TYPE: DNA
<213> ORGANISM: Artificial Sequence
<220> FEATURE:
<223> OTHER INFORMATION: Mouse IgKappa Signal Peptide

<400> SEQUENCE: 61
atgaaactgc ccgtgagact gctggtgctg atgttttgga ttcccgcttc ctcgagc  57

<210> SEQ ID NO 62
<211> LENGTH: 36
<212> TYPE: DNA
<213> ORGANISM: Artificial Sequence
<220> FEATURE:
<223> OTHER INFORMATION: Hinge hIgG4

<400> SEQUENCE: 62
gagagcaagt acggcccacc ctgccctcca tgtcca                        36

<210> SEQ ID NO 63
<211> LENGTH: 327
<212> TYPE: DNA
<213> ORGANISM: Artificial Sequence
<220> FEATURE:
<223> OTHER INFORMATION: Mutated CH2 human IgG4

<400> SEQUENCE: 63
gcaccacctg tggcaggacc ttccgtgttc ctgtttccac ccaagcctaa ggacacactg  60
atgatctccc ggaccccaga ggtgacatgc gtggtggtgg acgtgtctca ggaggacccc  120
gaggtgcagt tcaactggta cgtggatggc gtggaggtgc acaatgccaa gaccaagccc  180
cgcgaggagc agtttcagtc cacctaccgg gtggtgtctg tgctgacagt gctgcaccag  240
gactggctga acggcaagga gtataagtgc aaggtgagca taagggcct gccttcctct  300 atcgagaaga ccatctccaa ggccaag                                    327

<210> SEQ ID NO 64
<211> LENGTH: 321
<212> TYPE: DNA
<213> ORGANISM: Artificial Sequence
<220> FEATURE:
<223> OTHER INFORMATION: CH3 human IgG4

<400> SEQUENCE: 64
ggccagccca gagagcctca ggtgtacaca ctgcctccat ctcaggagga gatgaccaag  60
aaccaggtga gcctgacatg tctggtgaag ggcttctatc catccgacat cgccgtggag  120
tgggagtcta atggccagcc cgagaacaat tacaagacca caccccctgt gctggactcc  180
gatggctctt tctttctgta ttctcgcctg accgtggata gagccggtg gcaggagggc  240 aacgtgttca gctgctccgt gatgcacgag gccctgcaca atcactacac acagaagtct  300
ctgagcctgt ccctgggcaa g                                          321
```

<210> SEQ ID NO 65
<211> LENGTH: 57
<212> TYPE: DNA
<213> ORGANISM: Artificial Sequence
<220> FEATURE:
<223> OTHER INFORMATION: P2A Cleavage peptide

<400> SEQUENCE: 65
gccacaaact tctccctgct gaagcaggcc ggcgatgtgg aggagaatcc tggacca      57

<210> SEQ ID NO 66
<211> LENGTH: 939
<212> TYPE: DNA
<213> ORGANISM: Artificial Sequence
<220> FEATURE:
<223> OTHER INFORMATION: Truncated human CD19 Reporter

<400> SEQUENCE: 66
atgccacctc caaggctgct gttctttctg ctgtttctga ccccaatgga ggtgcggcca      60
gaggagccac tggtggtgaa ggtggaggag ggcgacaacg ccgtgctgca gtgtctgaag     120
ggcacaagcg atggccctac ccagcagctg acatggtcta gagagagccc tctgaagcca     180
ttcctgaagc tgtccctggg cctgccaggc ttaggaatcc atatgaggcc cctggctatc     240
tggctgttta tcttcaacgt gagccagcag atgggaggct ctatctgtg ccagccagga     300 ccacctagcg agaaggcatg gcagcctgga tggaccgtga acgtggaggg cagcggagag     360
ctgtttcgct ggaacgtgag cgacctggga ggcctgggat gtggcctgaa aaccggagc     420 tccgagggac cctctagccc tagcggcaag ctgatgtccc caaagctgta cgtgtgggcc     480
aaggatagac cagagatctg ggagggagag ccaccatgcc tgcctccaag ggacagcctg     540
aatcagtccc tgtctcagga tctgaccatg gcccccggct ctacactgtg gctgagctgt     600
ggagtgccac ctgacagcgt gtcccggggc cctctgagct ggacccacgt gcacccaaag     660
ggccccaagt ccctgctgtc tctggagctg aaggacgatc gccctgcccg ggacatgtgg     720
gtcatggaga caggcctgct gctgccacgc gccacagcac aggatgccgg caagtactat     780
tgccaccggg gcaacctgac catgagcttc cacctggaga tcacagccag acccgtgctg     840
tggcactggc tgctgaggac cggaggatgg aaggtgtccg ccgtgaccct ggcataccctg     900 attttctgtc tgtgctccct ggtgggcatc ctgcacctg                            939

<210> SEQ ID NO 67
<211> LENGTH: 741
<212> TYPE: DNA
<213> ORGANISM: Artificial Sequence
<220> FEATURE:
<223> OTHER INFORMATION: ScFV 15E7

<400> SEQUENCE: 67
gatgtgctga tgacccagat tccctttagc ctgccagtga gcctgggcga ccaggcctcc      60
atctcttgca gaagctccca gtccatcgtg cacaggtctg gcaacaccta cctggagtgg     120
tatctgcaga agcctggcca gtccccaaag ctgctgatct acaaggtgag caatagattc     180
tccggagtgc cagacaggtt tagcggctcc ggctctggca ccgatttcac actgaagatc     240
tcccgcgtgg aggcagagga tctgggcgtg tactattgct tccagggctc tcacctgccc     300
cctacatttg gcggcggcac cacactggag atcaagggag gaggaggcag cggcggagga     360
ggctccggcg gcggcggctc tcaggtgcag ctgcagcagc ctggagcaga gctggtgcgg     420
cccggctcta gcgtgaagct gtcttgtaag gccagcggct acaccttcac agactattgg     480

| | |
|---|---|
| atggattggg tgaagcagag gcctggacag ggcctggagt ggatcggcac catctaccca | 540 |
| agcgactcct ctacacacta taaccaggag tttaagggca aggccaccat gacagtggac | 600 |
| aagagctcct ctaccgccta tatgcacctg agctccctga catctgagga tagcgccgtg | 660 |
| tactattgcg cccgcgaggg cctggccggc gtgttctact ttgattattg gggccagggc | 720 |
| accacactga ccgtctcgag c | 741 |

<210> SEQ ID NO 68
<211> LENGTH: 726
<212> TYPE: DNA
<213> ORGANISM: Artificial Sequence
<220> FEATURE:
<223> OTHER INFORMATION: ScFV LFTT1

<400> SEQUENCE: 68

| | |
|---|---|
| gatattcaca tgactcagag ccctagttca ctgtccgcct cactgggggg aaaagtcacc | 60 |
| atcacctgta aagcatctca ggacatcaac aggtacatcg cctggtatca gcacaagcca | 120 |
| ggcaagggac ctaggctgct gatccacttc acctctacac tgcagagcgg catcccctcc | 180 |
| cggttcagcg gctccggctc tggaagagac tacagctttt ccatctctaa tctggagcct | 240 |
| gaggatatcg ccacctacta ttgcctgcag tatgacgatc tgcggacctt tggcggcggc | 300 |
| acaaagctgg agatcaaggg aggaggaggc tccggcggag aggctctgg cggcggcggc | 360 |
| agccagatcc agctggtgca gagcggccca gagctgaaga agcccggcga cagtgaagag | 420 |
| atctcttgta aggccagcgg ctacacattc accacatatg gcatgtcctg ggtgaagcag | 480 |
| gcacctggca agggcctgaa gtggatgggc tggatctaca cctattccgg cgtgccaaca | 540 |
| tacgccgacg atctggaggg ccggttcgcc ttttctctgg agacaagcgc cagcaccgcc | 600 |
| tacctgcaga tcaacaatct gaagaacgag gacaccgcca tattttgg cgccaggtg | 660 |
| cgggatggct attacagata cgctatggac tattggggac aggggacctc agtgactgtc | 720 |
| tcgagc | 726 |

<210> SEQ ID NO 69
<211> LENGTH: 3141
<212> TYPE: DNA
<213> ORGANISM: Artificial Sequence
<220> FEATURE:
<223> OTHER INFORMATION: LFTT1 HingeCH2CH3 hIgG4

<400> SEQUENCE: 69

| | |
|---|---|
| atgaaactgc ccgtgagact gctggtgctg atgttttgga ttcccgcttc ctcgagcgat | 60 |
| attcacatga ctcagagccc tagttcactg tccgcctcac tggggggaa agtcaccatc | 120 |
| acctgtaaag catctcagga catcaacagg tacatcgcct ggtatcagca caagccaggc | 180 |
| aagggaccta ggctgctgat ccacttcacc tctacactgc agagcggcat ccctcccgg | 240 |
| ttcagcggct ccggctctgg aagagactac agcttttcca tctctaatct ggagcctgag | 300 |
| gatatcgcca cctactattg cctgcagtat gacgatctgc ggacctttgg cggcggcaca | 360 |
| aagctggaga tcaagggagg aggaggctcc ggcggaggag gctctggcgg cggcggcagc | 420 |
| cagatccagc tggtgcagag cggcccagag ctgaagaagc ccggcgagac agtgaagatc | 480 |
| tcttgtaagg ccagcggcta cacattcacc acatatggca tgtcctgggt gaagcaggca | 540 |
| cctggcaagg gcctgaagtg gatgggctgg atctacacct attccggcgt gccaacatac | 600 |
| gccgacgatc tggagggccg gttcgccttt tctctggaga caagcgccag caccgcctac | 660 |
| ctgcagatca acaatctgaa gaacgaggac accgccacat attttgcgc cagggtgcgg | 720 |

```
gatggctatt acagatacgc tatggactat tggggacagg ggacctcagt gactgtctcg    780
agcgagagca agtacggccc accctgccct ccatgtccag caccacctgt ggcaggacct    840
tccgtgttcc tgtttccacc caagcctaag gacacactga tgatctcccg gacccccagag   900 gtgacatgcg tggtggtgga cgtgtctcag gaggacccccg aggtgcagtt caactggtac   960
gtggatggcg tggaggtgca caatgccaag accaagcccc gcgaggagca gtttcagtcc   1020
acctaccggg tggtgtctgt gctgacagtg ctgcaccagg actggctgaa cggcaaggag   1080
tataagtgca aggtgagcaa taagggcctg ccttcctcta tcgagaagac catctccaag   1140
gccaagggcc agcccagaga gcctcaggtg tacacactgc ctccatctca ggaggagatg   1200
accaagaacc aggtgagcct gacatgtctg gtgaagggct ctatccatc gacatcgcc    1260 gtggagtggg agtctaatgg ccagcccgag aacaattaca agaccacacc ccctgtgctg   1320
gactccgatg gctctttctt tctgtattct cgcctgaccg tggataagag ccggtggcag   1380
gagggcaacg tgttcagctg ctccgtgatg cacgaggccc tgcacaatca ctacacacag   1440
aagtctctga gcctgtccct gggcaagttt tgggtgctgg tggtggtggg aggcgtgctg   1500
gcctgttatt ctctgctggt gaccgtggcc ttcatcatct tttgggtgcg cagcaagcgg   1560
agccggctgc tgcactccga ctacatgaac atgaccccaa gacggcccgg accaacaagg   1620
aagcactacc agcctatgc accacccgc gatttttgcag cataccggag caagagaggc   1680
aggaagaagc tgctgtatat cttcaagcag cccttcatgc ggcccgtgca gaccacacag   1740
gaggaggacg gctgctcctg taggttccct gaagaggagg agggaggatg cgagctgaga   1800
gtgaagtttt ctaggagcgc cgatgcacca gcataccagc agggacagaa tcagctgtat   1860
aacgagctga atctgggcag gcgcgaggag tacgacgtgc tggataagag gagaggacgg   1920
gaccccgaga tgggaggcaa gccaaggcgc aagaaccccc aggagggcct gtacaatgag   1980
ctgcagaagg acaagatggc cgaggcctat agcgagatcg gcatgaaggg agagcggaga   2040
aggggcaagg gacacgatgg cctgtaccag ggcctgtcca ccgccacaaa ggacacctat   2100
gatgccctgc acatgcaggc cctgcctcca aggggcagcg agccacaaa ctttctccctg   2160 ctgaagcagg ccggcgatgt ggaggagaat cctggaccaa tgccacctcc aaggctgctg   2220
ttctttctgc tgtttctgac cccaatggag gtgcggccag aggagccact ggtggtgaag   2280
gtggaggagg cgacaacgc cgtgctgcag tgtctgaagg cacaagcga tggccctacc   2340 cagcagctga catggtctag agagagccct ctgaagccat tcctgaagct gtccctgggc   2400
ctgccaggct taggaatcca tatgaggccc ctggctatct ggctgtttat cttcaacgtg   2460
agccagcaga tgggaggctt ctatctgtgc cagccaggac cacctagcga aaggcatgg   2520 cagcctggat ggaccgtgaa cgtggaggc agcgagagc tgtttcgctg gaacgtgagc   2580
gacctgggag gctgggatg tggcctgaag aaccggagct ccgagggacc ctctagccct   2640
agcggcaagc tgatgtcccc aaagctgtac gtgtgggcca aggatagacc agagatctgg   2700
gagggagagc caccatgcct gcctccaagg gacagcctga tcagtccct gtctcaggat   2760 ctgaccatgg ccccccggctc tacactgtgg ctgagctgtg gagtgccacc tgacagcgtg   2820 tcccgggggcc ctctgagctg gacccacgtg cacccaaagg gccccaagtc cctgctgtct   2880
ctggagctga aggacgatcg ccctgcccgg gacatgtggg tcatggagac aggcctgctg   2940
ctgccacgcg ccacagcaca ggatgccggc aagtactatt gccaccgggg caacctgacc   3000
atgagcttcc acctggagat cacagccaga cccgtgctgt ggcactggct gctgaggacc   3060
```

```
ggaggatgga aggtgtccgc cgtgaccctg gcatacctga ttttctgtct gtgctccctg   3120
gtgggcatcc tgcacctgtg a                                              3141

<210> SEQ ID NO 70
<211> LENGTH: 2814
<212> TYPE: DNA
<213> ORGANISM: Artificial Sequence
<220> FEATURE:
<223> OTHER INFORMATION: LFTT1 CH3 hIgG4

<400> SEQUENCE: 70
atgaaactgc cgtgagagact gctggtgctg atgttttgga ttcccgcttc ctcgagcgat     60
attcacatga ctcagagccc tagttcactg tccgcctcac tgggggggaa agtcaccatc    120
acctgtaaag catctcagga catcaacagg tacatcgcct ggtatcagca aagccaggc     180 aagggaccta ggctgctgat ccacttcacc tctacactgc agagcggcat ccctcccgg     240 ttcagcggct ccggctctgg aagagactac agcttttcca tctctaatct ggagcctgag    300
gatatcgcca cctactattg cctgcagtat gacgatctgc cggacctttgg cggcggcaca   360 aagctggaga tcaagggagg aggaggctcc ggcggaggag gctctggcgg cggcggcagc    420
cagatccagc tggtgcagag cggcccagag ctgaagaagc ccggcgagac agtgaagatc    480
tcttgtaagg ccagcggcta cacattcacc acatatggca tgtcctgggt gaagcaggca    540
cctggcaagg gcctgaagtg gatgggctgg atctacacct attccggcgt gccaacatac    600
gccgacgatc tggagggccg gttcgccttt tctctggaga caagcgccag caccgcctac    660
ctgcagatca caatctgaa gaacgaggac accgccacat tttttgcgc cagggtgcgg     720 gatggctatt acagatacgc tatggactat ggggacaggg gacctcagt gactgtctcg     780 agcgagagca gtacggcccc acctgccct ccatgtccag ccagcccag agagcctcag      840 gtgtacacac tgcctccatc tcaggaggag atgaccaaga accaggtgag cctgacatgt    900
ctggtgaagg gcttctatcc atccgacatc gccgtggagt gggagtctaa tggccagccc    960
gagaacaatt acaagaccac ccccctgtg ctggactccg atggctcttt ctttctgtat    1020
tctcgcctga ccgtggataa gagccggtgg caggagggca acgtgttcag ctgctccgtg   1080
atgcacgagg ccctgcacaa tcactacaca cagaagtctc tgagcctgtc cctgggcaag    1140
ttttgggtgc tggtggtggt gggaggcgtg ctggcctgtt attctctgct ggtgaccgtg   1200
gccttcatca tcttttgggt gcgcagcaag cggagccggc tgctgcactc cgactacatg    1260
aacatgaccc caagacggcc cggaccaaca aggaagcact accagcctta tgcaccaccc    1320
cgcgattttg cagcataccg gagcaagaga ggcaggaaga agctgctgta tatcttcaag    1380
cagcccttca tgcggcccgt gcagaccaca caggaggagg acggctgctc ctgtaggttc    1440
cctgaagagg aggagggagg atgcgagctg agagtgaagt ttctaggag cgccgatgca    1500 ccagcatacc agcagggaca gaatcagctg tataacgagc tgaatctggg caggcgcgag    1560
gagtacgacg tgctggataa gaggagagga cgggaccccg atgggagg caagccaagg    1620 cgcaagaacc cccaggaggg cctgtacaat gagctgcaga aggacaagat ggccgaggcc   1680
tatagcgaga tcggcatgaa gggagagcgg agaaggggca aggacacga tggcctgtac    1740 cagggcctgt ccaccgccac aaaggacacc tatgatgccc tgcacatgca ggccctgcct    1800 ccaagggca gcgagccac aaacttctcc ctgctgaagc aggccggcga tgtggaggag    1860
aatcctggac caatgccacc tccaaggctg ctgttctttc tgctgtttct gacccaatg    1920 gaggtgcggc cagaggagcc actggtggtg aaggtggagg agggcgacaa cgccgtgctg   1980
```

| | |
|---|---|
| cagtgtctga agggcacaag cgatggccct acccagcagc tgacatggtc tagagagagc | 2040 |
| cctctgaagc cattcctgaa gctgtccctg ggcctgccag gcttaggaat ccatatgagg | 2100 |
| cccctggcta tctggctgtt tatcttcaac gtgagccagc agatgggagg cttctatctg | 2160 |
| tgccagccag gaccacctag cgagaaggca tggcagcctg gatggaccgt gaacgtggag | 2220 |
| ggcagcggag agctgtttcg ctggaacgtg agcgacctgg gaggcctggg atgtggcctg | 2280 |
| aagaaccgga gctccgaggg accctctagc cctagcggca agctgatgtc cccaaagctg | 2340 |
| tacgtgtggg ccaaggatag accagagatc tgggagggag agccaccatg cctgcctcca | 2400 |
| agggacagcc tgaatcagtc cctgtctcag gatctgacca tggcccccgg ctctacactg | 2460 |
| tggctgagct gtggagtgcc acctgacagc gtgtcccggg gccctctgag ctggacccac | 2520 |
| gtgcacccaa agggccccaa gtccctgctg tctctggagc tgaaggacga tcgccctgcc | 2580 |
| cgggacatgt gggtcatgga gacaggcctg ctgctgccac gcgccacagc acaggatgcc | 2640 |
| ggcaagtact attgccaccg gggcaacctg accatgagct ccacctggga gatcacagcc | 2700 |
| agaccgtgc tgtggcactg gctgctgagg accggaggat ggaaggtgtc cgccgtgacc | 2760 |
| ctggcatacc tgattttctg tctgtgctcc ctggtgggca tcctgcacct gtga | 2814 |

<210> SEQ ID NO 71
<211> LENGTH: 2493
<212> TYPE: DNA
<213> ORGANISM: Artificial Sequence
<220> FEATURE:
<223> OTHER INFORMATION: LFTT1 hIgG4

<400> SEQUENCE: 71

| | |
|---|---|
| atgaaactgc ccgtgagact gctggtgctg atgttttgga ttcccgcttc ctcgagcgat | 60 |
| attcacatga ctcagagccc tagttcactg tccgcctcac tgggggggaa agtcaccatc | 120 |
| acctgtaaag catctcagga catcaacagg tacatcgcct ggtatcagca caagccaggc | 180 |
| aagggaccta ggctgctgat ccacttcacc tctacactgc agagcggcat cccctcccgg | 240 |
| ttcagcggct ccggctctgg aagagactac agcttttcca tctctaatct ggagcctgag | 300 |
| gatatcgcca cctactattg cctgcagtat gacgatctgc ggacctttgg cggcggcaca | 360 |
| aagctggaga tcaagggagg aggaggctcc ggcggaggag gctctggcgg cggcggcagc | 420 |
| cagatccagc tggtgcagag cggccccgag ctgaagaagc ccggcgagac agtgaagatc | 480 |
| tcttgtaagg ccagcggcta cacattcacc acatatggca tgtcctgggt gaagcaggca | 540 |
| cctggcaagg gcctgaagtg gatgggctgg atctacacct attccggcgt gccaacatac | 600 |
| gccgacgatc tggagggccg gttcgccttt ctctctggaga caagcgccag caccgcctac | 660 |
| ctgcagatca caatctgaa gaacgaggac accgccacat attttgcgc cagggtgcgg | 720 |
| gatggctatt acagatacgc tatggactat ggggacaggg gacctcagt gactgtctcg | 780 |
| agcgagagca agtacggccc accctgccct ccatgtccat ttgggtgct ggtggtggtg | 840 |
| ggaggcgtgc tggcctgtta ttctctgctg gtgaccgtgg ccttcatcat cttttgggtg | 900 |
| cgcagcaagc ggagccggct gctgcactcc gactacatga acatgacccc aagacggccc | 960 |
| ggaccaacaa ggaagcacta ccagcccttat gcaccacccc gcgattttgc agcataccgg | 1020 |
| agcaagagag gcaggaagaa gctgctgtat atcttcaagc agcccttcat gcggcccgtg | 1080 |
| cagaccacac aggaggagga cggctgctcc tgtaggttcc ctgaagagga ggagggagga | 1140 |
| tgcgagctga gagtgaagtt ttctaggagc gccgatgcac cagcatacca gcagggacag | 1200 |

```
aatcagctgt ataacgagct gaatctgggc aggcgcgagg agtacgacgt gctggataag    1260
aggagaggac gggaccccga gatgggaggc aagccaaggc gcaagaaccc ccaggagggc    1320
ctgtacaatg agctgcagaa ggacaagatg gccgaggcct atagcgagat cggcatgaag    1380
ggagagcgga gaaggggcaa gggacacgat ggcctgtacc agggcctgtc caccgccaca    1440
aaggacacct atgatgccct gcacatgcag gccctgcctc aaggggcag cggagccaca    1500
aacttctccc tgctgaagca ggccggcgat gtggaggaga atcctggacc aatgccacct    1560
ccaaggctgc tgttctttct gctgtttctg accccaatgg aggtgcggcc agaggagcca    1620
ctggtggtga aggtgcagga gggcgacaac gccgtgctgc agtgtctgaa gggcacaagc    1680
gatggcccta cccagcagct gacatggtct agagagagcc ctctgaagcc attcctgaag    1740
ctgtccctgg gcctgccagg cttaggaatc catatgaggc ccctggctat ctggctgttt    1800
atcttcaacg tgagccagca gatgggaggc ttctatctgt gccagccagg accacctagc    1860
gagaaggcat ggcagcctgg atggaccgtg aacgtggagg gcagcggaga gctgtttcgc    1920
tggaacgtga gcgacctggg aggcctggga tgtggcctga gaaccggag ctccgaggga    1980
ccctctagcc ctagcggcaa gctgatgtcc ccaaagctgt acgtgtgggc caaggataga    2040
ccagagatct gggagggaga gccaccatgc ctgcctccaa gggacagcct gaatcagtcc    2100
ctgtctcagg atctgaccat ggccccggc tctacactgt ggctgagctg tggagtgcca    2160
cctgacagcg tgtcccgggg ccctctgagc tggacccacg tgcacccaaa gggccccaag    2220
tccctgctgt ctctggagct gaaggacgat cgccctgccc gggacatgtg ggtcatggag    2280
acaggcctgc tgctgccacg cgccacagca caggatgccg gcaagtacta ttgccaccgg    2340
ggcaacctga ccatgagctt ccacctggag atcacagcca gacccgtgct gtggcactgg    2400
ctgctgagga ccggaggatg gaaggtgtcc gccgtgaccc tggcatacct gattttctgt    2460
ctgtgctccc tggtgggcat cctgcacctg tga                                 2493

<210> SEQ ID NO 72
<211> LENGTH: 3156
<212> TYPE: DNA
<213> ORGANISM: Artificial Sequence
<220> FEATURE:
<223> OTHER INFORMATION: 15E7 CH2CH3 hIgG4

<400> SEQUENCE: 72
atgaaactgc ccgtgagact gctggtgctg atgttttgga ttcccgcttc ctcgagcgat     60
gtgctgatga cccagattcc ctttagcctg ccagtgagcc tgggcgacca ggcctccatc    120
tcttgcagaa gctcccagtc catcgtgcac aggtctggca cacctacct ggagtggtat    180
ctgcagaagc ctggccagtc cccaaagctg ctgatctaca aggtgagcaa tagattctcc    240
ggagtgccag acaggtttag cggctccggc tctggcaccg atttcacact gaagatctcc    300
cgcgtggagg cagaggatct gggcgtgtac tattgcttcc agggctctca cctgcccct    360
acatttggcg gcggcaccac actggagatc aaggaggag gagcagcgg cggaggaggc    420
tccggcggcg gcggctctca ggtgcagctg cagcagcctg gagcagagct ggtgcggccc    480
ggctctagcg tgaagctgtc ttgtaaggcc agcggctaca ccttcacaga ctattggatg    540
gattgggtga agcagaggcc tggacagggc ctggagtgga tcggcaccat ctacccaagc    600
gactcctcta cacactataa ccaggagttt aagggcaagg ccaccatgac agtggacaag    660
agctcctcta ccgcctatat gcacctgagc tccctgacat ctgaggatag cgccgtgtac    720
tattgcgccc gcgagggcct ggccggcgtg ttctactttg attattgggg ccagggcacc    780
```

```
acactgaccg tctcgagcga gagcaagtac ggcccaccct gccctccatg tccagcacca    840
cctgtggcag gaccttccgt gttcctgttt ccacccaagc ctaaggacac actgatgatc    900
tcccggaccc cagaggtgac atgcgtggtg gtggacgtgt ctcaggagga ccccgaggtg    960
cagttcaact ggtacgtgga tggcgtggag gtgcacaatg ccaagaccaa gccccgcgag   1020
gagcagtttc agtccaccta ccgggtggtg tctgtgctga cagtgctgca ccaggactgg   1080
ctgaacggca aggagtataa gtgcaaggtg agcaataagg gcctgccttc ctctatcgag   1140
aagaccatct ccaaggccaa gggccagccc agagagcctc aggtgtacac actgcctcca   1200
tctcaggagg agatgaccaa gaaccaggtg agcctgacat gtctggtgaa gggcttctat   1260
ccatccgaca tcgccgtgga gtgggagtct aatggccagc ccgagaacaa ttacaagacc   1320
acccccctg tgctggactc cgatggctct ttctttctgt attctcgcct gaccgtggat   1380
aagagccggt ggcaggaggg caacgtgttc agctgctccg tgatgcacga ggccctgcac   1440
aatcactaca cacagaagtc tctgagcctg tccctgggca gttttgggt gctggtggtg   1500
gtgggaggcg tgctggcctg ttattctctg ctggtgaccg tggccttcat catcttttgg   1560
gtgcgcagca gcggagccg gctgctgcac tccgactaca tgaacatgac cccaagacgg   1620
cccggaccaa caaggaagca ctaccagcct tatgcaccac cccgcgattt tgcagcatac   1680
cggagcaaga gaggcaggaa gaagctgctg tatatcttca gcagcccctt catgcggccc   1740
gtgcagacca cacaggagga ggacggctgc tcctgtaggt tccctgaaga ggaggaggga   1800
ggatgcgagc tgagagtgaa gttttctagg agcgccgatg caccagcata ccagcaggga   1860
cagaatcagc tgtataacga gctgaatctg ggcaggcgcg aggagtacga cgtgctggat   1920
aagaggagag gacgggaccc cgagatggga ggcaagccaa ggcgcaagaa ccccaggag   1980
ggcctgtaca atgagctgca gaaggacaag atggccgagg cctatagcga gatcggcatg   2040
aagggagagc ggagaagggg caagggacac gatggcctgt accagggcct gtccaccgcc   2100
acaaaggaca cctatgatgc cctgcacatg caggccctgc ctccaagggg cagcggagcc   2160
acaaacttct ccctgctgaa gcaggccggc gatgtggagg agaatcctgg accaatgcca   2220
cctccaaggc tgctgttctt tctgctgttt ctgacccaa tggaggtgcg gccagaggag   2280
ccactggtgg tgaaggtgga ggagggcgac aacgccgtgc tgcagtgtct gaagggcaca   2340
agcgatggcc ctacccagca gctgacatgg tctagagaga ccctctgaa gccattcctg   2400
aagctgtccc tgggcctgcc aggcttagga atccatatga ggcccctggc tatctggctg   2460
tttatcttca acgtgagcca gcagatggga ggcttctatc tgtgccagcc aggaccacct   2520
agcgagaagg catggcagcc tggatggacc gtgaacgtgg agggcagcgg agagctgttt   2580
cgctggaacg tgagcgacct gggaggcctg ggatgtggcc tgaagaaccg gagctccgag   2640
ggaccctcta gccctagcgg caagctgatg tccccaaagc tgtacgtgtg ggccaaggat   2700
agaccagaga tctgggaggg agagccacca tgcctgcctc aagggacag cctgaatcag   2760
tccctgtctc aggatctgac catggccccc ggctctacac tgtggctgag ctgtggagtg   2820
ccacctgaca gcgtgtcccg gggccctctg agctggaccc acgtgcaccc aaagggcccc   2880
aagtccctgc tgtctctgga gctgaaggac gatcgccctg cccgggacat gtgggtcatg   2940
gagacaggcc tgctgctgcc acgcgccaca gcacaggatg ccggcaagta ctattgccac   3000
cggggcaacc tgaccatgag cttccacctg gagatcacag ccagaccgt gctgtggcac   3060
tggctgctga ggaccggagg atggaaggtg tccgccgtga ccctggcata cctgattttc   3120
```

-continued

| | |
|---|---|
| tgtctgtgct ccctggtggg catcctgcac ctgtga | 3156 |

<210> SEQ ID NO 73
<211> LENGTH: 2829
<212> TYPE: DNA
<213> ORGANISM: Artificial Sequence
<220> FEATURE:
<223> OTHER INFORMATION: 15E7 CH3 hIgG4

<400> SEQUENCE: 73

| | |
|---|---|
| atgaaactgc ccgtgagact gctggtgctg atgttttgga ttcccgcttc ctcgagcgat | 60 |
| gtgctgatga cccagattcc ctttagcctg ccagtgagcc tgggcgacca ggcctccatc | 120 |
| tcttgcagaa gctcccagtc catcgtgcac aggtctggca cacctacct ggagtggtat | 180 |
| ctgcagaagc ctggccagtc cccaaagctg ctgatctaca aggtgagcaa tagattctcc | 240 |
| ggagtgccag acaggtttag cggctccggc tctggcaccg atttcacact gaagatctcc | 300 |
| cgcgtggagg cagaggatct gggcgtgtac tattgcttcc agggctctca cctgccccct | 360 |
| acatttggcg gcggcaccac actggagatc aaggaggag gaggcagcgg cggaggaggc | 420 |
| tccggcggcg gcggctctca ggtgcagctg cagcagcctg gagcagagct ggtgcggccc | 480 |
| ggctctagcg tgaagctgtc ttgtaaggcc agcggctaca ccttcacaga ctattggatg | 540 |
| gattgggtga agcagaggcc tggacagggc ctggagtgga tcggcaccat ctacccaagc | 600 |
| gactcctcta cacactataa ccaggagttt aagggcaagg ccaccatgac agtggacaag | 660 |
| agctcctcta ccgcctatat gcacctgagc tccctgacat ctgaggatag cgccgtgtac | 720 |
| tattgcgccc gcgagggcct ggccggcgtg ttctactttg attattgggg ccagggcacc | 780 |
| acactgaccg tctcgagcga gagcaagtac ggcccaccct gcctccatg tccaggccag | 840 |
| cccagagagc tcaggtgta cactgcct ccatctcagg aggagatgac caagaaccag | 900 |
| gtgagcctga catgtctggt gaagggcttc tatccatccg acatcgccgt ggagtgggag | 960 |
| tctaatggcc agcccgagaa caattacaag accacacccc ctgtgctgga ctccgatggc | 1020 |
| tctttctttc tgtattctcg cctgaccgtg gataagagcc ggtggcagga gggcaacgtg | 1080 |
| ttcagctgct ccgtgatgca cgaggccctg cacaatcact acacacagaa gtctctgagc | 1140 |
| ctgtccctgg gcaagttttg ggtgctggtg gtggtgggag gcgtgctggc ctgttattct | 1200 |
| ctgctggtga ccgtggcctt catcatcttt tgggtgcgca gcaagcggag ccggctgctg | 1260 |
| cactccgact acatgaacat gacccccaaga cggcccggac caacaaggaa gcactaccag | 1320 |
| ccttatgcac cacccgcga ttttgcagca taccggagca agagaggcag gaagaagctg | 1380 |
| ctgtatatct tcaagcagcc cttcatgcgg cccgtgcaga ccacacagga ggaggacggc | 1440 |
| tgctcctgta ggttccctga gaggaggag ggaggatgcg agctgagagt gaagtttttct | 1500 |
| aggagcgccg atgcaccagc ataccagcag ggacagaatc agctgtataa cgagctgaat | 1560 |
| ctgggcaggc gcgaggagta cgacgtgctg gataagagga gaggacggga ccccgagatg | 1620 |
| ggaggcaagc caaggcgcaa gaaccccag gagggcctgt acaatgagct gcagaaggac | 1680 |
| aagatggccg aggcctatag cgagatcggc atgaagggag agcggagaag gggcaaggga | 1740 |
| cacgatggcc tgtaccaggg cctgtccacc gccacaaagg acacctatga tgccctgcac | 1800 |
| atgcaggccc tgcctccaag gggcagcgga gccacaaact ctccctgct gaagcaggcc | 1860 |
| ggcgatgtgg aggagaatcc tggaccaatg ccacctccaa ggctgctgtt ctttctgctg | 1920 |
| tttctgaccc caatggaggt gcggccagag gagccactgg tggtgaaggt ggaggagggc | 1980 |
| gacaacgccg tgctgcagtg tctgaagggc acaagcgatg ccctaccca gcagctgaca | 2040 |

```
tggtctagag agagccctct gaagccattc ctgaagctgt ccctgggcct gccaggctta    2100
ggaatccata tgaggcccct ggctatctgg ctgtttatct tcaacgtgag ccagcagatg    2160
ggaggcttct atctgtgcca gccaggacca cctagcgaga aggcatggca gcctggatgg    2220
accgtgaacg tggagggcag cggagagctg tttcgctgga acgtgagcga cctgggaggc    2280
ctgggatgtg gcctgaagaa ccggagctcc gagggaccct ctagccctag cggcaagctg    2340
atgtccccaa agctgtacgt gtgggccaag gatagaccag atctggga gggagagcca    2400 ccatgcctgc tccaaggga cagcctgaat cagtccctgt ctcaggatct gaccatggcc    2460
cccggctcta cactgtggct gagctgtgga gtgccacctg acagcgtgtc ccggggccct    2520
ctgagctgga cccacgtgca cccaaagggc cccaagtccc tgctgtctct ggagctgaag    2580
gacgatcgcc ctgcccggga catgtgggtc atggagacag gctgctgct gccacgcgcc    2640 acagcacagg atgccggcaa gtactattgc caccggggca acctgaccat gagcttccac    2700
ctggagatca cagccagacc cgtgctgtgg cactggctgc tgaggaccgg aggatggaag    2760
gtgtccgccg tgaccctggc atacctgatt ttctgtctgt gctccctggt gggcatcctg    2820
cacctgtga                                                            2829

<210> SEQ ID NO 74
<211> LENGTH: 2508
<212> TYPE: DNA
<213> ORGANISM: Artificial Sequence
<220> FEATURE:
<223> OTHER INFORMATION: 15E7 hIgG4

<400> SEQUENCE: 74
atgaaactgc ccgtgagact gctggtgctg atgttttgga ttcccgcttc ctcgagcgat      60
gtgctgatga cccagattcc ctttagcctg ccagtgagcc tgggcgacca ggcctccatc     120
tcttgcagaa gctcccagtc catcgtgcac aggtctggca cacctacct ggagtggtat      180 ctgcagaagc ctggccagtc cccaaagctg ctgatctaca aggtgagcaa tagattctcc     240
ggagtgccag acaggtttag cggctccggc tctggcaccg atttcacact gaagatctcc     300
cgcgtggagg cagaggatct gggcgtgtac tattgcttcc agggctctca cctgccccct     360
acatttggcg gcggcaccac actggagatc aagggaggag gaggcagcgg cggaggaggc     420
tccggcggcg gcggctctca ggtgcagctg cagcagcctg agcagagct ggtgcggccc     480 ggctctagcg tgaagctgtc ttgtaaggcc agcggctaca ccttcacaga ctattggatg     540
gattgggtga gcagagagcc tggacagggc ctggagtgga tcggcaccat ctacccaagc     600
gactcctcta cacactataa ccaggagttt aagggcaagg ccaccatgac agtggacaag     660
agctcctcta ccgcctatat gcacctgagc tccctgacat ctgaggatag cgccgtgtac     720
tattgcgccc gcgagggcct ggccggcgtg ttctactttg attattgggg ccagggcacc     780
acactgaccg tctcgagcga gagcaagtac ggcccaccct gccctccatg tccattttgg     840
gtgctggtgg tggtgggagg cgtgctggcc tgttattctc tgctggtgac cgtggccttc     900
atcatctttt gggtgcgcag caagcggagc cggctgctgc actccgacta catgaacatg     960
accccaagac ggccccggacc aacaaggaag cactaccagc cttatgcacc ccccgcgat    1020 tttgcagcat accggagcaa gaggcagg aagaagctgc tgtatatctt caagcagccc     1080
ttcatgcggc ccgtgcagac cacacaggag gaggacggct gctcctgtag gttccctgaa    1140
gaggaggagg aggatgcga gctgagagtg aagttttcta ggagcgccga tgcaccagca    1200
```

```
taccagcagg gacagaatca gctgtataac gagctgaatc tgggcaggcg cgaggagtac    1260
gacgtgctgg ataagaggag aggacgggac cccgagatgg gaggcaagcc aaggcgcaag    1320 aaccccagg agggcctgta caatgagctg cagaaggaca agatggccga ggcctatagc     1380
gagatcggca tgaagggaga gcggagaagg ggcaagggac acgatggcct gtaccagggc    1440
ctgtccaccg ccacaaagga cacctatgat gccctgcaca tgcaggccct gcctccaagg    1500
ggcagcggag ccacaaactt ctccctgctg aagcaggccg cgatgtgga ggagaatcct     1560 ggaccaatgc cacctccaag gctgctgttc tttctgctgt ttctgacccc aatggaggtg    1620
cggccagagg agccactggt ggtgaaggtg gaggagggcg acaacgccgt gctgcagtgt    1680
ctgaagggca aagcgatgg ccctacccag cagctgacat ggtctagaga gagccctctg     1740
aagccattcc tgaagctgtc cctgggcctg ccaggcttag aatccatat gaggcccctg     1800 gctatctggc tgtttatctt caacgtgagc cagcagatgg gaggcttcta tctgtgccag    1860
ccaggaccac ctagcgagaa ggcatggcag cctggatgga ccgtgaacgt ggagggcagc    1920
ggagagctgt ttcgctggaa cgtgagcgac ctggaggcc tggatgtgg cctgaagaac      1980 cggagctccg agggaccctc tagccctagc ggcaagctga tgtccccaaa gctgtacgtg    2040
tgggccaagg atagaccaga gatctgggag ggagagccac catgcctgcc tccaagggac    2100
agcctgaatc agtccctgtc tcaggatctg accatggccc ccggctctac actgtggctg    2160
agctgtggag tgccacctga cagcgtgtcc cggggcccctc tgagctggac ccacgtgcac   2220
ccaaagggcc ccaagtccct gctgtctctg gagctgaagg acgatcgccc tgcccgggac    2280
atgtgggtca tggagacagg cctgctgctg ccacgcgcca cagcacagga tgccggcaag    2340
tactattgcc accggggcaa cctgaccatg agcttccacc tggagatcac agccagaccc    2400
gtgctgtggc actggctgct gaggaccgga ggatggaagg tgtccgccgt gaccctggca    2460
tacctgattt tctgtctgtg ctccctggtg ggcatcctgc acctgtga              2508
```

<210> SEQ ID NO 75
<211> LENGTH: 21
<212> TYPE: PRT
<213> ORGANISM: Artificial Sequence
<220> FEATURE:
<223> OTHER INFORMATION: mouse Ig

<400> SEQUENCE: 75

Met Glu Thr Asp Thr Leu Leu Leu Trp Val Leu Leu Leu Trp Val Pro
1               5                   10                  15

Gly Ser Thr Gly Asp
            20

<210> SEQ ID NO 76
<211> LENGTH: 20
<212> TYPE: PRT
<213> ORGANISM: Artificial Sequence
<220> FEATURE:
<223> OTHER INFORMATION: Human IL2 signal peptide

<400> SEQUENCE: 76

Met Tyr Arg Met Gln Leu Leu Ser Cys Ile Ala Leu Ser Leu Ala Leu
1               5                   10                  15

Val Thr Asn Ser
            20

<210> SEQ ID NO 77
<211> LENGTH: 19

```
<212> TYPE: PRT
<213> ORGANISM: Artificial Sequence
<220> FEATURE:
<223> OTHER INFORMATION: Human IgG2

<400> SEQUENCE: 77

Met Gly Trp Ser Cys Ile Ile Leu Phe Leu Val Ala Thr Ala Thr Gly
1               5                   10                  15

Val His Ser

<210> SEQ ID NO 78
<211> LENGTH: 17
<212> TYPE: PRT
<213> ORGANISM: Artificial Sequence
<220> FEATURE:
<223> OTHER INFORMATION: Gaussia luc

<400> SEQUENCE: 78

Met Gly Val Lys Val Leu Phe Ala Leu Ile Cys Ile Ala Val Ala Glu
1               5                   10                  15

Ala

<210> SEQ ID NO 79
<211> LENGTH: 24
<212> TYPE: DNA
<213> ORGANISM: Artificial Sequence
<220> FEATURE:
<223> OTHER INFORMATION: FlagTag

<400> SEQUENCE: 79
gactacaaag acgacgatga caag                                              24

<210> SEQ ID NO 80
<211> LENGTH: 132
<212> TYPE: DNA
<213> ORGANISM: Artificial Sequence
<220> FEATURE:
<223> OTHER INFORMATION: CD28 Transmembrane domain

<400> SEQUENCE: 80
ttctgggtgc gttctaagcg gagccgcctt ctccactctg actacatgaa catgacacca      60
cgtagaccgg gccctacacg gaaacactac cagccatatg caccaccccg ggactttgcc     120
gcttaccgta gc                                                         132

<210> SEQ ID NO 81
<211> LENGTH: 126
<212> TYPE: DNA
<213> ORGANISM: Artificial Sequence
<220> FEATURE:
<223> OTHER INFORMATION: 41BB domain

<400> SEQUENCE: 81
aagcggggtc gaaagaagct gttgtacatc tttaaacagc ctttcatgcg ccccgtgcag      60
acaactcaag aggaggatgg gtgttcatgt cgctttccag aggaggagga aggaggttgc     120
gagctg                                                                126

<210> SEQ ID NO 82
<211> LENGTH: 339
<212> TYPE: DNA
<213> ORGANISM: Artificial Sequence
<220> FEATURE:
<223> OTHER INFORMATION: CD3z endodomain
```

<400> SEQUENCE: 82

```
cgcgtgaagt tcagtagaag tgccgatgcc ccggcatacc aacaaggcca gaatcagctg      60
tacaacgagc tgaatctcgg caggcgggaa gaatacgacg tcctggataa gaggcgaggg     120
agggacccag agatgggcgg caaaccccag aggaggaaga atccgcagga gggtctttat     180
aatgaactgc agaaggataa gatggcggaa gcctattccg aaattgggat gaaaggggag     240
agaaggagag gaaaaggcca tgatgggctg tatcagggct tgagtacagc aaccaaagac     300
acttacgatg cactgcacat gcaggctttg ccacccagg                            339
```

<210> SEQ ID NO 83
<211> LENGTH: 568
<212> TYPE: PRT
<213> ORGANISM: Artificial Sequence
<220> FEATURE:
<223> OTHER INFORMATION: CD8a hinge

<400> SEQUENCE: 83

```
Met Ala Leu Pro Val Thr Ala Leu Leu Leu Pro Leu Ala Leu Leu Leu
1               5                   10                  15

His Ala Asp Asp Val Leu Met Thr Gln Ile Pro Phe Ser Leu Pro
            20                  25                  30

Val Ser Leu Gly Asp Gln Ala Ser Ile Ser Cys Arg Ser Gln Ser
        35                  40                  45

Ile Val His Arg Ser Gly Asn Thr Tyr Leu Glu Trp Tyr Leu Gln Lys
    50                  55                  60

Pro Gly Gln Ser Pro Lys Leu Leu Ile Tyr Lys Val Ser Asn Arg Phe
65                  70                  75                  80

Ser Gly Val Pro Asp Arg Phe Ser Gly Ser Gly Ser Gly Thr Asp Phe
                85                  90                  95

Thr Leu Lys Ile Ser Arg Val Glu Ala Glu Asp Leu Gly Val Tyr Tyr
            100                 105                 110

Cys Phe Gln Gly Ser His Leu Pro Pro Thr Phe Gly Gly Gly Thr Thr
        115                 120                 125

Leu Glu Ile Lys Gly Gly Gly Gly Ser Gly Gly Gly Gly Ser Gly Gly
    130                 135                 140

Gly Gly Ser Gln Val Gln Leu Gln Gln Pro Gly Ala Glu Leu Val Arg
145                 150                 155                 160

Pro Gly Ser Ser Val Lys Leu Ser Cys Lys Ala Ser Gly Tyr Thr Phe
                165                 170                 175

Thr Asp Tyr Trp Met Asp Trp Val Lys Gln Arg Pro Gly Gln Gly Leu
            180                 185                 190

Glu Trp Ile Gly Thr Ile Tyr Pro Ser Asp Ser Thr His Tyr Asn
        195                 200                 205

Gln Glu Phe Lys Gly Lys Ala Thr Met Thr Val Asp Lys Ser Ser Ser
    210                 215                 220

Thr Ala Tyr Met His Leu Ser Ser Leu Thr Ser Glu Asp Ser Ala Val
225                 230                 235                 240

Tyr Tyr Cys Ala Arg Glu Gly Leu Ala Gly Val Phe Tyr Phe Asp Tyr
                245                 250                 255

Trp Gly Gln Gly Thr Thr Leu Thr Val Ser Ser Ala Leu Ser Asn Ser
            260                 265                 270

Ile Met Tyr Phe Ser His Phe Val Pro Val Phe Leu Pro Ala Lys Pro
        275                 280                 285

Thr Thr Thr Pro Ala Pro Arg Pro Pro Thr Pro Ala Pro Thr Ile Ala
```

```
        290                 295                 300
Ser Gln Pro Leu Ser Leu Arg Pro Glu Ala Cys Arg Pro Ala Ala Gly
305                 310                 315                 320

Gly Ala Val His Thr Arg Gly Leu Asp Phe Ala Cys Asp Phe Trp Val
                325                 330                 335

Leu Val Val Val Gly Gly Val Leu Ala Cys Tyr Ser Leu Leu Val Thr
                340                 345                 350

Val Ala Phe Ile Ile Phe Trp Val Arg Ser Lys Arg Ser Arg Gly Gly
            355                 360                 365

His Ser Asp Tyr Met Asn Met Thr Pro Arg Arg Pro Gly Pro Thr Arg
        370                 375                 380

Lys His Tyr Gln Pro Tyr Ala Pro Pro Arg Asp Phe Ala Ala Tyr Arg
385                 390                 395                 400

Ser Lys Arg Gly Arg Lys Lys Leu Leu Tyr Ile Phe Lys Gln Pro Phe
                405                 410                 415

Met Arg Pro Val Gln Thr Thr Gln Glu Glu Asp Gly Cys Ser Cys Arg
                420                 425                 430

Phe Pro Glu Glu Glu Glu Gly Gly Cys Glu Leu Arg Val Lys Phe Ser
            435                 440                 445

Arg Ser Ala Asp Ala Pro Ala Tyr Gln Gln Gly Gln Asn Gln Leu Tyr
450                 455                 460

Asn Glu Leu Asn Leu Gly Arg Arg Glu Glu Tyr Asp Val Leu Asp Lys
465                 470                 475                 480

Arg Arg Gly Arg Asp Pro Glu Met Gly Gly Lys Pro Gln Arg Arg Lys
                485                 490                 495

Asn Pro Gln Glu Gly Leu Tyr Asn Glu Leu Gln Lys Asp Lys Met Ala
                500                 505                 510

Glu Ala Tyr Ser Glu Ile Gly Met Lys Gly Glu Arg Arg Arg Gly Lys
            515                 520                 525

Gly His Asp Gly Leu Tyr Gln Gly Leu Ser Thr Ala Thr Lys Asp Thr
        530                 535                 540

Tyr Asp Ala Leu His Met Gln Ala Leu Pro Pro Arg Gly Gly Gly Ser
545                 550                 555                 560

Asp Tyr Lys Asp Asp Asp Asp Lys
                565
```

<210> SEQ ID NO 84
<211> LENGTH: 1707
<212> TYPE: DNA
<213> ORGANISM: Artificial Sequence
<220> FEATURE:
<223> OTHER INFORMATION: CD8a hinge

<400> SEQUENCE: 84

| | | |
|---|---|---|
| atggctctcc ccgtgaccgc actgcttctg cctctggcgt tattgctaca cgccgccgac | 60 |
| gatgtcctga tgacacaaat cccatttagc ctgcctgtat ccctgggtga tcaggccagc | 120 |
| attagctgtc gctcctccca gtccatcgtt caccggtctg caacacgta tctggaatgg | 180 |
| tacctccaga aacccggcca atcccctaag ctccttattt acaaagtgag caatcgcttt | 240 |
| tctggagtgc ctgatagatt ctcaggaagt ggttcaggaa ctgacttcac ccttaagatt | 300 |
| agccgggttg aggccgagga tcttggtgtg tactactgct ttcaaggag tcaccttcct | 360 |
| cccacatttg gcggcggcac aactctggag atcaaaggtg gtggaggag cggtggaggt | 420 |
| ggaagtggcg gtggcggctc acaggtgcag ttgcagcaac ccggggccga actggtcaga | 480 |

```
ccgggctcct ctgtgaagct gtcatgcaag gctagtggct ataccttcac cgactattgg    540
atggattggg taaagcagcg gccaggacaa ggactggaat ggattgggac catttacccc    600
agcgacagtt ctacgcacta caatcaggag ttcaaaggca aggctacaat gacagtggac    660
aagtccagtt ctacagccta catgcacctt tctagcctca catcagagga ttccgcagtg    720
tactattgtg cacgtgaagg cctggctgga gtgttttact tcgactactg gggacagggg    780
accaccttga cggttagctc cgccctgtcc aacagcatta tgtacttctc acatttcgtt    840
cctgtgtttc tgcccgcaaa acctactaca accccctgccc ctcgaccacc aactccagct    900
cccactatag cctctcagcc cctgtctctc agaccagagg cctgtaggcc tgctgcggga    960
ggagccgtgc atacccgcgg gttggacttc gcctgcgatt tctgggtgct ggttgtagta   1020
ggcggagtct tggcctgtta ttcactgttg gttacagtgg cctttatcat attctgggtc   1080
cgctccaaga gaagccgggg cgggcatagc gactacatga acatgactcc ccgacgccca   1140
ggccccacca gaaagcacta tcagccatac gctccaccta gggattttgc ggcatatcgg   1200
agcaaacgtg gcaggaagaa gctcctgtat atcttcaaac agcccttcat gcggcccgtc   1260
cagactacgc aggaagagga cggttgcagc tgcagatttc ggaagaggag gaaggtggg    1320
tgtgaactcc gggtgaagtt tagccggagt gcagatgctc cagcgtacca acagggccag   1380
aatcagctct ataacgaact gaatctggga aggagggagg aatatgatgt cctggataag   1440
cgacgcgggc gcgatcccga gatgggcggg aaacccccaaa gacgtaagaa tccgcaggag   1500
gggttgtaca cgaactgca aaggacaaa atggctgagg cctattccga gatcggaatg    1560
aaagggaaa ggaggagagg caaggggcat gacggcctgt atcaggggct gtctactgca    1620
accaaagaca cctacgacgc actgcacatg caggcacttc cgccacgagg cggagggagc   1680
gactacaaag acgacgatga caagtga                                      1707
```

<210> SEQ ID NO 85
<211> LENGTH: 533
<212> TYPE: PRT
<213> ORGANISM: Artificial Sequence
<220> FEATURE:
<223> OTHER INFORMATION: CD28 hinge domain

<400> SEQUENCE: 85

Met Ala Leu Pro Val Thr Ala Leu Leu Leu Pro Leu Ala Leu Leu Leu
1               5                   10                  15

His Ala Ala Asp Ile His Met Thr Gln Ser Pro Ser Ser Leu Ser Ala
                20                  25                  30

Ser Leu Gly Gly Lys Val Thr Ile Thr Cys Lys Ala Ser Gln Asp Ile
        35                  40                  45

Asn Arg Tyr Ile Ala Trp Tyr Gln His Lys Pro Gly Lys Gly Pro Arg
    50                  55                  60

Leu Leu Ile His Phe Thr Ser Thr Leu Gln Ser Gly Ile Pro Ser Arg
65                  70                  75                  80

Phe Ser Gly Ser Gly Ser Gly Arg Asp Tyr Ser Phe Ser Ile Ser Asn
                85                  90                  95

Leu Glu Pro Glu Asp Ile Ala Thr Tyr Tyr Cys Leu Gln Tyr Asp Asp
                100                 105                 110

Leu Arg Thr Phe Gly Gly Gly Thr Lys Leu Glu Ile Lys Gly Gly Gly
            115                 120                 125

Gly Ser Gly Gly Gly Gly Ser Gly Gly Gly Gly Ser Gln Ile Gln Leu
    130                 135                 140

Val Gln Ser Gly Pro Glu Leu Lys Lys Pro Gly Glu Thr Val Lys Ile
145                 150                 155                 160

Ser Cys Lys Ala Ser Gly Tyr Thr Phe Thr Thr Tyr Gly Met Ser Trp
            165                 170                 175

Val Lys Gln Ala Pro Gly Lys Gly Leu Lys Trp Met Gly Trp Ile Tyr
            180                 185                 190

Thr Tyr Ser Gly Val Pro Thr Tyr Ala Asp Asp Leu Glu Gly Arg Phe
            195                 200                 205

Ala Phe Ser Leu Glu Thr Ser Ala Ser Thr Ala Tyr Leu Gln Ile Asn
    210                 215                 220

Asn Leu Lys Asn Glu Asp Thr Ala Thr Tyr Phe Cys Ala Arg Val Arg
225                 230                 235                 240

Asp Gly Tyr Tyr Arg Tyr Ala Met Asp Tyr Trp Gly Gln Gly Thr Ser
            245                 250                 255

Val Thr Val Ser Ser Cys Lys Ile Glu Val Met Tyr Pro Pro Pro Tyr
            260                 265                 270

Leu Asp Asn Glu Lys Ser Asn Gly Thr Ile Ile His Val Lys Gly Lys
    275                 280                 285

His Leu Cys Pro Ser Pro Leu Phe Pro Gly Pro Ser Lys Pro Phe Trp
    290                 295                 300

Val Leu Val Val Val Gly Gly Val Leu Ala Cys Tyr Ser Leu Leu Val
305                 310                 315                 320

Thr Val Ala Phe Ile Ile Phe Trp Val Arg Ser Lys Arg Ser Arg Leu
            325                 330                 335

Leu His Ser Asp Tyr Met Asn Met Thr Pro Arg Arg Pro Gly Pro Thr
            340                 345                 350

Arg Lys His Tyr Gln Pro Tyr Ala Pro Pro Arg Asp Phe Ala Ala Tyr
            355                 360                 365

Arg Ser Lys Arg Gly Arg Lys Lys Leu Leu Tyr Ile Phe Lys Gln Pro
            370                 375                 380

Phe Met Arg Pro Val Gln Thr Thr Gln Glu Glu Asp Gly Cys Ser Cys
385                 390                 395                 400

Arg Phe Pro Glu Glu Glu Glu Gly Gly Cys Glu Leu Arg Val Lys Phe
                405                 410                 415

Ser Arg Ser Ala Asp Ala Pro Ala Tyr Gln Gln Gly Gln Asn Gln Leu
            420                 425                 430

Tyr Asn Glu Leu Asn Leu Gly Arg Arg Glu Glu Tyr Asp Val Leu Asp
            435                 440                 445

Lys Arg Arg Gly Arg Asp Pro Glu Met Gly Gly Lys Pro Gln Arg Arg
450                 455                 460

Lys Asn Pro Gln Glu Gly Leu Tyr Asn Glu Leu Gln Lys Asp Lys Met
465                 470                 475                 480

Ala Glu Ala Tyr Ser Glu Ile Gly Met Lys Gly Glu Arg Arg Arg Gly
            485                 490                 495

Lys Gly His Asp Gly Leu Tyr Gln Gly Leu Ser Thr Ala Thr Lys Asp
            500                 505                 510

Thr Tyr Asp Ala Leu His Met Gln Ala Leu Pro Pro Arg Asp Tyr Lys
            515                 520                 525

Asp Asp Asp Asp Lys
            530

<210> SEQ ID NO 86
<211> LENGTH: 1602
<212> TYPE: DNA

```
<213> ORGANISM: Artificial Sequence
<220> FEATURE:
<223> OTHER INFORMATION: CD28 hinge domain

<400> SEQUENCE: 86
atggctctcc ctgtaaccgc actccttctg ccattggctc tcctgcttca tgccgccgat    60
atccatatga cccagagtcc aagctctctg agcgctagcc tgggcggcaa agtgaccata   120
acatgcaagg ctagccagga cattaaccgg tacatagcct ggtaccagca taagcccgga   180
aaaggcccca gactgctgat ccacttcacc tccacactgc agtccgggat tccctcacga   240
ttctccggat caggttcagg tcgagactac tcctttagca tttccaacct cgaacctgag   300
gacatcgcca catactactg tctgcagtat gacgaccttc gcacttttgg cggtggaact   360
aaactggaga tcaagggcgg aggtggttcc ggaggcggcg ggtctggagg tggcgggagt   420
cagattcagc ttgtacaatc tgggcctgag ctgaagaaac ccggagaaac cgtcaagatc   480
agctgcaaag caagtgggta ctctttcacg acgtatggca tgtcttgggt caagcaagct   540
cctgggaaag ggctgaaatg gatgggctgg atttacacct attctggagt tcctacatat   600
gccgacgatc tggaagggcg ctttgccttc agcctggaga ctagcgcctc aaccgcttat   660
ttgcagatca acaacctcaa gaacgaagat acggcgacct atttctgtgc cagagttcgg   720
gatggctact atagatacgc catggattat tggggccaag gtacatccgt gaccgtttca   780
agctgcaaga tcgaagtgat gtaccctcct ccctatctcg acaatgagaa atccaatgga   840
accattatac acgtcaaggg gaagcacctg tgtcccagcc ctctgtttcc gggaccctct   900
aaaccatttt gggtgctggt ggtggtagga ggagttctcg cgtgctatag cctgttggtg   960
actgtcgcat tcatcatctt ctgggtgcgt tctaagcgga gccgccttct ccactctgac  1020
tacatgaaca tgacaccacg tagaccgggc cctacacgga aacactacca gccatatgca  1080
ccaccccggg actttgccgc ttaccgtagc aagcggggtc gaaagaagct gttgtacatc  1140
tttaaacagc ctttcatgcg ccccgtgcag acaactcaag aggaggatgg gtgttcatgt  1200
cgctttccag aggaggagga aggaggttgc gagctgcgcg tgaagttcag tagaagtgcc  1260
gatgccccgg cataccaaca aggccagaat cagctgtaca acgagctgaa tctcggcagg  1320
cgggaagaat acgacgtcct ggataagagg cgagggaggg acccagagat gggcggcaaa  1380
ccccagagga ggaagaatcc gcaggagggt ctttataatg aactgcagaa ggataagatg  1440
gcggaagcct attccgaaat tgggatgaaa ggggagagaa ggagaggaaa aggccatgat  1500
gggctgtatc agggcttgag tacagcaacc aaagacactt acgatgcact gcacatgcag  1560
gctttgccac ccagggatta caaggatgac gacgacaaat ga                     1602
```